US006312922B1

(12) United States Patent
Edwards et al.

(10) Patent No.: US 6,312,922 B1
(45) Date of Patent: Nov. 6, 2001

(54) COMPLEMENTARY DNAS

(75) Inventors: Jean-Baptiste Dumas Milne Edwards, Paris; Aymeric Duclert, Saint Maur; Lydie Bougueleret, Vanves, all of (FR)

(73) Assignee: Genset, Paris (FR)

( * ) Notice: Subject to any disclaimer, the term of this patent is extended or adjusted under 35 U.S.C. 154(b) by 0 days.

(21) Appl. No.: 09/247,155

(22) Filed: Feb. 9, 1999

Related U.S. Application Data

(60) Provisional application No. 60/099,273, filed on Sep. 4, 1998, provisional application No. 60/096,116, filed on Aug. 10, 1998, provisional application No. 60/081,563, filed on Apr. 13, 1998, and provisional application No. 60/074,121, filed on Feb. 9, 1998.

(51) Int. Cl.⁷ ............................. C12N 15/63; C12N 1/21; C12N 5/10; C12N 15/12
(52) U.S. Cl. ..................... 435/69.1; 435/325; 435/419; 435/252.3; 435/254.11; 435/320.1; 536/23.1; 536/23.2
(58) Field of Search ................................ 435/252.3, 69.1, 435/325, 419, 254.11, 320.1; 536/23.5, 23.1, 23.2

(56) References Cited

FOREIGN PATENT DOCUMENTS 625 572    11/1994  (EP) .
WO 96/34981  11/1996  (WO) .

OTHER PUBLICATIONS

Matthews et al. Analytical strategies for the use of DNA probes. Analytical Biochemistry vol. 169 pp. 1–25, 1988.*
Genbank Accession No. AA400536, 1997.*
Genbank Accession No. AA281637, 1997.*
Genbank Accession No. AA402000, 1997.*
Genbank Accession No. G28389, 1996.*
Genbank Accession No. AA340672, 1997.*
Genbank Accession No. AA152481, 1996.*
Genbank Accession No. AA029276, 1997.*
Genbank Accession No. N21474, 1995.*
Genbank Accession No. AA281340, 1997.*
Genbank Accession No. AD000833, 1988.*
Adams et al., "Initial assessment of human gene diversity and expression patterns based upon 83 million nucleotides of cDNA sequence", Nature, 377 (Supp):3–17 (Sep. 28, 1995).
Carninci et al., "High–Efficiency Full–Length cDNA Cloning by Biotinylated CAP Trapper", Genomics, 37 : 327–336 (1996).
Hillier et al., "Generation and Analysis of 280,000 Human Expressed Sequence Tags", Genome Research, 6: 807–828 (1996).
Kato et al., "Construction of a human full–length cDNA bank", Gene, 150: 243–250 (1994).
Nomura, et al., "Prediction of the Coding Sequences of Unidentified Human Genes. I. The Coding Sequences of 40 New Genes (KIAA0001–KIAA0040) Deduced by Analysis of Randomly Samples cDNA Clones from Human Immature Myeloid Cell Line KG–1", DNA Research 1, 27–35 (1994).
Von Heijne, Nucleic Acid Research, 14, 4683–90 (1986).

* cited by examiner

Primary Examiner—John S. Brusca
(74) Attorney, Agent, or Firm—Knoibbe, Martens, Olson & Bear, LLP

(57) ABSTRACT

The sequences of extended cDNAs encoding secreted proteins are disclosed. The extended cDNAs can be used to express secreted proteins or portions thereof or to obtain antibodies capable of specifically binding to the secreted proteins. The extended cDNAs may also be used in diagnostic, forensic, gene therapy, and chromosome mapping procedures. The extended cDNAs may also be used to design expression vectors and secretion vectors.

33 Claims, 10 Drawing Sheets

| Minimum signal peptide score | false positive rate | false negative rate | proba(0.1) | proba(0.2) |
|---|---|---|---|---|
| 3.5 | 0.121 | 0.036 | 0.467 | 0.664 |
| 4 | 0.096 | 0.06 | 0.519 | 0.708 |
| 4.5 | 0.078 | 0.079 | 0.565 | 0.745 |
| 5 | 0.062 | 0.098 | 0.615 | 0.782 |
| 5.5 | 0.05 | 0.127 | 0.659 | 0.813 |
| 6 | 0.04 | 0.163 | 0.694 | 0.836 |
| 6.5 | 0.033 | 0.202 | 0.725 | 0.855 |
| 7 | 0.025 | 0.248 | 0.763 | 0.878 |
| 7.5 | 0.021 | 0.304 | 0.78 | 0.889 |
| 8 | 0.015 | 0.368 | 0.816 | 0.909 |
| 8.5 | 0.012 | 0.418 | 0.836 | 0.92 |
| 9 | 0.009 | 0.512 | 0.856 | 0.93 |
| 9.5 | 0.007 | 0.581 | 0.863 | 0.934 |
| 10 | 0.006 | 0.679 | 0.835 | 0.919 |

FIG. 2

| Minimum signal peptide score | All ESTs | New ESTs | ESTs matching public EST closer than 40 bp from beginning | ESTs extending known mRNA more than 40 bp | ESTs extending public EST more than 40 bp |
|---|---|---|---|---|---|
| 3.5 | 2674 | 947 | 599 | 23 | 150 |
| 4 | 2278 | 784 | 499 | 23 | 126 |
| 4.5 | 1943 | 647 | 425 | 22 | 112 |
| 5 | 1657 | 523 | 353 | 21 | 96 |
| 5.5 | 1417 | 419 | 307 | 19 | 80 |
| 6 | 1190 | 340 | 238 | 18 | 68 |
| 6.5 | 1035 | 280 | 186 | 18 | 60 |
| 7 | 893 | 219 | 161 | 15 | 48 |
| 7.5 | 753 | 173 | 132 | 12 | 36 |
| 8 | 636 | 133 | 101 | 11 | 29 |
| 8.5 | 543 | 104 | 83 | 8 | 26 |
| 9 | 456 | 81 | 63 | 6 | 24 |
| 9.5 | 364 | 57 | 48 | 6 | 18 |
| 10 | 303 | 47 | 35 | 6 | 15 |

FIG. 4

| Tissue | All ESTs | New ESTs | ESTs matching public EST closer than 40 bp from beginning | ESTs extending known mRNA more than 40 bp | ESTs extending public EST more than 40 bp |
|---|---|---|---|---|---|
| Brain | 329 | 131 | 75 | 3 | 24 |
| Cancerous prostate | 134 | 40 | 37 | 1 | 6 |
| Cerebellum | 17 | 9 | 1 | 0 | 6 |
| Colon | 21 | 11 | 4 | 0 | 0 |
| Dystrophic muscle | 41 | 18 | 8 | 0 | 1 |
| Fetal brain | 70 | 37 | 16 | 0 | 1 |
| Fetal kidney | 227 | 116 | 46 | 1 | 19 |
| Fetal liver | 13 | 7 | 2 | 0 | 0 |
| Heart | 30 | 15 | 7 | 0 | 1 |
| Hypertrophic prostat | 86 | 23 | 22 | 2 | 2 |
| Kidney | 10 | 7 | 3 | 0 | 0 |
| Large intestine | 21 | 8 | 4 | 0 | 1 |
| Liver | 23 | 9 | 6 | 0 | 0 |
| Lung | 24 | 12 | 4 | 0 | 1 |
| Lung (cells) | 57 | 38 | 6 | 0 | 4 |
| Lymph ganglia | 163 | 60 | 23 | 2 | 12 |
| Lymphocytes | 23 | 6 | 4 | 0 | 2 |
| Muscle | 33 | 16 | 6 | 0 | 4 |
| Normal prostate | 181 | 61 | 45 | 7 | 11 |
| Ovary | 90 | 57 | 12 | 1 | 2 |
| Pancreas | 48 | 11 | 6 | 0 | 1 |
| Placenta | 24 | 5 | 1 | 0 | 0 |
| Prostate | 34 | 16 | 4 | 0 | 2 |
| Spleen | 56 | 28 | 10 | 0 | 1 |
| Substantia nigra | 108 | 47 | 27 | 1 | 6 |
| Surrenals | 15 | 3 | 3 | 1 | 0 |
| Testis | 131 | 68 | 25 | 1 | 8 |
| Thyroid | 17 | 8 | 2 | 0 | 2 |
| Umbilical cord | 55 | 17 | 12 | 1 | 3 |
| Uterus | 28 | 15 | 3 | 0 | 2 |
| Non tissue-specific | 568 | 48 | 177 | 2 | 28 |
| Total | 2677 | 947 | 601 | 23 | 150 |

Promoter sequence P15B4 (861 bp):

| Matrix | Position | Orientation | Score | Length | Sequence |
|---|---|---|---|---|---|
| NFY_Q6 | -748 | - | 0.956 | 11 | GGACCAATCAT |
| MZF1_01 | -738 | + | 0.962 | 8 | CCTGGGGA |
| CMYB_01 | -684 | + | 0.994 | 9 | TGACCGTTG |
| VMYB_02 | -682 | - | 0.985 | 9 | TCCAACGGT |
| STAT_01 | -673 | + | 0.968 | 9 | TTCCTGGAA |
| STAT_01 | -673 | - | 0.951 | 9 | TTCCAGGAA |
| MZF1_01 | -556 | - | 0.956 | 8 | TTGGGGGA |
| IK2_01 | -451 | + | 0.965 | 12 | GAATGGGATTTC |
| MZF1_01 | -424 | + | 0.986 | 8 | AGAGGGGA |
| SRY_02 | -398 | - | 0.955 | 12 | GAAAACAAAACA |
| MZF1_01 | -216 | + | 0.960 | 8 | GAAGGGGA |
| MYOD_Q6 | -190 | + | 0.981 | 10 | AGCATCTGCC |
| DELTAEF1_01 | -176 | + | 0.958 | 11 | TCCCACCTTCC |
| S8_01 | 5 | - | 0.992 | 11 | GAGGCAATTAT |
| MZF1_01 | 16 | + | 0.986 | 8 | AGAGGGGA |

Promoter sequence P29B6 (555 bp):

| Matrix | Position | Orientation | Score | Length | Sequence |
|---|---|---|---|---|---|
| ARNT_01 | -311 | + | 0.964 | 16 | GGACTCACGTGCTGCT |
| NMYC_01 | -309 | + | 0.965 | 12 | ACTCACGTGCTG |
| USF_01 | -309 | + | 0.985 | 12 | ACTCACGTGCTG |
| USF_01 | -309 | - | 0.985 | 12 | CAGCACGTGAGT |
| NMYC_01 | -309 | - | 0.956 | 12 | CAGCACGTGAGT |
| MYCMAX_02 | -309 | - | 0.972 | 12 | CAGCACGTGAGT |
| USF_C | -307 | + | 0.997 | 8 | TCACGTGC |
| USF_C | -307 | - | 0.991 | 8 | GCACGTGA |
| MZF1_01 | -292 | - | 0.968 | 8 | CATGGGGA |
| ELK1_02 | -105 | + | 0.963 | 14 | CTCTCCGGAAGCCT |
| CETS1P54_01 | -102 | + | 0.974 | 10 | TCCGGAAGCC |
| AP1_Q4 | -42 | - | 0.963 | 11 | AGTGACTGAAC |
| AP1FJ_Q2 | -42 | + | 0.961 | 11 | AGTGACTGAAC |
| PADS_C | 45 | + | 1.000 | 9 | TGTGGTCTC |

Promoter sequence P13H2 (546 bp):

| Matrix | Position | Orientation | Score | Length | Sequence |
|---|---|---|---|---|---|
| CMYB_01 | -502 | + | 0.983 | 9 | TGTCAGTTG |
| MYOD_Q6 | -501 | - | 0.961 | 10 | CCCAACTGAC |
| S8_01 | -444 | - | 0.960 | 11 | AATAGAATTAG |
| S8_01 | -425 | + | 0.966 | 11 | AACTAAATTAG |
| DELTAEF1_01 | -390 | - | 0.960 | 11 | GCACACCTCAG |
| GATA_C | -364 | - | 0.964 | 11 | AGATAAATCCA |
| CMYB_01 | -349 | + | 0.958 | 9 | CTTCAGTTG |
| GATA1_02 | -343 | + | 0.959 | 14 | TTGTAGATAGGACA |
| GATA_C | -339 | + | 0.953 | 11 | AGATAGGACAT |
| TAL1ALPHAE47_01 | -235 | + | 0.973 | 16 | CATAACAGATGGTAAG |
| TAL1BETAE47_01 | -235 | + | 0.983 | 16 | CATAACAGATGGTAAG |
| TAL1BETAITF2_01 | -235 | + | 0.978 | 16 | CATAACAGATGGTAAG |
| MYOD_Q6 | -232 | + | 0.954 | 10 | ACCATCTGTT |
| GATA1_04 | -217 | - | 0.953 | 13 | TCAAGATAAAGTA |
| IK1_01 | -126 | + | 0.963 | 13 | AGTTGGGAATTCC |
| IK2_01 | -126 | + | 0.985 | 12 | AGTTGGGAATTC |
| CREL_01 | -123 | + | 0.962 | 10 | TGGGAATTCC |
| GATA1_02 | -96 | - | 0.950 | 14 | TCAGTGATATGGCA |
| SRY_02 | -41 | + | 0.951 | 12 | TAAAACAAAACA |
| E2F_02 | -33 | + | 0.957 | 8 | TTTAGCGC |
| MZF1_01 | -5 | - | 0.975 | 8 | TGAGGGGA |

FIG. 10

97.8% identity in 92 aa overlap

```
                    10        20        30        40        50        60
SEQ ID NO:120  MASLGHILVFCVGLLTMAKAESPKEHDPFTYDYQSLQIGGLVIAGILFILGILIVLSRRC
               ::..: :::::::::::::::::::::::::::::::::::::::::::::::::::::
SEQ ID NO:180  MAPLHHILVFCVGLLTMAKAESPKEHDPFTYDYQSLQIGGLVIAGILFILGILIVLSRRC
                    10        20        30        40        50        60

70        80        90
SEQ ID NO:120  RCKFNQQQRTGEPDEEEGTFRSSIRRLSTRRR
               ::::::::::::::::::::::::::::::::
SEQ ID NO:180  RCKFNQQQRTGEPDEEEGTFRSSIRRLSTRRR
                    70        80        90
```

FIG. 11

98.6% identity in 210 aa overlap

```
                                                10        20        30
SEQ ID NO:121                              MLTLLGLSLILAGLIVGGACIYKHFMPKST
                                           ::::::::.:::::::::::::.::::::
SEQ ID NO:181  LLSRTVRTQILTGKELRVATQEKEGSSGRCMLTLLGLSFILAGLIVGGACIYKYFMPKST
                    30        40        50        60        70        80

40        50        60        70        80        90
SEQ ID NO:121  IYRGEMCFFDSEDPANSLRGGEPNFLPVTEEADIREDDNIAIIDVPVPSFSDSDPAAIIH
               ::::::::::::::::::::::::::::::::::::::::::::::::::::::::::::
SEQ ID NO:181  IYRGEMCFFDSEDPANSLRGGEPNFLPVTEEADIREDDNIAIIDVPVPSFSDSDPAAIIH
                    90       100       110       120       130       140

100       110       120       130       140       150
SEQ ID NO:121  DFEKGMTAYLDLLLGNCYLMPLNTSIVMPPENLVELFGKLASGRYLPQTYVVREDLVAVE
               :::::::::::::::::::::::::::::::: :::::::::::::::::::::::::::
SEQ ID NO:181  DFEKGMTAYLDLLLGNCYLMPLNTSIVMPPKNLVELFGKLASGRYLPQTYVVREDLVAVE
                   150       160       170       180       190       200

160       170       180       190       200       210
SEQ ID NO:121  EIRDVSNLGIFIYQLCNNRKSFRLRRRDLLLGFNKRAIDKCWKIRHFPNEFIVETKICQE
               ::::::::::::::::::::::::::::::::::::::::::::::::::::::::::::
SEQ ID NO:181  EIRDVSNLGIFIYQLCNNRKSFRLRRRDLLLGFNKRAIDKCWKIRHFPNEFIVETKICQE
                   210       220       230       240       250       260
```

FIG. 12

```
83.4% identity in 211 aa overlap
                                         10        20        30
SEQ ID NO:128                    LWWFWLLWTVLILFSCCCAFRHRRAKLRLQ
                                 ::::::::::::::::::::::::::::::
SEQ ID NO:182  ELCPGVNTQPYLCETGHCCGETGCCTYYYELWWFWLLWTVLILFSCCCAFRHRRAKLRLQ
                  70        80        90       100       110       120

40        50        60        70        80        90
SEQ ID NO:128  QQQRQREINLLAYHGACHGAGPFPTGSLLDLRLLSTFKPPAYEDVVHRPGTPPPPYTVAP
               ::::::::::::::::::::: :::::::::::::::.:::::::::::.::::::::.:
SEQ ID NO:182  QQQRQREINLLAYHGACHGAGPVPTGSLLDLRLLSAFKPPAYEDVVHHPGTPPPPYTVGP
                 130       140       150       160       170       180

100       110       120       130       140       150
SEQ ID NO:128  GRPLTASSEQTCCSSSSSCPAHFEGTNVEGVSSHQSAPPHQEGEPGAGVTPASTPPSCRY
               :  :  :..:::  :  :::.:::.:::::::::::.::: :::::::::..:. .::::::
SEQ ID NO:182  GYPWTTSSECTRCSSESSCSAHLEGTNVEGVSSQQSALPHQEGEPRAGLSPVHIPPSCRY
                 190       200       210       220       230       240

160       170       180       190       200       210
SEQ ID NO:128  RRLTGDSGIELCPCPASGEGEPVKEVRVSATLPDLEDYSPCALPPESVPQIFPMGLSSSE
               ::::::::::::::::::..:::::.:.:.::.::::::::::::.:::.:. ::::.::
SEQ ID NO:182  RRLTGDSGIELCPCPDSSEGEPLKEARASASQPDLEDHSPCALPPDSVSQVPPMGLASSC
                 250       260       270       280       290       300

SEQ ID NO:128  GDIP
               :
SEQ ID NO:182  GTSHK
```

COMPLEMENTARY DNAS

RELATED APPLICATIONS

The present application claims priority from U.S. Provisional Patent Aplication Ser. No. 60/074,121 filed Feb. 9, 1998, U.S. Provisional Patent Aplication Ser. No. 60/081,563, filed Apr. 13, 1998, U.S. Provisional Patent Aplication Ser. No. 60/096,116, filed Aug. 10, 1998, and U.S. Provisional Patent Aplication Ser. No. 60/099,273 filed Sep. 4, 1998 the disclosures of which are incorporated herein by reference in their entirety.

Table I lists the SEQ ID Nos. of the extended cDNAs in the present application, the SEQ ID Nos. of the extended cDNAs in the provisional applications, and the identities of the provisional applications in which the extended cDNAs were disclosed.

BACKGROUND OF THE INVENTION

The estimated 50,000–100,000 genes scattered along the human chromosomes offer tremendous promise for the understanding, diagnosis, and treatment of human diseases. In addition, probes capable of specifically hybridizing to loci distributed throughout the human genome find applications in the construction of high resolution chromosome maps and in the identification of individuals.

In the past, the characterization of even a single human gene was a painstaking process, requiring years of effort. Recent developments in the areas of cloning vectors, DNA sequencing, and computer technology have merged to greatly accelerate the rate at which human genes can be isolated, sequenced, mapped, and characterized. Cloning vectors such as yeast artificial chromosomes (YACs) and bacterial artificial chromosomes (BACs) are able to accept DNA inserts ranging from 300 to 1000 kilobases (kb) or 100–400 kb in length respectively, thereby facilitating the manipulation and ordering of DNA sequences distributed over great distances on the human chromosomes. Automated DNA sequencing machines permit the rapid sequencing of human genes. Bioinformatics software enables the comparison of nucleic acid and protein sequences, thereby assisting in the characterization of human gene products.

Currently, two different approaches are being pursued for identifying and characterizing the genes distributed along the human genome. In one approach, large fragments of genomic DNA are isolated, cloned, and sequenced. Potential open reading frames in these genomic sequences are identified using bio-informatics software. However, this approach entails sequencing large stretches of human DNA which do not encode proteins in order to find the protein encoding sequences scattered throughout the genome. In addition to requiring extensive sequencing, the bio-informatics software may mischaracterize the genomic sequences obtained. Thus, the software may produce false positives in which non-coding DNA is mischaracterizedas coding DNA or false negatives in which coding DNA is mislabeled as non-coding DNA.

An alternative approach takes a more direct route to identifying and characterizing human genes. In this approach, complementary DNAs (cDNAs) are synthesized from isolated messenger RNAs (mRNAs) which encode human proteins. Using this approach, sequencing is only performed on DNA which is derived from protein coding portions of the genome. Often, only short stretches of the cDNAs are sequenced to obtain sequences called expressed sequence tags (ESTs). The ESTs may then be used to isolate or purify extended cDNAs which include sequences adjacent to the EST sequences. The extended cDNAs may contain all of the sequence of the EST which was used to obtain them or only a portion of the sequence of the EST which was used to obtain them. In addition, the extended cDNAs may contain the full coding sequence of the gene from which the EST was derived or, alternatively, the extended cDNAs may include portions of the coding sequence of the gene from which the EST was derived. It will be appreciated that there may be several extended cDNAs which include the EST sequence as a result of alternate splicing or the activity of alternative promoters.

In the past, the short EST sequences which could be used to isolate or purify extended cDNAs were often obtained from oligo-dT primed cDNA libraries. Accordingly, they mainly corresponded to the 3' untranslated region of the mRNA. In part, the prevalence of EST sequences derived from the 3' end of the mRNA is a result of the fact that typical techniques for obtaining cDNAs, are not well suited for isolating cDNA sequences derived from the 5' ends of mRNAs. (Adams et al., *Nature* 377:174, 1996, Hillier et al., *Genome Res.* 6:807–828, 1996).

In addition, in those reported instances where longer cDNA sequences have been obtained, the reported sequences typically correspond to coding sequences and do not include the full 5' untranslated region of the mRNA from which the cDNA is derived. Such incomplete sequences may not include the first exon of the mRNA, particularly in situations where the first exon is short. Furthermore, they may not include some exons, often short ones, which are located upstream of splicing sites. Thus, there is a need to obtain sequences derived from the 5' ends of mRNAs which can be used to obtain extended cDNAs which may include the 5' sequences contained in the 5' ESTs.

While many sequences derived from human chromosomes have practical applications, approaches based on the identification and characterization of those chromosomal sequences which encode a protein product are particularly relevant to diagnostic and therapeutic uses. Of the 50,000–100,000 protein coding genes, those genes encoding proteins which are secreted from the cell in which they are synthesized, as well as the secreted proteins themselves, are particularly valuable as potential therapeutic agents. Such proteins are often involved in cell to cell communication and may be responsible for producing a clinically relevant response in their target cells.

In fact, several secretory proteins, including tissue plasminogen activator, G-CSF, GM-CSF, erythropoietin, human growth hormone, insulin, interferon-α, interferon-β, interferon-γ, and interleukin-2, are currently in clinical use. These proteins are used to treat a wide range of conditions, including acute myocardial infarction, acute ischemic stroke, anemia, diabetes, growth hormone deficiency, hepatitis, kidney carcinoma, chemotherapy induced neutropenia and multiple sclerosis. For these reasons, extended cDNAs encoding secreted proteins or portions thereof represent a particularly valuable source of therapeutic agents. Thus, there is a need for the identification and characterizationof secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably linking the signal sequences to a gene encoding the protein for which secretion is desired. This may prove beneficial in gene therapy strategies in which it is desired to deliver a particular gene product to cells other than the cell in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' portions of the genes for secretory proteins which encode signal peptides.

Public information on the number of human genes for which the promoters and upstream regulatory regions have been identified and characterized is quite limited. In part, this may be due to the difficulty of isolating such regulatory sequences. Upstream regulatory sequences such as transcription factor binding sites are typically too short to be utilized as probes for isolating promoters from human genomic libraries. Recently, some approaches have been developed to isolate human promoters. One of them consists of making a CpG island library (Cross, S. H. et al., Purification of CpG Islands using a Methylated DNA Binding Column, Nature Genetics 6: 236–244 (1994)). The second consists of isolating human genomic DNA sequences containing SpeI binding sites by the use of SpeI binding protein. (Mortlock et al., Genome Res. 6:327–335, 1996). Both of these approaches have their limits due to a lack of specificity or of comprehensiveness.

5' ESTs and extended cDNAs obtainable therefrom may be used to efficiently identify and isolate upstream regulatory regions which control the location, developmental stage, rate, and quantity of protein synthesis, as well as the stability of the mRNA. (Theil et al., BioFactors 4:87–93, (1993). Once identified and characterized, these regulatory regions may be utilized in gene therapy or protein purification schemes to obtain the desired amount and locations of protein synthesis or to inhibit, reduce, or prevent the synthesis of undesirable gene products.

In addition, ESTs containing the 5' ends of secretory protein genes or extended cDNAs which include sequences adjacent to the sequences of the ESTs may include sequences useful as probes for chromosome mapping and the identification of individuals. Thus, there is a need to identify and characterize the sequences upstream of the 5' coding sequences of genes encoding secretory proteins.

SUMMARY OF THE INVENTION

The present invention relates to purified, isolated, or recombinant extended cDNAs which encode secreted proteins or fragments thereof. Preferably, the purified, isolated or recombinant cDNAs contain the entire open reading frame of their corresponding mRNAs, including a start codon and a stop codon. For example, the extended cDNAs may include nucleic acids encoding the signal peptide as well as the mature protein. Alternatively, the extended cDNAs may contain a fragment of the open reading frame. In some embodiments, the fragment may encode only the sequence of the mature protein. Alternatively, the fragment may encode only a portion of the mature protein. A further aspect of the present invention is a nucleic acid which encodes the signal peptide of a secreted protein.

The present extended cDNAs were obtained using ESTs which include sequences derived from the authentic 5' ends of their corresponding mRNAs. As used herein the terms "EST" or "5' EST" refer to the short cDNAs which were used to obtain the extended cDNAs of the present invention. As used herein, the term "extended cDNA" refers to the cDNAs which include sequences adjacent to the 5' EST used to obtain them. The extended cDNAs may contain all or a portion of the sequence of the EST which was used to obtain them. The term "corresponding mRNA" refers to the mRNA which was the template for the cDNA synthesis which produced the 5' EST. As used herein, the term "purified" does not require absolute purity; rather, it is intended as a relative definition. Individual extended cDNA clones isolated from a cDNA library have been conventionally purified to electrophoretic homogeneity. The sequences obtained from these clones could not be obtained directly either from the library or from total human DNA. The extended cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$–$10^6$ fold purification of the native message. Purification of starting material or natural material to at least one order of magnitude, preferably two or three orders, and more preferably four or five orders of magnitude is expressly contemplated.

As used herein, the term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "recombinant" means that the extended cDNA is adjacent to "backbone" nucleic acid to which it is not adjacent in its natural environment. Additionally, to be "enriched" the extended cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched extended cDNAs represent 15% or more of the number of nucleic acid inserts in the population of recombinant backbone molecules. More preferably, the enriched extended cDNAs represent 50% or more of the number of nucleic acid inserts in the population of recombinant backbone molecules. In a highly preferred embodiment, the enriched extended cDNAs represent 90% or more of the number of nucleic acid inserts in the population of recombinant backbone molecules. "Stringent", "moderate," and "low" hybridization conditions are as defined in Example 29.

Unless otherwise indicated, a "complementary" sequence is fully complementary. Thus, extended cDNAs encoding secreted polypeptides or fragments thereof which are present in cDNA libraries in which one or more extended cDNAs encoding secreted polypeptides or fragments thereof make up 5% or more of the number of nucleic acid inserts in the backbone molecules are "enriched recombinant extended cDNAs" as defined herein. Likewise, extended cDNAs encoding secreted polypeptides or fragments thereof which are in a population of plasmids in which one or more extended cDNAs of the present invention have been inserted such that they represent 5% or more of the number of inserts in the plasmid backbone are "enriched recombinant extended cDNAs" as defined herein. However, extended cDNAs encoding secreted polypeptides or fragments thereof which are in cDNA libraries in which the extended cDNAs encoding secreted polypeptides or fragments thereof constitute less than 5% of the number of nucleic acid inserts in the population of backbone molecules, such as libraries in which backbone molecules having a cDNA insert encoding a secreted polypeptide are extremely rare, are not "enriched recombinant extended cDNAs."

In particular, the present invention relates to extended cDNAs which were derived from genes encoding secreted proteins. As used herein, a "secreted" protein is one which, when expressed in a suitable host cell, is transported across or through a membrane, including transport as a result of signal peptides in its amino acid sequence. "Secreted" proteins include without limitation proteins secreted wholly (e.g. soluble proteins), or partially (e.g. receptors) from the cell in which they are expressed. "Secreted" proteins also include without limitation proteins which are transported across the membrane of the endoplasmic reticulum.

Extended cDNAs encoding secreted proteins may include nucleic acid sequences, called signal sequences, which encode signal peptides which direct the extracellular secretion of the proteins encoded by the extended cDNAs. Generally, the signal peptides are located at the amino termini of secreted proteins.

Secreted proteins are translated by ribosomes associated with the "rough" endoplasmic reticulum. Generally, secreted proteins are co-translationally transferred to the membrane of the endoplasmic reticulum. Association of the ribosome with the endoplasmic reticulum during translation of secreted proteins is mediated by the signal peptide. The signal peptide is typically cleaved following its co-translational entry into the endoplasmic reticulum. After delivery to the endoplasmic reticulum, secreted proteins may proceed through the Golgi apparatus. In the Golgi apparatus, the proteins may undergo post-translational modification before entering secretory vesicles which transport them across the cell membrane.

The extended cDNAs of the present invention have several important applications. For example, they may be used to express the entire secreted protein which they encode. Alternatively, they may be used to express portions of the secreted protein. The portions may comprise the signal peptides encoded by the extended cDNAs or the mature proteins encoded by the extended cDNAs (i.e. the proteins generated when the signal peptide is cleaved off). The portions may also comprise polypeptides having at least 10 consecutive amino acids encoded by the extended cDNAs. Alternatively, the portions may comprise at least 15 consecutive amino acids encoded by the extended cDNAs. In some embodiments, the portions may comprise at least 25 consecutive amino acids encoded by the extended cDNAs. In other embodiments, the portions may comprise at least 40 amino acids encoded by the extended cDNAs.

Antibodies which specifically recognize the entire secreted proteins encoded by the extended cDNAs or fragments thereof having at least 10 consecutive amino acids, at least 15 consecutive amino acids, at least 25 consecutive amino acids, or at least 40 consecutive amino acids may also be obtained as described below. Antibodies which specifically recognize the mature protein generated when the signal peptide is cleaved may also be obtained as described below. Similarly, antibodies which specifically recognize the signal peptides encoded by the extended cDNAs may also be obtained.

In some embodiments, the extended cDNAs include the signal sequence. In other embodiments, the extended cDNAs may include the full coding sequence for the mature protein (i.e. the protein generated when the signal polypeptide is cleaved off). In addition, the extended cDNAs may include regulatory regions upstream of the translation start site or downstream of the stop codon which control the amount, location, or developmental stage of gene expression. As discussed above, secreted proteins are therapeutically important. Thus, the proteins expressed from the cDNAs may be useful in treating or controlling a variety of human conditions. The extended cDNAs may also be used to obtain the corresponding genomic DNA. The term "corresponding genomic DNA" refers to the genomic DNA which encodes mRNA which includes the sequence of one of the strands of the extended cDNA in which thymidine residues in the sequence of the extended cDNA are replaced by uracil residues in the mRNA.

The extended cDNAs or genomic DNAs obtained therefrom may be used in forensic procedures to identify individuals or in diagnostic procedures to identify individuals having genetic diseases resulting from abnormal expression of the genes corresponding to the extended cDNAs. In addition, the present invention is useful for constructing a high resolution map of the human chromosomes.

The present invention also relates to secretion vectors capable of directing the secretion of a protein of interest. Such vectors may be used in gene therapy strategies in which it is desired to produce a gene product in one cell which is to be delivered to another location in the body. Secretion vectors may also facilitate the purification of desired proteins.

The present invention also relates to expression vectors capable of directing the expression of an inserted gene in a desired spatial or temporal manner or at a desired level. Such vectors may include sequences upstream of the extended cDNAs such as promoters or upstream regulatory sequences.

In addition, the present invention may also be used for gene therapy to control or treat genetic diseases. Signal peptides may also be fused to heterologous proteins to direct their extracellular secretion.

One embodiment of the present invention is a purified or isolated nucleic acid comprising the sequence of one of SEQ ID NOs: 40–84 and 130–154 or a sequence complementary thereto. In one aspect of this embodiment, the nucleic acid is recombinant.

Another embodiment of the present invention is a purified or isolated nucleic acid comprising at least 10 consecutive bases of the sequence of one of SEQ ID NOs: 40–84 and 130–154 or one of the sequences complementary thereto. In one aspect of this embodiment, the nucleic acid comprises at least 15, 25, 30, 40, 50, 75, or 100 consecutive bases of one of the sequences of SEQ ID NOs: 40–84 and 130–154 or one of the sequences complementary thereto. The nucleic acid may be a recombinant nucleic acid.

Another embodiment of the present invention is a purified or isolated nucleic acid of at least 15 bases capable of hybridizing under stringent conditions to the sequence of one of SEQ ID NOs: 40–84 and 130–154 or a sequence complementary to one of the sequences of SEQ ID NOs: 40–84 and 130–154. In one aspect of this embodiment, the nucleic acid is recombinant.

Another embodiment of the present invention is a purified or isolated nucleic acid comprising the full coding sequences of one of SEQ ID Nos: 40–84 and 130–154 wherein the full coding sequence optionally comprises the sequence encoding signal peptide as well as the sequence encoding mature protein. In a preferred embodiment, the isolated or purified nucleic acid comprises the full coding sequence of one of SEQ ID Nos. 40–59,61–73, 75, 77–82, and 130–154 wherein the full coding sequence comprises the sequence encoding signal peptide and the sequence encoding mature protein. In one aspect of this embodiment, the nucleic acid is recombinant.

A further embodiment of the present invention is a purified or isolated nucleic acid comprising the nucleotides of one of SEQ ID NOs: 40–84 and 130–154 which encode a mature protein. In a preferred embodiment, the purified or isolated nucleic acid comprises the nucleotides of one of SEQ ID NOs: 40–59, 61–75, 77–82, and 130–154 which encode a mature protein. In one aspect of this embodiment, the nucleic acid is recombinant.

Yet another embodiment of the present invention is a purified or isolated nucleic acid comprising the nucleotides of one of SEQ ID NOs: 40–84 and 130–154 which encode the signal peptide. In a preferred embodiment, the purified or isolated nucleic acid comprises the nucleotides of SEQ ID NOs: 40–59, 61–73, 75–82, 84, and 130–154 which encode the signal peptide. In one aspect of this embodiment, the nucleic acid is recombinant.

Another embodiment of the present invention is a purified or isolated nucleic acid encoding a polypeptide having the sequence of one of the sequences of SEQ ID NOs: 85–129 and 155–179.

Another embodiment of the present invention is a purified or isolated nucleic acid encoding a polypeptide having the sequence of a mature protein included in one of the sequences of SEQ ID NOs: 85–129 and 155–179. In a preferred embodiment, the purified or isolated nucleic acid encodes a polypeptide having the sequence of a mature protein included in one of the sequences of SEQ ID NOs: 85–104, 106–120, 122–127, and 155–179.

Another embodiment of the present invention is a purified or isolated nucleic acid encoding a polypeptide having the sequence of a signal peptide included in one of the sequences of SEQ ID NOs: 85–129 and 155–179. In a preferred embodiment, the purified or isolated nucleic acid encodes a polypeptide having the sequence of a signal peptide included in one of the sequences of SEQ ID NOs: 85–104, 106–118, 120–127, 129, and 155–179.

Yet another embodiment of the present invention is a purified or isolated protein comprising the sequence of one of SEQ ID NOs: 85–129 and 155–179.

Another embodiment of the present invention is a purified or isolated polypeptide comprising at least 10 consecutive amino acids of one of the sequences of SEQ ID NOs: 85–129 and 155–179. In one aspect of this embodiment, the purified or isolated polypeptide comprises at least 15, 20, 25, 35, 50, 75, 100, 150 or 200 consecutive amino acids of one of the sequences of SEQ ID NOs: 85–129 and 155–179. In still another aspect, the purified or isolated polypeptide comprises at least 25 consecutive amino acids of one of the sequences of SEQ ID NOs: 85–129 and 155–179.

Another embodiment of the present invention is an isolated or purified polypeptide comprising a signal peptide of one of the polypeptides of SEQ ID NOs: 85–129 and 155–179. In a preferred embodiment, the isolated or purified polypeptide comprises a signal peptide of one of the polypeptides of SEQ ID NOs: 85–104, 106–118, 120–127, 129, and 155–179.

Yet another embodiment of the present invention is an isolated or purified polypeptide comprising a mature protein of one of the polypeptides of SEQ ID NOs: 85–129 and 155–179. In a preferred embodiment, the isolated or purified polypeptide comprises a mature protein of one of the polypeptides of SEQ ID NOs: 85–104, 106–120, 122–127, and 155–179. In a preferred embodiment, the purified or isolated nucleic acid encodes a polypeptide having the sequence of a mature protein included in one of the sequences of SEQ ID NOs: 85–104, 106–120, 122–127, and 155–179.

A further embodiment of the present invention is a method of making a protein comprising one of the sequences of SEQ ID NO: 85–129 and 155–179, comprising the steps of obtaining a cDNA comprising one of the sequences of sequence of SEQ ID NO: 40–84 and 130–154, inserting the cDNA in an expression vector such that the cDNA is operably linked to a promoter, and introducing the expression vector into a host cell whereby the host cell produces the protein encoded by said cDNA. In one aspect of this embodiment, the method further comprises the step of isolating the protein.

Another embodiment of the present invention is a protein obtainable by the method described in the preceding paragraph.

Another embodiment of the present invention is a method of making a protein comprising the amino acid sequence of the mature protein contained in one of the sequences of SEQ ID NOs: 85–104, 106–120, 122–127, and 155–179 comprising the steps of obtaining a cDNA comprising one of the nucleotides sequence of sequence of SEQ ID NOs: 40–59, 61–75, 77–82, and 130–154 which encode for the mature protein, inserting the cDNA in an expression vector such that the cDNA is operably linked to a promoter, and introducing the expression vector into a host cell whereby the host cell produces the mature protein encoded by the cDNA. In one aspect of this embodiment, the method further comprises the step of isolating the protein.

Another embodiment of the present invention is a mature protein obtainable by the method described in the preceding paragraph.

In a preferred embodiment, the above method comprises a method of making a protein comprising the amino acid sequence of the mature protein contained in one of the sequences of SEQ ID NOs. 85–104, 106–120, 122–127 and 155–179, comprising the steps of obtaining a cDNA comprising one of the nucleotide sequences of SEQ ID Nos. 40–59, 61–75, 77–82 and 130–154 which encode for the mature protein, inserting the cDNA in an expression vector such that the cDNA is operably linked to a promoter, and introducing the expression vector into a host cell whereby the host cell produces the mature protein encoded by the cDNA. In one aspect of this embodiment, the method further comprises the step of isolating the protein.

Another embodiment of the present invention is a host cell containing the purified or isolated nucleic acids comprising the sequence of one of SEQ ID NOs: 40–84 and 130–154 or a sequence complementary thereto described herein.

Another embodiment of the present invention is a host cell containing the purified or isolated nucleic acids comprising the full coding sequences of one of SEQ ID NOs: 40–59, 61–73, 75, 77–82, and 130–154, wherein the full coding sequence comprises the sequence encoding signal peptide and the sequence encoding mature protein described herein.

Another embodiment of the present invention is a host cell containing the purified or isolated nucleic acids comprising the nucleotides of one of SEQ ID NOs: 40–84 and 130–154 which encode a mature protein which are described herein. Preferably, the host cell contains the purified or isolated nucleic acids comprising the nucleotides of one of SEQ ID NOs: 40–59, 61–75, 77–82, and 130–154 which encode a mature protein.

Another embodiment of the present invention is a host cell containing the purified or isolated nucleic acids comprising the nucleotides of one of SEQ ID NOs: 40–84 and 130–154 which encode the signal peptide which are described herein. Preferably, the host cell contains the purified or isolated nucleic acids comprising the nucleotides of one of SEQ ID Nos.: 40–59, 61–73, 75–82, 84, and 130–154 which encode the signal peptide.

Another embodiment of the present invention is a purified or isolated antibody capable of specifically binding to a protein having the sequence of one of SEQ ID NOs: 85–129 and 155–179. In one aspect of this embodiment, the antibody is capable of binding to a polypeptide comprising at least 10 consecutive amino acids of the sequence of one of SEQ ID NOs: 85–129 and 155–179.

Another embodiment of the present invention is an array of cDNAs or fragments thereof of at least 15 nucleotides in length which includes at least one of the sequences of SEQ ID NOs: 40–84 and 130–154, or one of the sequences complementary to the sequences of SEQ ID NOs: 40–84 and 130–154, or a fragment thereof of at least 15 consecutive nucleotides. In one aspect of this embodiment, the array includes at least two of the sequences of SEQ ID NOs: 40–84 and 130–154, the sequences complementary to the sequences of SEQ ID NOs: 40–84 and 130–154, or fragments thereof of at least 15 consecutive nucleotides. In another aspect of this embodiment, the array includes at least five of the sequences of SEQ ID NOs: 40–84 and 130–154, the sequences complementary to the sequences of SEQ ID NOs: 40–84 and 130–154, or fragments thereof of at least 15 consecutive nucleotides.

A further embodiment of the invention encompasses purified polynucleotides comprising an insert from a clone deposited in a deposit having an accession number selected from the group consisting of the accession numbers listed in Table VI or a fragment thereof comprising a contiguous span of at least 8, 10, 12, 15, 20, 25, 40, 60, 100, or 200 nucleotides of said insert. An additional embodiment of the invention encompasses purified polypeptides which comprise, consist of, or consist essentially of an amino acid sequence encoded by the insert from a clone deposited in a deposit having an accession number selected from the group consisting of the accession numbers listed in Table VI, as well as polypeptides which comprise a fragment of said amino acid sequence consisting of a signal peptide, a mature protein, or a contiguous span of at least 5, 8, 10, 12, 15, 20, 25, 40, 60, 100, or 200 amino acids encoded by said insert.

An additional embodiment of the invention encompasses purified polypeptides which comprise a contiguous span of at least 5, 8, 10, 12, 15, 20, 25, 40, 60, 100, or 200 amino acids of SEQ ID NOs: 85–129 and 155–179, wherein said contiguous span comprises at least one of the amino acid positions which was not shown to be identical to a public sequence in any of FIGS. 10 to 12. Also encompassed by the invention are purified polynuculeotides encoding said polypeptides.

Another embodiment of the present invention is a computer readable medium having stored thereon a sequence selected from the group consisting of a cDNA code of SEQID NOs. 40–84 and 130–154 and a polypeptide code of SEQ ID NOs. 85–129 and 155–179.

Another embodiment of the present invention is a computer system comprising a processor and a data storage device wherein the data storage device has stored thereon a sequence selected from the group consisting of a cDNA code of SEQID NOs. 40–84 and 130–154 and a polypeptide code of SEQ ID NOs. 85–129 and 155–179. In some embodiments the computer system further comprises a sequence comparer and a data storage device having reference sequences stored thereon. For example, the sequence comparer may comprise a computer program which indicates polymorphisms. In other aspects of the computer system, the system further comprises an identifier which identifies features in said sequence.

Another embodiment of the present invention is a method for comparing a first sequence to a reference sequence wherein the first sequence is selected from the group consisting of a cDNA code of SEQID NOs. 40–84 and 130–154 and a polypeptide code of SEQ ID NOs. 85–129 and 155–179 comprising the steps of reading the first sequence and the reference sequence through use of a computer program which compares sequences and determining differences between the first sequence and the reference sequence with the computer program. In some embodiments of the method, the step of determining differences between the first sequence and the reference sequence comprises identifying polymorphisms.

Another embodiment of the present invention is a method for identifying a feature in a sequence selected from the group consisting of a cDNA code of SEQID NOs. 40–84 and 130–154 and a polypeptide code of SEQ ID NOs. 85–129 and 155–179 comprising the steps of reading the sequence through the use of a computer program which identifies features in sequences and identifying features in the sequence with said computer program.

BRIEF DESCRIPTION OF THE DRAWINGS

FIG. 2 is an analysis of the 43 amino terminal amino acids of all human SwissProt proteins to determine the frequency of false positives and false negatives using the techniques for signal peptide identification described herein.

FIG. 4 shows the distribution of 5' ESTs in each category and the number of 5' ESTs in each category having a given minimum von Heijne's score.

FIG. 5 shows the tissues from which the mRNAs corresponding to the 5' ESTs in each of the categories described herein were obtained.

FIG. 9 describes the transcription factor binding sites present in each of these promoters.

FIG. 10 is an alignment of the proteins of SEQ ID NOs: 120 and 180 wherein the signal peptide is in italics, the predicted transmembrane segment is underlined, the experimentally determined transmembrane segment is double-underlined, and the ATP1G/PLMN/MAT8 signature is in bold.

FIG. 11 is an alignment of the proteins of SEQ ID NOs: 121 and 181 wherein the predicted transmembrane segment is underlined.

FIG. 12 is an alignment of the proteins of SEQ ID NOs: 128 and 182 wherein the PPPY motif is in bold.

DETAILED DESCRIPTION OF THE PREFERRED EMBODIMENT

I. Obtaining 5' ESTs

Figure 1:
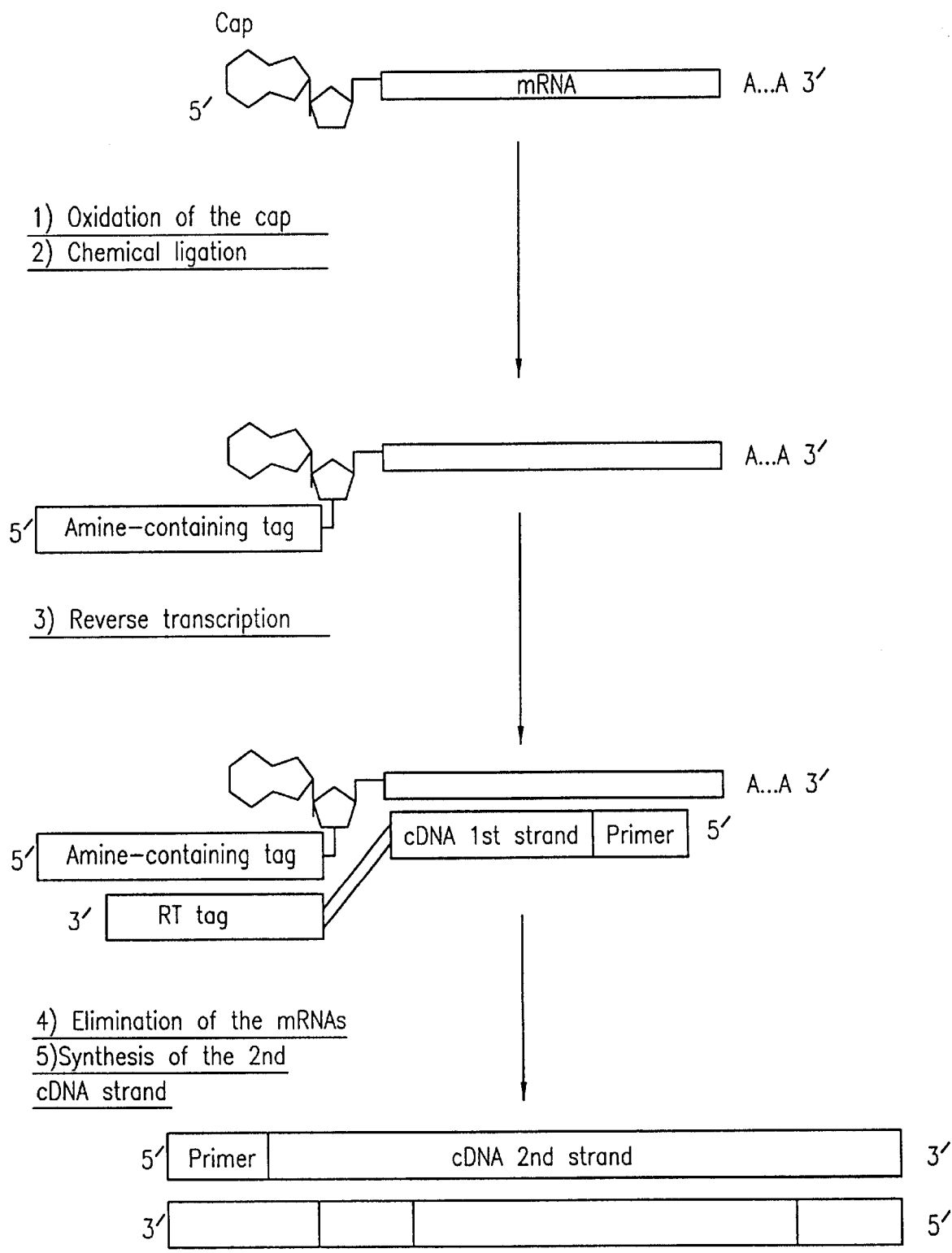
FIG. 1 is a summary of a procedure for obtaining cDNAs which have been selected to include the 5' ends of the mRNAs from which they are derived.

The present extended cDNAs were obtained using 5' ESTs which were isolated as described below.

A. Chemical Methods for Obtaining mRNAs having Intact 5' Ends

In order to obtain the 5' ESTs used to obtain the extended cDNAs of the present invention, mRNAs having intact 5' ends must be obtained. Currently, there are two approaches for obtaining such mRNAs. One of these approaches is a chemical modification method involving derivatization of the 5' ends of the mRNAs and selection of the derivatized mRNAs. The 5' ends of eucaryotic mRNAs possess a structure referred to as a "cap" which comprises a guanosine methylated at the 7 position. The cap is joined to the first transcribed base of the mRNA by a 5', 5'-triphosphate bond. In some instances, the 5' guanosine is methylated in both the 2 and 7 positions. Rarely, the 5' guanosine is trimethylated at the 2, 7 and 7 positions. In the chemical method for obtaining mRNAs having intact 5' ends, the 5' cap is specifically derivatized and coupled to a reactive group on an immobilizing substrate. This specific derivatization is based on the fact that only the ribose linked to the methylated guanosine at the 5' end of the mRNA and the ribose linked to the base at the 3' terminus of the mRNA, possess 2', 3'-cis diols. Optionally, where the 3' terminal ribose has a 2', 3'-cis diol, the 2', 3'-cis diol at the 3' end may be chemically modified, substituted, converted, or eliminated, leaving only the ribose linked to the methylated guanosine at the 5' end of the mRNA with a 2', 3'-cis diol. A variety of techniques are available for eliminating the 2', 3'-cis diol on the 3' terminal ribose. For example, controlled alkaline hydrolysis may be used to generate mRNA fragments in which the 3' terminal ribose is a 3'-phosphate, 2'-phosphate or (2', 3')-cyclophosphate. Thereafter, the fragment which includes the original 3' ribose may be eliminated from the mixture through chromatography on an oligo-dT column. Alternatively, a base which lacks the 2', 3'-cis diol may be added to the 3' end of the mRNA using an RNA ligase such as T4 RNA ligase. Example I below describes a method for ligation of pCp to the 3' end of messenger RNA.

EXAMPLE 1

Ligation of the Nucleoside Diphosphate pCp to the 3' End of Messenger RNA

1 μg of RNA was incubated in a final reaction medium of 10 μl in the presence of U of $T_4$ phage RNA ligase in the buffer provided by the manufacturer(Gibco-BRL), 40 U of the RNase inhibitor RNasin (Promega) and, 2 μl of $^{32}$pCp (Amersham #PB 10208).

The incubation was performed at 37° C. for 2 hours or overnight at 7–8° C.

Following modification or elimination of the 2', 3'-cis diol at the 3' ribose, the 2', 3'-cis diol present at the 5' end of the mRNA may be oxidized using reagents such as $NaBH_4$, $NaBH_3CN$, or sodium periodate, thereby converting the 2', 3'-cis diol to a dialdehyde. Example 2 describes the oxidation of the 2', 3'-cis diol at the 5' end of the mRNA with sodium periodate.

EXAMPLE 2

Oxidation of 2', 3'-cis diol at the 5' End of the mRNA 0.1 OD unit of either a capped oligoribonucleotide of 47 nucleotides (including the cap) or an uncapped oligoribonucleotide of 46 nucleotides were treated as follows. The oligoribonucleotides were produced by in vitro transcription using the transcription kit "AmpliScribe T7" (Epicentre Technologies). As indicated below, the DNA template for the RNA transcript contained a single cytosine. To synthesize the uncapped RNA, all four NTPs were included in the in vitro transcription reaction. To obtain the capped RNA, GTP was replaced by an analogue of the cap, m7G(5')ppp (5')G. This compound, recognized by polymerase, was incorporated into the 5' end of the nascent transcript during the step of initiation of transcription but was not capable of incorporation during the extension step. Consequently, the resulting RNA contained a cap at its 5' end. The sequences of the oligoribonucleotides produced by the in vitro transcription reaction were:

+Cap:
5'm7GpppGCAUCCUACUCCCAUCCAAUUCCACCCUA (SEQ ID NO:1)
ACUCCUCCCAUCUCCAC-3'

-Cap:
5'-pppGCAUCCUACUCCCAUCCAAUUCCACCCUAAC (SEQ ID NO:2)
UCCUCCCAUCUCCAC-3'

The oligoribonucleotides were dissolved in 9 μl of acetate buffer (0.1 M sodium acetate, pH 5.2) and 3μl of freshly prepared 0.1M sodium periodate solution. The mixture was incubated for 1 hour in the dark at 4° C. or room temperature. Thereafter, the reaction was stopped by adding 4 μl of 10% ethylene glycol. The product was ethanol precipitated, resuspended in 10 μl or more of water or appropriate buffer and dialyzed against water.

The resulting aldehyde groups may then be coupled to molecules having a reactive amine group, such as hydrazine, carbazide, thiocarbazide or semicarbazide groups, in order to facilitate enrichment of the 5' ends of the mRNAs. Molecules having reactive amine groups which are suitable for use in selecting mRNAs having intact 5' ends include avidin, proteins, antibodies, vitamins, ligands capable of specifically binding to receptor molecules, or oligonucleotides. Example 3 below describes the coupling of the resulting dialdehyde to biotin.

EXAMPLE 3

Coupling of the Dialdehyde with Biotin

The oxidation product obtained in Example 2 was dissolved in 50 μl of sodium acetate at a pH of between 5 and 5.2 and 50 μl of freshly prepared 0.02M solution of biotin hydrazide in a methoxyethanol/watermixture (1:1) of formula:

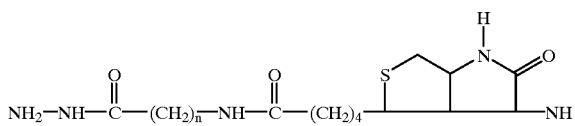

In the compound used in these experiments, n=5. However, it will be appreciated that other commercially available hydrazides may also be used, such as molecules of the formula above in which n varies from 0 to 5.

The mixture was then incubated for 2 hours at 37° C. Following the incubation, the mixture was precipitated with ethanol and dialyzed against distilled water.

Example 4 demonstrates the specificity of the biotinylation reaction.

EXAMPLE 4

Specificity of Biotinylation

The specificity of the biotinylation for capped mRNAs was evaluated by gel electrophoresis of the following samples:

Sample 1. The 46 nucleotide uncapped in vitro transcript prepared as in Example 2 and labeled with $^{32}$pCp as described in Example 1.

Sample 2. The 46 nucleotide uncapped in vitro transcript prepared as in Example 2, labeled with $^{32}$pCp as described in Example 1, treated with the oxidation reaction of Example 2, and subjected to the biotinylation conditions of Example 3.

Sample 3. The 47 nucleotide capped in vitro transcript prepared as in Example 2 and labeled with $^{32}$pCp as described in Example 1.

Sample 4. The 47 nucleotide capped in vitro transcript prepared as in Example 2, labeled with $^{32}$pCp as described in Example 1, treated with the oxidation reaction of Example 2, and subjected to the biotinylation conditions of Example 3.

Samples 1 and 2 had indentical migration rates, demonstrating that the uncapped RNAs were not oxidized and biotinylated. Sample 3 migrated more slowly than Samples 1 and 2, while Sample 4 exhibited the slowest migration. The difference in migration of the RNAs in Samples 3 and 4 demonstrates that the capped RNAs were specifically biotinylated.

In some cases, mPNAs having intact 5' ends may be enriched by binding the molecule containing a reactive amine group to a suitable solid phase substrate such as the inside of the vessel containing the mRNAs, magnetic beads, chromatography matrices, or nylon or nitrocellulose membranes. For example, where the molecule having a reactive amine group is biotin, the solid phase substrate may be coupled to avidin or streptavidin. Alternatively, where the molecule having the reactive amine group is an antibody or receptor ligand, the solid phase substrate may be coupled to the cognate antigen or receptor. Finally, where the molecule having a reactive amine group comprises an oligonucleotide, the solid phase substrate may comprise a complementary oligonucleotide.

The mRNAs having intact 5' ends may be released from the solid phase following the enrichment procedure. For example, where the dialdehyde is coupled to biotin hydrazide and the solid phase comprises streptavidin, the mRNAs may be released from the solid phase by simply heating to 95 degrees Celsius in 2% SDS. In some methods, the molecule having a reactive amine group may also be cleaved from the mRNAs having intact 5' ends following enrichment. Example 5 describes the capture of biotinylated mRNAs with streptavidin coated beads and the release of the biotinylated mRNAs from the beads following enrichment.

EXAMPLE 5

Capture and Release of Biotinylated mRNAs Using Strepatividin Coated Beads

The streptavidin-coated magnetic beads were prepared according to the manufacturer's instructions (CPG Inc., USA). The biotinylated mRNAs were added to a hybridization buffer (1.5M NaCl, pH 5–6). After incubating for 30 minutes, the unbound and nonbiotinylated material was removed. The beads were washed several times in water with 1% SDS. The beads obtained were incubated for 15 minutes at 95° C. in water containing 2% SDS.

Example 6 demonstrates the efficiency with which biotinylated mRNAs were recovered from the streptavidin coated beads.

EXAMPLE 6

Efficiency of Recovery of Biotinylated mRNAs

The efficiency of the recovery procedure was evaluated as follows. RNAs were labeled with $^{32}$pCp, oxidized, biotinylated and bound to streptavidin coated beads as described above. Subsequently, the bound RNAs were incubated for 5, 15 or 30 minutes at 95° C. in the presence of 2% SDS.

The products of the reaction were analyzed by electrophoresis on 12% polyacrylamide gels under denaturing conditions (7 M urea). The gels were subjected to autoradiography. During this manipulation, the hydrazone bonds were not reduced.

Increasing amounts of nucleic acids were recovered as incubation times in 2% SDS increased, demonstrating that biotinylated mRNAs were efficiently recovered.

In an alternative method for obtaining mRNAs having intact 5' ends, an oligonucleotide which has been derivatized to contain a reactive amine group is specifically coupled to mRNAs having an intact cap. Preferably, the 3' end of the mRNA is blocked prior to the step in which the aldehyde groups are joined to the derivatized oligonucleotide, as described above, so as to prevent the derivatized oligonucleotide from being joined to the 3' end of the mRNA. For example, pCp may be attached to the 3' end of the mRNA using T4 RNA ligase. However, as discussed above, blocking the 3' end of the mRNA is an optional step. Derivatized oligonucleotides may be prepared as described below in Example 7.

EXAMPLE 7

Derivatization of the Oligonucleotide

An oligonucleotide phosphorylated at its 3' end was converted to a 3' hydrazide in 3' by treatment with an aqueous solution of hydrazine or of dihydrazide of the formula $H_2N(R1)NH_2$ at about 1 to 3M, and at pH 4.5, in the presence of a carbodiimide type agent soluble in water such as 1-ethyl-3-(3-dimethylaminopropyl)carbodiimide at a final concentration of 0.3M at a temperature of 8° C. overnight.

The derivatized oligonucleotide was then separated from the other agents and products using a standard technique for isolating oligonucleotides.

As discussed above, the mRNAs to be enriched may be treated to eliminate the 3' OH groups which may be present thereon. This may be accomplished by enzymatic ligation of sequences lacking a 3' OH, such as pCp, as described above in Example 1. Alternatively, the 3' OH groups may be eliminated by alkaline hydrolysis as described in Example 8 below.

EXAMPLE 8

Alkaline Hydrolysis of mRNA

The mRNAs may be treated with alkaline hydrolysis as follows. In a total volume of 100 µl of 0.1N sodium hydroxide, 1.5 µg mRNA is incubated for 40 to 60 minutes at 4° C. The solution is neutralized with acetic acid and precipitated with ethanol.

Following the optional elimination of the 3' OH groups, the diol groups at the 5' ends of the mRNAs are oxidized as described below in Example 9.

EXAMPLE 9

Oxidation of Diols

Up to 1 OD unit of RNA was dissolved in 9 µl of buffer (0.1 M sodium acetate, pH 6–7 or water) and 3 µl of freshly prepared 0.1M sodium periodate solution. The reaction was incubated for 1 h in the dark at 4° C. or room temperature. Following the incubation, the reaction was stopped by adding 4 µl of 10% ethylene glycol. Thereafter the mixture was incubated at room temperature for 15 minutes. After ethanol precipitation, the product was resuspended in 10 µl or more of water or appropriate buffer and dialyzed against water.

Following oxidation of the diol groups at the 5' ends of the mRNAs, the derivatized oligonucleotide was joined to the resulting aldehydes as described in Example 10.

EXAMPLE 10

Reaction of Aldehydes with Derivatized Oligonucleotides

The oxidized mRNA was dissolved in an acidic medium such as 50 µl of sodium acetate pH 4–6. 50 µl of a solution of the derivatized oligonucleotide was added such that an mRNA:derivatized oligonucleotide ratio of 1:20 was obtained and mixture was reduced with a borohydride. The mixture was allowed to incubate for 2 h at 37° C. or overnight (14 h) at 10° C. The mixture was ethanol precipitated, resuspended in 10 µl or more of water or appropriate buffer and dialyzed against distilled water. If desired, the resulting product may be analyzed using acrylamide gel electrophoresis, HPLC analysis, or other conventional techniques.

Following the attachment of the derivatized oligonucleotide to the mRNAs, a reverse transcription reaction may be performed as described in Example 11 below.

EXAMPLE 11

Reverse Transcription of mRNAs

An oligodeoxyribonucleotide was derivatized as follows. 3 OD units of an oligodeoxyribonucleotide of sequence ATCAAGAATTCGCACGAGACCATTA (SEQ ID NO:3) having 5' -OH and 3'-P ends were dissolved in 70 µl of a 1.5 M hydroxybenzotriazole solution, pH 5.3, prepared in dimethylformamide/water (75:25) containing 2 µg of 1-ethyl-3-(3-dimethylaminopropyl)carbodiimide. The mixture was incubated for 2 h 30 min at 22° C. The mixture was then precipitated twice in $LiClO_4$/acetone. The pellet was resuspended in 200 µl of 0.25M hydrazine and incubated at 8° C. from 3 to 14 h. Following the hydrazine reaction, the mixture was precipitated twice in $LiClO_4$/acetone.

The messenger RNAs to be reverse transcribed were extracted from blocks of placenta having sides of 2 cm which had been stored at −80° C. The mRNA was extracted using conventional acidic phenol techniques. Oligo-dT chromatography was used to purify the mRNAs. The integrity of the mRNAs was checked by Northern-blotting.

The diol groups on 7 µg of the placental mRNAs were oxidized as described above in Example 9. The derivatized oligonucleotide was joined to the mRNAs as described in Example 10 above except that the precipitation step was replaced by an exclusion chromatography step to remove derivatized oligodeoxyribonucleotides which were not joined to mRNAs. Exclusion chromatography was performed as follows:

10 ml of AcA34 (BioSepra#230151)gel were equilibrated in 50 ml of a solution of 10 mM Tris pH 8.0, 300 mM NaCl, 1 mM EDTA, and 0.05% SDS. The mixture was allowed to sediment. The supernatant was eliminated and the gel was resuspended in 50 ml of buffer. This procedure was repeated 2 or 3 times.

A glass bead (diameter 3 mm) was introduced into a 2 ml disposable pipette (length 25 cm). The pipette was filled with the gel suspension until the height of the gel stabilized at 1 cm from the top of the pipette. The column was then equilibrated with 20 ml of equilibration buffer(10 mM Tris HCl pH 7.4,20 mM NaCl).

10 µl of the mRNA which had been reacted with the derivatized oligonucleotide were mixed in 39 µl of 10 mM urea and 2 µl of blue-glycerol buffer, which had been prepared by dissolving 5 mg of bromophenol blue in 60% glycerol (v/v), and passing the mixture through a filter with a filter of diameter 0.45 µm.

The column was loaded. As soon as the sample had penetrated, equilibration buffer was added. 100 µl fractions were collected. Derivatized oligonucleotide which had not been attached to mRNA appeared in fraction 16 and later fractions. Fractions 3 to 15 were combined and precipitated with ethanol.

The mRNAs which had been reacted with the derivatized oligonucleotide were spotted on a nylon membrane and hybridized to a radioactive probe using conventional techniques. The radioactive probe used in these hybridizations was an oligodeoxy ribonucleotide of sequence TAATGGTCTCGTGCGAATTCTTGAT(SEQ ID NO:4) which was anticomplementary to the derivatized oligonucleotide and was labeled at its 5' end with $^{32}$P. 1/10th of the mRNAs which had been reacted with the derivatized oligonucleotide was spotted in two spots on the membrane and the membrane was visualized by autoradiography after hybridization of the probe. A signal was observed, indicating that the derivatized oligonucleotide had been joined to the mRNA.

The remaining 9/10 of the mRNAs which had been reacted with the derivatized oligonucleotide was reverse transcribed as follows. A reverse transcription reaction was carried out with reverse transcriptase following the manufacturer's instructions. To prime the reaction, 50 pmol of nonamers with random sequence were used.

A portion of the resulting cDNA was spotted on a positively charged nylon membrane using conventional methods. The cDNAs were spotted on the membrane after the cDNA:RNA heteroduplexes had been subjected to an alkaline hydrolysis in order to eliminate the RNAs. An oligonucleotide having a sequence identical to that of the derivatized oligonucleotide was labeled at its 5' end with $^{32}P$ and hybridized to the cDNA blots using conventional techniques. Single-stranded cDNAs resulting from the reverse transcription reaction were spotted on the membrane. As controls, the blot contained 1 pmol, 100 fmol, 50 fmol, 10 fmol and 1 fmol respectively of a control oligodeoxyribonucleotide of sequence identical to that of the derivatized oligonucleotide. The signal observed in the spots containing the cDNA indicated that approximately 15 fmol of the derivatized oligonucleotide had been reverse transcribed.

These results demonstrate that the reverse transcription can be performed through the cap and, in particular, that reverse transcriptase crosses the 5'-P-P-P-5' bond of the cap of eukaryotic messenger RNAs.

The single stranded cDNAs obtained after the above first strand synthesis were used as template for PCR reactions. Two types of reactions were carried out. First, specific amplification of the mRNAs for the alpha globin, dehydrogenase, pp15 and elongation factor E4 were carried out using the following pairs of oligodeoxy ribonucleotide primers.

```
         alpha-globin
GLO-S:   CCG ACA AGA CCA ACG TCA AGG CCG C      (SEQ ID NO:5)
GLO-As:  TCA CCA GCA GGC AGT GGC TTA GGA G 3'   (SEQ ID NO:6)

dehydrogenase
3 DH-S:  AGT GAT TCC TGC TAC TTT GGA TGG C      (SEQ ID NO:7)
3 DH-As: GCT TGG TCT TGT TCT GGA GTT TAG A      (SEQ ID NO:8)

pp15
PP15-S:  TCC AGA ATG GGA GAC AAG CCA ATT T      (SEQ ID NO:9)
PP15-As: AGG GAG GAG GAA ACA GCG TGA GTC C      (SEQ ID NO:10)

Elongation factor E4
EFA1-S:  ATG GGA AAG GAA AAG ACT CAT ATC A      (SEQ ID NO:11)
EF1A-As: AGC AGC AAC AAT CAG GAC AGC ACA G      (SEQ ID NO:12)
```

Non specific amplifications were also carried out with the antisense (_As) oligodeoxyribonucleotides of the pairs described above and a primer chosen from the sequence of the derivatized oligodeoxyribonucleotide (ATCAAGAATTCGCACGAGACCATTA)(SEQ ID NO: 13).

A 1.5% agarose gel containing the following samples corresponding to the PCR products of reverse transcription was stained with ethidium bromide. (½0th of the products of reverse transcription were used for each PCR reaction).

Sample 1: The products of a PCR reaction using the globin primers of SEQ ID NOs 5 and 6 in the presence of cDNA.

Sample 2: The products of a PCR reaction using the globin primers of SEQ ID NOs 5 and 6 in the absence of added cDNA.

Sample 3: The products of a PCR reaction using the dehydrogenase primers of SEQ ID NOs 7 and 8 in the presence of cDNA.

Sample 4: The products of a PCR reaction using the dehydrogenase primers of SEQ ID NOs 7 and 8 in the absence of added cDNA.

Sample 5: The products of a PCR reaction using the pp15 primers of SEQ ID NOs 9 and 10 in the presence of cDNA.

Sample 6: The products of a PCR reaction using the pp15 primers of SEQ ID NOs 9 and 10 in the absence of added cDNA.

Sample 7: The products of a PCR reaction using the EIE4 primers of SEQ ID NOs 11 and 12 in the presence of added cDNA.

Sample 8: The products of a PCR reaction using the EIE4 primers of SEQ ID NOs 11 and 12 in the absence of added cDNA.

In Samples 1, 3, 5 and 7, a band of the size expected for the PCR product was observed, indicating the presence of the corresponding sequence in the cDNA population.

PCR reactions were also carried out with the antisense oligonucleotides of the globin and dehydrogenase primers (SEQ ID NOs 6 and 8) and an oligonucleotide whose sequence corresponds to that of the derivatized oligonucleotide. The presence of PCR products of the expected size in the samples corresponding to samples 1 and 3 above indicated that the derivatized oligonucleotide had been incorporated.

The above examples summarize the chemical procedure for enriching mRNAs for those having intact 5' ends. Further detail regarding the chemical approaches for obtaining mRNAs having intact 5' ends are disclosed in International Application No. WO96/3498 1, published Nov. 7, 1996, which is incorporated herein by reference.

Strategies based on the above chemical modifications to the 5' cap structure may be utilized to generate cDNAs which have been selected to include the 5' ends of the mRNAs from which they are derived. In one version of such procedures, the 5' ends of the mRNAs are modified as described above. Thereafter, a reverse transcription reaction is conducted to extend a primer complementary to the mRNA to the 5' end of the mRNA. Single stranded RNAs are eliminated to obtain a population of cDNA/mRNA heteroduplexes in which the mRNA includes an intact 5' end. The resulting heteroduplexes may be captured on a solid phase coated with a molecule capable of interacting with the molecule used to derivatize the 5' end of the mRNA. Thereafter, the strands of the heteroduplexes are separated to recover single stranded first cDNA strands which include the 5' end of the mRNA. Second strand cDNA synthesis may then proceed using conventional techniques. For example, the procedures disclosed in WO 96/34981 or in Carninci, P. et al. High-Efficiency Full-Length cDNA Cloning by Biotinylated CAP Trapper. Genomics 37:327–336 (1996), the disclosures of which are incorporated herein by reference, may be employed to select cDNAs which include the sequence derived from the 5' end of the coding sequence of the mRNA.

Following ligation of the oligonucleotide tag to the 5' cap of the mRNA, a reverse transcription reaction is conducted to extend a primer complementary to the mRNA to the 5' end of the mRNA. Following elimination of the RNA component of the resulting heteroduplex using standard techniques, second strand cDNA synthesis is conducted with a primer complementary to the oligonucleotide tag.

FIG. 1 summarizes the above procedures for obtaining cDNAs which have been selected to include the 5' ends of the mRNAs from which they are derived.

B. Enzymatic Methods for Obtaining mRNAs having Intact 5' Ends

Other techniques for selecting cDNAs extending to the 5' end of the mRNA from which they are derived are fully enzymatic. Some versions of these techniques are disclosed in Dumas Milne Edwards J.B. (Doctoral Thesis of Paris VI University, Le clonage des ADNc complets: difficultes et perspectives nouvelles. Apports pour l'etude de la regulation de l'expression de la tryptophane hydroxylase de rat, Dec. 20, 1993), EPO 625572 and Kato et al. Construction of a Human Full-Length cDNA Bank. Gene 150:243–250 (1994), the disclosures of which are incorporated herein by reference.

Briefly, in such approaches, isolated mRNA is treated with alkaline phosphatase to remove the phosphate groups present on the 5' ends of uncapped incomplete mRNAs. Following this procedure, the cap present on full length mRNAs is enzymatically removed with a decapping enzyme such as T4 polynucleotide kinase or tobacco acid pyrophosphatase. An oligonucleotide, which may be either a DNA oligonucleotide or a DNA-RNA hybrid oligonucleotide having RNA at its 3' end, is then ligated to the phosphate present at the 5' end of the decapped mRNA using T4 RNA ligase. The oligonucleotide may include a restriction site to facilitate cloning of the cDNAs following their synthesis. Example 12 below describes one enzymatic method based on the doctoral thesis of Dumas.

EXAMPLE 12

Enzymatic Approach for Obtaining 5' ESTs

Twenty micrograms of PolyA+RNA were dephosphorylated using Calf Intestinal Phosphatase (Biolabs). After a phenol chloroform extraction, the cap structure of mRNA was hydrolysed using the Tobacco Acid Pyrophosphatase (purified as described by Shinshi et al., Biochemistry 15: 2185–2190, 1976) and a hemi 5'DNA/RNA-3' oligonucleotide having an unphosphorylated 5' end, a stretch of adenosine ribophosphate at the 3' end, and an EcoRI site near the 5' end was ligated to the 5'P ends of mRNA using the T4 RNA ligase (Biolabs). Oligonucleotides suitable for use in this procedure are preferably 30–50 bases in length. Oligonucleotides having an unphosphorylated 5' end may be synthesized by adding a fluorochrome at the 5' end. The inclusion of a stretch of adenosine ribophosphates at the 3' end of the oligonucleotide increases ligation efficiency. It will be appreciated that the oligonucleotide may contain cloning sites other than EcoRI.

Following ligation of the oligonucleotide to the phosphate present at the 5' end of the decapped mRNA, first and second strand cDNA synthesis may be carried out using conventional methods or those specified in EPO 625,572 and Kato et al. Construction of a Human Full-Length cDNA Bank. Gene 150:243–250 (1994), and Dumas Milne Edwards, supra, the disclosures of which are incorporated herein by reference. The resulting cDNA may then be ligated into vectors such as those disclosed in Kato et al. Construction of a Human Full-Length cDNA Bank. Gene 150:243–250 (1994) or other nucleic acid vectors known to those skilled in the art using techniques such as those described in Sambrook et al., Molecular Cloning: A Laboratory Manual 2d Ed., Cold Spring Harbor Laboratory Press, 1989, the disclosure of which is incorporated herein by reference.

II. Characterizationof 5' ESTs

The above chemical and enzymatic approaches for enriching mRNAs having intact 5' ends were employed to obtain 5' ESTs. First, mRNAs were prepared as described in Example 13 below.

EXAMPLE 13

Preparation of mRNA

Total human RNAs or PolyA+RNAs derived from 29 different tissues were respectively purchased from LABIMO and CLONTECH and used to generate 44 cDNA libraries as described below. The purchased RNA had been isolated from cells or tissues using acid guanidium thiocyanate-phenol-chloroform extraction (Chomczyniski, P and Sacchi, N., Analytical Biochemistry 162:156–159, 1987). PolyA+ RNA was isolated from total RNA (LABIMO) by two passes of oligodT chromatography, as described by Aviv and Leder (Aviv, H. and Leder, P., Proc. Natl. Acad. Sci. USA 69:1408–1412, 1972) in order to eliminate ribosomal RNA.

The quality and the integrity of the poly A+ were checked. Northern blots hybridized with a globin probe were used to confirm that the mRNAs were not degraded. Contamination of the PolyA+mRNAs by ribosomal sequences was checked using RNAs blots and a probe derived from the sequence of the 28S RNA. Preparations of mRNAs with less than 5% of ribosomal RNAs were used in library construction. To avoid constructing libraries with RNAs contaminated by exogenous sequences (prokaryotic or fungal), the presence of bacterial 16S ribosomal sequences or of two highly expressed mRNAs was examined using PCR.

Following preparation of the mRNAs, the above described chemical and/or the enzymatic procedures for enriching mRNAs having intact 5' ends discussed above were employed to obtain 5' ESTs from various tissues. In both approaches an oligonucleotide tag was attached to the cap at the 5' ends of the mRNAs. The oligonucleotide tag had an EcoRI site therein to facilitate later cloning procedures.

Following attachment of the oligonucleotide tag to the mRNA by either the chemical or enzymatic methods, the integrity of the mRNA was examined by performing a Northern blot with 200–500 ng of mRNA using a probe complementary to the oligonucleotidetag.

EXAMPLE 14 cDNA Synthesis Using mRNA Templates Having Intact 5' Ends

For the mRNAs joined to oligonucleotide tags using both the chemical and enzymatic methods, first strand cDNA synthesis was performed using reverse transcriptase with random nonamers as primers. In order to protect internal EcoRI sites in the cDNA from digestion at later steps in the procedure, methylated dCTP was used for first strand synthesis. After removal of RNA by an alkaline hydrolysis, the first strand of cDNA was precipitated using isopropanol in order to eliminate residual primers.

For both the chemical and the enzymatic methods, the second strand of the cDNA was synthesized with a Klenow fragment using a primer corresponding to the 5' end of the ligated oligonucleotide described in Example 12. Preferably, the primer is 20–25 bases in length. Methylated dCTP was also used for second strand synthesis in order to protect internal EcoRI sites in the cDNA from digestion during the cloning process.

Following cDNA synthesis, the cDNAs were cloned into pBlueScript as described in Example 15 below.

EXAMPLE 15

Insertion of cDNAs into BlueScript

Following second strand synthesis, the ends of the cDNA were blunted with T4 DNA polymerase (Biolabs) and the cDNA was digested with EcoRI. Since methylated dCTP was used during cDNA synthesis, the EcoRI site present in the tag was the only site which was hemi-methylated. Consequently, only the EcoRI site in the oligonucleotide tag was susceptible to EcoRI digestion. The cDNA was then size fractionated using exclusion chromatography (AcA, Biosepra). Fractions corresponding to cDNAs of more than 150 bp were pooled and ethanol precipitated. The cDNA was directionally cloned into the SmaI and EcoRI ends of the phagemid pBlueScript vector (Stratagene). The ligation mixture was electroporated into bacteria and propagated under appropriate antibiotic selection.

Clones containing the oligonucleotide tag attached were selected as described in Example 16 below.

EXAMPLE 16

Selection of Clones Having the Oligonucleotide Tag Attached Thereto

The plasmid DNAs containing 5' EST libraries made as described above were purified (Qiagen). A positive selection of the tagged clones was performed as follows. Briefly, in this selection procedure, the plasmid DNA was converted to single stranded DNA using gene II endonuclease of the phage F1 in combination with an exonuclease (Chang et al., Gene 127:95–8, 1993) such as exonuclease III or T7 gene 6 exonuclease. The resulting single stranded DNA was then purified using paramagnetic beads as described by Fry et al., Biotechniques, 13: 124–131, 1992. In this procedure, the single stranded DNA was hybridized with a biotinylated oligonucleotide having a sequence corresponding to the 3' end of the oligonucleotide described in Example 13. Preferably, the primer has a length of 20–25 bases. Clones including a sequence complementary to the biotinylated oligonucleotide were captured by incubation with streptavidin coated magnetic beads followed by magnetic selection. After capture of the positive clones, the plasmid DNA was released from the magnetic beads and converted into double stranded DNA using a DNA polymerase such as the ThermoSequenase obtained from Amersham Pharmacia Biotech. Alternatively, protocols such as the Gene Trapper kit (Gibco BRL) may be used. The double stranded DNA was then electroporated into bacteria. The percentage of positive clones having the 5' tag oligonucleotide was estimated to typically rank between 90 and 98% using dot blot analysis.

Following electroporation, the libraries were ordered in 384-microtiter plates (MTP). A copy of the MTP was stored for future needs. Then the libraries were transferred into 96 MTP and sequenced as described below.

EXAMPLE 17

Sequencing of Inserts in Selected Clones

Plasmid inserts were first amplified by PCR on PE 9600 thermocyclers (Perkin-Elmer), using standard SETA-A and SETA-B primers (Genset SA), AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers used were either T7 or 21M13 (available from Genset SA) as appropriate. The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data from the 44 cDNA libraries made as described above were transferred to a proprietary database, where quality control and validation steps were performed. A proprietary base-caller ("Trace"), working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector or ligation oligonucleotides were automatically removed from the EST sequences. However, the resulting EST sequences may contain 1 to 5 bases belonging to the above mentioned sequences at their 5' end. If needed, these can easily be removed on a case by case basis.

Thereafter, the sequences were transferred to the proprietary NETGENE™ Database for further analysis as described below.

Following sequencing as described above, the sequences of the 5' ESTs were entered in a proprietary database called NETGENE™ for storage and manipulation. It will be appreciated by those skilled in the art that the data could be stored and manipulated on any medium which can be read and accessed by a computer. Computer readable media include magnetically readable media, optically readable media, or electronically readable media. For example, the computer readable media may be a hard disc, a floppy disc, a magnetic tape, CD-ROM, RAM, or ROM as well as other types of other media known to those skilled in the art.

In addition, the sequence data may be stored and manipulated in a variety of data processor programs in a variety of formats. For example, the sequence data may be stored as text in a word processing file, such as MicrosoftWORD or WORDPERFECT or as an ASCII file in a variety of database programs familiar to those of skill in the art, such as DB2, SYBASE, or ORACLE.

The computer readable media on which the sequence information is stored may be in a personal computer, a network, a server or other computer systems known to those skilled in the art. The computer or other system preferably includes the storage media described above, and a processor for accessing and manipulating the sequence data.

Once the sequence data has been stored it may be manipulated and searched to locate those stored sequences which contain a desired nucleic acid sequence or which encode a protein having a particular functional domain. For example, the stored sequence information may be compared to other known sequences to identify homologies, motifs implicated in biological function, or structural motifs.

Programs which may be used to search or compare the stored sequences include the MacPattern (EMBL), BLAST, and BLAST2 program series (NCBI), basic local alignment search tool programs for nucleotide (BLASTN) and peptide (BLASTX) comparisons (Altschul et al, J. Mol. Biol. 215: 403 (1990)) and FASTA (Pearson and Lipman, Proc. Natl. Acad. Sci. USA, 85: 2444 (1988)). The BLAST programs then extend the alignments on the basis of defined match and mismatch criteria.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Before searching the cDNAs in the NETGENE™ database for sequence motifs of interest, cDNAs derived from mRNAs which were not of interest were identified and eliminated from further consideration as described in Example 18 below.

EXAMPLE 18

Elimination of Undesired Sequences from Further Consideration

5' ESTs in the NETGENE™ database which were derived from undesired sequences such as transfer RNAs, ribosomal RNAs, mitochondrial RNAs, procaryotic RNAs, fungal RNAs, Alu sequences, L1 sequences, or repeat sequences were identified using the FASTA and BLASTN programs with the parameters listed in Table II.

To eliminate 5' ESTs encoding tRNAs from further consideration, the 5' EST sequences were compared to the sequences of 1190 known tRNAs obtained from EMBL release 38, of which 100 were human. The comparison was performed using FASTA on both strands of the 5' ESTs. Sequences having more than 80% homology over more than 60 nucleotides were identified as tRNA. Of the 144,341 sequences screened, 26 were identified as tRNAs and eliminated from further consideration.

To eliminate 5' ESTs encoding rRNAs from further consideration, the 5' EST sequences were compared to the sequences of 2497 known rRNAs obtained from EMBL release 38, of which 73 were human. The comparison was performed using BLASTN on both strands of the 5' ESTs with the parameter S=108. Sequences having more than 80% homology over stretches longer than 40 nucleotides were identified as rRNAs. Of the 144,341 sequences screened, 3,312 were identified as rRNAs and eliminated from further consideration.

To eliminate 5' ESTs encoding mtRNAs from further consideration, the 5' EST sequences were compared to the sequences of the two known mitochondrial genomes for which the entire genomic sequences are available and all sequences transcribed from these mitochondrial genomes including tRNAs, rRNAs, and mRNAs for a total of 38 sequences. The comparison was performed using BLASTN on both strands of the 5' ESTs with the parameter S=108. Sequences having more than 80% homology over stretches longer than 40 nucleotides were identified as mtRNAs. Of the 144,341 sequences screened, 6,110 were identified as mtRNAs and eliminated from further consideration.

Sequences which might have resulted from exogenous contaminants were eliminated from further consideration by comparing the 5' EST sequences to release 46 of the EMBL bacterial and fungal divisions using BLASTN with the parameter S=144. All sequences having more than 90% homology over at least 40 nucleotides were identified as exogenous contaminants. Of the 42 cDNA libraries examined, the average percentages of procaryotic and fungal sequences contained therein were 0.2% and 0.5% respectively. Among these sequences, only one could be identified as a sequence specific to fungi. The others were either fungal or procaryotic sequences having homologies with vertebrate sequences or including repeat sequences which had not been masked during the electronic comparison.

In addition, the 5' ESTs were compared to 6093 Alu sequences and 1115 L1 sequences to mask 5' ESTs containing such repeat sequences from further consideration. 5' ESTs including THE and MER repeats, SSTR sequences or satellite, micro-satellite, or telomeric repeats were also eliminated from further consideration. On average, 11.5% of the sequences in the libraries contained repeat sequences. Of this 11.5%, 7% contained Alu repeats, 3.3% contained L1 repeats and the remaining 1.2% were derived from the other types of repetitive sequences which were screened. These percentages are consistent with those found in cDNA libraries prepared by other groups. For example, the cDNA libraries of Adams et al. contained between 0% and 7.4% Alu repeats depending on the source of the RNA which was used to prepare the cDNA library (Adams et al., Nature 377:174,1996).

The sequences of those 5' ESTs remaining after the elimination of undesirable sequences were compared with the sequences of known human mRNAs to determine the accuracy of the sequencing procedures described above.

EXAMPLE 19

Measurement of Sequencing Accuracy by Comparison to Known Sequences

To further determine the accuracy of the sequencing procedure described above, the sequences of 5' ESTs derived from known sequences were identified and compared to the known sequences. First, a FASTA analysis with overhangs shorter than 5 bp on both ends was conducted on the 5' ESTs to identify those matching an entry in the public human mRNA database. The 6655 5' ESTs which matched a known human mRNA were then realigned with their cognate mRNA and dynamic programming was used to include substitutions, insertions, and deletions in the list of "errors" which would be recognized. Errors occurring in the last 10 bases of the 5' EST sequences were ignored to avoid the inclusion of spurious cloning sites in the analysis of sequencing accuracy.

This analysis revealed that the sequences incorporated in the NETGENE™ database had an accuracy of more than 99.5%.

To determine the efficiency with which the above selection procedures select cDNAs which include the 5' ends of their corresponding mRNAs, the following analysis was performed.

EXAMPLE 20

Determination of Efficiency of 5' EST Selection

To determine the efficiency at which the above selection procedures isolated 5' ESTs which included sequences close to the 5' end of the mRNAs from which they were derived, the sequences of the ends of the 5' ESTs which were derived from the elongation factor 1 subunit α and ferritin heavy chain genes were compared to the known cDNA sequences for these genes. Since the transcription start sites for the elongation factor 1 subunit α and ferritin heavy chain are well characterized, they may be used to determine the percentage of 5' ESTs derived from these genes which included the authentic transcription start sites.

For both genes, more than 95% of the cDNAs included sequences close to or upstream of the 5' end of the corresponding mRNAs.

To extend the analysis of the reliability of the procedures for isolating 5' ESTs from ESTs in the NETGENE™ database, a similar analysis was conducted using a database composed of human mRNA sequences extracted from GenBank database release 97 for comparison. For those 5' ESTs derived from mRNAs included in the GeneBank database, more than 85% had their 5' ends close to the 5' ends of the known sequence. As some of the mRNA sequences available in the GenBank database are deduced from genomic sequences, a 5' end matching with these sequences will be counted as an internal match. Thus, the method used here underestimates the yield of ESTs including the authentic 5' ends of their corresponding mRNAs.

The EST libraries made above included multiple 5' ESTs derived from the same mRNA. The sequences of such 5' ESTs were compared to one another and the longest 5' ESTs for each mRNA were identified. Overlapping cDNAs were assembled into continuous sequences (contigs). The resulting continuous sequences were then compared to public databases to gauge their similarity to known sequences, as described in Example 21 below.

EXAMPLE 21

Clustering of the 5' ESTs and Calculation of Novelty Indices for cDNA Libraries

For each sequenced EST library, the sequences were clustered by the 5' end. Each sequence in the library was compared to the others with BLASTN2 (direct strand, parameters S=107). ESTs with High Scoring Segment Pairs (HSPs) at least 25 bp long, having 95% identical bases and beginning closer than 10 bp from each EST 5' end were grouped. The longest sequence found in the cluster was used as representative of the cluster. A global clustering between libraries was then performed leading to the definition of super-contigs.

To assess the yield of new sequences within the EST libraries, a novelty rate (NR) was defined as: NR=100 X (Number of new unique sequences found in the library/Total number of sequences from the library). Typically, novelty rating range between 10% and 41% depending on the tissue from which the EST library was obtained. For most of the libraries, the random sequencing of 5' EST libraries was pursued until the novelty rate reached 20%.

Following characterization as described above, the collection of 5' ESTs in NETGENE™ was screened to identify those 5' ESTs bearing potential signal sequences as described in Example 22 below.

EXAMPLE 22

Identification of Potential Signal Sequences in 5' ESTs

The 5' ESTs in the NETGENE™ database were screened to identify those having an uninterrupted open reading frame (ORF) longer than 45 nucleotides beginning with an ATG codon and extending to the end of the EST. Approximately half of the cDNA sequences in NETGENE™ contained such an ORF. The ORFs of these 5' ESTs were searched to identify potential signal motifs using slight modifications of the procedures disclosed in Von Heijne, G. A New Method for Predicting Signal Sequence Cleavage Sites. Nucleic Acids Res. 14:4683–4690 (1986), the disclosure of which is incorporated herein by reference. Those 5' EST sequences encoding a 15 amino acid long stretch with a score of at least 3.5 in the Von Heijne signal peptide identification matrix were considered to possess a signal sequence. Those 5' ESTs which matched a known human mRNA or EST sequence and had a 5' end more than 20 nucleotides downstream of the known 5' end were excluded from further analysis. The remaining cDNAs having signal sequences therein were included in a database called SIGNALTAG™.

To confirm the accuracy of the above method for identifying signal sequences, the analysis of Example 23 was performed.

EXAMPLE 23

Confirmation of Accuracy of Identification of Potential Signal Sequences in 5' ESTs The accuracy of the above procedure for identifying signal sequences encoding signal peptides was evaluated by applying the method to the 43 amino terminal amino acids of all human SwissProt proteins. The computed Von Heijne score for each protein was compared with the known characterization of the protein as being a secreted protein or a non-secreted protein. In this manner, the number of non-secreted proteins having a score higher than 3.5 (false positives) and the number of secreted proteins having a score lower than 3.5 (false negatives) could be calculated.

Figure 3:
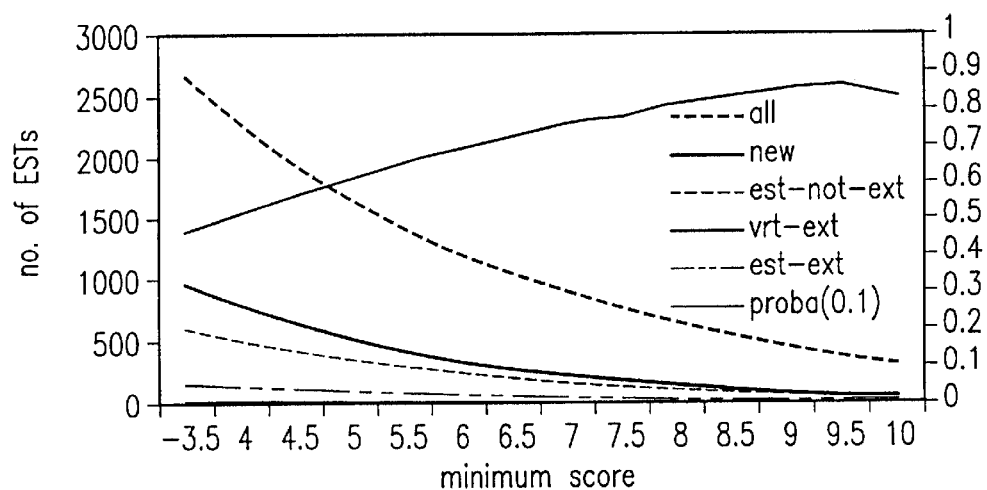
FIG. 3 shows the distribution of von Heijne scores for 5' ESTs in each of the categories described herein and the probability that these 5' ESTs encode a signal peptide.

Using the results of the above analysis, the probability that a peptide encoded by the 5' region of the mRNA is in fact a genuine signal peptide based on its Von Heijne's score was calculated based on either the assumption that 10% of human proteins are secreted or the assumption that 20% of human proteins are secreted. The results of this analysis are shown in FIGS. 2 and 3.

Using the above method of identifying secretory proteins, 5' ESTs for human glucagon, gamma interferon induced monokine precursor, secreted cyclophilin-like protein, human pleiotropin, and human biotinidase precursor all of which are polypeptides which are known to be secreted, were obtained. Thus, the above method successfully identified those 5' ESTs which encode a signal peptide.

To confirm that the signal peptide encoded by the 5' ESTs actually functions as a signal peptide, the signal sequences from the 5' ESTs may be cloned into a vector designed for the identification of signal peptides. Some signal peptide identification vectors are designed to confer the ability to grow in selective medium on host cells which have a signal sequence operably inserted into the vector. For example, to confirm that a 5' EST encodes a genuine signal peptide, the signal sequence of the 5' EST may be inserted upstream and in frame with a non-secreted form of the yeast invertase gene in signal peptide selection vectors such as those described in U.S. Pat. No. 5,536,637, the disclosure of which is incorporated herein by reference. Growth of host cells containing signal sequence selection vectors having the signal sequence from the 5' EST inserted therein confirms that the 5' EST encodes a genuine signal peptide.

Alternatively, the presence of a signal peptide may be confirmed by cloning the extended cDNAs obtained using the ESTs into expression vectors such as pXT1 (as described below), or by constructing promoter-signal sequence-reporter gene vectors which encode fusion proteins between the signal peptide and an assayable reporter protein. After introduction of these vectors into a suitable host cell, such as COS cells or NIH 3T3 cells, the growth medium may be harvested and analyzed for the presence of the secreted protein. The medium from these cells is compared to the medium from cells containing vectors lacking the signal sequence or extended cDNA insert to identify vectors which encode a functional signal peptide or an authentic secreted protein.

Those 5' ESTs which encoded a signal peptide, as determined by the method of Example 22 above, were further grouped into four categories based on their homology to known sequences. The categorization of the 5' ESTs is described in Example 24 below.

EXAMPLE 24

Categorization of 5' ESTs Encoding a Signal Peptide

Those 5' ESTs having a sequence not matching any known vertebrate sequence nor any publicly available EST sequence were designated "new." Of the sequences in the SIGNALTAG™ database, 947 of the 5' ESTs having a Von Heijne's score of at least 3.5 fell into this category.

Those 5' ESTs having a sequence not matching any vertebrate sequence but matching a publicly known EST were designated "EST-ext", provided that the known EST sequence was extended by at least 40 nucleotides in the 5' direction. Of the sequences in the SIGNALTAG™ database, 150 of the 5' ESTs having a Von Heijne's score of at least 3.5 fell into this category.

Those ESTs not matching any vertebrate sequence but matching a publicly known EST without extending the known EST by at least 40 nucleotides in the 5' direction were designated "EST." Of the sequences in the SIGNALTAG™ database, 599 of the 5' ESTs having a Von Heijne's score of at least 3.5 fell into this category.

Those 5' ESTs matching a human mRNA sequence but extending the known sequence by at least 40 nucleotides in the 5' direction were designated "VERT-ext." Of the sequences in the SIGNALTAG™ database, 23 of the 5' ESTs having a Von Heijne's score of at least 3.5 fell into this category. Included in this category was a 5' EST which extended the known sequence of the human translocase mRNA by more than 200 bases in the 5' direction. A 5' EST which extended the sequence of a human tumor suppressor gene in the 5' direction was also identified.

FIG. 4 shows the distribution of 5' ESTs in each category and the number of 5' ESTs in each category having a given minimum von Heijne's score.

Each of the 5' ESTs was categorized based on the tissue from which its corresponding mRNA was obtained, as described below in Example 25.

EXAMPLE 25

Categorization of Expression Patterns

FIG. 5 shows the tissues from which the mRNAs corresponding to the 5' ESTs in each of the above described categories were obtained.

In addition to categorizing the 5' ESTs by the tissue from which the cDNA library in which they were first identified was obtained, the spatial and temporal expression patterns of the mRNAs corresponding to the 5' ESTs, as well as their expression levels, may be determined as described in Example 26 below. Characterization of the spatial and temporal expression patterns and expression levels of these mRNAs is useful for constructing expression vectors capable of producing a desired level of gene product in a desired spatial or temporal manner, as will be discussed in more detail below.

In addition, 5' ESTs whose corresponding mRNAs are associated with disease states may also be identified. For example, a particular disease may result from lack of expression, over expression, or under expression of an mRNA corresponding to a 5' EST. By comparing mRNA expression patterns and quantities in samples taken from healthy individuals with those from individuals suffering from a particular disease, 5' ESTs responsible for the disease may be identified.

It will be appreciated that the results of the above characterization procedures for 5' ESTs also apply to extended cDNAs (obtainable as described below) which contain sequences adjacent to the 5' ESTs. It will also be appreciated that if it is desired to defer characterization until extended cDNAs have been obtained rather than characterizing the ESTs themselves, the above characterization procedures can be applied to characterize the extended cDNAs after their isolation.

EXAMPLE 26

Evaluation of Expression Levels and Patterns of mRNAs Corresponding to 5' ESTs or Extended cDNAs Expression levels and patterns of mRNAs corresponding to 5' ESTs or extended cDNAs (obtainable as described below) may be analyzed by solution hybridization with long probes as described in International Patent Application No. WO 97/05277, the entire contents of which are hereby incorporated by reference. Briefly, a 5' EST, extended cDNA, or fragment thereof corresponding to the gene encoding the mRNA to be characterized is inserted at a cloning site immediately downstream of a bacteriophage (T3, T7 or SP6) RNA polymerase promoter to produce antisense RNA. Preferably, the 5' EST or extended cDNA has 100 or more nucleotides. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

The 5' ESTs, extended cDNAs, or fragments thereof may also be tagged with nucleotide sequences for the serial analysis of gene expression (SAGE) as disclosed in UK Patent Application No. 2 305 241 A, the entire contents of which are incorporated by reference. In this method, cDNAs are prepared from a cell, tissue, organism or other source of nucleic acid for which it is desired to determine gene expression patterns. The resulting cDNAs are separated into two pools. The cDNAs in each pool are cleaved with a first restriction endonuclease, called an "anchoring enzyme," having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer and an internal restriction site for a "tagging endonuclease" is ligated to the digested cDNAs in the first pool. Digestion with the second endonuclease produces short "tag" fragments from the cDNAs.

A second oligonucleotide having a second sequence for hybridization of an amplification primer and an internal restriction site is ligated to the digested cDNAs in the second pool. The cDNA fragments in the second pool are also digested with the "tagging endonuclease" to generate short "tag" fragments derived from the cDNAs in the second pool. The "tags" resulting from digestion of the first and second pools with the anchoring enzyme and the tagging endonuclease are ligated to one another to produce "ditags." In some embodiments, the ditags are concatamerized to produce ligation products containing from 2 to 200 ditags. The tag sequences are then determined and compared to the sequences of the 5' ESTs or extended cDNAs to determine which 5' ESTs or extended cDNAs are expressed in the cell, tissue, organism, or other source of nucleic acids from which the tags were derived. In this way, the expression pattern of the 5' ESTs or extended cDNAs in the cell, tissue, organism, or other source of nucleic acids is obtained.

Quantitative analysis of gene expression may also be performed using arrays. As used herein, the term array means a one dimensional, two dimensional, or multidimensional arrangement of full length cDNAs (i.e. extended cDNAs which include the coding sequence for the signal peptide, the coding sequence for the mature protein, and a stop codon), extended cDNAs, 5' ESTs or fragments of the full length cDNAs, extended cDNAs, or 5' ESTs of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full length cDNAs, extended cDNAs, 5' ESTs, or fragments thereof in a complementary DNA microarray as described by Schena et al. (*Science* 270:467–470, 1995; *Proc. Natl. Acad. Sci. U.S.A.* 93:10614–10619, 1996). Full length cDNAs, extended cDNAs, 5' ESTs or fragments thereof are amplified by PCR and arrayed from 96-well microtiter plates onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm² microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the expression of genes may also be performed with full length cDNAs, extended cDNAs, 5' ESTs, or fragments thereof in complementary DNA arrays as described by Pietu et al. (Genome Research 6:492–503, 1996). The full length cDNAs, extended cDNAs, 5' ESTs or fragments thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of the 5' ESTs or extended cDNAs can be done through high density nucleotide arrays as described by Lockhart et al. (Nature Biotechnology 14: 1675–1680, 1996) and Sosnowsky et al. (Proc. Natl. Acad. Sci. 94:1119–1123,1997). Oligonucleotides of 15–50 nucleotides corresponding to sequences of the 5' ESTs or extended cDNAs are synthesized directly on the chip (Lockhart et al., supra) or synthesized and then addressed to the chip (Sosnowski et al., supra). Preferably, the oligonucleotidesare about 20 nucleotides in length.

cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Natl. Acad. Sci. 94:1119–1123)., the dyes or labeling compounds are detected and quantified. Duplicate hybridizations are performed. Comparative analysis of the intensity of the signal originating from cDNA probes on the same target oligonucleotide in different cDNA samples indicates a differential expression of the mRNA corresponding to the 5' EST or extended cDNA from which the oligonucleotide sequence has been designed.

III. Use of 5' ESTs to Clone Extended cDNAs and to Clone the Corresponding Genomic DNAs Once 5' ESTs which include the 5' end of the corresponding mRNAs have been selected using the procedures described above, they can be utilized to isolate extended cDNAs which contain sequences adjacent to the 5' ESTs. The extended cDNAs may include the entire coding sequence of the protein encoded by the corresponding mRNA, including the authentic translation start site, the signal sequence, and the sequence encoding the mature protein remaining after cleavage of the signal peptide. Such extended cDNAs are referred to herein as "full length cDNAs." Alternatively, the extended cDNAs may include only the sequence encoding the mature protein remaining after cleavage of the signal peptide, or only the sequence encoding the signal peptide.

Example 27 below describes a general method for obtaining extended cDNAs. Example 28 below describes the cloning and sequencing of several extended cDNAs, including extended cDNAs which include the entire coding sequence and authentic 5' end of the corresponding mRNA for several secreted proteins.

The methods of Examples 27, 28, and 29 can also be used to obtain extended cDNAs which encode less than the entire coding sequence of the secreted proteins encoded by the genes corresponding to the 5' ESTs. In some embodiments, the extended cDNAs isolated using these methods encode at least 10 amino acids of one of the proteins encoded by the sequences of SEQ ID NOs: 40–84 and 130–154. In further embodiments, the extended cDNAs encode at least 20 amino acids of the proteins encoded by the sequences of SEQ ID NOs: 40–84 and 130–154. In further embodiments, the extended cDNAs encode at least 30 amino amino acids of the sequences of SEQ ID NOs: 40–84 and 130–154. In a preferred embodiment, the extended cDNAs encode a full length protein sequence, which includes the protein coding sequences of SEQ ID NOs: 40–84 and 130–154.

EXAMPLE 27

General Method for Using 5' ESTs to Clone and Sequence Extended cDNAs

The following general method has been used to quickly and efficiently isolate extended cDNAs including sequence adjacent to the sequences of the 5' ESTs used to obtain them. This method may be applied to obtain extended cDNAs for any 5' EST in the NETGENE™ database, including those 5' ESTs encoding secreted proteins. The method is summarized in FIG. 6.

1. Obtaining Extended cDNAs
a) First Strand Synthesis

The method takes advantage of the known 5' sequence of the mRNA. A reverse transcription reaction is conducted on purified mRNA with a poly 14dT primer containing a 49 nucleotide sequence at its 5' end allowing the addition of a known sequence at the end of the cDNA which corresponds to the 3' end of the mRNA. For example, the primer may have the following sequence: 5'-ATC GTT GAG ACT CGT ACC AGC AGA GTC ACG AGA GAG ACT ACA CGG TAC TGG TTT TTT TTT TTT TTVN-3' (SEQ ID NO:14). Those skilled in the art will appreciate that other sequences may also be added to the poly dT sequence and used to prime the first strand synthesis. Using this primer and a reverse transcriptase such as the Superscript II (Gibco BRL) or Rnase H Minus M-MLV (Promega) enzyme, a reverse transcript anchored at the 3' polyA site of the RNAs is generated.

After removal of the mRNA hybridized to the first cDNA strand by alkaline hydrolysis, the products of the alkaline hydrolysis and the residual poly dT primer are eliminated with an exclusion column such as an AcA34 (Biosepra) matrix as explained in Example 11.

b) Second Strand Synthesis

A pair of nested primers on each end is designed based on the known 5' sequence from the 5' EST and the known 3' end added by the poly dT primer used in the first strand synthesis. Software used to design primers are either based on GC content and melting temperatures of oligonucleotides, such as OSP (Illier and Green, *PCR Meth. Appl.* 1:124–128, 1991), or based on the octamer frequency disparity method (Griffais et al., *Nucleic Acids Res.* 19: 3887–3891, 1991 such as PC-Rare (http://bioinformatics.weizmann.ac.il/software/PC-Rare/doc/manuel.html).

Preferably, the nested primers at the 5' end are separated from one another by four to nine bases. The 5' primer sequences may be selected to have melting temperatures and specificities suitable for use in PCR.

Preferably, the nested primers at the 3' end are separated from one another by four to nine bases. For example, the nested 3' primers may have the following sequences: (5'-CCA GCA GAG TCA CGA GAG AGA CTA CAC GG-3' (SEQ ID NO:15), and 5'-CAC GAG AGA GAC TAC ACG GTA CTG G-3' (SEQ ID NO:]6). These primers were selected because they have melting temperatures and specificities compatible with their use in PCR. However, those skilled in the art will appreciate that other sequences may also be used as primers.

The first PCR run of 25 cycles is performed using the Advantage Tth Polymerase Mix (Clontech) and the outer primer from each of the nested pairs. A second 20 cycle PCR using the same enzyme and the inner primer from each of the nested pairs is then performed on 1/2500 of the first PCR product. Thereafter, the primers and nucleotides are removed.

2. Sequencing of Full Length Extended cDNAs or Fragments Thereof

Due to the lack of position constraints on the design of 5' nested primers compatible for PCR use using the OSP software, amplicons of two types are obtained. Preferably, the second 5' primer is located upstream of the translation initiation codon thus yielding a nested PCR product containing the whole coding sequence. Such a full length extended cDNA undergoes a direct cloning procedure as described in section a below. However, in some cases, the second 5' primer is located downstream of the translation initiation codon, thereby yielding a PCR product containing only part of the ORF. Such incomplete PCR products are submitted to a modified procedure described in section b below.

a) Nested PCR Products Containing Complete ORFs

When the resulting nested PCR product contains the complete coding sequence, as predicted from the 5' EST sequence, it is cloned in an appropriate vector such as pED6dpc2, as described in section 3.

b) Nested PCR Products Containing Incomplete ORFs

When the amplicon does not contain the complete coding sequence, intermediate steps are necessary to obtain both the complete coding sequence and a PCR product containing the full coding sequence. The complete coding sequence can be assembled from several partial sequences determined directly from different PCR products as described in the following section.

Figure 6:
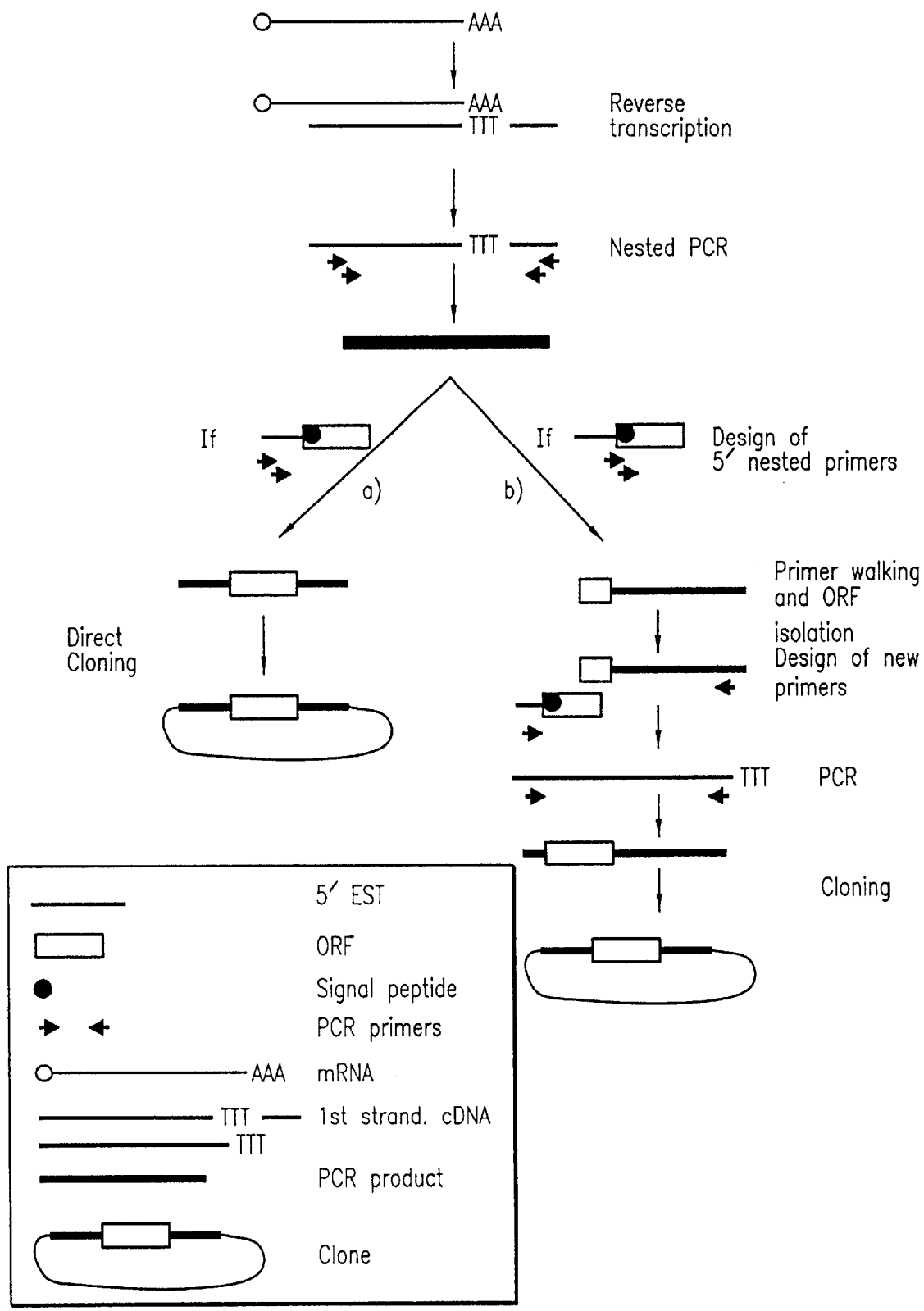
FIG. 6 illustrates a method for obtaining extended cDNAs.

Once the full coding sequence has been completely determined, new primers compatible for PCR use are designed to obtain amplicons containing the whole coding region. However, in such cases, 3' primers compatible for PCR use are located inside the 3' UTR of the corresponding mRNA, thus yielding amplicons which lack part of this region, i.e. the polyA tract and sometimes the polyadenylation signal, as illustrated in FIG. 6. Such full length extended cDNAs are then cloned into an appropriate vector as described in section 3.

c) Sequencing Extended cDNAs

Sequencing of extended cDNAs can be performed using a Die Terminator approach with the AmpliTaq DNA polymerase FS kit available from Perkin Elmer.

In order to sequence PCR fragments, primer walking is performed using software such as OSP to choose primers and automated computer software such as ASMG (Sutton et al., *Genome Science Technol.* 1: 9–19, 1995) to construct contigs of walking sequences including the initial 5' tag using minimum overlaps of 32 nucleotides. Preferably, primer walking is performed until the sequences of full length cDNAs are obtained.

Completion of the sequencing of a given extended cDNA fragment is assessed as follows. Since sequences located after a polyA tract are difficult to determine precisely in the case of uncloned products, sequencing and primer walking processes for PCR products are interrupted when a polyA tract is identified in extended cDNAs obtained as described in case b. The sequence length is compared to the size of the nested PCR product obtained as described above. Due to the limited accuracy of the determination of the PCR product size by gel electrophoresis, a sequence is considered complete if the size of the obtained sequence is at least 70% the size of the first nested PCR product. If the length of the sequence determined from the computer analysis is not at least 70% of the length of the nested PCR product, these PCR products are cloned and the sequence of the insertion is determined. When Northern blot data are available, the size of the mRNA detected for a given PCR product is used to finally assess that the sequence is complete. Sequences which do not fulfill the above criteria are discarded and will undergo a new isolation procedure.

Sequence data of all extended cDNAs are then transferred to a proprietary database, where quality controls and validation steps are carried out as described in example 15.

3. Cloning of Full Length Extended cDNAs

Figure 7:
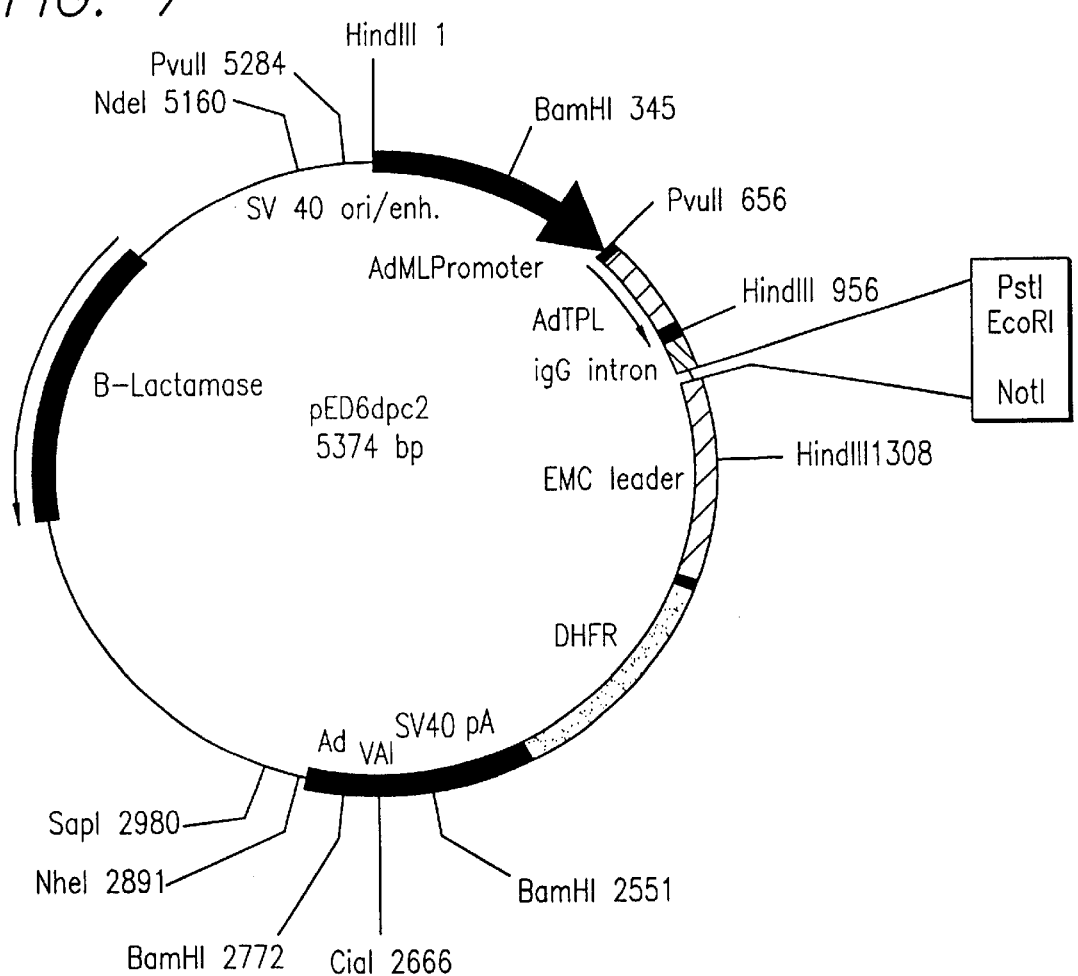
FIG. 7 is a map of pED6dpc2.

The PCR product containing the full coding sequence is then cloned in an appropriate vector. For example, the extended cDNAs can be cloned into the expression vector pED6dpc2 (DiscoverEase, Genetics Institute, Cambridge, Mass.) as follows. The structure of pED6dpc2 is shown in FIG. 7. pED6dpc2 vector DNA is prepared with blunt ends by performing an EcoRI digestion followed by a fill in reaction. The blunt ended vector is dephosphorylated. After removal of PCR primers and ethanol precipitation, the PCR product containing the full coding sequence or the extended cDNA obtained as described above is phosphorylated with a kinase subsequently removed by phenol-Sevag extraction and precipitation. The double stranded extended cDNA is then ligated to the vector and the resulting expression plasmid introduced into appropriate host cells.

Since the PCR products obtained as described above are blunt ended molecules that can be cloned in either direction, the orientation of several clones for each PCR product is determined. Then, 4 to 10 clones are ordered in microtiter plates and subjected to a PCR reaction using a first primer located in the vector close to the cloning site and a second primer located in the portion of the extended cDNA corresponding to the 3' end of the mRNA. This second primer may be the antisense primer used in anchored PCR in the case of direct cloning (case a) or the antisense primer located inside the 3'UTR in the case of indirect cloning (case b). Clones in which the start codon of the extended cDNA is operably linked to the promoter in the vector so as to permit expression of the protein encoded by the extended cDNA are conserved and sequenced. In addition to the ends of cDNA inserts, approximately 50 bp of vector DNA on each side of the cDNA insert are also sequenced.

The cloned PCR products are then entirely sequenced according to the aforementioned procedure. In this case, contig assembly of long fragments is then performed on walking sequences that have already contigated for uncloned PCR products during primer walking. Sequencing of cloned amplicons is complete when the resulting contigs include the whole coding region as well as overlapping sequences with vector DNA on both ends.

4. Computer Analysis of Full Length Extended cDNA

Sequences of all full length extended cDNAs may then be subjected to further analysis as described below and using the parameters found in Table II with the following modifications. For screening of miscellaneous subdivisions of Genbank, FASTA was used instead of BLASTN and 15 nucleotide of homology was the limit instead of 17. For Alu detection, BLASTN was used with the following parameters: S=72; identity=70%; and length=40 nucleotides. Polyadenylation signal and polyA tail which were not search for the 5' ESTs were searched. For polyadenylation signal detection the signal (AATAAA) was searched with one permissible mismatch in the last fifty nucleotides preceding the 5' end of the polyA. For the polyA, a stretch of 8 amino acids in the last 20 nucleotides of the sequence was searched with BLAST2N in the sense strand with the following parameters (W=6, S=10, E=1000, and identity=90%). Finally, patented sequences and ORF homologies were searched using, respectively, BLASTN and BLASTP on GenSEQ (Derwent's database of patented nucleotide sequences) and SWISSPROT for ORFs with the following parameters (W=8 and B=10). Before examining the extended full length cDNAs for sequences of interest, extended cDNAs which are not of interest are searched as follows.

a) Elimination of Undesired Sequences

Although 5' ESTs were checked to remove contaminants sequences as described in Example 18, a last verification was carried out to identify extended cDNAs sequences derived from undesired sequences such as vector RNAs, transfer RNAs, ribosomal rRNAs, mitochondrial RNAs, prokaryotic RNAs and fungal RNAs using the FASTA and BLASTN programs on both strands of extended cDNAs as described below.

To identify the extended cDNAs encoding vector RNAs, extended cDNAs are compared to the known sequences of vector RNA using the FASTA program. Sequences of extended cDNAs with more than 90% homology over stretches of 15 nucleotides are identified as vector RNA.

To identify the extended cDNAs encoding tRNAs, extended cDNA sequences were compared to the sequences of 1190 known tRNAs obtained from EMBL release 38, of which 100 were human. Sequences of extended cDNAs having more than 80% homology over 60 nucleotides using FASTA were identified as tRNA.

To identify the extended cDNAs encoding rRNAs, extended cDNA sequences were compared to the sequences of 2497 known rRNAs obtained from EMBL release 38, of which 73 were human. Sequences of extended cDNAs having more than 80% homology over stretches longer than 40 nucleotides using BLASTN were identified as rRNAs.

To identify the extended cDNAs encoding mtRNAs, extended cDNA sequences were compared to the sequences of the two known mitochondrial genomes for which the entire genomic sequences are available and all sequences transcribed from these mitochondrial genomes including tRNAs, rRNAs, and mRNAs for a total of 38 sequences. Sequences of extended cDNAs having more than 80% homology over stretches longer than 40 nucleotides using BLASTN were identified as mtRNAs.

Sequences which might have resulted from other exogenous contaminants were identified by comparing extended cDNA sequences to release 105 of Genbank bacterial and fungal divisions. Sequences of extended cDNAs having more than 90% homology over 40 nucleotides using BLASTN were identified as exogenous prokaryotic or fungal contaminants.

In addition, extended cDNAs were searched for different repeat sequences, including Alu sequences, L1 sequences, THE and MER repeats, SSTR sequences or satellite, microsatellite, or telomeric repeats. Sequences of extended cDNAs with more than 70% homology over 40 nucleotide stretches using BLASTN were identified as repeat sequences and masked in further identification procedures. In addition, clones showing extensive homology to repeats, i.e., matches of either more than 50 nucleotides if the homology was at least 75% or more than 40 nucleotides if the homology was at least 85% or more than 30 nucleotides if the homology was at least 90%, were flagged.

b) Identification of Structural Features

Structural features, e.g. polyA tail and polyadenylation signal, of the sequences of full length extended cDNAs are subsequently determined as follows.

A polyA tail is defined as a homopolymeric stretch of at least 11 A with at most one alternative base within it. The polyA tail search is restricted to the last 20 nt of the sequence and limited to stretches of 11 consecutive A's because sequencing reactions are often not readable after such a polyA stretch. Stretches with 100% homology over 6 nucleotides are identified as polyA tails.

To search for a polyadenylation signal, the polyA tail is clipped from the full-length sequence. The 50 bp preceding the polyA tail are first searched for the canonic polyadenylation AAUAAA signal and, if the canonic signal is not detected, for the alternative AUUAAA signal (Sheets et al., Nuc. Acids Res. 18: 5799–5805, 1990). If neither of these consensus polyadenylation signals is found, the canonic motif is searched again allowing one mismatch to account for possible sequencing errors. More than 85% of identified polyadenylation signals of either type actually ends 10 to 30 bp from the polyA tail. Alternative AUUAAA signals represents approximately 15% of the total number of identified polyadenylation signals.

To search for a polyadenylation signal, the polyA tail is clipped from the full-length sequence. The 50 bp preceding the polyA tail are searched for the canonic polyadenylation AAUAAA signal allowing one mismatch to account for possible sequencing errors and known variation in the canonical sequence of the polyadenylation signal.

c) Identification of Functional Features

Functional features, e.g. ORFs and signal sequences, of the sequences of full length extended cDNAs were subsequently determined as follows.

The 3 upper strand frames of extended cDNAs are searched for ORFs defined as the maximum length fragments beginning with a translation initiation codon and ending with a stop codon. ORFs encoding at least 20 amino acids are preferred.

Each found ORF is then scanned for the presence of a signal peptide in the first 50 amino-acids or, where appropriate, within shorter regions down to 20 amino acids or less in the ORF, using the matrix method of von Heijne (Nuc. Acids Res. 14: 4683–4690 (1986)), the disclosure of which is incorporated herein by reference and the modification described in Example 22.

d) Homology to Either Nucleotidic or Proteic Sequences

Sequences of full length extended cDNAs are then compared to known sequences on a nucleotidic or proteic basis.

Sequences of full length extended cDNAs are compared to the following known nucleic acid sequences: vertebrate sequences, EST sequences, patented sequences and recently identified sequences available at the time of filing the priority documents. Full length cDNA sequences are also compared to the sequences of a private database (Genset internal sequences) in order to find sequences that have already been identified by applicants. Sequences of full length extended cDNAs with more than 90% homology over 30 nucleotides using either BLASTN or BLAST2N as indicated in Table III are identified as sequences that have already been described. Matching vertebrate sequences are subsequently examined using FASTA; full length extended cDNAs with more than 70% homology over 30 nucleotides are identified as sequences that have already been described.

ORFs encoded by full length extended cDNAs as defined in section c) are subsequently compared to known amino acid sequences found in public databases using Swissprot, PIR and Genptept releases available at the time of filing the priority documents for the present application. These analyses were performed using BLASTP with the parameter W=8 and allowing a maximum of 10 matches. Sequences of full length extended cDNAs showing extensive homology to known protein sequences are recognized as already identified proteins.

In addition, the three-frame conceptual translation products of the top strand of full length extended cDNAs are compared to publicly known amino acid sequences of Swissprot using BLASTX with the parameter E=0.001. Sequences of full length extended cDNAs with more than 70% homology over 30 amino acid stretches are detected as already identified proteins.

As used herein the term "cDNA codes of SEQ ID NOs. 40–84 and 130–154" encompasses the nucleotide sequences of SEQ ID NOs. 40–84 and 130–154, fragments of SEQ ID NOs. 40–84 and 130–154, nucleotide sequences homologous to SEQ ID NOs. 40–84 and 130–154 or homologous to fragments of SEQ ID NOs. 40–84 and 130–154, and sequences complementary to all of the preceding sequences. The fragments include portions of SEQ ID NOs. 40–84 and 130–154 comprising at least 10, 15, 20, 25, 30, 35, 40, 50, 75, 100, 150, 200, 300, 400, or 500 consecutive nucleotides of SEQ ID NOs. 40–84 and 130–154. Preferably, the fragments are novel fragments. Homologous sequences and fragments of SEQ ID NOs. 40–84 and 130–154 refer to a sequence having at least 99%, 98%, 97%, 96%, 95%, 90%, 85%, 80%, or 75% homology to these sequences. Homology may be determined using any of the computer programs and parameters described herein, including BLAST2N with the default parameters or with any modified parameters. Homologous sequences also include RNA sequences in which uridines replace the thymines in the cDNA codes of SEQ ID NOs. 40–84 and 130–154. The homologous sequences may be obtained using any of the procedures described herein or may result from the correction of a sequencing error as described above. It will be appreciated that the cDNA codes of SEQ ID NOs. 40–84 and 130–154 can be represented in the traditional single character format (See the inside back cover of Starrier, Lubert. *Biochemistry*, $3^{rd}$ edition. W. H Freeman & Co., New York.) or in any other format which records the identity of the nucleotides in a sequence.

As used herein the term "polypeptide codes of SEQ ID NOS. 85–129 and 155–179" encompasses the polypeptide sequence of SEQ ID NOs. 85–129 and 155–179 which are encoded by the extended cDNAs of SEQ ID NOs. 40–84 and 130–154, polypeptide sequences homologous to the polypeptides of SEQ ID NOS. 85–129 and 155–179, or fragments of any of the preceding sequences. Homologous polypeptide sequences refer to a polypeptide sequence having at least 99%, 98%, 97%, 96%, 95%, 90%, 85%, 80%, 75% homology to one of the polypeptide sequences of SEQ ID NOS. 85–129 and 155–179. Homology may be determined using any of the computer programs and parameters described herein, including FASTA with the default parameters or with any modified parameters. The homologous sequences may be obtained using any of the procedures described herein or may result from the correction of a sequencing error as described above. The polypeptide fragments comprise at least 5, 10, 15, 20, 25, 30, 35, 40, 50, 75, 100, or 150 consecutive amino acids of the polypeptides of SEQ ID NOS. 85–129 and 155–179. Preferably, the fragments are novel fragments. It will be appreciated that the polypeptide codes of the SEQ ID NOS. 85–129 and 155–179 can be represented in the traditional single character format or three letter format (See the inside back cover of Starrier, Lubert. *Biochemistry*, 3$^{rd}$ edition. W. H Freeman & Co., New York.) or in any other format which relates the identity of the polypeptides in a sequence.

It will be appreciated by those skilled in the art that the cDNA codes of SEQ ID NOs. 40–84 and 130–154 and polypeptide codes of SEQ ID NOS. 85–129 and 155–179 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the cDNA codes of SEQ ID NOs. 40–84 and 130–154, one or more of the polypeptide codes of SEQ ID NOS. 85–129 and 155–179. Another aspect of the present invention is a computer readable medium having recorded thereon at least 2, 5, 10, 15, 20, 25, 30, or 50 cDNA codes of SEQ ID NOs. 40–84 and 130–154. Another aspect of the present invention is a computer readable medium having recorded thereon at least 2, 5, 10, 15, 20, 25, 30, or 50 polypeptide codes of SEQ ID NOS. 85–129 and 155–179.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the sequence information described herein. As used herein, "a computer system" refers to the hardware components, software components, and data storage components used to analyze the nucleotide sequences of the cDNA codes of SEQ ID NOs. 40–84 and 130–154, or the amino acid sequences of the polypeptide codes of SEQ ID NOS. 85–129 and 155–179. The computer system preferably includes the computer readable media described above, and a processor for accessing and manipulating the sequence data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory (preferably implemented as RAM) and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, etc. In some embodiments, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the cDNA codes of SEQ ID NOs. 40–84 and 130–154, or the amino acid sequences of the polypeptide codes of SEQ ID NOS. 85–129 and 155–179 (such as search tools, compare tools, and modeling tools etc.) may reside in main memory during execution.

In some embodiments, the computer system may further comprise a sequence comparer for comparing the above-described cDNA codes of SEQ ID NOs. 40–84 and 130–154 or polypeptide codes of SEQ ID NOS. 85–129 and 155–179 stored on a computer readable medium to reference nucleotide or polypeptide sequences stored on a computer readable medium. A "sequence comparer" refers to one or more programs which are implemented on the computer system to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of the cDNA codes of SEQ ID NOs. 40–84 and 130–154, or the amino acid sequences of the polypeptide codes of SEQ ID NOS. 85–129 and 155–179 stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Accordingly, one aspect of the present invention is a computer system comprising a processor, a data storage device having stored thereon a cDNA code of SEQ ID NOs. 40–84 and 130–154 or a polypeptide code of SEQ ID NOS. 85–129 and 155–179, a data storage device having retrievably stored thereon reference nucleotide sequences or polypeptide sequences to be compared to the cDNA code of SEQ ID NOs. 40–84 and 130–154 or polypeptide code of SEQ ID NOS. 85–129 and 155–179 and a sequence comparer for conducting the comparison. The sequence comparer may indicate a homology level between the sequences compared or identify structural motifs in the above described cDNA code of SEQ ID NOs. 40–84 and 130–154 and polypeptide codes of SEQ ID NOS. 85–129 and 155–179 or it may identify structural motifs in sequences which are compared to these cDNA codes and polypeptide codes. In some embodiments, the data storage device may have stored thereon the sequences of at least 2, 5, 10, 15, 20, 25, 30, or 50 of the cDNA codes of SEQ ID NOs. 40–84 and 130–154 or polypeptide codes of SEQ ID NOS. 85–129 and 155–179.

Another aspect of the present invention is a method for determining the level of homology between a cDNA code of SEQ ID NOs. 40–84 and 130–154 and a reference nucleotide sequence, comprising the steps of reading the cDNA code and the reference nucleotide sequence through the use of a computer program which determines homology levels and determining homology between the cDNA code and the reference nucleotide sequence with the computer program. The computer program may be any of a number of computer programs for determining homology levels, including those specifically enumerated below, including BLAST2N with the default parameters or with any modified parameters. The method may be implemented using the computer systems described above. The method may also be performed by reading 2, 5, 10, 15, 20, 25, 30, or 50 of the above described cDNA codes of SEQ ID NOs. 40–84 and 130–154 through use of the computer program and determining homology between the cDNA codes and reference nucleotide sequences.

Alternatively, the computer program may be a computer program which compares the nucleotide sequences of the cDNA codes of the present invention, to reference nucleotide sequences in order to determine whether the cDNA code of SEQ ID NOs. 40–84 and 130–154 differs from a reference nucleic acid sequence at one or more positions. Optionally such a program records the length and identity of inserted, deleted or substituted nucleotides with respect to the sequence of either the reference polynucleotide or the cDNA code of SEQ ID NOs. 40–84 and 130–154. In one embodiment, the computer program may be a program which determines whether the nucleotide sequences of the cDNA codes of SEQ ID NOs. 40–84 and 130–154 contain a single nucleotide polymorphism (SNP) with respect to a reference nucleotide sequence. This single nucleotide polymorphism may comprise a single base substitution, insertion, or deletion.

Another aspect of the present invention is a method for determining the level of homology between a polypeptide code of SEQ ID NOS. 85–129 and 155–179 and a reference polypeptide sequence, comprising the steps of reading the polypeptide code of SEQ ID NOS. 85–129 and 155–179 and the reference polypeptide sequence through use of a computer program which determines homology levels and determining homology between the polypeptide code and the reference polypeptide sequence using the computer program.

Accordingly, another aspect of the present invention is a method for determining whether a cDNA code of SEQ ID NOs. 40–84 and 130–154 differs at one or more nucleotides from a reference nucleotide sequence comprising the steps of reading the cDNA code and the reference nucleotide sequence through use of a computer program which identifies differences between nucleic acid sequences and identifying differences between the cDNA code and the reference nucleotide sequence with the computer program. In some embodiments, the computer program is a program which identifies single nucleotide polymorphisms. The method may be implemented by the computer systems described above. The method may also be performed by reading at least 2, 5, 10, 15, 20, 25, 30, or 50 of the cDNA codes of SEQ ID NOs. 40–84 and 130–154 and the reference nucleotide sequences through the use of the computer program and identifying differences between the cDNA codes and the reference nucleotide sequences with the computer program.

In other embodiments the computer based system may further comprise an identifier for identifying features within the nucleotide sequences of the cDNA codes of SEQ ID NOs. 40–84 and 130–154 or the amino acid sequences of the polypeptide codes of SEQ ID NOS. 85–129 and 155–179.

An "identifier" refers to one or more programs which identifies certain features within the above-described nucleotide sequences of the cDNA codes of SEQ ID NOs. 40–84 and 130–154 or the amino acid sequences of the polypeptide codes of SEQ ID NOS. 85–129 and 155–179. In one embodiment, the identifier may comprise a program which identifies an open reading frame in the cDNAs codes of SEQ ID NOs. 40–84 and 130–154.

In another embodiment, the identifier may comprise a molecular modeling program which determines the 3-dimensional structure of the polypeptides codes of SEQ ID NOS. 85–129 and 155–179. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of the polypeptide codes of SEQ ID NOS. 85–129 and 155–179. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins:Structure, Function, and Genetics, Supplement 1:38–42 (1997)).

The results of the molecular modeling analysis may then be used in rational drug design techniques to identify agents which modulate the activity of the polypeptide codes of SEQ ID NOS. 85–129 and 155–179.

Accordingly, another aspect of the present invention is a method of identifying a feature within the cDNA codes of SEQ ID NOs. 40–84 and 130–154 or the polypeptide codes of SEQ ID NOS. 85–129 and 155–179 comprising reading the cDNA code(s) or the polypeptide code(s) through the use of a computer program which identifies features therein and identifying features within the cDNA code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the cDNA codes of SEQ ID NOs. 40–84 and 130–154 or the polypeptide codes of SEQ ID NOS. 85–129 and 155–179 through the use of the computer program and identifying features withing the cDNA codes or polypeptide codes with the computer program.

The cDNA codes of SEQ ID NOs. 40–84 and 130–154 or the polypeptide codes of SEQ ID NOS. 85–129 and 155–179 may be stored and manipulated in a variety of data processor programs in a variety of formats. For example, the cDNA codes of SEQ ID NOs. 40–84 and 130–154 or the polypeptide codes of SEQ ID NOS. 85–129 and 155–179 may be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the cDNA codes of SEQ ID NOs. 40–84 and 130–154 or the polypeptide codes of SEQ ID NOS. 85–129 and 155–179. The following list is intended not to limit the invention but to provide guidance to programs and databases which are useful with the cDNA codes of SEQ ID NOs. 40–84 and 130–154 or the polypeptide codes of SEQ ID NOS. 85–129 and 155–179. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol* 215: 403 (1990)), FASTA (Pearson and Lipman, *Proc. Natl Acad. Sci.* USA, 85: 2444 (1988)), FASTDB (Brutlag et al. Comp. App. Biosci. 6:237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

5. Selection of Cloned Full Length Sequences of the Present Invention

Cloned full length extended cDNA sequences that have already been characterized by the aforementioned computer analysis are then submitted to an automatic procedure in order to preselect full length extended cDNAs containing sequences of interest.

a) Automatic Sequence Preselection

All complete cloned full length extended cDNAs clipped for vector on both ends are considered. First, a negative selection is operated in order to eliminate unwanted cloned sequences resulting from either contaminants or PCR artifacts as follows. Sequences matching contaminant sequences such as vector RNA, tRNA, mtRNA, rRNA sequences are discarded as well as those encoding ORF sequences exhibiting extensive homology to repeats as defined in section 4 a). Sequences obtained by direct cloning using nested primers on 5' and 3' tags (section 1. case a) but lacking polyA tail are discarded. Only ORFs containing a signal peptide and ending either before the polyA tail (case a) or before the end of the cloned 3'UTR (case b) are kept. Then, ORFs containing unlikely mature proteins such as mature proteins which size is less than 20 amino acids or less than 25% of the immature protein size are eliminated.

In the selection of the ORF, priority was given to the ORF and the frame corresponding to the polypeptides described in SignalTag Patents (U.S. Pat. No. 6,222,029, and application Ser. Nos. 08/905,135; 08/905,051; 08/905,144; 08/905,279; 08/904,468; 08/905,134; and 08/905,133). If the ORF was not found among the ORFs described in the SignalTag Patents, the ORF encoding the signal peptide with the highest score according to Von Heijne method as defined in Example 22 was chosen. If the scores were identical, then the longest ORF was chosen.

Sequences of full length extended cDNA clones are then compared pairwise with BLAST after masking of the repeat sequences. Sequences containing at least 90% homology over 30 nucleotides are clustered in the same class. Each cluster is then subjected to a cluster analysis that detects sequences resulting from internal priming or from alternative splicing, identical sequences or sequences with several frameshifts. This automatic analysis serves as a basis for manual selection of the sequences.

b) Manual Sequence Selection

Manual selection can be carried out using automatically generated reports for each sequenced full length extended cDNA clone. During this manual procedure, a selection is operated between clones belonging to the same class as follows. ORF sequences encoded by clones belonging to the same class are aligned and compared. If the homology between nucleotidic sequences of clones belonging to the same class is more than 90% over 30 nucleotide stretches or if the homology between amino acid sequences of clones belonging to the same class is more than 80% over 20 amino acid stretches, than the clones are considered as being identical. The chosen ORF is the best one according to the criteria mentioned below. If the nucleotide and amino acid homologies are less than 90% and 80% respectively, the clones are said to encode distinct proteins which can be both selected if they contain sequences of interest.

Selection of full length extended cDNA clones encoding sequences of interest is performed using the following criteria. Structural parameters (initial tag, polyadenylation site and signal) are first checked. Then, homologies with known nucleic acids and proteins are examined in order to determine whether the clone sequence match a known nucleic/proteic sequence and, in the latter case, its covering rate and the date at which the sequence became public. If there is no extensive match with sequences other than ESTs or genomic DNA, or if the clone sequence brings substantial new information, such as encoding a protein resulting from alternative slicing of an mRNA coding for an already known protein, the sequence is kept. Examples of such cloned full length extended cDNAs containing sequences of interest are described in Example 28. Sequences resulting from chimera or double inserts as assessed by homology to other sequences are discarded during this procedure.

EXAMPLE 28

Cloning and Sequencing of Extended cDNAs

The procedure described in Example 27 above was used to obtain the extended cDNAs of the present invention. Using this approach, the full length cDNA of SEQ ID NO:17 was obtained. This cDNA falls into the "EST-ext" category described above and encodes the signal peptide MKKVLL-LITAILAVAVG (SEQ ID NO: 18) having a von Heijne score of 8.2.

The full length cDNA of SEQ ID NO: 19 was also obtained using this procedure. This cDNA falls into the "EST-ext" category described above and encodes the signal peptide MWWFQQGLSFLPSALVIWTSA(SEQ ID NO:20) having a von Heijne score of 5.5.

Another full length cDNA obtained using the procedure described above has the sequence of SEQ ID NO:21. This cDNA, falls into the "EST-ext" category described above and encodes the signal peptide MVLTTLPSANSANSPVN-MPTTGPNSLSYASSA LSPCLT (SEQ ID NO:22) having a von Heijne score of 5.9.

The above procedure was also used to obtain a full length cDNA having the sequence of SEQ ID NO:23. This cDNA falls into the "EST-ext" category described above and encodes the signal peptide ILSTVTALTFAXA (SEQ ID NO:24) having a von Heijne score of 5.5.

The full length cDNA of SEQ ID NO:25 was also obtained using this procedure. This cDNA falls into the "new" category described above and encodes a signal peptide LVLTLCTLPLAVA(SEQ ID NO:26) having a von Heijne score of 10.1.

The full length cDNA of SEQ ID NO:27 was also obtained using this procedure. This cDNA falls into the "new" category described above and encodes a signal peptide LWLLFFLVTAIHA(SEQ ID NO:28) having a von Heijne score of 10.7.

The above procedures were also used to obtain the extended cDNAs of the present invention. 5' ESTs expressed in a variety of tissues were obtained as described above. The appended sequence listing provides the tissues from which the extended cDNAs were obtained. It will be appreciated that the extended cDNAs may also be expressed in tissues other than the tissue listed in the sequence listing.

5' ESTs obtained as described above were used to obtain extended cDNAs having the sequences of SEQ ID NOs: 40–84 and 130–154. Table IV provides the sequence identification numbers of the extended cDNAs of the present invention, the locations of the full coding sequences in SEQ ID NOs: 40–84 and 130–154 (i.e. the nucleotides encoding both the signal peptide and the mature protein, listed under the heading FCS location in Table IV), the locations of the nucleotides in SEQ ID NOs: 40–84 and 130–154 which encode the signal peptides (listed under the heading SigPep Location in Table IV), the locations of the nucleotides in SEQ ID NOs: 40–84 and 130–154 which encode the mature proteins generated by cleavage of the signal peptides (listed under the heading Mature Polypeptide Location in Table IV), the locations in SEQ ID NOs: 40–84 and 130–154 of stop codons (listed under the heading Stop Codon Location in Table IV), the locations in SEQ ID NOs: 40–84 and 130–154 of polyA signals (listed under the heading Poly A Signal Location in Table IV) and the locations of polyA sites (listed under the heading Poly A Site Location in Table IV).

The polypeptides encoded by the extended cDNAs were screened for the presence of known structural or functional motifs or for the presence of signatures, small amino acid sequences which are well conserved amongst the members of a protein family. The conserved regions have been used to derive consensus patterns or matrices included in the PROSITE data bank, in particular in the file prosite.dat (Release 13.0 of November 1995, located at http://expasy.hcuge.ch/sprot/prosite.html. Prosite_convert and prosite_scan programs (http://ulrec3.unil.ch/ftpserveur/prosite_scan)were used to find signatures on the extended cDNAs.

For each pattern obtained with the prosite_convert program from the prosite.dat file, the accuracy of the detection on a new protein sequence has been tested by evaluating the frequency of irrelevant hits on the population of human secreted proteins included in the data bank SWISSPROT. The ratio between the number of hits on shuffled proteins (with a window size of 20 amino acids) and the number of hits on native (unshuffled) proteins was used as an index. Every pattern for which the ration was greater than 20% (one hit on shuffled proteins for 5 hits on native proteins) was skipped during the search with prosite_scan. The program used to shuffle protein sequences (db_shuffled) and the program used to determine the statistics for each pattern in the protein data banks (prosite_statistics)are available on the ftp site http://ulrec3.unil.ch/ftpserveur/prosite_scan.

Table V lists the sequence identification numbers of the polypeptides of SEQ ID NOs: 85–129 and 155–179, the locations of the amino acid residues of SEQ ID NOs: 85–129 and 155–179 in the full length polypeptide (second column), the locations of the amino acid residues of SEQ ID NOs: 85–129 and 155–179 in the signal peptides (third column), and the locations of the amino acid residues of SEQ ID NOs: 85–129 and 155–179 in the mature polypeptide created by cleaving the signal peptide from the full length polypeptide (fourth column).

The nucleotide sequences of the sequences of SEQ ID NOs: 40–84 and 130–154 and the amino acid sequences encoded by SEQ ID NOs: 40–84 and 130–154 (i.e. amino acid sequences of SEQ ID NOs: 85–129 and 155–179) are provided in the appended sequence listing. In some instances, the sequences are preliminary and may include some incorrect or ambiguous sequences or amino acids. The sequences of SEQ ID NOs: 40–84 and 130–154 can readily be screened for any errors therein and any sequence ambiguities can be resolved by resequencing a fragment containing such errors or ambiguities on both strands. Sequences containing such errors will generally be at least 95%, at least 96%, at least 97%, at least 98%, or at least 99% homologous to the sequences of SEQ ID Nos. 85–129 and 155–179 and such sequences are included in the nucleic acids and polypeptides of the present invention. Nucleic acid fragments for resolving sequencing errors or ambiguities may be obtained from the deposited clones or can be isolated using the techniques described herein. Resolution of any such ambiguities or errors may be facilitated by using primers which hybridize to sequences located close to the ambiguous or erroneous sequences. For example, the primers may hybridize to sequences within 50–75 bases of the ambiguity or error. Upon resolution of an error or ambiguity, the corresponding corrections can be made in the protein sequences encoded by the DNA containing the error or ambiguity. The amino acid sequence of the protein encoded by a particular clone can also be determined by expression of the clone in a suitable host cell, collecting the protein, and determining its sequence.

For each amino acid sequence, Applicants have identified what they have determined to be the reading frame best identifiable with sequence information available at the time of filing. Some of the amino acid sequences may contain "Xaa" designators. These "Xaa" designators indicate either (1) a residue which cannot be identified because of nucleotide sequence ambiguity or (2) a stop codon in the determined sequence where Applicants believe one should not exist (if the sequence were determined more accurately).

Cells containing the extended cDNAs (SEQ ID NOs: 40–84 and 130–154) of the present invention in the vector pED6dpc2, are maintained in permanent deposit by the inventors at Genset, S.A., 24 Rue Royale, 75008 Paris, France.

Pools of cells containing the extended cDNAs (SEQ ID NOs: 40–84), from which cells containig a particular polynucleotide are obtainable, were deposited on Oct. 15, 1998 with the American Type Culture Collection (ATCC), 10801 University Blvd., Manassas, Va., U.S.A, 20110-2209. Each extended cDNA clone has been transfected into separate bacterial cells (E-coli) for this composite deposit. Table VI lists the deposit numbers of the clones of SEQ ID Nos: 40–84 A pool of cells designated SignalTag 28011999, which contains the clones of SEQ ID NOs 71–84 was mailed to the European Collection of Cell Cultures, (ECACC) Vaccine Research and Production Laboratory, Public Health Laboratory Service, Centre for Applied Microbiology and Research, Porton Down, Salisbury, Wiltshire SP4 OJG, United Kingdom on Jan. 28, 1999 and was received on Jan. 29, 1999. This pool of cells has the ECACC Accession # XXXXXX. One or more pools of cells containing the extended cDNAs of SEQ ID Nos: 130–154, from which the cells containing a particular polynicleotide is obtainable, will be deposited with the European Collection of Cell Cultures, Vaccine Research and Production Laboratory, Public Health Laboratory Service, Centre for Applied Microbiology and Research, Porton Down, Salisbury, Wiltshire SP4 OJG, United Kingdom and will be assigned ECACC deposit number XXXXXXX. Table VII provides the internal designation number assigned to each SEQ ID NO. and indicates whether the sequence is a nucleic acid sequence or a protein sequence.

Each extended cDNA can be removed from the pED6dpc2 vector in which it was deposited by performing a NotI, PstIa double digestion to produce the appropriate fragment for each clone. The proteins encoded by the extended cDNAs may also be expressed from the promoter in pED6dpc2.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The design of the oligonucleotide probe should preferably follow these parameters:

(a) It should be designed to an area of the sequence which has the fewest ambiguous bases ("N's"), if any;

(b) Preferably, the probe is designed to have a $T_m$ of approx. 80° C. (assuming 2 degrees for each A or T and 4 degrees for each G or C). However, probes having melting temperatures between 40° C. and 80° C. may also be used provided that specificity is not lost.

The oligonucleotide should preferably be labeled with $\gamma$-[$^{32}$P]ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantified by measurement in a scintillation counter. Preferably, specific activity of the resulting probe should be approximately $4 \times 10^6$ dpm/pmole.

The bacterial culture containing the pool of full-length clones should preferably be thawed and 100 $\mu$l of the stock used to inoculate a sterile culture flask containing 25 ml of sterile L-broth containing ampicillin at 100 ug/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 $\mu$g/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20× stock is 175.3 g Na citrate/liter, 88.2 g Na citrate/liter, adjusted to pH 7.0 with NaOH) containing 0.5% SDS, 100 pg/ml of yeast RNA, and 10 mM EDTA (approximately 10 mL per 150 mm filter). Preferably, the probe is then added to the hybridization mix at a concentration greater than or equal to $1 \times 10^6$ dpm/mL. The filter is then preferably incubated at 65° C. with gentle agitation overnight. The filter is then preferably washed in 500 mL of 2×SSC/0. 1% SDS at room temperature with gentle shaking for 15 minutes. A third wash with 0.1×SSC/ 0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

The plasmid DNA obtained using these procedures may then be manipulated using standard cloning techniques familiar to those skilled in the art. Alternatively, a PCR can be done with primers designed at both ends of the extended cDNA insertion. For example, a PCR reaction may be conducted using a primer having the sequence GGCCATA-CACTTGAGTGAC (SEQ ID NO:38) and a primer having the sequence ATATAGACAAACGCACACC (SEQ. ID NO:39). The PCR product which corresponds to the extended cDNA can then be manipulated using standard cloning techniques familiar to those skilled in the art.

In addition to PCR based methods for obtaining extended cDNAs, traditional hybridization based methods may also be employed. These methods may also be used to obtain the genomic DNAs which encode the mRNAs from which the 5' ESTs were derived, mRNAs corresponding to the extended cDNAs, or nucleic acids which are homologous to extended cDNAs or 5' ESTs. Example 29 below provides an example of such methods.

EXAMPLE 29

Methods for Obtaining Extended cDNAs or
Nucleic Acids Homologous to Extended cDNAs or
5' ESTs 5' ESTs or extended cDNAs of the present invention may also be used to isolate extended cDNAs or nucleic acids homologous to extended cDNAs from a cDNA library or a genomic DNA library. Such cDNA library or genomic DNA library may be obtained from a commercial source or made using other techniques familiar to those skilled in the art. One example of such cDNA library construction is as follows.

PolyA+ RNAs are prepared and their quality checked as described in Example 13. Then, polyA+ RNAs are ligated to an oligonucleotide tag using either the chemical or enzymatic methods described in above sections 1 and 2. In both cases, the oligonucleotide tag may contain a restriction site such as Eco RI to facilitate further subcloning procedures. Northern blotting is then performed to check the size of ligatured mRNAs and to ensure that the mRNAs were actually tagged.

As described in Example 14, first strand synthesis is subsequently carried out for mRNAs joined to the oligonucleotide tag replacing the random nonamers by an oligodT primer. For instance, this oligodT primer may contain an internal tag of 4 nucleotides which is different from one tissue to the other. Alternatively, the oligonucleotide of SEQ ID NO:14 may be used. Following second strand synthesis using a primer contained in the oligonucleotide tag attached to the 5' end of mRNA, the blunt ends of the obtained double stranded full length DNAs are modified into cohesive ends to allow subcloning into the Eco RI and Hind III sites of a Bluescript vector using the addition of a Hind III adaptor to the 3' end of full length DNAs.

The extended full length DNAs are then separated into several fractions according to their sizes using techniques familiar to those skilled in the art. For example, electrophoretic separation may be applied in order to yield 3 or 6 different fractions. Following gel extraction and purification, the DNA fractions are subcloned into Bluescript vectors, transformed into competent bacteria and propagated under appropriate antibiotic conditions.

Such full length cDNA libraries may then be sequenced as follows or used in screening procedures to obtain nucleic acids homologous to extended cDNAs or 5' ESTs as described below.

The 5' end of extended cDNA isolated from the full length cDNA libraries or of nucleic acid homologous thereto may then be sequenced as described in example 27. In a first step, the sequence corresponding to the 5' end of the mRNA is obtained; If this sequence either corresponds to a Signal-Tag™ 5' EST or fulfills the criteria to be one, the cloned insert is subcloned into an appropriate vector such as pED6dpc2, double-sequenced and submitted to the analysis and selection procedures described in Example 27.

Such cDNA or genomic DNA libraries may be used to isolate extended cDNAs obtained from 5' EST or nucleic acids homologous to extended cDNAs or 5' EST as follows. The cDNA library or genomic DNA library is hybridized to a detectable probe comprising at least 10 consecutive nucleotides from the 5' EST or extended cDNA using conventional techniques. Preferably, the probe comprises at least 12, 15, or 17 consecutive nucleotides from the 5' EST or extended cDNA. More preferably, the probe comprises at least 20 to 30 consecutive nucleotides from the 5' EST or extended cDNA. In some embodiments, the probe comprises at least 40, at least 50, at least 75, at least 100, at least 150, or at least 200 consecutive nucleotides from the 5' EST or extended cDNA.

Techniques for identifying cDNA clones in a cDNA library which hybridize to a given probe sequence are disclosed in Sambrook et al, *Molecular Cloning: A Laboratory Manual 2d Ed.*, Cold Spring Harbor Laboratory Press, 1989, the disclosure of which is incorporated herein by reference. The same techniques may be used to isolate genomic DNAs.

Briefly, cDNA or genomic DNA clones which hybridize to the detectable probe are identified and isolated for further manipulation as follows. A probe comprising at least 10 consecutive nucleotides from the 5' EST or extended cDNA is labeled with a detectable label such as a radioisotope or a fluorescent molecule. Preferably, the probe comprises at least 12, 15, or 17 consecutive nucleotides from the 5' EST or extended cDNA. More preferably, the probe comprises 20 to 30 consecutive nucleotides from the 5' EST or extended cDNA. In some embodiments, the probe comprises at least 40, at least 50, at least 75, at least 100, at least 150, or at least 200 consecutive nucleotides from the 5' EST or extended cDNA.

Techniques for labeling the probe are well known and include phosphorylation with polynucleotide kinase, nick translation, in vitro transcription, and non radioactive techniques. The cDNAs or genomic DNAs in the library are transferred to a nitrocellulose or nylon filter and denatured. After blocking of non specific sites, the filter is incubated with the labeled probe for an amount of time sufficient to allow binding of the probe to cDNAs or genomic DNAs containing a sequence capable of hybridizing thereto.

By varying the stringency of the hybridization conditions used to identify extended cDNAs or genomic DNAs which hybridize to the detectable probe, extended cDNAS having different levels of homology to the probe can be identified and isolated as described below.

1. Identification of Extended cDNA or Genomic DNA Sequences Having a High Degree of Homology to the Labeled Probe To identify extended cDNAs or genomic DNAs having a high degree of homology to the probe sequence, the melting temperature of the probe may be calculated using the following formulas:

For probes between 14 and 70 nucleotides in length the melting temperature (Tm) is calculated using the formula: Tm=81.5+16.6(log[Na+])+0.41(fractionG+C)−(600/N) where N is the length of the probe.

If the hybridization is carried out in a solution containing formamide, the melting temperature may be calculated using the equation Tm=81.5+16.6(log [Na+])+0.41(fraction G+C)−(0.63% formamide)−(600/N) where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to extended cDNAs or genomic DNAs containing sequences complementary thereto or homologous thereto.

For probes over 200 nucleotides in length, the hybridization may be carried out at 15–25° C. below the Tm. For shorterprobes, such as oligonucleotide probes, the hybridization may be conducted at 15–25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

Extended cDNAs, nucleic acids homologous to extended cDNAs or 5' ESTs, or genomic DNAs which have hybridized to the probe are identified by autoradiography or other conventional techniques.

2. Obtaining Extended cDNA or Genomic DNA Sequences Having Lower Degrees of Homology to the Labeled Probe The above procedure may be modified to identify extended cDNAs, nucleic acids homologous to extended cDNAs, or genomic DNAs having decreasing levels of homology to the probe sequence. For example, to obtain extended cDNAs, nucleic acids homologous to extended cDNAs, or genomic DNAs of decreasing homology to the detectable probe, less stringent conditions may be used. For example, the hybridization temperature may be decreased in increments of 5° C. from 68° C. to 42° C. in a hybridization buffer having a sodium concentration of approximately 1M. Following hybridization, the filter may be washed with 2×SSC, 0.5% SDS at the temperature of hybridization. These conditions are considered to be "moderate" conditions above 50° C. and "low" conditions 30 below 50° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide.

Extended cDNAs, nucleic acids homologous to extended cDNAs, or genomic DNAs which have hybridized to the probe are identified by autoradiography.

3. Determination of the Degree of Homology between the Obtained Extended cDNAs or Genomic DNAs and the Labeled Probe To determine the level of homology between the hybridized nucleic acid and the extended cDNA or 5' EST from which the probe was derived, the nucleotide sequences of the hybridized nucleic acid and the extended cDNA or 5' EST from which the probe was derived are compared. The sequences of the extended cDNA or 5' EST and the homologous sequences may be stored on a computer readable medium as described in Example 17 above and may be compared using any of a variety of algorithms familiar to those skilled in the art. For example, if it is desired to obtain nucleic acids homologous to extended cDNAs, such as allelic variants thereof or nucleic acids encoding proteins related to the proteins encoded by the extended cDNAs, the level of homology between the hybridized nucleic acid and the extended cDNA or 5' EST used as the probe may be determined using algorithms such as BLAST2N; parameters may be adapted depending on the sequence length and degree of homology studied. For example, the default parameters or the parameters in Table I and II may be used to determine homology levels.

Alternatively, the level of homology between the hybridized nucleic acid and the extended cDNA or 5' EST from which the probe was derived may be determined using the FASTDB algorithm described in Brutlag et al. Comp. App. Biosci. 6:237–245, 1990. In such analyses the parameters may be selected as follows: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the sequence which hybridizes to the probe, whichever is shorter. Because the FASTDB program does not consider 5' or 3' truncations when calculating homology levels, if the sequence which hybridizes to the probe is truncated relative to the sequence of the extended cDNA or 5' EST from which the probe was derived the homology level is manually adjusted by calculating the number of nucleotides of the extended cDNA or 5' EST which are not matched or aligned with the hybridizing sequence, determining the percentage of total nucleotides of the hybridizing sequence which the non-matched or non-aligned nucleotides represent, and subtracting this percentage from the homology level. For example, if the hybridizing sequence is 700 nucleotides in length and the extended cDNA sequence is 1000 nucleotides in length wherein the first 300 bases at the 5' end of the extended cDNA are absent from the hybridizing sequence, and wherein the overlapping 700 nucleotides are identical, the homology level would be adjusted as follows. The non-matched, non-aligned 300 bases represent 30% of the length of the extended cDNA. If the overlapping 700 nucleotides are 100% identical, the adjusted homology level would be 100−30=70% homology. It should be noted that the preceding adjustments are only made when the non-matched or non-aligned nucleotides are at the 5' or 3' ends. No adjustments are made if the non-matched or non-aligned sequences are internal or under any other conditions.

For example, using the above methods, nucleic acids having at least 95% nucleic acid homology, at least 96% nucleic acid homology, at least 97% nuleic acid homology, at least 98% nucleic acid homology, at least 99% nucleic acid homology, or more than 99% nucleic acid homology to the extended cDNA or 5' EST from which the probe was derived may be obtained and identified. Such nucleic acids may be allelic variants or related nucleic acids from other species. Similarly, by using progressively less stringent hybridization conditions one can obtain and identify nucleic acids having at least 90%, at least 85%, at least 80% or at least 75% homology to the extended cDNA or 5' EST from which the probe was derived.

To determine whether a clone encodes a protein having a given amount of homology to the protein encoded by the extended cDNA or 5' EST, the amino acid sequence encoded by the extended cDNA or 5' EST is compared to the amino acid sequence encoded by the hybridizing nucleic acid. The sequences encoded by the extended cDNA or 5' EST and the sequences encoded by the homologous sequences may be stored on a computer readable medium as described in Example 17 above and may be compared using any of a variety of algorithms familiar to those skilled in the art. Homology is determined to exist when an amino acid sequence in the extended cDNA or 5' EST is closely related to an amino acid sequence in the hybridizing nucleic acid. A sequence is closely related when it is identical to that of the extended cDNA or 5' EST or when it contains one or more amino acid substitutions therein in which amino acids having similar characteristics have been substituted for one another. Using the above methods and algorithms such as FASTA with parameters depending on the sequence length and degree of homology studied, for example the default parameters or the parameters in Table I and II, one can obtain nucleic acids encoding proteins having at least 99%, at least 98%, at least 97%, at least 96%, at least 95%, at least 90%, at least 85%, at least 80% or at least 75% homology to the proteins encoded by the extended cDNA or 5' EST from which the probe was derived. In some embodiments, the homology levels can be determined using the "default" opening penalty and the "default" gap penalty, and a scoring matrix such as PAM 250 (a standard scoring matrix; see Dayhoff et al., in: Atlas of Protein Sequence and Structure, Vol. 5, Supp. 3 (1978)).

Alternatively, the level of homology may be determined using the FASTDB algorithm described by Brutlag et al. Comp. App. Biosci. 6:237–245, 1990. In such analyses the parameters may be selected as follows: Matrix=PAM 0, k-tuple=2, Mismatch Penalty=1, Joining Penalty=20, Randomization Group Length=0, Cutoff Score=1, Window Size=Sequence Length, Gap Penalty=5, Gap Size Penalty= 0.05, Window Size=500 or the length of the homologous sequence, whichever is shorter. If the homologous amino acid sequence is shorter than the amino acid sequence encoded by the extended cDNA or 5' EST as a result of an N terminal and/or C terminal deletion the results may be manually corrected as follows. First, the number of amino acid residues of the amino acid sequence encoded by the extended cDNA or 5' EST which are not matched or aligned with the homologous sequence is determined. Then, the percentage of the length of the sequence encoded by the extended cDNA or 5' EST which the non-matched or non-aligned amino acids represent is calculated. This percentage is subtracted from the homology level. For example wherein the amino acid sequence encoded by the extended cDNA or 5' EST is 100 amino acids in length and the length of the homologous sequence is 80 amino acids and wherein the amino acid sequence encoded by the extended cDNA or 5' EST is truncated at the N terminal end with respect to the homologous sequence, the homology level is calculated as follows. In the preceding scenario there are 20 non-matched, non-aligned amino acids in the sequence encoded by the extended cDNA or 5' EST. This represents 20% of the length of the amino acid sequence encoded by the extended cDNA or 5' EST. If the remaining amino acids are 1005 identical between the two sequences, the homology level would be 100%–20%=80% homology. No adjustments are made if the non-matched or non-aligned sequences are internal or under any other conditions.

In addition to the above described methods, other protocols are available to obtain extended cDNAs using 5' ESTs as outlined in the following paragraphs.

Extended cDNAs may be prepared by obtaining mRNA from the tissue, cell, or organism of interest using mRNA preparation procedures utilizing polyA selection procedures or other techniques known to those skilled in the art. A first primer capable of hybridizing to the polyA tail of the mRNA is hybridized to the mRNA and a reverse transcription reaction is performed to generate a first cDNA strand.

The first cDNA strand is hybridized to a second primer containing at least 10 consecutive nucleotides of the sequences of the 5' EST for which an extended cDNA is desired. Preferably, the primer comprises at least 12, 15, or 17 consecutive nucleotides from the sequences of the 5' EST. More preferably, the primer comprises 20 to 30 consecutive nucleotides from the sequences of the 5' EST. In some embodiments, the primer comprises more than 30 nucleotides from the sequences of the 5' EST. If it is desired to obtain extended cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RT-PCR may be performed as described above using primers from both ends of the cDNA to be obtained.

Extended cDNAs containing 5' fragments of the mRNA may be prepared by hybridizing an mRNA comprising the sequence of the 5' EST for which an extended cDNA is desired with a primer comprising at least 10 consecutive nucleotides of the sequences complementary to the 5' EST and reverse transcribing the hybridized primer to make a first cDNA strand from the mRNAs. Preferably, the primer comprises at least 12, 15, or 17 consecutive nucleotides from the 5' EST. More preferably, the primer comprises 20 to 30 consecutive nucleotides from the 5' EST.

Thereafter, a second cDNA strand complementary to the first cDNA strand is synthesized. The second cDNA strand may be made by hybridizing a primer complementary to sequences in the first cDNA strand to the first cDNA strand and extending the primer to generate the second cDNA strand.

The double stranded extended cDNAs made using the methods described above are isolated and cloned. The extended cDNAs may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in *Current Protocols in Molecular Biology*, John Wiley 503 Sons, Inc. 1997 and Sambrook et al., Molecular Cloning: A Laboratory Manual, Second Edition, Cold Spring Harbor Laboratory Press, 1989, the entire disclosures of which are incorporated herein by reference.

Alternatively, other procedures may be used for obtaining full length cDNAs or extended cDNAs. In one approach, full length or extended cDNAs are prepared from mRNA and cloned into double stranded phagemids as follows. The cDNA library in the double stranded phagemids is then rendered single stranded by treatment with an endonuclease, such as the Gene II product of the phage F 1, and an exonuclease (Chang et al, *Gene* 127:95–8,1993). A biotinylated oligonucleotide comprising the sequence of a 5' EST, or a fragment containing at least 10 nucleotides thereof, is hybridized to the single stranded phagemids. Preferably, the fragment comprises at least 12, 15, or 17 consecutive nucleotides from the 5' EST. More preferably, the fragment comprises 20–30 consecutive nucleotides from the 5' EST. In some procedures, the fragment may comprise at least 40, at least 50, at least 75, at least 100, at least 150, or at least 200 consuctive nucleotides from the 5' EST.

Hybrids between the biotinylated oligonucleotide and phagemids having inserts containing the 5' EST sequence are isolated by incubating the hybrids with streptavidin coated paramagnetic beads and retrieving the beads with a magnet (Fry et al., *Biotechniques,* 13: 124–131, 1992). Therafter, the resulting phagemids containing the 5' EST sequence are released from the beads and converted into double stranded DNA using a primer specific for the 5' EST sequence. Alternatively, protocols such as the Gene Trapper kit (Gibco BRL) may be used. The resulting double stranded DNA is transformed into bacteria. Extended cDNAs containing the 5' EST sequence are identified by colony PCR or colony hybridization.

Using any of the above described methods in section III, a plurality of extended cDNAs containing full length protein coding sequences or sequences encoding only the mature protein remaining after the signal peptide is cleaved off may be provided as cDNA libraries for subsequent evaluation of the encoded proteins or use in diagnostic assays as described below.

IV. Expression of Proteins Encoded by Extended cDNAs Isolated Using 5' ESTs

Extended cDNAs containing the full protein coding sequences of their corresponding mRNAs or portions thereof, such as cDNAs encoding the mature protein, may be used to express the secreted proteins or portions thereof which they encode as described in Example 30 below. If desired, the extended cDNAs may contain the sequences encoding the signal peptide to facilitate secretion of the expressed protein. It will be appreciated that a plurality of extended cDNAs containing the full protein coding sequences or portions thereof may be simultaneously cloned into expression vectors to create an expression library for analysis of the encoded proteins as described below.

EXAMPLE 30

Expression of the Proteins Encoded by Extended cDNAs or Portions Thereof

To express the proteins encoded by the extended cDNAs or portions thereof, nucleic acids containing the coding sequence for the proteins or portions thereof to be expressed are obtained as described in Examples 27–29 and cloned into a suitable expression vector. If desired, the nucleic acids may contain the sequences encoding the signal peptide to facilitate secretion of the expressed protein. For example, the nucleic acid may comprise the sequence of one of SEQ ID NOs: 40–84 and 130–154 listed in Table IV and in the accompanying sequence listing. Alternatively, the nucleic acid may comprise those nucleotides which make up the full coding sequence of one of the sequences of SEQ ID NOs: 40–84 and 130–154 as defined in Table IV above.

It will be appreciated that should the extent of the full coding sequence (i.e. the sequence encoding the signal peptide and the mature protein resulting from cleavage of the signal peptide) differ from that listed in Table IV as a result of a sequencing error, reverse transcription or amplification error, mRNA splicing, post-translational modification of the encoded protein, enzymatic cleavage of the encoded protein, or other biological factors, one skilled in the art would be readily able to identify the extent of the full coding sequences in the sequences of SEQ ID NOs. 40–84 and 130–154. Accordingly, the scope of any claims herein relating to nucleic acids containing the full coding sequence of one of SEQ ID NOs. 40–84 and 130–154 is not to be construed as excluding any readily identifiable variations from or equivalents to the full coding sequences listed in Table IV Similarly, should the extent of the full length polypeptides differ from those indicated in Table V as a result of any of the preceding factors, the scope of claims relating to polypeptides comprising the amino acid sequence of the full length polypeptides is not to be construed as excluding any readily identifiable variations from or equivalents to the sequences listed in Table V.

Alternatively, the nucleic acid used to express the protein or portion thereof may comprise those nucleotides which encode the mature protein (i.e. the protein created by cleaving the signal peptide off) encoded by one of the sequences of SEQ ID NOs: 40–84 and 130–154 as defined in Table IV above.

It will be appreciated that should the extent of the sequence encoding the mature protein differ from that listed in Table IV as a result of a sequencing error, reverse transcription or amplification error, mRNA splicing, post-translational modification of the encoded protein, enzymatic cleavage of the encoded protein, or other biological factors, one skilled in the art would be readily able to identify the extent of the sequence encoding the mature protein in the sequences of SEQ ID NOs. 40–84 and 130–154. Accordingly, the scope of any claims herein relating to nucleic acids containing the sequence encoding the mature protein encoded by one of SEQ ID Nos. 40–84 and 130–154 is not to be construed as excluding any readily identifiable variations from or equivalents to the sequences listed in Table IV. Thus, claims relating to nucleic acids containing the sequence encoding the mature protein encompass equivalents to the sequences listed in Table IV, such as sequences encoding biologically active proteins resulting from post-translational modification, enzymatic cleavage, or other readily identifiable variations from or equivalents to the secreted proteins in addition to cleavage of the signal peptide. Similarly, should the extent of the mature polypeptides differ from those indicated in Table V as a result of any of the preceding factors, the scope of claims relating to polypeptides comprising the sequence of a mature protein included in the sequence of one of SEQ ID NOs. 85–129 and 155–179 is not to be construed as excluding any readily identifiable variations from or equivalents to the sequences listed in Table V. Thus, claims relating to polypeptides comprising the sequence of the mature protein encompass equivalents to the sequences listed in Table IV, such as biologically active proteins resulting from post-translational modification, enzymatic cleavage, or other readily identifiable variations from or equivalents to the secreted proteins in addition to cleavage of the signal peptide. It will also be appreciated that should the biologically active form of the polypeptides included in the sequence of one of SEQ ID NOs. 85–129 and 155–179 or the nucleic acids encoding the biologically active form of the polypeptides differ from those identified as the mature polypeptide in Table V or the nucleotides encoding the mature polypeptide in Table IV as a result of a sequencing error, reverse transcription or amplification error, mRNA splicing, post-translational modification of the encoded protein, enzymatic cleavage of the encoded protein, or other biological factors, one skilled in the art would be readily able to identify the amino acids in the biologically active form of the polypeptides and the nucleic acids encoding the biologically active form of the polypeptides. In such instances, the claims relating to polypetides comprising the mature protein included in one of SEQ ID NOs. 85–129 and 155–179 or nucleic acids comprising the nucleotides of one of SEQ ID NOs. 40–84 and 130–154 encoding the mature protein shall not be construed to exclude any readily identifiable variations from the sequences listed in Table IV and Table V.

In some embodiments, the nucleic acid used to express the protein or portion thereof may comprise those nucleotides which encode the signal peptide encoded by one of the sequences of SEQ ID NOs: 40–84 and 130–154 as defined in Table IV above.

It will be appreciated that should the extent of the sequence encoding the signal peptide differ from that listed in Table IV as a result of a sequencing error, reverse transcription or amplification error, mRNA splicing, post-translationalmodification of the encoded protein, enzymatic cleavage of the encoded protein, or other biological factors, one skilled in the art would be readily able to identify the extent of the sequence encoding the signal peptide in the sequences of SEQ ID NOs. 40–84 and 130–154. Accordingly, the scope of any claims herein relating to nucleic acids containing the sequence encoding the signal peptide encoded by one of SEQ ID Nos. 40–84 and 130–154 is not to be construed as excluding any readily identifiable variations from the sequences listed in Table IV. Similarly, should the extent of the signal peptides differ from those indicated in Table V as a result of any of the preceding factors, the scope of claims relating to polypeptides comprising the sequence of a signal peptide included in the sequence of one of SEQ ID NOs. 85–129 and 155–179 is not to be construed as excluding any readily identifiable variations from the sequences listed in Table V.

Alternatively, the nucleic acid may encode a polypeptide comprising at least 10 consecutive amino acids of one of the sequences of SEQ ID NOs: 85–129 and 155–179. In some embodiments, the nucleic acid may encode a polypeptide comprising at least 15 consecutive amino acids of one of the sequences of SEQ ID NOs: 85–129 and 155–179. In other embodiments, the nucleic acid may encode a polypeptide comprising at least 25 consecutiveamino acids of one of the sequences of SEQ ID NOs: 85–129 and 155–179. In other embodiments, the nucleic acid may encode a polypeptide comprising at least 60, at least 75, at least 100 or more than 100 consecutive amino acids of one of the sequences of SEQ ID Nos: 85–129 and 155–179.

The nucleic acids inserted into the expression vectors may also contain sequences upstream of the sequences encoding the signal peptide, such as sequences which regulate expression levels or sequences which confer tissue specific expression.

The nucleic acid encoding the protein or polypeptide to be expressed is operably linked to a promoter in an expression vector using conventional cloning technology. The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767, incorporated herein by this reference.

The following is provided as one exemplary method to express the proteins encoded by the extended cDNAs corresponding to the 5' ESTs or the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the extended cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The extended cDNA or portion thereof encoding the polypeptide to be expressed is obtained by PCR from the bacterial vector using oligonucleotide primers complementary to the extended cDNA or portion thereof and containing restriction endonuclease sequences for Pst I incorporated into the 5' primer and BglII at the 5' end of the corresponding cDNA 3' primer, taking care to ensure that the extended cDNA is positioned in frame with the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Alternatively, the extended cDNAs may be cloned into pED6dpc2 as described above. The resulting pED6dpc2 constructs may be transfected into a suitable host cell, such as COS 1 cells. Methotrexate resistant cells are selected and expanded. Preferably, the protein expressed from the extended cDNA is released into the culture medium thereby facilitating purification.

Proteins in the culture medium are separated by gel electrophoresis. If desired, the proteins may be ammonium sulfate precipitated or separated based on size or charge prior to electrophoresis.

As a control, the expression vector lacking a cDNA insert is introduced into host cells or organisms and the proteins in the medium are harvested. The secreted proteins present in the medium are detected using techniques such as Coomassie or silver staining or using antibodies against the protein encoded by the extended cDNA. Coomassie and silver staining techniques are familiar to those skilled in the art.

Antibodies capable of specifically recognizing the protein of interest may be generated using synthetic 15-mer peptides having a sequence encoded by the appropriate 5' EST, extended cDNA, or portion thereof. The synthetic peptides are injected into mice to generate antibody to the polypeptide encoded by the 5' EST, extended cDNA, or portion thereof.

Secreted proteins from the host cells or organisms containing an expression vector which contains the extended cDNA derived from a 5' EST or a portion thereof are compared to those from the control cells or organism. The presence of a band in the medium from the cells containing the expression vector which is absent in the medium from the control cells indicates that the extended cDNA encodes a secreted protein. Generally, the band corresponding to the protein encoded by the extended cDNA will have a mobility near that expected based on the number of amino acids in the open reading frame of the extended cDNA. However, the band may have a mobility different than that expected as a result of modifications such as glycosylation, ubiquitination, or enzymatic cleavage.

Alternatively, if the protein expressed from the above expression vectors does not contain sequences directing its secretion, the proteins expressed from host cells containing an expression vector containing an insert encoding a secreted protein or portion thereof can be compared to the proteins expressed in host cells containing the expression vector without an insert. The presence of a band in samples from cells containing the expression vector with an insert which is absent in samples from cells containing the expression vector without an insert indicates that the desired protein or portion thereof is being expressed. Generally, the band will have the mobility expected for the secreted protein or portion thereof. However, the band may have a mobility different than that expected as a result of modifications such as glycosylation, ubiquitination, or enzymatic cleavage.

The protein encoded by the extended cDNA may be purified using standard immunochromatography techniques. In such procedures, a solution containing the secreted protein, such as the culture medium or a cell extract, is applied to a column having antibodies against the secreted protein attached to the chromatography matrix. The secreted protein is allowed to bind the immunochromatography column. Thereafter, the column is washed to remove non-specifically bound proteins. The specifically bound secreted protein is then released from the column and recovered using standard techniques.

If antibody production is not possible, the extended cDNA sequence or portion thereof may be incorporated into expression vectors designed for use in purification schemes employing chimeric polypeptides. In such strategies the coding sequence of the extended cDNA or portion thereof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites may be engineered between the β-globin gene or the nickel binding polypeptide and the extended cDNA or portion thereof. Thus, the two polypeptides of the chimera may be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

Following expression and purification of the secreted proteins encoded by the 5' ESTs, extended cDNAs, or fragments thereof, the purified proteins may be tested for the ability to bind to the surface of various cell types as described in Example 31 below. It will be appreciated that a plurality of proteins expressed from these cDNAs may be included in a panel of proteins to be simultaneously evaluated for the activities specifically described below, as well as other biological roles for which assays for determining activity are available.

EXAMPLE 31

Analysis of Secreted Proteins to Determine Whether they Bind to the Cell Surface The proteins encoded by the 5' ESTs, extended cDNAs, or fragments thereof are cloned into expression vectors such as those described in Example 30. The proteins are purified by size, charge, immunochromatography or other techniques familiar to those skilled in the art. Following purification, the proteins are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected by autoradiography. Alternatively, unlabeled proteins may be incubated with the cells and detected with antibodies having a detectable label, such as a fluorescent molecule, attached thereto.

Specificity of cell surface binding may be analyzed by conducting a competition analysis in which various amounts of unlabeled protein are incubated along with the labeled protein. The amount of labeled protein bound to the cell surface decreases as the amount of competitive unlabeled protein increases. As a control, various amounts of an unlabeled protein unrelated to the labeled protein is included in some binding reactions. The amount of labeled protein bound to the cell surface does not decrease in binding reactions containing increasing amounts of unrelated unlabeled protein, indicating that the protein encoded by the cDNA binds specifically to the cell surface.

As discussed above, secreted proteins have been shown to have a number of important physiological effects and, consequently, represent a valuable therapeutic resource. The secreted proteins encoded by the extended cDNAs or portions thereof made according to Examples 27–29 may be evaluated to determine their physiological activities as described below.

EXAMPLE 32

Assaying the Proteins Expressed from Extended cDNAs or Portions Thereof for Cytokine Cell Proliferationor Cell Differentiation Activity As discussed above, secreted proteins may act as cytokines or may affect cellular proliferation or differentiation. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7c and CMK. The proteins encoded by the above extended cDNAs or portions thereof may be evaluated for their ability to regulate T cell or thymocyte proliferation in assays such as those described above or in the following references, which are incorporated herein by reference: Current Protocols in Immunology, Ed. by J. E. Coligan et al., Greene Publishing Associates and Wiley-Interscience; Takai et al. J. Immunol. 137:3494–3500, 1986. Bertagnolli et al. J. Immunol. 145:1706–1712, 1990. Bertagnolli et al., Cellular Immunology 133:327–341,1991. Bertagnolli,et al. J. Immunol. 149:3778–3783,1992; Bowman et al., J. Immunol. 152:1756–1761,1994.

In addition, numerous assays for cytokine production and/or the proliferation of spleen cells, lymph node cells and thymocytes are known. These include the techniques disclosed in Current Protocols in Immunology. J. E. Coligan et al. Eds., Vol 1 pp. 3.12.1–3.12.14 John Wiley and Sons, Toronto. 1994; and Schreiber, R. D. Current Protocols in Immunology., supra Vol 1 pp. 6.8.1–6.8.8, John Wiley and Sons, Toronto. 1994.

The proteins encoded by the cDNAs may also be assayed for the ability to regulate the proliferation and differentiation of hematopoietic or lymphopoietic cells. Many assays for such activity are familiar to those skilled in the art, including the assays in the following references, which are incorporated herein by reference: Bottomly, K., Davis, L. S. and Lipsky, P. E., Measurement of Human and Murine Interleukin 2 and Interleukin 4, Current Protocols in Immunology., J. E. Coligan et al. Eds. Vol 1 pp. 6.3.1–6.3.12, John Wiley and Sons, Toronto. 1991; deVries et al., J. Exp. Med. 173:1205–1211,1991; Moreau et al., Nature 36:690–692, 1988; Greenberger et al., Proc. Natl. Acad. Sci. U.S.A. 80:2931–2938,1983; Nordan, R., Measurement of Mouse and Human Interleukin 6 Current Protocols in Immunology. J. E. Coligan et al. Eds. Vol 1 pp. 6.6.1–6.6.5, John Wiley and Sons, Toronto. 1991; Smith et al., Proc. Natl. Acad. Sci. U.S.A. 83:1857–1861, 1986; Bennett, F., Giannotti, J., Clark, S. C. and Turner, K. J., Measurement of Human Interleukin 11 Current Protocols in Immunology. J. E. Coligan et al. Eds. Vol 1 pp. 6.15.1 John Wiley and Sons, Toronto. 1991; Ciarletta, A., Giannotti, J., Clark, S. C. and Turner, K. J., Measurement of Mouse and Human Interleukin 9 Current Protocols in Immunology. J. E. Coligan et al., Eds. Vol 1 pp. 6.13.1, John Wiley and Sons, Toronto. 1991.

The proteins encoded by the cDNAs may also be assayed for their ability to regulate T-cell responses to antigens. Many assays for such activity are familiar to those skilled in the art, including the assays described in the following references, which are incorporated herein by reference: Chapter 3 (In Vitro Assays for Mouse Lymphocyte Function), Chapter 6 (Cytokines and Their Cellular Receptors) and Chapter 7, (Immunologic Studies in Humans) in Current Protocols in Immunology, J. E. Coligan et al. Eds. Greene Publishing Associates and Wiley-Interscience; Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512,1988.

Those proteins which exhibit cytokine, cell proliferation, or cell differentiation activity may then be formulated as pharmaceuticals and used to treat clinical conditions in which induction of cell proliferation or differentiation is beneficial. Alternatively, as described in more detail below, genes encoding these proteins or nucleic acids regulating the expression of these proteins may be introduced into appropriate host cells to increase or decrease the expression of the proteins as desired.

EXAMPLE 33

Assaying the Proteins Expressed from Extended cDNAs or Portions Thereof for Activity as Immune System Regulators The proteins encoded by the cDNAs may also be evaluated for their effects as immune regulators. For example, the proteins may be evaluated for their activity to influence thymocyte or splenocyte cytotoxicity. Numerous assays for such activity are familiar to those skilled in the art including the assays described in the following references, which are incorporated herein by reference: Chapter 3 (In Vitro Assays for Mouse Lymphocyte Function 3.1–3.19) and Chapter 7 (Immunologic studies in Humans) in Current Protocols in Immunology, J. E. Coligan et al. Eds, Greene Publishing Associates and Wiley-Interscience;Herrmann et al., Proc. Natl. Acad. Sci. USA 78:2488–2492, 1981; Herrmann et al., J. Immunol. 128:1968–1974, 1982; Handa et al., J. Immunol. 135:1564–1572,1985; Takai et al., J. Immunol. 137:3494–3500,1986; Takai et al., J. Immunol. 140:508–512, 1988; Herrmann et al., Proc. Natl. Acad. Sci. USA 78:2488–2492,1981; Herrmann et al., J. Immunol. 128:1968–1974,1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512,1988; Bertagnolli et al., Cellular Immunology 133:327–341, 1991; Brown et al., J. Immunol. 153:3079–3092,1994.

The proteins encoded by the cDNAs may also be evaluated for their effects on T-cell dependent immunoglobulin responses and isotype switching. Numerous assays for such activity are familiar to those skilled in the art, including the assays disclosed in the following references, which are incorporated herein by reference: Maliszewski, J. Immunol. 144:3028–3033, 1990; Mond, J. J. and Brunswick, M Assays for B Cell Function: In vitro Antibody Production, Vol 1 pp. 3.8.1–3.8.16 in Current Protocols in Immunology. J. E. Coligan et al Eds., John Wiley and Sons, Toronto. 1994.

The proteins encoded by the cDNAs may also be evaluated for their effect on immune effector cells, including their effect on Thl cells and cytotoxic lymphocytes. Numerous assays for such activity are familiar to those skilled in the art, including the assays disclosed in the following references, which are incorporated herein by reference: Chapter 3 (In Vitro Assays for Mouse Lymphocyte Function 3.1–3.19) and Chapter 7 (Immunologic Studies in Humans) in Current Protocols in Immunology, J. E. Coligan et al. Eds., Greene Publishing Associates and Wiley-Interscience; Takai et al., J. Immunol. 137:3494–3500,1986; Takai et al.; J. Immunol. 140:508–512,1988; Bertagnolliet al., J. Immunol. 149:3778–3783,1992.

The proteins encoded by the cDNAs may also be evaluated for their effect on dendritic cell mediated activation of naive T-cells. Numerous assays for such activity are familiar to those skilled in the art, including the assays disclosed in the following references, which are incorporated herein by reference: Guery et al., J. Immunol. 134:536–544,1995; Inaba et al., Journal of Experimental Medicine 173:549–559,1991; Macatonia et al., Journal of Immunology 154:5071–5079,1995; Porgador et al., Journal of Experimental Medicine 182:255–260,1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640,1990.

The proteins encoded by the cDNAs may also be evaluated for their influence on the lifetime of lymphocytes. Numerous assays for such activity are familiar to those skilled in the art, including the assays disclosed in the following references, which are incorporated herein by reference: Darzynkiewicz et al., Cytometry 13:795–808, 1992; Gorczycaet al., Leukemia 7:659–670, 1993; Gorczycaet al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648,1992.

Assays for proteins that influence early steps of T-cell commitment and development include, without limitation, those described in: Antica et al., Blood 84:111–117, 1994; Fine et al., Cellular immunology 155:111–122, 1994; Galy et al., Blood 85:2770–2778,1995; Toki et al., Proc. Nat. Acad Sci. USA 88:7548–7551,1991.

Those proteins which exhibit activity as immune system regulators activity may then be formulated as pharmaceuticals and used to treat clinical conditions in which regulation of immune activity is beneficial. For example, the protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses, in a number of ways. Down regulation may be in the form of inhibiting or blocking an immune response already in progress or may involve preventing the induction of an immune response. The functions of activated T-cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVfID can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/pr/pr mice or NZB hybrid mice, murine autoimmuno collagen arthritis, diabetes mellitus in OD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory form of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. The infected cells would now be capable of delivering a costimulatory signal to T cells in vivo, thereby activating the T cells.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1 -like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acids encoding all or a portion of (e.g., a cytoplasmic-domain truncated portion) of an MHC class I $\alpha$ chain protein and $\beta_2$ macroglobulin protein or an MHC class II $\alpha$ chain protein and an MHC class II $\beta$ chain protein to thereby express MHC class I or MHC class II proteins on the cell surface. Expression of the appropriate class II or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain,can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject. Alternatively, as described in more detail below, genes encoding these proteins or nucleic acids regulating the expression of these proteins may be introduced into appropriate host cells to increase or decrease the expression of the proteins as desired.

EXAMPLE 34

Assaying the Proteins Expressed from Extended cDNAs or Portions Thereof for Hematopoiesis Regulating Activity The proteins encoded by the extended cDNAs or portions thereof may also be evaluated for their hematopoiesis regulating activity. For example, the effect of the proteins on embryonic stem cell differentiation may be evaluated. Numerous assays for such activity are familiar to those skilled in the art, including the assays disclosed in the following references, which are incorporated herein by reference: Johansson et al. Cellular Biology 15:141–151, 1995; Keller et al., Molecular and Cellular Biology 13:473–486,1993; McClanahan et al., Blood 81:2903–2915, 1993.

The proteins encoded by the extended cDNAs or portions thereof may also be evaluated for their influence on the lifetime of stem cells and stem cell differentiation. Numerous assays for such activity are familiar to those skilled in the art, including the assays disclosed in the following references, which are incorporated herein by reference: Freshney, M. G. Methylcellulose Colony Forming Assays, in Culture of Hematopoietic Cells. R. I. Freshney, et al. Eds. pp. 265–268, Wiley-Liss, Inc., New York, N.Y. 1994; Hirayama et al., Proc. Natl. Acad. Sci. USA 89:5907–5911, 1992; McNiece, I. K. and Briddell, R. A. Primitive Hematopoietic Colony Forming Cells with High Proliferative Potential, in Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Ploemacher, R. E. Cobblestone Area Forming Cell Assay, In Culture of Hematopoietic Cells. R. I. Freshney, et al. Eds. pp. 1–21, Wiley-Liss, Inc., New York, N.Y. 1994; Spooncer, E., Dexter, M. and Allen, T. Long Term Bone Marrow Cultures in the Presence of Stromal Cells, in Culture of Hematopoietic Cells. R. I. Freshney, et al. Eds. pp. 163–179, Wiley-Liss, Inc., New York, NY. 1994; and Sutherland, H. J. Long Term Culture Initiating Cell Assay, in Culture of Hematopoietic Cells. R. I. Freshney, et al. Eds. pp. 139–162, Wiley-Liss, Inc., New York, N.Y. 1994.

Those proteins which exhibit hematopoiesis regulatory activity may then be formulated as pharmaceuticals and used to treat clinical conditions in which regulation of hematopoeisis is beneficial. For example, a protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapyto stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantion, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy. Alternatively, as described in more detail below, genes encoding these proteins or nucleic acids regulating the expression of these proteins may be introduced into appropriate host cells to increase or decrease the expression of the proteins as desired.

EXAMPLE 35

Assaying the Proteins Expressed from Extended cDNAs or Portions Thereof for Regulation of Tissue Growth The proteins encoded by the extended cDNAs or portions thereof may also be evaluated for their effect on tissue growth. Numerous assays for such activity are familiar to those skilled in the art, including the assays disclosed in International Patent Publication No. WO95/16035, International Patent Publication No. WO95/05846 and International Patent Publication No. WO91/07491, which are incorporated herein by reference.

Assays for wound healing activity include, without limitation, those described in: Winter, *Epidermal Wound Healing*, pps. 71–112 (Maibach, H1 and Rovee, DT, eds.), Year Book Medical Publishers, Inc., Chicago, as modified by Eaglstein and Mertz, J. Invest. Dermatol 71 :382–84 (1978) which are incorporated herein by reference.

Those proteins which are involved in the regulation of tissue growth may then be formulated as pharmaceuticals and used to treat clinical conditions in which regulation of tissue growth is beneficial. For example, a protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis. such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligamentcells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e., for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds. including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium) muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to generate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokinc damage.

A protein of the present invention may also be useful for promoting or inhibiting differentiation of tissues described above from precursor tissues or cells; or for inhibiting the growth of tissues described above.

Alternatively, as described in more detail below, genes encoding these proteins or nucleic acids regulating the expression of these proteins may be introduced into appropriate host cells to increase or decrease the expression of the proteins as desired.

EXAMPLE 36

Assaying the Proteins Expressed from Extended cDNAs or Portions Thereof for Regulation of Reproductive Hormones or Cell Movement The proteins encoded by the extended cDNAs or portions thereof may also be evaluated for their ability to regulate reproductive hormones, such as follicle stimulating hormone. Numerous assays for such activity are familiar to those skilled in the art, including the assays disclosed in the following references, which are incorporated herein by reference: Vale et al., Endocrinology 91:562–572,1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986. Chapter 6.12 (Measurement of Alpha and Beta Chemokines) Current Protocols in Immunology, J. E. Coligan et al. Eds. Greene Publishing Associates and Wiley-Intersciece; Taub et al. J. Clin. Invest. 95:1370–1376, 1995; Lind et al. APMIS 103:140–146, 1995; Muller et al. Eur. J. Immunol. 25:1744–1748; Gruber et al. J. of Immunol. 152:5860–5867, 1994; Johnston et al. J. of Immunol. 153: 1762–1768,1994.

Those proteins which exhibit activity as reproductive hormones or regulators of cell movement may then be formulated as pharmaceuticals and used to treat clinical conditions in which regulation of reproductive hormones or cell movement are beneficial. For example, a protein of the present invention may also exhibit activin- or inhibin-related activities. Inhibins are characterized by their ability to inhibit the release of follicle stimulating hormone (FSH), while activins are characterized by their ability to stimulate the release of folic stimulating hormone (FSH). Thus, a protein of the present invention, alone or in heterodimers with a member of the inhibin (x family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-B group, may be useful as a fertility inducing therapeutic, based upon the ability of activin molecules in stimulating FSH release from cells of the anterior pituitary. See, for example, U.S. Pat. No. 4,798,885, the disclosure of which is incorporated herein by reference. A protein of the invention may also be useful for advancement of the onset of fertility in sexually immature mammals, so as to increase the lifetime reproductive performance of domestic animals such as cows, sheep and pigs.

Alternatively, as described in more detail below, genes encoding these proteins or nucleic acids regulating the expression of these proteins may be introduced into appropriate host cells to increase or decrease the expression of the proteins as desired.

EXAMPLE 36A

Assaying the Proteins Expressed from Extended cDNAs or Portions Thereof for Chemotactic/ Chemokinetic Activity The proteins encoded by the extended cDNAs or portions thereof may also be evaluated for chemotactic/chemokinetic activity. For example, a protein of the present invention may have chemotactic or chemokinetic activity (e.g., act as a chemokine) for mammalian cells, including, for example, monocytes, fibroblasts, neutrophils, T-cells, mast cells, cosinophils, epithelial and/or endothelial cells. Chemotactic and chmokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhension of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokincs 6.12.1–6.12.28; Taub et al. J. Clin. Invest. 95:1370–1376, 1995; Lind et al. APMIS 103:140–146, 1995; Mueller et al Eur. J. Immunol. 25:1744–1748; Gruber et al. J. of Immunol. 152:5860–5867,1994; Johnston et al. J. of Immunol, 153:1762–1768,1994.

EXAMPLE 37

Assaying the Proteins Expressed from Extended cDNAs or Portions Thereof for Regulation of Blood Clotting The proteins encoded by the extended cDNAs or portions thereof may also be evaluated for their effects on blood clotting. Numerous assays for such activity are familiar to those skilled in the art, including the assays disclosed in the following references, which are incorporated herein by reference: Linet et al., J. Clin. Pharmacol. 26:131–140, 1986; Burdick et al., Thrombosis Res. 45:413–419, 1987; Humphrey et al., Fibrinolysis 5:71–79(1991); Schaub, Prostaglandins 35:467–474,1988.

Those proteins which are involved in the regulation of blood clotting may then be formulated as pharmaceuticals and used to treat clinical conditions in which regulation of blood clotting is beneficial. For example, a protein of the invention may also exhibit hemostatic or thrombolytic activity. As a result, such a protein is expected to be useful in treatment of various coagulations disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as,for example, infarction of cardiac and central nervous system vessels (e.g., stroke). Alternatively, as described in more detail below, genes encoding these proteins or nucleic acids regulating the expression of these proteins may be introduced into appropriate host cells to increase or decrease the expression of the proteins as desired.

EXAMPLE 38

Assaying the Proteins Expressed from Extended cDNAs or Portions Thereof for Involvement in Receptor/Ligand Interactions The proteins encoded by the extended cDNAs or a portion thereof may also be evaluated for their involvement in receptor/ligand interactions. Numerous assays for such involvement are familiar to those skilled in the art, including the assays disclosed in the following references, which are incorporated herein by reference: Chapter 7.28 (Measurement of Cellular Adhesion under Static Conditions 7.28.1–7.28.22) in Current Protocols in Immunology, J. E. Coligan et al. Eds. Greene Publishing Associates and Wiley-Interscience;Takai et al., Proc. Natl. Acad. Sci. USA 84:6864–6868,1987; Bierer et al., J. Exp. Med. 168:1145–1156,1988; Rosenstein et al., J. Exp. Med. 169:149–160, 1989; Stoltenborg et al., J. Immunol. Methods 175:59–68,1994; Stitt et al., Cell 80:661–670, 1995; Gyuris et al., *Cell* 75:791–803,1993.

For example, the proteins of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune respones). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

EXAMPLE 38A

Assaying the Proteins Expressed from Extended cDNAs or Portions Thereof for Anti-Inflammatory Activity The proteins encoded by the extended cDNAs or a portion thereof may also be evaluated for anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusioninury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

EXAMPLE 38B

Assaying the Proteins Expressed from Extended cDNAs or Portions Thereof for Tumor Inhibition Activity The proteins encoded by the extended cDNAs or a portion thereof may also be evaluated for tumor inhibition activity.

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogencsis), by causing production of other factors, agents or cell types which inhibit tumor growth, or by suppressing, climinating or inhibiting factors, agents or cell types which promote tumor growth.

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

EXAMPLE 39

Identification of Proteins which Interact with Polypeptides Encoded by Extended cDNAs Proteins which interact with the polypeptides encoded by extended cDNAs or portions thereof, such as receptor proteins, may be identified using two hybrid systems such as the Matchmaker Two Hybrid System 2 (Catalog No. K1604-1, Clontech). As described in the manual accompanying the Matchmaker Two Hybrid System 2 (Catalog No. K1604-1, Clontech), which is incorporated herein by reference, the extended cDNAs or portions thereof, are inserted into an expression vector such that they are in frame with DNA encoding the DNA binding domain of the yeast transcriptional activator GAL4. cDNAs in a cDNA library which encode proteins which might interact with the polypeptides encoded by the extended cDNAs or portions thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the extended cDNAs or portions thereof.

Alternatively, the system described in Lustig et al., Methods in Enzymology 283: 83–99 (1997), the disclosure of which is incorporated herein by reference, may be used for identifying molecules which interact with the polypeptides encoded by extended cDNAs. In such systems, in vitro transcription reactions are performed on a pool of vectors containing extended cDNA inserts cloned downstream of a promoter which drives in vitro transcription. The resulting pools of mRNAs are introduced into Xenopus laevis oocytes. The oocytes are then assayed for a desired acitivity.

Alternatively, the pooled in vitro transcription products produced as described above may be translated in vitro. The pooled in vitro translation products can be assayed for a desired activity or for interaction with a known polypeptide.

Proteins or other molecules interacting with polypeptides encoded by extended cDNAs can be found by a variety of additional techniques. In one method, affinity columns containing the polypeptide encoded by the extended cDNA or a portion thereof can be constructed. In some versions, of this method the affinity column contains chimeric proteins in which the protein encoded by the extended cDNA or a portion thereof is fused to glutathione S-transferase. A mixture of cellular proteins or pool of expressed proteins as described above and is applied to the affinity column. Proteins interacting with the polypeptide attached to the column can then be isolated and analyzed on 2-D electrophoresis gel as described in Ramunsen et al. Electrophoresis, 18, 588–598 (1997), the disclosure of which is incorporated herein by reference. Alternatively, the proteins retained on the affinity column can be purified by electrophoresis based methods and sequenced. The same method can be used to isolate antibodies, to screen phage display products, or to screen phage display human antibodies.

Proteins interacting with polypeptides encoded by extended cDNAs or portions thereof can also be screened by using an Optical Biosensor as described in Edwards & Leatherbarrow, Analytical Biochemistry, 246, 1–6 (1997), the disclosure of which is incorporated herein by reference. The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred manometers from the sensor surface). In these screening assays, the target molecule can be one of the polypeptides encoded by extended cDNAs or a portion thereof and the test sample can be a collection of proteins extracted from tissues or cells, a pool of expressed proteins, combinatorial peptide and/or chemical libraries,or phage displayed peptides. The tissues or cells from which the test proteins are extracted can originate from any species.

In other methods, a target protein is immobilized and the test population is a collection of unique polypeptides encoded by the extended cDNAs or portions thereof.

To study the interaction of the proteins encoded by the extended cDNAs or portions thereof with drugs, the microdialysis coupled to HPLC method described by Wang et al., Chromatographia, 44, 205–208(1997) or the affinity capillary electrophoresis method described by Busch et al., J. Chromatogr. 777:311–328 (1997), the disclosures of which are incorporated herein by referenc can be used.

The system described in U.S. Pat. No. 5,654,150, the disclosure of which is incorporated herein by reference, may also be used to identify molecules which interact with the polypeptides encoded by the extended cDNAs. In this system, pools of extended cDNAs are transcribed and translated in vitro and the reaction products are assayed for interaction with a known polypeptide or antibody.

It will be appreciated by those skilled in the art that the proteins expressed from the extended cDNAs or portions may be assayed for numerous activities in addition to those specifically enumerated above. For example, the expressed proteins may be evaluated for applications involving control and regulation of inflammation, tumor proliferation or metastasis, infection, or other clinical conditions. In addition, the proteins expressed from the extended cDNAs or portions thereof may be useful as nutritional agents or cosmetic agents.

The proteins expressed from the extended cDNAs or portions thereof may be used to generate antibodies capable of specifically binding to the expressed protein or fragments thereof as described in Example 40 below. The antibodies may be capable of binding a full length protein encoded by one of the sequences of SEQ ID NOs: 40–59, 61–73, 75, 77–82, and 130–154, a mature protein encoded by one of the sequences of SEQ ID NOs: 40–59, 61–75, 77–82, and 130–154, or a signal peptide encoded by one of the sequences of SEQ ID Nos. 40–59, 61–73, 75–82, 84 and 130–154. Alternatively, the antibodies may be capable of binding fragments of the proteins expressed from the extended cDNAs which comprise at least 10 amino acids of the sequences of SEQ ID NOs: 85–129 and 155–179. In some embodiments, the antibodies may be capable of binding fragments of the proteins expressed from the extended cDNAs which comprise at least 15 amino acids of the sequences of SEQ ID NOs: 85–129 and 155–179. In other embodiments, the antibodies may be capable of binding fragments of the proteins expressed from the extended cDNAs which comprise at least 25 amino acids of the sequences of SEQ ID NOs: 85–129 and 155–179. In further embodiments, the antibodies may be capable of binding fragments of the proteins expressed from the extended cDNAs which comprise at least 40 amino acids of the sequences of SEQ ID NOs: 85–129 and 155–179.

EXAMPLE 40

Production of an Antibody to a Human Protein

Substantially pure protein or polypeptide is isolated from the transfected or transformed cells as described in Example 30. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21–2.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, 0. et al., Chap. 19 in: Handbook of Experimental Immunology D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitativelyor qualitatively to identify the presence of antigen in a biological sample. The antibodies may also be used in therapeutic compositions for killing cells expressing the protein or reducing the levels of the protein in the body.

V. Use of Extended cDNAs or Portions Thereof as Reagents

The extended cDNAs of the present invention may be used as reagents in isolation procedures, diagnostic assays, and forensic procedures. For example, sequences from the extended cDNAs (or genomic DNAs obtainable therefrom) may be detectably labeled and used as probes to isolate other sequences capable of hybridizing to them. In addition, sequences from the extended cDNAs (or genomic DNAs obtainable therefrom) may be used to design PCR primers to be used in isolation, diagnostic, or forensic procedures.

EXAMPLE 41

Preparation of PCR Primers and Amplification of DNA

The extended cDNAs (or genomic DNAs obtainable therefrom) may be used to prepare PCR primers for a variety of applications, including isolation procedures for cloning nucleic acids capable of hybridizing to such sequences, diagnostic techniques and forensic techniques. The PCR primers are at least 10 bases, and preferably at least 12, 15, or 17 bases in length. More preferably, the PCR primers are at least 20–30 bases in length. In some embodiments, the PCR primers may be more than 30 bases in length. It is preferred that the primer pairs have approximately the same G/C ratio, so that melting temperatures are approximately the same. A variety of PCR techniques are familiar to those skilled in the art. For a review of PCR technology, see Molecular Cloning to Genetic Engineering White, B. A. Ed. in Methods in Molecular Biology 67: Humana Press, Totowa 1997. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

EXAMPLE 42

Use of Extended cDNAs as Probes

Probes derived from extended cDNAs or portions thereof (or genomic DNAs obtainable therefrom) may be labeled with detectable labels familiar to those skilled in the art, including radioisotopes and non-radioactive labels, to provide a detectable probe. The detectable probe may be single stranded or double stranded and may be made using techniques known in the art, including in vitro transcription, nick translation, or kinase reactions. A nucleic acid sample containing a sequence capable of hybridizing to the labeled probe is contacted with the labeled probe. If the nucleic acid in the sample is double stranded, it may be denatured prior to contacting the probe. In some applications, the nucleic acid sample may be immobilized on a surface such as a nitrocellulose or nylon membrane. The nucleic acid sample may comprise nucleic acids obtained from a variety of sources, including genomic DNA, cDNA libraries, RNA, or tissue samples.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described in Example 30 above.

PCR primers made as described in Example 41 above may be used in forensic analyses, such as the DNA fingerprinting techniques described in Examples 43–47 below. Such analyses may utilize detectable probes or primers based on the sequences of the extended cDNAs isolated using the 5' ESTs (or genomic DNAs obtainable therefrom).

EXAMPLE 43

Forensic Matching by DNA Sequencing

In one exemplary method, DNA samples are isolated from forensic specimens of, for example, hair, semen, blood or skin cells by conventional methods. A panel of PCR primers based on a number of the extended cDNAs (or genomic DNAs obtainable therefrom), is then utilized in accordance with Example 41 to amplify DNA of approximately 100–200 bases in length from the forensic specimen. Corresponding sequences are obtained from a test subject. Each of these identification DNAs is then sequenced using standard techniques, and a simple database comparison determines the differences, if any, between the sequences from the subject and those from the sample. Statistically significant differences between the suspect's DNA sequences and those from the sample conclusively prove a lack of identity. This lack of identity can be proven, for example, with only one sequence. Identity, on the other hand, should be demonstrated with a large number of sequences, all matching. Preferably, a minimum of 50 statistically identical sequences of 100 bases in length are used to prove identity between the suspect and the sample.

EXAMPLE 44

Positive Identification by DNA Sequencing

The technique outlined in the previous example may also be used on a larger scale to provide a unique fingerprint-type identification of any individual. In this technique, primers are prepared from a large number of sequences from Table IV and the appended sequence listing. Preferably, 20 to 50 different primers are used. These primers are used to obtain a corresponding number of PCR-generated DNA segments from the individual in question in accordance with Example 41. Each of these DNA segments is sequenced, using the methods set forth in Example 43. The database of sequences generated through this procedure uniquely identifies the individual from whom the sequences were obtained. The same panel of primers may then be used at any later time to absolutely correlate tissue or other biological specimen with that individual.

EXAMPLE 45

Southern Blot Forensic Identification

The procedure of Example 44 is repeated to obtain a panel of at least 10 amplified sequences from an individual and a specimen. Preferably, the panel contains at least 50 amplified sequences. More preferably, the panel contains 100 amplified sequences. In some embodiments, the panel contains 200 amplified sequences. This PCR-generated DNA is then digested with one or a combination of, preferably, four base specific restriction enzymes. Such enzymes are commercially available and known to those of skill in the art. After digestion, the resultant gene fragments are size separated in multiple duplicate wells on an agarose gel and transferred to nitrocellulose using Southern blotting techniques well known to those with skill in the art. For a review of Southern blotting see Davis et al. (Basic Methods in Molecular Biology, 1986, Elsevier Press. pp 62–65).

A panel of probes based on the sequences of the extended cDNAs (or genomic DNAs obtainable therefrom), or fragments thereof of at least 10 bases, are radioactively or calorimetrically labeled using methods known in the art, such as nick translation or end labeling, and hybridized to the Southern blot using techniques known in the art (Davis et al., supra). Preferably, the probe comprises at least 12, 15, or 17 consecutive nucleotides from the extended cDNA (or genomic DNAs obtainable therefrom). More preferably, the probe comprises at least 20–30 consecutive nucleotides from the extended cDNA (or genomic DNAs obtainable therefrom). In some embodiments, the probe comprises more than 30 nucleotides from the extended cDNA (or genomic DNAs obtainable therefrom). In other embodiments, the probe comprises at least 40, at least 50, at least 75, at least 100, at least 150, or at least 200 consecutive nucleotides from the extended cDNA (or genomic DNAs obtainable therefrom).

Preferably, at least 5 to 10 of these labeled probes are used, and more preferably at least about 20 or 30 are used to provide a unique pattern. The resultant bands appearing from the hybridization of a large sample of extended cDNAs (or genomic DNAs obtainable therefrom) will be a unique identifier. Since the restriction enzyme cleavage will be different for every individual, the band pattern on the Southern blot will also be unique. Increasing the number of extended cDNA probes will provide a statistically higher level of confidence in the identification since there will be an increased number of sets of bands used for identification.

EXAMPLE 46

Dot Blot Identification Procedure

Another technique for identifying individuals using the extended cDNA sequences disclosed herein utilizes a dot blot hybridizationtechnique.

Genomic DNA is isolated from nuclei of subject to be identified. Oligonucleotide probes of approximately 30 bp in length are synthesized that correspond to at least 10, preferably 50 sequences from the extended cDNAs or genomic DNAs obtainable therefrom. The probes are used to hybridize to the genomic DNA through conditions known to those in the art. The oligonucleotides are end labeled with $p^{32}$ using polynucleotide kinase (Pharmacia). Dot Blots are created by spotting the genomic DNA onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al. supra). The $^{32}P$ labeled DNA fragments are sequentially hybridized with successively stringent conditions to detect minimal differences between the 30 bp sequence and the DNA. Tetramethylammonium chloride is useful for identifying clones containing small numbers of nucleotide mismatches (Wood et al., Proc. Natl. Acad. Sci. USA 82(6):1585–1588 (1985)) which is hereby incorporated by reference. A unique pattern of dots distinguishes one individual from another individual.

Extended cDNAs or oligonucleotides containing at least 10 consecutive bases from these sequences can be used as probes in the following alternative fingerprinting technique. Preferably, the probe comprises at least 12, 15, or 17 consecutive nucleotides from the extended cDNA (or genomic DNAs obtainable therefrom). More preferably, the probe comprises at least 20–30 consecutive nucleotides from the extended cDNA (or genomic DNAs obtainable therefrom). In some embodiments, the probe comprises more than 30 nucleotides from the extended cDNA (or genomic DNAs obtainable therefrom). In other embodiments, the probe comprises at least 40, at least 50, at least 75, at least 100, at least 150, or at least 200 consecutive nucleotides from the extended cDNA (or genomic DNAs obtainable therefrom).

Preferably, a plurality of probes having sequences from different genes are used in the alternative fingerprinting technique. Example 47 below provides a representative alternative fingerprinting procedure in which the probes are derived from extended cDNAs.

EXAMPLE 47

Alternative "Fingerprint" Identification Technique 20-mer oligonucleotidesare prepared from a large number, e.g. 50, 100, or 200, of extended cDNA sequences (or genomic DNAs obtainable therefrom) using commercially available oligonucleotide services such as Genset, Paris, France. Cell samples from the test subject are processed for DNA using techniques well known to those with skill in the art. The nucleic acid is digested with restriction enzymes such as EcoRI and XbaI. Following digestion, samples are applied to wells for electrophoresis. The procedure, as known in the art, may be modified to accommodate polyacrylamide electrophoresis, however in this example, samples containing 5 ug of DNA are loaded into wells and separated on 0.8% agarose gels. The gels are transferred onto nitrocellulose using standard Southern blotting techniques.

10 ng of each of the oligonucleotides are pooled and end-labeled with $P^{32}$. The nitrocellulose is prehybridized with blocking solution and hybridized with the labeled probes. Following hybridization and washing, the nitrocellulose filter is exposed to X-Omat AR X-ray film. The resulting hybridization pattern will be unique for each individual.

It is additionally contemplated within this example that the number of probe sequences used can be varied for additional accuracy or clarity.

The antibodies generated in Examples 30 and 40 above may be used to identify the tissue type or cell species from which a sample is derived as described above.

EXAMPLE 48

Identification of Tissue Types or Cell Species by Means of Labeled Tissue Specific Antibodies Identification of specific tissues is accomplished by the visualization of tissue specific antigens by means of antibody preparations according to Examples 30 and 40 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

A. Immunohistochemical Techniques

Purified, high-titer antibodies, prepared as described above, are conjugated to a detectable marker, as described, for example, by Fudenberg, H., Chap. 26 in: Basic 503 Clinical Immunology, 3rd Ed. Lange, Los Altos, Calif. (1980) or Rose, N. et al., Chap. 12 in: Methods in Immunodiagnosis, 2d Ed. John Wiley 503 Sons, New York (1980).

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibodycomplexes achieved by means of an electron microscope. In yet another approach, the antibodies are radiolabeled, with, for example $^{125}I$ and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 μm, unfixed) of the unknown tissue and known control, are mounted and each slide covered with different dilutions of the antibody preparation. Sections of known and unknown tissues should also be treated with preparations to provide a positive control, a negative control, for example, pre-immune sera, and a control for non-specific staining, for example, buffer.

Treated sections are incubated in a humid chamber for 30 min at room temperature, rinsed, then washed in buffer for 30–45 min. Excess fluid is blotted away, and the marker developed.

If the tissue specific antibody was not labeled in the first incubation, it can be labeled at this time in a second antibody-antibody reaction, for example, by adding fluorescein- or enzyme-conjugated antibody against the immunoglobulin class of the antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. et al., Section 19-2 in: Basic Methods in Molecular Biology (P. Leder, ed), Elsevier, New York (1986), using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 μl, and containing from about 1 to 100 μg protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., (above) Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 30 and 40. In this procedure, as in procedure A above, appropriate positive and negative sample and reagent controls are run.

In either procedure A or B, a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

The visualization of tissue specific antigen binding at levels above those seen in control tissues to one or more tissue specific antibodies, prepared from the gene sequences identified from extended cDNA sequences, can identify tissues of unknown origin, for example, forensic samples, or differentiated tumor tissue that has metastasized to foreign bodily sites.

In addition to their applications in forensics and identification, extended cDNAs (or genomic DNAs obtainable therefrom) may be mapped to their chromosomal locations. Example 49 below describes radiation hybrid (RH) mapping of human chromosomal regions using extended cDNAs. Example 50 below describes a representative procedure for mapping an extended cDNA (or a genomic DNA obtainable therefrom) to its location on a human chromosome. Example 51 below describes mapping of extended cDNAs (or genomic DNAs obtainable therefrom) on metaphase chromosomes by Fluorescence In Situ Hybridization(FISH).

EXAMPLE 49

Radiation hybrid mapping of Extended cDNAs to the human genome

Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. (*Genomics* 4:509–517, 1989) and Cox et al., (*Science* 250:245–250, 1990), the entire contents of which are hereby incorporated by reference. The random and independent nature of the subclones permits efficient mapping of any human genome marker. Human DNA isolated from a panel of 80–100 cell lines provides a mapping reagent for ordering extended cDNAs (or genomic DNAs obtainable therefrom). In this approach, the frequency of breakage between markers is used to measure distance, allowing construction of fine resolution maps as has been done using conventional ESTs (Schuler et al., *Science* 274:540–546, 1996, hereby incorporated by reference).

RH mapping has been used to generate a high-resolution whole genome radiation hybrid map of human chromosome 17q22–q25.3 across the genes for growth hormone (GH) and thymidine kinase (TK) (Foster et al., *Genomics* 33:185–192, 1996), the region surrounding the Gorlin syndrome gene (Obermayr et al., *Eur. J Hum. Genet.* 4:242–245, 1996), 60 loci covering the entire short arm of chromosome 12 (Raeymaekers et al., *Genomics* 29:170–178, 1995), the region of human chromosome 22 containing the neurofibromatosistype 2 locus (Frazer et al., *Genomics* 14:574–584, 1992) and 13 loci on the long arm of chromosome 5 (Warrington et al., *Genomics* 11:701–708,1991).

EXAMPLE 50

Mapping of Extended cDNAs to Human Chromosomes using PCR techniques

Extended cDNAs (or genomic DNAs obtainable therefrom) may be assigned to human chromosomes using PCR based methodologies. In such approaches, oligonucleotide primer pairs are designed from the extended cDNA sequence (or the sequence of a genomic DNA obtainable therefrom) to minimize the chance of amplifying through an intron. Preferably, the oligonucleotide primers are 18–23 bp in length and are designed for PCR amplification. The creation of PCR primers from known sequences is well known to those with skill in the art. For a review of PCR technology see Erlich, H. A., PCR Technology; Principles and Applications for DNA Amplification. 1992. W.H. Freeman and Co., New York.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 μCu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the distance between the ends of the primer sequences in the extended cDNA from which the primers are derived, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given extended cDNA (or genomic DNA obtainable therefrom). DNA is isolated from the somatic hybrids and used as starting templates for PCR reactions using the primer pairs from the extended cDNAs (or genomic DNAs obtainable therefrom). Only those somatic cell hybrids with chromosomes containing the human gene corresponding to the extended cDNA (or genomic DNA obtainable therefrom) will yield an amplified fragment. The extended cDNAs (or genomic DNAs obtainable therefrom) are assigned to a chromosome by analysis of the segregation pattern of PCR products from the somatic hybrid DNA templates. The single human chromosome present in all cell hybrids that give rise to an amplified fragment is the chromosome containing that extended cDNA (or genomic DNA obtainable therefrom). For a review of techniques and analysis of results from somatic cell gene mapping experiments. (See Ledbetter et al., Genomics 6:475–481 (1990).)

Alternatively, the extended cDNAs (or genomic DNAs obtainable therefrom) may be mapped to individual chromosomes using FISH as described in Example 51 below.

EXAMPLE 51

Mapping of Extended 5' ESTs to Chromosomes Using Fluorescence in situ Hybridization Fluorescence in situ hybridization allows the extended cDNA (or genomic DNA obtainable therefrom) to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of an extended cDNA (or genomic DNA obtainable therefrom) is obtained by FISH as described by Cherif et al. (*Proc. Natl. Acad. Sci. U.S.A.,* 87:6639–6643, 1990). Metaphase chromosomes are prepared from phytohemagglutinin(PHA)-stimulatedblood cell donors. PHA-stimulated lymphocytes from healthy males are cultured for 72 h in RPMI-1640 medium. For synchronization, methotrexate (10 $\mu$M) is added for 17 h, followed by addition of 5-bromodeoxyuridine (5-BudR, 0.1 mM) for 6 h. Colcemid (1 $\mu$g/ml) is added for the last 15 min before harvesting the cells. Cells are collected, washed in RPMI, incubated with a hypotonic solution of KCl (75 mM) at 37° C. for 15 min and fixed in three changes of methanol:aceticacid (3:1). The cell suspension is dropped on to a glass slide and air dried. The extended cDNA (or genomic DNA obtainable therefrom) is labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5–10 mm.

Slides kept at -20° C. are treated for 1 h at 37° C. with RNase A (100 $\mu$g/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 $\mu$g/100 ml in 20 mM Tris-HCl, 2 mM $CaCl_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular extended cDNA (or genomic DNA obtainable therefrom) may be localized to a particular cytogenetic R-band on a given chromosome.

Once the extended cDNAs (or genomic DNAs obtainable therefrom) have been assigned to particular chromosomes using the techniques described in Examples 49–51 above, they may be utilized to construct a high resolution map of the chromosomes on which they are located or to identify the chromosomes in a sample.

EXAMPLE 52

Use of Extended cDNAs to Construct or Expand Chromosome Maps

Chromosome mapping involves assigning a given unique sequence to a particular chromosome as described above. Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the extended cDNAs (or genomic DNAs obtainable therefrom) are obtained. This approach is described in Ramaiah Nagaraja et al. Genome Research 7:210–222, March 1997. Briefly, in this approach each chromosome is broken into overlapping pieces which are inserted into the YAC vector. The YAC inserts are screened using PCR or other methods to determine whether they include the extended cDNA (or genomic DNA obtainable therefrom) whose position is to be determined. Once an insert has been found which includes the extended cDNA (or genomic DNA obtainable therefrom), the insert can be analyzed by PCR or other methods to determine whether the insert also contains other sequences known to be on the chromosome or in the region from which the extended cDNA (or genomic DNA obtainable therefrom) was derived. This process can be repeated for each insert in the YAC library to determine the location of each of the extended cDNAs (or genomic DNAs obtainable therefrom) relative to one another and to other known chromosomal markers.

In this way, a high resolution map of the distribution of numerous unique markers along each of the organisms chromosomes may be obtained.

As described in Example 53 below extended cDNAs (or genomic DNAs obtainable therefrom) may also be used to identify genes associated with a particular phenotype, such as hereditary disease or drug response.

EXAMPLE 53

Identification of Genes Associated with Hereditary Diseases or Drug Response

This example illustrates an approach useful for the association of extended cDNAs (or genomic DNAs obtainable therefrom) with particular phenotypic characteristics. In this example, a particular extended cDNA (or genomic DNA obtainable therefrom) is used as a test probe to associate that extended cDNA (or genomic DNA obtainable therefrom) with a particular phenotypic characteristic.

Extended cDNAs (or genomic DNAs obtainable therefrom) are mapped to a particular location on a human chromosome using techniques such as those described in Examples 49 and 50 or other techniques known in the art. A search of Mendelian Inheritance in Man (V. McKusick, Mendelian Inheritance in Man (available on line through Johns Hopkins University Welch Medical Library) reveals the region of the human chromosome which contains the extended cDNA (or genomic DNA obtainable therefrom) to be a very gene rich region containing several known genes and several diseases or phenotypes for which genes have not been identified. The gene corresponding to this extended cDNA (or genomic DNA obtainable therefrom) thus becomes an immediate candidate for each of these genetic diseases.

Cells from patients with these diseases or phenotypes are isolated and expanded in culture. PCR primers from the extended cDNA (or genomic DNA obtainable therefrom) are used to screen genomic DNA, mRNA or cDNA obtained from the patients. Extended cDNAs (or genomic DNAs obtainable therefrom) that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the extended cDNA may be responsible for the genetic disease.

VI. Use of Extended cDNAs (or Genomic DNAs Obtainable therefrom) to Construct Vectors The present extended cDNAs (or genomic DNAs obtainable therefrom) may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described in Example 54 below.

EXAMPLE 54

Construction of Secretion Vectors

The secretion vectors of the present invention include a promoter capable of directing gene expression in the host cell, tissue, or organism of interest. Such promoters include the Rous Sarcoma Virus promoter, the SV40 promoter, the human cytomegalovirus promoter, and other promoters familiar to those skilled in the art.

A signal sequence from an extended cDNA (or genomic DNA obtainable therefrom), such as one of the signal sequences in SEQ ID NOs: 40–59, 61–73, 75–82, 84, and 130–154 as defined in Table IV above, is operably linked to the promoter such that the mRNA transcribed from the promoter will direct the translation of the signal peptide. The host cell, tissue, or organism may be any cell, tissue, or organism which recognizes the signal peptide encoded by the signal sequence in the extended cDNA (or genomic DNA obtainable therefrom). Suitable hosts include mammalian cells, tissues or organisms, avian cells, tissues, or organisms, insect cells, tissues or organisms, or yeast.

In addition, the secretion vector contains cloning sites for inserting genes encoding he proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA signal such that the polyA signal is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediatedtransfection, viral particles or as naked DNA. The protein encoded by the inserted gene is then purified or enriched from the supernatant using conventional techniques such as ammonium sulfate precipitation, immunoprecipitation, immunochromatography, size exclusion chromatography, ion exchange chromatography, and hplc. Alternatively,the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and fused to the signal sequence. The vector is introduced into an appropriate host cell. The protein expressed from the promoter is secreted extracellularly, thereby producing a therapeutic effect.

The extended cDNAs or 5' ESTs may also be used to clone sequences located upstream of the extended cDNAs or 5' ESTs which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion. Example 55 describes a method for cloning sequences upstream of the extended cDNAs or 5' ESTs.

EXAMPLE 55

Use of Extended cDNAs or 5' ESTs to Clone Upstream Sequences from Genomic DNA

Sequences derived from extended cDNAs or 5' ESTs may be used to isolate the promoters of the corresponding genes using chromosome walking techniques. In one chromosome walking technique, which utilizes the GenomeWalker# kit available from Clontech, five genomic DNA samples are each digested with a different restriction enzyme which has a 6 base recognition site and leaves a blunt end. Following digestion, oligonucleotide adapters are ligated to each end of the resulting genomic DNA fragments.

For each of the five genomic DNA libraries, a first PCR reaction is performed according to the manufacturer's instructions (which are incorporated herein by reference) using an outer adaptor primer provided in the kit and an outer gene specific primer. The gene specific primer should be selected to be specific for the extended cDNA or 5' EST of interest and should have a melting temperature, length, and location in the extended cDNA or ' EST which is consistent with its use in PCR reactions. Each first PCR reaction contains 5 ng of genomic DNA, 5 µl of 10×Tth reaction buffer, 0.2 mM of each dNTP, 0.2 µM each of outer adaptor primer and outer gene specific primer, 1.1 mM of Mg(OAc)$_2$, and 1 µl of the Tth polymerase 50×mix in a total volume of 50 µl. The reaction cycle for the first PCR reaction is as follows: 1 min @ 94° C./2 sec @ 94° C., 3 min@72° C. (7 cycles)/2 sec @ 94° C., 3 min@67° C. (32 cycles)/5 min @ 67° C.

The product of the first PCR reaction is diluted and used as a template for a second PCR reaction according to the manufacturer's instructions using a pair of nested primers which are located internally on the amplicon resulting from the first PCR reaction. For example, 5 µl of the reaction product of the first PCR reaction mixture may be diluted 180 times. Reactions are made in a 50 µl volume having a composition identical to that of the first PCR reaction except the nested primers are used. The first nested primer is specific for the adaptor, and is provided with the GenomeWalker™ kit. The second nested primer is specific for the particular extended cDNA or 5' EST for which the promoter is to be cloned and should have a melting temperature, length, and location in the extended cDNA or 5' EST which is consistent with its use in PCR reactions. The reaction parameters of the second PCR reaction are as follows: 1 min @ 94° C./2 sec @ 94° C., 3 min @ 72° C. (6 cycles)/2 sec @ 94° C., 3 min @ 67° C. (25 cycles)/5 min @ 67° C.

The product of the second PCR reaction is purified, cloned, and sequenced using standard techniques. Alternatively, two or more human genomic DNA libraries can be constructed by using two or more restriction enzymes. The digested genomic DNA is cloned into vectors which can be converted into single stranded, circular, or linear DNA. A biotinylated oligonucleotide comprising at least 15 nucleotides from the extended cDNA or 5' EST sequence is hybridized to the single stranded DNA. Hybrids between the biotinylated oligonucleotide and the single stranded DNA containing the extended cDNA or EST sequence are isolated as described in Example 29 above. Thereafter, the single stranded DNA containing the extended cDNA or EST sequence is released from the beads and converted into double stranded DNA using a primer specific for the extended cDNA or 5' EST sequence or a primer corresponding to a sequence included in the cloning vector. The resulting double stranded DNA is transformed into bacteria. DNAs containing the 5' EST or extended cDNA sequences are identified by colony PCR or colony hybridization.

Once the upstream genomic sequences have been cloned and sequenced as described above, prospective promoters and transcription start sites within the upstream sequences may be identified by comparing the sequences upstream of the extended cDNAs or 5' ESTs with databases containing known transcription start sites, transcription factor binding sites, or promoter sequences.

In addition, promoters in the upstream sequences may be identified using promoter reporter vectors as described in Example 56.

EXAMPLE 56

Identification of Promoters in Cloned Upstream Sequences

The genomic sequences upstream of the extended cDNAs or 5' ESTs are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the extended cDNAs or 5' ESTs are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Appropriate host cells for the promoter reporter vectors may be chosen based on the results of the above described determination of expression patterns of the extended cDNAs and ESTs. For example, if the expression pattern analysis indicates that the mRNA corresponding to a particular extended cDNA or 5' EST is expressed in fibroblasts, the promoter reporter vector may be introduced into a human fibroblast cell line.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

EXAMPLE 57

Cloning and Identification of Promoters

Using the method described in Example 55 above with 5' ESTs, sequences upstream of several genes were obtained. Using the primer pairs GGG AAG ATG GAG ATA GTA TTG CCT G (SEQ ID NO:29) and CTG CCA TGT ACA TGA TAG AGA GAT TC (SEQ ID NO:30), the promoter having the internal designation P13H2 (SEQ ID NO:3 1) was obtained.

Using the primer pairs GTA CCA GGGG ACT GTG ACC ATT GC (SEQ ID NO:32) and CTG TGA CCA TTG CTC CCA AGA GAG (SEQ ID NO:33), the promoter having the internal designation P 1 5B4 (SEQ ID NO:34) was obtained.

Using the primer pairs CTG GGA TGG AAG GCA CGG TA (SEQ ID NO:35) and GAG ACC ACA CAG CTA GAC AA (SEQ ID NO:36), the promoter having the internal designation P29B6 (SEQ ID NO:37) was obtained.

Figure 8:
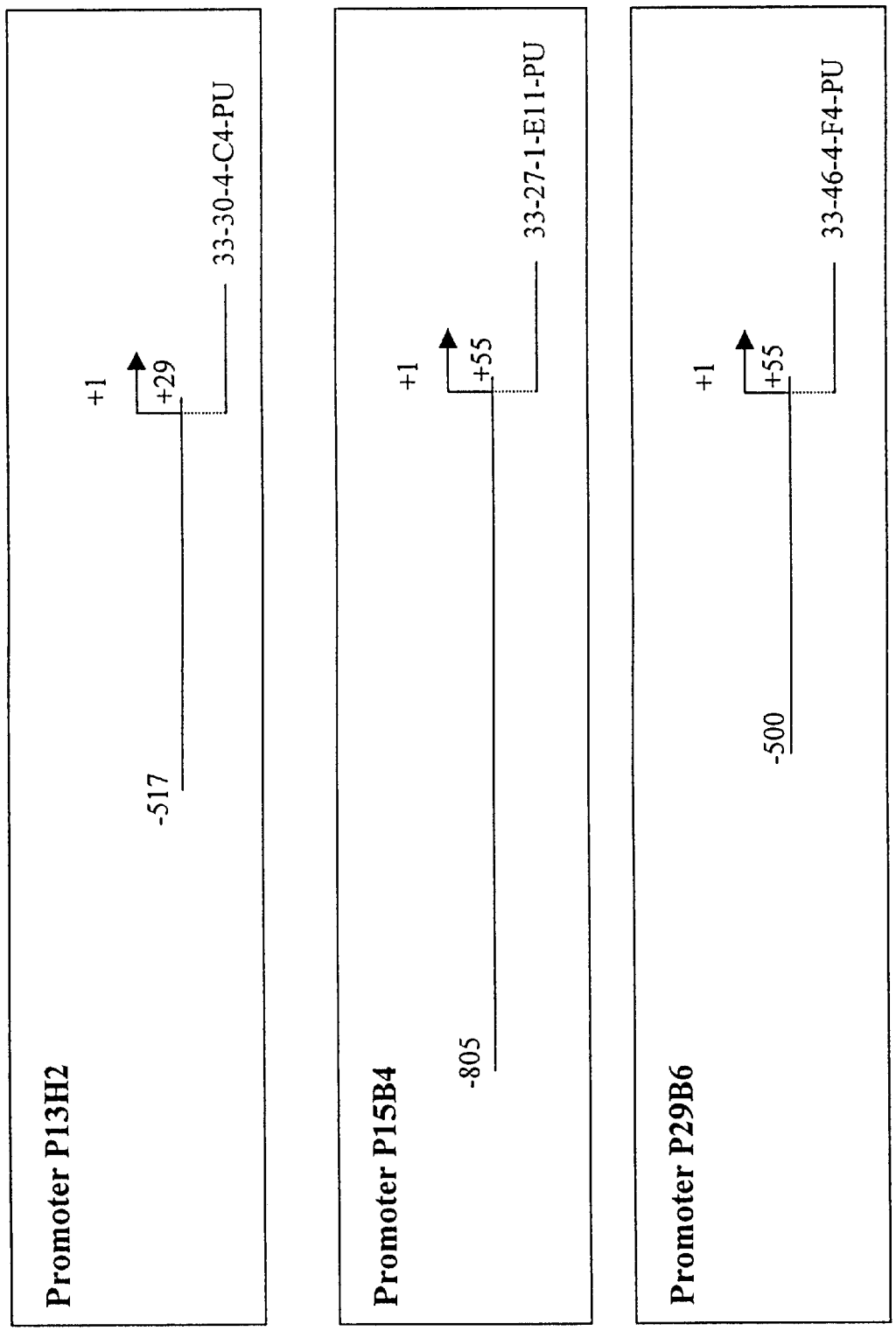
FIG. 8 provides a schematic description of the promoters isolated and the way they are assembled with the corresponding 5' tags.

FIG. 8 provides a schematic description of the promoters isolated and the way they are assembled with the corresponding 5' tags. The upstream sequences were screened for the presence of motifs resembling transcription factor binding sites or known transcription start sites using the computer program MatInspector release 2.0, August 1996.

FIG. 9 describes the transcription factor binding sites present in each of these promoters. The columns labeled matrice provides the name of the MatInspector matrix used. The column labeled position provides the 5' postion of the promoter site. Numeration of the sequence starts from the transcription site as determined by matching the genomic sequence with the 5' EST sequence. The column labeled "orientation" indicates the DNA strand on which the site is found, with the + strand being the coding strand as determined by matching the genomic sequence with the sequence of the 5' EST. The column labeled "score" provides the MatInspector score found for this site. The column labeled "length" provides the length of the site in nucleotides. The column labeled "sequence" provides the sequence of the site found.

The promoters and other regulatory sequences located upstream of the extended cDNAs or 5' ESTs may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described in Example 26 above. For example, if a promoter which confers a high level of expression in muscle is desired, the promoter sequence upstream of an extended cDNA or 5' EST derived from an mRNA which is expressed at a high level in muscle, as determined by the method of Example 26, may be used in the expression vector.

Preferably, the desired promoter is placed near multiple restriction sites to facilitate the cloning of the desired insert downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Following the identification of promoter sequences using the procedures of Examples 55–57, proteins which interact with the promoter may be identified as described in Example 58 below.

EXAMPLE 58

Identification of Proteins Which Interact with Promoter Sequences, Upstream Regulatory Sequences, or mRNA Sequences within the promoter region which are likely to bind transcription factors may be identified by homology to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art. Nucleic acids encoding proteins which interact with sequences in the promoter may be identified using one-hybrid systems such as those described in the manual accompanying the Matchmaker One-Hybrid System kit avalilabe from Clontech (Catalog No. K1603-1), the disclosure of which is incorporated herein by reference. Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

VII. Use of Extended cDNAs (or Genomic DNAs Obtainable Therefrom) in Gene Therapy The present invention also comprises the use of extended cDNAs (or genomic DNAs obtainable therefrom) in gene therapy strategies, including antisense and triple helix strategies as described in Examples 57 and 58 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 59

Preparation and Use of Antisense Oligonucleotides

The antisense nucleic acid molecules to be used in gene therapy may be either DNA or RNA sequences. They may comprise a sequence complementary to the sequence of the extended cDNA (or genomic DNA obtainable therefrom). The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., Ann. Rev. Biochem. 55:569–597 (1986) and Izant and Weintraub, Cell 36:1007–1015 (1984), which are hereby incorporated by reference.

In some strategies, antisense molecules are obtained from a nucleotide sequence encoding a protein by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies are described by Rossi et al., Pharmacol. Ther. 50(2):245–254, (1991).

Various types of antisense oligonucleotides complementary to the sequence of the extended cDNA (or genomic DNA obtainable therefrom) may be used. In one preferred embodiment, stable and semi-stable antisense oligonucleotides described in International Application No. PCT WO94/23026, hereby incorporated by reference, are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotidecovalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense molecules are introduced onto cell samples at a number of different concentrations preferably between $1 \times 10^{-10}$M to $1 \times 10^{-4}$M. Once the minimum concentration that can adequately control gene expression is identified, the optimized dose is translated into a dosage suitable for use in vivo. For example, an inhibiting concentration in culture of $1 \times 10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

The extended cDNAs of the present invention (or genomic DNAs obtainable therefrom) may also be used in gene therapy approaches based on intracellular triple helix formation. Triple helix oligonucleotides are used to inhibit transcription from a genome. They are particularly useful for studying alterations in cell activity as it is associated with a particular gene. The extended cDNAs (or genomic DNAs obtainable therefrom) of the present invention or, more preferably, a portion of those sequences, can be used to inhibit gene expression in individuals having diseases associated with expression of a particular gene. Similarly, a portion of the extended cDNA (or genomic DNA obtainable therefrom) can be used to study the effect of inhibiting transcription of a particular gene within a cell. Traditionally, homopurine sequences were considered the most useful for triple helix strategies. However, homopyrimidine sequences can also inhibit gene expression. Such homopyrimidine oligonucleotides bind to the major groove at homopurine- :homopyrimidinesequences. Thus, both types of sequences from the extended cDNA or from the gene corresponding to the extended cDNA are contemplated within the scope of this invention.

EXAMPLE 60

Preparation and use of Triple Helix Probes

The sequences of the extended cDNAs (or genomic DNAs obtainable therefrom) are scanned to identify 10-mer to 20-mer homopyrimidine or homopurine stretches which could be used in triple-helix based strategies for inhibiting gene expression. Following identification of candidate homopyrimidine or homopurine stretches, their efficiency in inhibiting gene expression is assessed by introducing varying amounts of oligonucleotides containing the candidate sequences into tissue culture cells which normally express the target gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced gene expression using techniques such as Northern blotting, RNase protection assays, or PCR based strategies to monitor the transcription levels of the target gene in cells which have been treated with the oligonucleotide. The cell functions to be monitored are predicted based upon the homologies of the target gene corresponding to the extended cDNA from which the oligonucleotide was derived with known gene sequences that have been associated with a particular function. The cell functions can also be predicted based on the presence of abnormal physiologies within cells derived from individuals with a particular inherited disease, particularly when the extended cDNA is associated with the disease using techniques described in Example 53.

The oligonucleotides which are effective in inhibiting gene expression in tissue culture cells may then be introduced in vivo using the techniques described above and in Example 59 at a dosage calculated based on the in vitro results, as described in Example 59.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (Science 245:967–971 (1989), which is hereby incorporated by this reference).

EXAMPLE 61

Use of Extended cDNAs to Express an Encoded Protein in a Host Organism

The extended cDNAs of the present invention may also be used to express an encoded protein in a host organism to produce a beneficial effect. In such procedures, the encoded protein may be transiently expressed in the host organism or stably expressed in the host organism. The encoded protein may have any of the activities described above. The encoded protein may be a protein which the host organism lacks or, alternatively, the encoded protein may augment the existing levels of the protein in the host organism.

A full length extended cDNA encoding the signal peptide and the mature protein, or an extended cDNA encoding only the mature protein is introduced into the host organism. The extended cDNA may be introduced into the host organism using a variety of techniques known to those of skill in the art. For example, the extended cDNA may be injected into the host organism as naked DNA such that the encoded protein is expressed in the host organism, thereby producing a beneficial effect.

Alternatively, the extended cDNA may be cloned into an expression vector downstream of a promoter which is active in the host organism. The expression vector may be any of the expression vectors designed for use in gene therapy, including viral or retroviral vectors.

The expression vector may be directly introduced into the host organism such that the encoded protein is expressed in the host organism to produce a beneficial effect. In another approach, the expression vector may be introduced into cells in vitro. Cells containing the expression vector are thereafter selected and introduced into the host organism, where they express the encoded protein to produce a beneficial effect.

EXAMPLE 62

Use of Signal Peptides Encoded by 5' Ests or Sequences Obtained Therefrom to Import Proteins into Cells The short core hydrophobic region (h) of signal peptides encoded by the 5' ESTS or extended cDNAs derived from the 5' ESTs of the present invention may also be used as a carrier to import a peptide or a protein of interest, so-called cargo, into tissue culture cells (Lin et al., *J. Biol. Chem.*, 270: 14225–14258 (1995); Du et al., *J Peptide Res.*, 51: 235–243 (1998); Rojas et al., *Nature Biotech.*, 16: 370–375 (1998)).

When cell permeable peptides of limited size (approximately up to 25 amino acids) are to be translocated across cell membrane, chemical synthesis may be used in order to add the h region to either the C-terminus or the N-terminus to the cargo peptide of interest. Alternatively, when longer peptides or proteins are to be imported into cells, nucleic acids can be genetically engineered, using techniques familiar to those skilled in the art, in order to link the extended cDNA sequence encoding the h region to the 5' or the 3' end of a DNA sequence coding for a cargo polypeptide. Such genetically engineered nucleic acids are then translated either in vitro or in vivo after transfection into appropriate cells, using conventional techniques to produce the resulting cell permeable polypeptide. Suitable hosts cells are then simply incubated with the cell permeable polypeptide which is then translocated across the membrane.

This method may be applied to study diverse intracellular functions and cellular processes. For instance, it has been used to probe functionally relevant domains of intracellular proteins and to examine protein-protein interactions involved in signal transduction pathways (Lin et al., supra; Lin et al., *J. Biol. Chem.*, 271: 5305–5308 (1996); Rojas et al., *J. Biol. Chem.*, 271: 27456–27461 (1996); Liu et al., *Proc. Natl. Acad. Sci. USA*, 93: 11819–11824 (1996); Rojas et al., *Bioch. Biophys. Res. Commun.*, 234: 675–680 (1997)).

Such techniques may be used in cellular therapy to import proteins producing therapeutic effects. For instance, cells isolated from a patient may be treated with imported therapeutic proteins and then re-introduced into the host organism.

Alternatively, the h region of signal peptides of the present invention could be used in combination with a nuclear localization signal to deliver nucleic acids into cell nucleus. Such oligonucleotides may be antisense oligonucleotides or oligonucleotides designed to form triple helixes, as described in examples 59 and 60 respectively, in order to inhibit processing and maturation of a target cellular RNA.

EXAMPLE 63

Reassembling & Resequencing of Clones

Full length cDNA clones obtained by the procedure described in Example 27 were double-sequenced. These sequences were assembled and the resulting consensus sequences were then reanalyzed. Open reading frames were reassigned following essentially the same process as the one described in Example 27.

After this reanalysis process a few abnormalities were revealed. The sequence presented in SEQ ID NO: 84 is apparently unlikely to be genuine full length cDNAs. This clone is more probably a 3' truncated cDNA sequence based on homology studies with existing protein sequences. Similarly, the sequences presented in SEQ ID NOs: 60, 76, 83 and 84 may also not be genuine full length cDNAs based on homology studies with existing protein sequences. Although these sequences encode a potential start methionine, except for SEQ ID NO:60, they could represent a 5' truncated cDNA.

Finally, after the reassignment of open reading frames for the clones, new open reading frames were chosen in some instances. For example, in the case of SEQ ID NOs: 60, 74 and 83 the new open reading frames were no longer predicted to contain a signal peptide.

As discussed above, Table IV provides the sequence identification numbers of the extended cDNAs of the present invention, the locations of the full coding sequences in SEQ ID NOs: 40–84 and 130–154 (i.e. the nucleotides encoding both the signal peptide and the mature protein, listed under the heading FCS location in Table IV), the locations of the nucleotides in SEQ ID NOs: 40–84 and 130–154 which encode the signal peptides (listed under the heading SigPep Location in Table IV), the locations of the nucleotides in SEQ ID NOs: 40–84 and 130–154 which encode the mature proteins generated by cleavage of the signal peptides (listed under the heading Mature Polypeptide Location in Table IV), the locations in SEQ ID NOs: 40–84 and 130–154 of stop codons (listed under the heading Stop Codon Location in Table IV) the locations in SEQ ID NOs: 40–84 and 130–154 of polyA signals (listed under the heading g PolyA Signal Location in Table IV) and the locations of polyA sites (listed under the heading PolyA Site Location in Table IV).

As discussed above, Table V lists the sequence identification numbers of the polypeptides of SEQ ID NOs: 85–129 and 155–179, the locations of the amino acid residues of SEQ ID NOs: 85–129 and 155–179 in the full length polypeptide (second column), the locations of the amino acid residues of SEQ ID NOs: 85–129 and 155–179 in the signal peptides (third column), and the locations of the amino acid residues of SEQ ID NOs: 85–129 and 155–179 in the mature polypeptide created by cleaving the signal peptide from the full length polypeptide (fourth column). In Table V, and in the appended sequence listing, the first amino acid of the mature protein resulting from cleavage of the signal peptide is designated as amino acid number 1 and the first amino acid of the signal peptide is designated with the appropriate negative number, in accordance with the regulations governing sequence listings.

Example 64

Functional Analysis of Predicted Protein Sequences

Following double-sequencing, new contigs were assembled for each of the extended cDNAs of the present invention and each was compared to known sequences available at the time of filing. These sequences originate from the following databases Genbank (release 108 and daily releases up to Oct. 15, 1998), Genseq (release 32) PIR (release 53) and Swissprot (release 35). The predicted proteins of the present invention matching known proteins were further classified into 3 categories depending on the level of homology.

The first category contains proteins of the present invention exhibiting more than 80% identical amino acid residues on the whole length of the matched protein. They are clearly close homologues which most probably have the same function or a very similar function as the matched protein.

The second category contains proteins of the present invention exhibiting more remote homologies (30 to 80% over the whole protein) indicating that the protein of the present invention is susceptible to have a function similar to the one of the matched protein.

The third category contains proteins exhibiting either high homology (90 to 100%) to a short domain or more remote homology (40 to 60%) to a larger domain of a known protein indicating that the matched protein and the protein of the invention may share similar features.

It should be noted that the numbering of amino acids in the protein sequences discussed in FIGS. 10 to 12, and Table VIII, the first methionine encountered is designated as amino acid number 1. In the appended sequence listing, the first amino acid of the mature protein resulting from cleavage of the signal peptide is designated as amino acid number 1 and the first amino acid of the signal peptide is designated with the appropriate negative number, in accordance with the regulations governing sequence listings.

In addition, all of the corrected amino acid sequences (SEQ ID NOs: 85–129 and 155–179) were scanned for the presence of known protein signatures and motifs. This search was performed against the Prosite 15.0 database, using the Proscan software from the GCG package. Functional signatures and their locations are indicated in Table VIII.

A) Proteins Which are Closely Related to Known Proteins
Protein of SEQ ID NO: 120 (Internal Designation 26-44-1-B5-CL3 1)

The protein of SEQ ID NO: 120 encoded by the extended cDNA SEQ ID NO: 75 isolated from ovary shows extensive homology to a human protein called phospholemman or PLM and its homologues in rodent and canine species. PLM is encoded by the nucleic acid sequence of Genbank accession number U72245 and has the amino acid sequence of SEQ ID NO: 180. Phospholemman is a prominent plasma membrane protein whose phosphorylation correlates with an increase in contractility of myocardium and skeletal muscle. Initially described as a simple chloride channel, it has recently been shown to be a channel for taurine that acts as an osmolyte in the regulation of cell volume (Moorman et al, *Adv Exp. Med. Biol.*, 442:219–228 (1998)).

As shown by the alignment in FIG. 10 between tha protein of SEQ ID NO: 120 and PLM, the amino acid residues are identical except for positions 3 and 5 in the 92 amino acid long matched protein. The substitution of a proline residue at position 3 par another neutral residue, serine, is conservative. In addition, the protein of the invention also exhibits the typical ATP1G /PLM/MAT8 PROSITE signature (position 27 to 40 in bold in FIG. 10) for a family containing mostly proteins known to be either chloride channels or chloride channel regulators In addition, the protein of invention contains 2 short transmembrane segments from positions 1 to 21 and from 37 to 57 as predicted by the software TopPred II (Claros and von Heijne, CABIOS applic. Notes, 10:685–686 (1994)). The first segment (in italic) corresponds to the signal peptide of PLM and the second transmembrane domains (underlined) matches the transmembrane region (double-underlined) shown to be the chloride channel itself (Chen et al., Circ. Res., 82:367–374 (1998)).

Taken together, these data suggest that the protein of SEQ ID NO: 120 may be involved in the regulation of cell volume and in tissue contractility. Thus, this protein may be useful in diagnosing and/or treating several types of disorders including, but not limited to, cancer, diarrhea, fertility disorders, and in contractility disorders including muscle disorders, pulmonary disorders and myocardial disorders.

Proteins of SEQ ID NOs: 121 (Internal Designation 47-4-4-C6-CL2 3)

The protein of SEQ ID NO: 121 encoded by the extended cDNA SEQ ID NO: 76 found in substantia nigra shows extensive homology with the human E25 protein. The E25 protein is encoded by the nucleic acid sequence of Genbank accession number AF038953 and has the amino acid sequence of SEQ ID NO: 181. The matched protein might be involved in the development and differentiation of haematopoietic stem/progenitor cells. In addition, it is the human homologue of a murine protein thought to be involved in chondro-osteogenic differentiation and belonging to a novel multigene family of integral membrane proteins (Deleersnijder et al, J. Biol. Chem., 271:19475–19482 (1996)).

As shown by the alignments in FIG. 11 between the protein of SEQ ID NO:121 and E25, the amino acid residues are identical except for positions 9, 24 and 121 in the 263 amino acid long matched sequence. All these substitutions are conservative. In addition, the protein of invention contains one short transmembrane segment from positions 1 to 21 (underlined in FIG. 11) matching the one predicted for the murine E25 protein as predicted by the software TopPred II (Claros and von Heijne, CABIOS applic. Notes, 10:685–686 (1994)).

Taken together, these data suggest that the protein of SEQ ID NO: 121 may be involved in cellular proliferation and differentiation, and/or in haematopoiesis. Thus, this protein may be useful in diagnosing and/or treating several types of disorders including, but not limited to, cancer, hematological, chondro-osteogenic and embryogenetic disorders.

Proteins of SEQ ID NO: 128 (Internal Designation 58-34-2-H8-CL1 3)

The protein of SEQ ID NO: 128 encoded by the extended cDNA SEQ ID NO: 83 isolated from kidney shows extensive homology to the murine WW-domain binding protein 1 or WWBP-1. WWBP-1 is encoded by the nucleic acid sequence of Genbank accession number U40825 and has the amino acid sequence of SEQ ID NO: 182. This protein is expressed in placenta, lung, liver and kidney is thought to play a role in intracellular signaling by binding to the WW domain of the Yes protooncogene-associated protein via its so-called PY domain (Chen and Sudol, Proc. Natl. Acad. Sci., 92:7819–7823 (1995)). The WW—PY domains are thought to represent a new set of modular protein-binding sequences just like the SH3—PXXP domains (Sudol et al., FEBS Lett., 369 :67–71 (1995)).

As shown by the alignments of FIG. 12 between the protein of SEQ ID NO:128 and WWBP-1, the amino acid residues are identical to those of the 305 amino acid long matched protein except for positions 53, 66, 78, 89, 92, 94, 96, 100, 102, 106, 110, 113, 124, 128, 136, 139, 140, 142–144, 166, 168, 173, 176, 178, 181, 182, 188, 196, 199, 201, 202, 207 and 210 of the matched protein. 68% of these substitutions are conservative. Indeed the histidine-rich PY domain is present in the protein of the invention (positions 82–86 in bold in FIG. 12).

Taken together, these data suggest that the protein of SEQ ID NO: 128 may play a role in intracellular signaling. Thus, this protein may be useful in diagnosing and/or treating several types of disorders including, but not limited to, cancer, neurodegenerative diseases, cardiovascular disorders, hypertension, renal injury and repair and septic shock.

B) Proteins Which are Remotely Related to Proteins with Known Functions

Protein of SEQ ID NO: 97 (Internal Designation 108-004-5-0-G6-FL)

The protein SEQ ID NO: 97 found in liver encoded by the extended cDNA SEQ ID NO: 52 shows homology to a lectin-like oxidized LDL receptor (LOX-1) found in human, bovine and murine species. Such type 11 proteins with a C-lectin-like domain, expressed in vascular endothelium and vascular-rich organs, bind and internalize oxidatively modified low-density lipoproteins (Sawamura et al, Nature, 386:73–77, (1997)). The oxidized lipoproteins have been implicated in the pathogenesis of atherosclerosis, a leading cause of death in industrialized countries (see review by Parthasarathy et al, Biochem. Pharmacol. 56:279–284 (1998)). In addition, type II membrane proteins with a C-terminus C-type lectin domain, also known as carbohydrate-recognition domains, also include proteins involved in target-cell recognition and cell activation.

The protein of invention has the typical structure of a type II protein belonging to the C-type lectin family. Indeed, it contains a short 31 -amino-acid-long N-terminal tail, a transmembrane segment from positions 32 to 52 matching the one predicted for human LOX-1 and a large 177-amino-acid-long C-terminal tail as predicted by the software Top-Pred II (Claros and von Heijne, CABIOS applic. Notes, 10:685–686 (1994)). All six cysteines of LOX-1 C-type lectin domain are also conserved in the protein of the invention (positions 102, 113, 130, 195, 208 and 216) although the characteristic PROSITE signature of this family is not. The LOX-1 protein is encoded by the nucleic acid sequence of Genbank accession number: AB010710.

Taken together, these data suggest that the protein of SEQ ID NO: 97 may be involved in the metabolism of lipids and/or in cell-cell or cell-matrix interactions and/or in cell activation. Thus, this protein or part therein, may be useful in diagnosing and treating several disorders including, but not limited to, cancer, hyperlipidaemia, cardiovascular disorders and neurodegenerative disorders.

Protein of SEQ ID NO: 111 (Internal Designation 108-008-5-0-G12-FL)

The protein SEQ ID NO: 111 encoded by the extended cDNA SEQ ID NO:66 shows homology to a mitochondrial protein found in Saccharomyces Cerevisiae (PIR:S72254) which is similar to E. Coli ribosomal protein L36. The typical PROSITE signature for ribosomal L36 is present in the protein of the invention (positions 76–102) except for a substitution of a tryptophane residue instead of a valine, leucine, isoleucine, methionine or asparagine residue.

Taken together, these data suggest that the protein of SEQ ID NO: 111 may be involved in protein biosynthesis. Thus, this protein may be useful in diagnosing and/or treating several types of disorders including, but not limited to, cancer.

Protein of SEQ ID NO: 94 (Internal Designation 108-004-5-0-D10-FL)

The protein SEQ ID NO: 94 encoded by the extended cDNA SEQ ID NO: 49 shows remote homology to a subfamily of beta4-galactosyltransferases widely conserved in animals (human, rodents, cow and chicken). Such enzymes, usually type II membrane proteins located in the endoplasmic reticulum or in the Golgi apparatus, catalyzes the biosynthesis of glycoproteins, glycolipid glycans and lactose. Their characteristic features defined as those of subfamily A in Breton et cil, *J. Biochem.*, 123:1000–1009 (1998) are pretty well conserved in the protein of the invention, especially the region I containing the DVD motif (positions 163–165) thought to be involved either in UDP binding or in the catalytic process itself.

In addition, the protein of invention has the typical structure of a type II protein. Indeed, it contains a short 28-amino-acid-long N-terminal tail, a transmembrane segment from positions 29 to 49 and a large 278-amino-acid-long C-terminal tail as predicted by the software TopPred II (Claros and von Heijne, *CABIOS applic. Notes*, 10:685–686 (1994)).

Taken together, these data suggest that the protein of SEQ ID NO: 94 may play a role in the biosynthesis of polysaccharides, and of the carbohydrate moieties of glycoproteins and glycolipids and/or in cell-cell recognition. Thus, this protein may be useful in diagnosing and/or treating several types of disorders including, but not limited to, cancer, atherosclerosis, cardiovascular disorders, autoimmune disorders and rheumatic diseases including rheumatoid arthritis.

Protein of SEQ ID NO: 104 (Internal Designation 108-006-5-0-G2-FL)

The protein of SEQ ID NO: 104 encoded by the extended cDNA SEQ ID NO: 59 shows homology to a neuronal murine protein NP15.6 whose expression is developmentally regulated. NP15.6 protein is encoded by the nucleic acid sequence of Genbank accession number Y08702.

Taken together, these data suggest that the protein of SEQ ID NO: 104 may be involved in cellular proliferation and differentiation. Thus, this protein may be useful in diagnosing and/or treating several types of disorders including, but not limited to, cancer, neurodegenerative disorders and embryogenetic disorders.

C) Proteins Homologous to a Domain of a Protein with known Function

Protein of SEQ ID NO: 113 (Internal Designation 108-009-5-0-A2-FL)

The protein of SEQ ID NO: 113 encoded by the extended cDNA SEQ ID NO: 68 shows extensive homology to the bZIP family of transcription factors, and especially to the human luman protein. (Lu et al., *Mol. Cell. Biol.*, 17:5117–5126 (1997)). The human luman protein is encoded by the nucleic acid sequence of Genbank accession number: AF009368. The match include the whole bZIP domain composed of a basic DNA-binding domain and of a leucine zipper allowing protein dimerization. The basic domain is conserved in the protein of the invention as shown by the characteristic PROSITE signature (positions 224–237) except for a conservative substitution of a glutamic acid with an aspartic acid in position 233. The typical PROSITE signature for leucine zipper is also present (positions 259 to 280). Secreted proteins may have nucleic acid binding domain as shown by a nematode protein thought to regulate gene expression which exhibits zinc fingers as well as a functional signal peptide (Holst and Zipfel, *J. Biol. Chem.*, 27116275–16733, 1996).

Taken together, these data suggest that the protein of SEQ ID NO: 113 may bind to DNA, hence regulating gene expression as a transcription factor. Thus, this protein may be useful in diagnosing and/or treating several types of disorders including, but not limited to, cancer.

Proteins of SEQ ID NO: 129 (Internal Designation 76-13-3-A9-CL1 1)

The protein of SEQ ID NO: 129 encoded by the extended cDNA SEQ ID NO: 84 shows homology with part of a human seven transmembrane protein. The human seven transmembrane protein is encoded by the nucleic acid sequence of Genbank accession number Y11395. The matched protein potentially associated to stomatin may act as a G-protein coupled receptor and is likely to be important for the signal transduction in neurons and haematopoietic cells (Mayer et al, *Biochem. Biophys. Acta.*, 1395:301–308 (1998)).

Taken together, these data suggest that the protein of SEQ ID NO: 129 may be involved in signal transduction. Thus, this protein may be useful in diagnosing and/or treating several types of disorders including, but not limited to, cancer, neurodegenerative diseases, cardiovascular disorders, hypertension, renal injury and repair and septic shock.

Proteins of SEQ ID NO: 95 (Internal Designation 108-004-5-0-E8-FL)

The protein of SEQ ID NO: 95 encoded by the extended cDNA SEQ ID NO: 50 exhibit the typical PROSITE signature for amino acid permeases (positions 5 to 66) which are integral membrane proteins involved in the transport of amino acids into the cell. In addition, the protein of invention has a transmembrane segment from positions 9 to 29 as predicted by the software TopPred II (Claros and von Heijne, *CABIOS applic. Notes*, 10:685–686 (1994)).

Taken together, these data suggest that the protein of SEQ ID NO: 95 may be involved in amino acid transport. Thus, this protein may be useful in diagnosing and/or treating several types of disorders including, but not limited to, cancer, aminoacidurias, neurodegenerative diseases, anorexia, chronic fatigue, coronary vascular disease, diphtheria, hypoglycemia, male infertility, muscular and myopathies.

As discussed above, the extended cDNAs of the present invention or portions thereof can be used for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support, including for examination for expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins or polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercializationas research products.

Methods for performing the uses listed above are well known to those skilled in the art. References disclosing such methods include without limitation "Molecular Cloning; A Laboratory Manual", 2d ed., Cole Spring Harbor Laboratory Press, Sambrook, J., E. F. Fritsch and T. Maniatis eds., 1989, and "Methods in Enzymology; Guide to Molecular Cloning Techniques", Academic Press, Berger, S. L. and A. R. Kimmel eds., 1987.

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE I

| SEQ ID NO. in Present Application | Provisional Application Disclosing Sequence | SEQ ID NO. in Provisional Application |
|---|---|---|
| 40 | U.S. Application No. 60/096,116, filed on August 10, 1998 | 40 |
| 41 | U.S. Application No. 60/096,116, filed on August 10, 1998 | 41 |
| 42 | U.S. Application No. 60/099,273, filed on September 4, 1998 | 62 |
| 43 | U.S. Application No. 60/099,273, filed on September 4, 1998 | 47 |
| 44 | U.S. Application No. 60/099,273, filed on September 4, 1998 | 43 |
| 45 | U.S. Application No. 60/096,116, filed on August 10, 1998 | 42 |
| 46 | U.S. Application No. 60/096,116, filed on August 10, 1998 | 43 |
| 47 | U.S. Application No. 60/099,273, filed on September 4, 1998 | 45 |
| 48 | U.S. Application No. 60/099,273, filed on September 4, 1998 | 44 |
| 49 | U.S. Application No. 60/099,273, filed on September 4, 1998 | 50 |
| 50 | U.S. Application No. 60/099,273, filed on September 4, 1998 | 49 |
| 51 | U.S. Application No. 60/096,116, filed on August 10, 1998 | 44 |
| 52 | U.S. Application No. 60/096,116, filed on August 10, 1998 | 45 |
| 53 | U.S. Application No. 60/096,116, filed on August 10, 1998 | 46 |
| 54 | U.S. Application No. 60/099,273, filed on September 4, 1998 | 51 |
| 55 | U.S. Application No. 60/099,273, filed on September 4, 1998 | 59 |
| 56 | U.S. Application No. 60/099,273, filed on September 4, 1998 | 61 |
| 57 | U.S. Application No. 60/099,273, filed on September 4, 1998 | 53 |
| 58 | U.S. Application No. 60/099,273, filed on September 4, 1998 | 52 |
| 59 | U.S. Application No. 60/099,273, filed on September 4, 1998 | 54 |
| 60 | U.S. Application No. 60/096,116, filed on August 10, 1998 | 47 |
| 61 | U.S. Application No. 60/099,273, filed on September 4, 1998 | 63 |
| 62 | U.S. Application No. 60/099,273, filed on September 4, 1998 | 46 |
| 63 | U.S. Application No. 60/096,116, filed on August 10, 1998 | 48 |
| 64 | U.S. Application No. 60/099,273, filed on September 4, 1998 | 58 |
| 65 | U.S. Application No. 60/099,273, filed on September 4, 1998 | 56 |
| 66 | U.S. Application No. 60/096,116, filed on August 10, 1998 | 49 |
| 67 | U.S. Application No. 60/099,273, filed on September 4, 1998 | 57 |
| 68 | U.S. Application No. 60/099,273, filed on September 4, 1998 | 55 |
| 69 | U.S. Application No. 60/099,273, filed on September 4, 1998 | 42 |
| 70 | U.S. Application No. 60/099,273, filed on September 4, 1998 | 41 |
| 71 | U.S. Application No. 60/099,273, filed on September 4, 1998 | 48 |
| 72 | U.S. Application No. 60/099,273, filed on September 4, 1998 | 60 |
| 73 | U.S. Application No. 60/096,116, filed on August 10, 1998 | 50 |
| 74 | U.S. Application No. 60/099,273, filed on September 4, 1998 | 40 |
| 75 | U.S. Application No. 60/074,121, filed on February 9, 1998 | 42 |
| 76 | U.S. Application No. 60/074,121, filed on February 9, 1998 | 56 |
| 77 | U.S. Application No. 60/074,121, filed on February 9, 1998 | 57 |
| 78 | U.S. Application No. 60/081,563, filed on April 13, 1998 | 84 |
| 79 | U.S. Application No. 60/081,563, filed on April 13, 1998 | 69 |

TABLE I-continued

| SEQ ID NO. in Present Application | Provisional Application Disclosing Sequence | SEQ ID NO. in Provisional Application |
|---|---|---|
| 80 | U.S. Application No. 60/074,121, filed on February 9, 1998 | 62 |
| 81 | U.S. Application No. 60/081,563, filed on April 13, 1998 | 79 |
| 82 | U.S. Application No. 60/074,121, filed on February 9, 1998 | 64 |
| 83 | U.S. Application No. 60/081,563, filed on April 13, 1998 | 51 |
| 84 | U.S. Application No. 60/074,121, filed on February 9, 1998 | 71 |
| 130 | U.S. Application No. 60/081,563, filed on April 13, 1998 | 40 |
| 131 | U.S. Application No. 60/081,563, filed on April 13, 1998 | 41 |
| 132 | U.S. Application No. 60/081,563, filed on April 13, 1998 | 42 |
| 133 | U.S. Application No. 60/081,563, filed on April 13, 1998 | 43 |
| 134 | U.S. Application No. 60/081,563, filed on April 13, 1998 | 44 |
| 135 | U.S. Application No. 60/081,563, filed on April 13, 1998 | 45 |
| 136 | U.S. Application No. 60/081,563, filed on April 13, 1998 | 46 |
| 137 | U.S. Application No. 60/081,563, filed on April 13, 1998 | 47 |
| 138 | U.S. Application No. 60/081,563, filed on April 13, 1998 | 48 |
| 139 | U.S. Application No. 60/081,563, filed on April 13, 1998 | 49 |
| 140 | U.S. Application No. 60/081,563, filed on April 13, 1998 | 50 |
| 141 | U.S. Application No. 60/081,563, filed on April 13, 1998 | 53 |
| 142 | U.S. Application No. 60/081,563, filed on April 13, 1998 | 54 |
| 143 | U.S. Application No. 60/081,563, filed on April 13, 1998 | 55 |
| 144 | U.S. Application No. 60/081,563, filed on April 13, 1998 | 56 |
| 145 | U.S. Application No. 60/081,563, filed on April 13, 1998 | 57 |
| 146 | U.S. Application No. 60/081,563, filed on April 13, 1998 | 58 |
| 147 | U.S. Application No. 60/081,563, filed on April 13, 1998 | 59 |
| 148 | U.S. Application No. 60/081,563, filed on April 13, 1998 | 60 |
| 149 | U.S. Application No. 60/081,563, filed on April 13, 1998 | 61 |
| 150 | U.S. Application No. 60/081,563, filed on April 13, 1998 | 62 |
| 151 | U.S. Application No. 60/081,563, filed on April 13, 1998 | 63 |
| 152 | U.S. Application No. 60/081,563, filed on April 13, 1998 | 64 |
| 153 | U.S. Application No. 60/081,563, filed on April 13, 1998 | 65 |
| 154 | U.S. Application No. 60/081,563, filed on April 13, 1998 | 66 |

TABLE II

Parameters used for each step of EST analysis

| Step | Search Characteristics | | | Selection Characteristics | |
|---|---|---|---|---|---|
| | Program | Strand | Parameters | Identity (%) | Length (bp) |
| Miscellaneous | Blastn | both | S = 61 X = 16 | 90 | 17 |
| tRNA | Fasta | both | — | 80 | 60 |
| rRNA | Blastn | both | S = 108 | 80 | 40 |
| mtRNA | Blastn | both | S = 108 | 80 | 40 |
| Procaryotic | Blastn | both | S = 144 | 90 | 40 |
| Fungal | Blastn | both | S = 144 | 90 | 40 |
| Alu | fasta* | both | — | 70 | 40 |
| L1 | Blastn | both | S = 72 | 70 | 40 |
| Repeats | Blastn | both | S = 72 | 70 | 40 |
| Promoters | Blastn | top | S = 54 X = 16 | 90 | 15† |
| Vertebrate | fasta* | both | S = 108 | 90 | 30 |
| ESTs | Blatsn | both | S = 108 X = 16 | 90 | 30 |
| Proteins | blastx☆ | top | E = 0.001 | — | — |

*use "Quick Fast" Database Scanner
† alignment further constrained to begin closer than 10bp to EST&5' end
☆ using BLOSUM62 substitution matrix

TABLE III

Parameters used for each step of extended cDNA analysis

| | Search characteristics | | | Selection characteristics | | |
|---|---|---|---|---|---|---|
| Step | Program | Strand | Parameters | Identity (%) | Length (bp) | Comments |
| miscellaneous* | FASTA | both | — | 90 | 15 | |
| tRNA$ | FASTA | both | — | 80 | 90 | |
| rRNA$ | BLASTN | both | S = 108 | 80 | 40 | |
| mtRNA$ | BLASTN | both | S = 108 | 80 | 40 | |
| Procaryotic$ | BLASTN | both | S = 144 | 90 | 40 | |
| Fungal* | BLASTN | both | S = 144 | 90 | 40 | |
| Alu* | BLASTN | both | S = 72 | 70 | 40 | max 5 matches, masking |
| L1$ | BLASTN | both | S = 72 | 70 | 40 | max 5 matches, masking |
| Repeats$ | BLASTN | both | S = 72 | 70 | 40 | masking |
| PolyA | BLAST2N | top | W = 6, 5 = 10, E = 1000 | 90 | 8 | in the last 20 nucleotides |
| Polyadenylation signal | — | top | AATAAA allowing 1 mismatch | | | in the 50 nucleotides preceding the 5' end of the polA |
| Vertibrate* | BLASTN then FASTA | both | — | 90 then 70 | 30 | first BLASTN and then FASTA on matching sequences |
| ESTs* | BLAST2N | both | — | 90 | 30 | |
| Geneseq | BLASTN | both | W = 8, B = 10 | 90 | 30 | |
| ORF | BLASTP | top | W = 8, B = 10 | — | — | on ORF proteins, max 10 matches |
| Proteins* | BLASTX | top | E = 0.001 | 70 | 30 | |

$steps common to EST analysis and using the same algorithms and parameters
*steps also used in EST analysis but with different algorithms and/or parameters

TABLE IV

| Id | FCS Location | SigPep Location | Mature Polypeptide Location | Stop Codon Location | PolyA Signal Location | PolyA Site Location |
|---|---|---|---|---|---|---|
| 40 | 35 through 568 | 35 through 100 | 101 through 568 | 569 | 667 through 672 | 685 through 699 |
| 41 | 68 through 337 | 68 through 124 | 125 through 337 | 338 | 462 through 467 | 482 through 497 |
| 42 | 39 through 413 | 39 through 83 | 84 through 413 | 414 | 566 through 571 | 583 through 598 |
| 43 | 235 through 642 | 235 through 336 | 337 through 642 | 643 | 1540 through 1545 | 1564 through 1579 |
| 44 | 42 through 755 | 42 through 200 | 201 through 755 | 756 | 860 through 865 | 878 through 893 |
| 45 | 23 through 340 | 23 through 235 | 236 through 340 | 341 | 611 through 616 | 629 through 644 |
| 46 | 12 through 380 | 12 through 263 | 264 through 380 | 381 | — | 523 through 538 |
| 47 | 8 through 232 | 8 through 154 | 155 through 232 | 233 | — | 737 through 752 |
| 48 | 183 through 422 | 183 through 302 | 303 through 422 | 423 | 505 through 510 | 523 through 537 |
| 49 | 24 through 1004 | 24 through 170 | 171 through 1004 | 1005 | — | 1586 through 1602 |
| 50 | 80 through 784 | 80 through 139 | 140 through 784 | 785 | 910 through 915 | 933 through 948 |
| 51 | 67 through 222 | 67 through 159 | 160 through 222 | 223 | — | 673 through 687 |
| 52 | 46 through 732 | 46 through 186 | 187 through 732 | 733 | 781 through 786 | 806 through 821 |
| 53 | 81 through 356 | 81 through 152 | 153 through 356 | 357 | 406 through 411 | 429 through 445 |
| 54 | 72 through 1346 | 72 through 140 | 141 through 1346 | 1347 | 1482 through 1487 | 1502 through 1517 |
| 55 | 194 through 454 | 194 through 379 | 380 through 454 | 455 | — | 1545 through 1560 |
| 56 | 48 through 494 | 48 through 347 | 348 through 494 | 495 | 1031 through 1036 | 1051 through 1066 |
| 57 | 111 through 671 | 111 through 215 | 216 through 671 | 672 | 990 through 995 | 1045 through 1061 |
| 58 | 5 through 373 | 5 through 82 | 83 through 373 | 374 | 1986 through 1991 | 2010 through 2025 |
| 59 | 14 through 472 | 14 through 319 | 320 through 472 | 473 | 555 through 560 | 576 through 591 |
| 60 | 2 through 217 | — | 2 through 217 | 218 | 489 through 494 | 529 through 544 |
| 61 | 51 through 575 | 51 through 110 | 111 through 575 | 576 | 1653 through 1658 | 1674 through 1689 |
| 62 | 69 through 977 | 69 through 128 | 129 through 977 | 978 | 1676 through 1081 | 1096 through 1111 |
| 63 | 44 through 238 | 44 through 160 | 161 through 238 | 239 | 443 through 448 | 540 through 554 |
| 64 | 114 through 524 | 114 through 164 | 165 through 524 | 525 | 1739 through 1744 | 1758 through 1773 |
| 65 | 26 through 487 | 26 through 64 | 65 through 487 | 488 | 883 through 888 | 901 through 917 |
| 66 | 80 through 388 | 80 through 187 | 188 through 388 | 389 | 609 through 614 | 627 through 641 |
| 67 | 186 through 443 | 186 through 407 | 408 through 443 | 444 | 827 through 832 | 839 through 854 |
| 68 | 75 through 1259 | 75 through 1004 | 1005 through 1259 | 1260 | 1536 through 1541 | 1553 through 1568 |
| 69 | 98 through 376 | 98 through 151 | 152 through 376 | 377 | 471 through 476 | 491 through 506 |
| 70 | 72 through 254 | 72 through 134 | 135 through 254 | 255 | 506 through 511 | 528 through 542 |
| 71 | 148 through 1140 | 148 through 240 | 241 through 1140 | 1141 | 1590 through 1595 | 1614 through 1629 |
| 72 | 109 through 738 | 109 through 405 | 406 through 738 | 739 | 1633 through 1638 | 1650 through 1665 |
| 73 | 55 through 291 | 55 through 255 | 256 through 291 | 292 | 390 through 395 | 410 through 425 |
| 74 | 25 through 276 | — | 25 through 276 | 277 | 508 through 513 | 533 through 546 |
| 75 | 32 through 307 | 32 through 91 | 92 through 307 | 308 | 452 through 457 | 472 through 485 |
| 76 | 46 through 675 | 46 through 87 | 88 through 675 | 676 | 1363 through 1368 | 1382 through 1394 |

TABLE IV-continued

| Id | FCS Location | SigPep Location | Mature Polypeptide Location | Stop Codon Location | PolyA Signal Location | PolyA Site Location |
|---|---|---|---|---|---|---|
| 77 | 329 through 943 | 329 through 745 | 746 through 943 | 944 | — | 1322 through 1333 |
| 78 | 27 through 281 | 27 through 77 | 78 through 281 | 282 | — | — |
| 79 | 61 through 405 | 61 through 213 | 214 through 405 | 406 | 675 through 680 | 692 through 703 |
| 80 | 137 through 379 | 137 through 229 | 230 through 379 | 380 | 728 through 733 | 755 through 768 |
| 81 | 37 through 741 | 37 through 153 | 154 through 741 | 742 | 969 through 974 | 994 through 1007 |
| 82 | 80 through 265 | 80 through 142 | 143 through 265 | 266 | 491 through 496 | 517 through 527 |
| 83 | 612 through 644 | — | 612 through 644 | 645 | 829 through 834 | 850 through 861 |
| 84 | 61 through 228 | 61 through 162 | 163 through 228 | 229 | 208 through 213 | — |
| 130 | 15 through 311 | 15 through 110 | 111 through 311 | 312 | 507 through 512 | 531 through 542 |
| 131 | 50 through 529 | 50 through 130 | 131 through 529 | 530 | 877 through 882 | 899 through 909 |
| 132 | 240 through 416 | 240 through 305 | 306 through 416 | 417 | 1117 through 1122 | 1139 through 1149 |
| 133 | 111 through 446 | 111 through 254 | 255 through 446 | 447 | 890 through 895 | 909 through 921 |
| 134 | 123 through 455 | 123 through 290 | 291 through 455 | 456 | 886 through 891 | 904 through 916 |
| 135 | 2 through 433 | 2 through 232 | 233 through 433 | 434 | 488 through 493 | 510 through 520 |
| 136 | 34 through 363 | 34 through 87 | 58 through 363 | 364 | 536 through 541 | 558 through 568 |
| 137 | 50 through 286 | 50 through 157 | 158 through 286 | 287 | 385 through 390 | 405 through 416 |
| 138 | 50 through 637 | 50 through 151 | 152 through 637 | 638 | — | 1277 through 1289 |
| 139 | 72 through 602 | 72 through 125 | 126 through 602 | 603 | — | 704 through 715 |
| 140 | 120 through 434 | 120 through 185 | 186 through 434 | 435 | 899 through 904 | 918 through 931 |
| 141 | 4 through 447 | 4 through 147 | 148 through 447 | 448 | 858 through 863 | 880 through 891 |
| 142 | 28 through 804 | 28 through 96 | 97 through 804 | 805 | — | 806 through 817 |
| 143 | 27 through 359 | 27 through 212 | 213 through 359 | 360 | 988 through 993 | 1009 through 1020 |
| 144 | 25 through 957 | 25 through 93 | 94 through 957 | 958 | 1368 through 1373 | 1388 through 1399 |
| 145 | 47 through 319 | 47 through 226 | 227 through 319 | 320 | — | 656 through 666 |
| 146 | 80 through 940 | 80 through 130 | 131 through 940 | 941 | 1101 through 1106 | 1119 through 1130 |
| 147 | 146 through 457 | 146 through 292 | 293 through 457 | 458 | 442 through 447 | 465 through 475 |
| 148 | 100 through 351 | 100 through 207 | 208 through 351 | 352 | — | 940 through 949 |
| 149 | 177 through 569 | 177 through 236 | 237 through 569 | 570 | — | 931 through 939 |
| 150 | 67 through 459 | 67 through 135 | 136 through 459 | 460 | 856 through 861 | 875 through 887 |
| 151 | 65 through 1069 | 65 through 112 | 113 through 1069 | 1070 | 1978 through 1983 | 1999 through 2010 |
| 152 | 70 through 321 | 70 through 234 | 235 through 321 | 322 | 364 through 369 | 375 through 387 |
| 153 | 38 through 877 | 38 through 91 | 92 through 877 | 878 | 947 through 952 | 974 through 983 |
| 154 | 51 through 470 | 51 through 203 | 204 through 470 | 471 | 1585 through 1590 | 1604 through 1614 |

TABLE V

| Id | Full Length Polypeptide Location | Signal Peptide Location | Mature Polypeptide Location |
|---|---|---|---|
| 85 | −22 through 156 | −22 through −1 | 1 through 156 |
| 86 | −19 through 71 | −19 through −1 | 1 through 71 |
| 87 | −15 through 110 | −15 through −1 | 1 through 110 |
| 88 | −34 through 102 | −34 through −1 | 1 through 102 |
| 89 | −53 through 185 | −53 through −1 | 1 through 185 |
| 90 | −71 through 35 | −71 through −1 | 1 through 35 |
| 91 | −84 through 39 | −84 through −1 | 1 through 39 |
| 92 | −49 through 26 | −49 through −1 | 1 through 26 |
| 93 | −40 through 40 | −40 through −1 | 1 through 40 |
| 94 | −49 through 278 | −49 through −1 | 1 through 278 |
| 95 | −20 through 215 | −20 through −1 | 1 through 215 |
| 96 | −31 through 21 | −31 through −1 | 1 through 21 |
| 97 | −47 through 182 | −47 through −1 | 1 through 182 |
| 98 | −24 through 68 | −24 through −1 | 1 through 68 |
| 99 | −23 through 402 | −23 through −1 | 1 through 402 |
| 100 | −62 through 25 | −62 through −1 | 1 through 25 |
| 101 | −100 through 49 | −100 through −1 | 1 through 49 |
| 102 | −35 through 152 | −35 through −1 | 1 through 152 |
| 103 | −26 through 97 | −26 through −1 | 1 through 97 |
| 104 | −102 through 51 | −102 through −1 | 1 through 51 |
| 105 | 1 through 72 | — | 1 through 72 |
| 106 | −20 through 155 | −20 through −1 | 1 through 155 |
| 107 | −20 through 283 | −20 through −1 | 1 through 283 |
| 108 | −39 through 26 | −39 through −1 | 1 through 26 |
| 109 | −17 through 120 | −17 through −1 | 1 through 120 |
| 110 | −13 through 141 | −13 through −1 | 1 through 141 |
| 111 | −36 through 67 | −36 through −1 | 1 through 67 |
| 112 | −74 through 12 | −74 through −1 | 1 through 12 |
| 113 | −310 through 85 | −310 through −1 | 1 through 85 |
| 114 | −18 through 75 | −18 through −1 | 1 through 75 |
| 115 | −21 through 40 | −21 through −1 | 1 through 40 |
| 116 | −31 through 300 | −31 through −1 | 1 through 300 |
| 117 | −99 through 111 | −99 through −1 | 1 through 111 |
| 118 | −67 through 12 | −67 through −1 | 1 through 12 |
| 119 | 1 through 84 | — | 1 through 84 |
| 120 | −20 through 72 | −20 through −1 | 1 through 72 |
| 121 | −14 through 196 | −14 through −1 | 1 through 196 |
| 122 | −139 through 66 | −139 through −1 | 1 through 66 |
| 123 | −17 through 68 | −17 through −1 | 1 through 68 |
| 124 | −51 through 64 | −51 through −1 | 1 through 64 |
| 125 | −31 through 50 | −31 through −1 | 1 through 50 |
| 126 | −39 through 196 | −39 through −1 | 1 through 196 |
| 127 | −21 through 41 | −21 through −1 | 1 through 41 |
| 128 | 1 through 11 | — | 1 through 11 |
| 129 | −34 through 22 | −34 through −1 | 1 through 22 |
| 155 | −32 through 67 | −32 through −1 | 1 through 67 |
| 156 | −27 through 133 | −27 through −1 | 1 through 133 |
| 157 | −22 through 37 | −22 through −1 | 1 through 37 |
| 158 | −48 through 64 | −48 through −1 | 1 through 64 |
| 159 | −56 through 55 | −56 through −1 | 1 through 55 |
| 160 | −77 through 67 | −77 through −1 | 1 through 67 |
| 161 | −18 through 92 | −18 through −1 | 1 through 92 |
| 162 | −36 through 43 | −36 through −1 | 1 through 43 |
| 163 | −34 through 162 | −34 through −1 | 1 through 162 |
| 164 | −18 through 159 | −18 through −1 | 1 through 159 |
| 165 | −22 through 83 | −22 through −1 | 1 through 83 |
| 166 | −48 through 100 | −48 through −1 | 1 through 100 |
| 167 | −23 through 236 | −23 through −1 | 1 through 236 |
| 168 | −62 through 49 | −62 through −1 | 1 through 49 |
| 169 | −23 through 288 | −23 through −1 | 1 through 288 |
| 170 | −60 through 31 | −60 through −1 | 1 through 31 |
| 171 | −17 through 270 | −17 through −1 | 1 through 270 |

TABLE V-continued

| Id | Full Length Polypeptide Location | Signal Peptide Location | Mature Polypeptide Location |
|---|---|---|---|
| 172 | −49 through 55 | −49 through −1 | 1 through 55 |
| 173 | −36 through 48 | −36 through −1 | 1 through 48 |
| 174 | −20 through 111 | −20 through −1 | 1 through 111 |
| 175 | −23 through 108 | −23 through −1 | 1 through 108 |
| 176 | −16 through 319 | −16 through −1 | 1 through 319 |
| 177 | −55 through 29 | −55 through −1 | 1 through 29 |
| 178 | −18 through 262 | −18 through −1 | 1 through 262 |
| 179 | −51 through 89 | −51 through −1 | 1 through 89 |

TABLE VI

| Id | Collection refs | Deposit Name |
|---|---|---|
| 40 | ATCC# 98921 | SignalTag 121–144 |
| 41 | ATCC# 98921 | SignalTag 121–144 |
| 42 | ATCC# 98919 | SignalTag 145–165 |
| 43 | ATCC# 98919 | SignalTag 145–165 |
| 44 | ATCC# 98919 | SignalTag 145–165 |
| 45 | ATCC# 98921 | SignalTag 121–144 |
| 46 | ATCC# 98921 | SignalTag 121–144 |
| 47 | ATCC# 98919 | SignalTag 145–165 |
| 48 | ATCC# 98919 | SignalTag 145–165 |
| 49 | ATCC# 98919 | SignalTag 145–165 |
| 50 | ATCC# 98919 | SignalTag 145–165 |
| 51 | ATCC# 98921 | SignalTag 121–144 |
| 52 | ATCC# 98921 | SignalTag 121–144 |
| 53 | ATCC# 98921 | SignalTag 121–144 |
| 54 | ATCC# 98919 | SignalTag 145–165 |
| 55 | ATCC# 98919 | SignalTag 145–165 |
| 56 | ATCC# 98919 | SignalTag 145–165 |
| 57 | ATCC# 98919 | SignalTag 145–165 |
| 58 | ATCC# 98919 | SignalTag 145–165 |
| 59 | ATCC# 98919 | SignalTag 145–165 |
| 60 | ATCC# 98921 | SignalTag 121–144 |
| 61 | ATCC# 98919 | SignalTag 145–165 |
| 62 | ATCC# 98919 | SignalTag 145–165 |
| 63 | ATCC# 98921 | SignalTag 121–144 |
| 64 | ATCC# 98919 | SignalTag 145–165 |
| 65 | ATCC# 98919 | SignalTag 145–165 |
| 66 | ATCC# 98921 | SignalTag 121–144 |
| 67 | ATCC# 98919 | SignalTag 145–165 |
| 68 | ATCC# 98919 | SignalTag 145–165 |
| 69 | ATCC# 98919 | SignalTag 145–165 |
| 70 | ATCC# 98919 | SignalTag 145–165 |
| 71 | ECACC# 99012901 | Signal Tag 28011 999 |
| 72 | ECACC# 99012901 | Signal Tag 28011 999 |
| 73 | ECACC# 99012901 | Signal Tag 28011 999 |
| 74 | ECACC# 99012901 | Signal Tag 28011 999 |
| 75 | ECACC# 99012901 | Signal Tag 28011 999 |
| 76 | ECACC# 99012901 | Signal Tag 28011 999 |
| 77 | ECACC# 99012901 | Signal Tag 28011 999 |
| 78 | ECACC# 99012901 | Signal Tag 28011 999 |
| 79 | ECACC# 99012901 | Signal Tag 28011 999 |
| 80 | ECACC# 99012901 | Signal Tag 28011 999 |
| 81 | ECACC# 99012901 | Signal Tag 28011 999 |
| 82 | ECACC# 99012901 | Signal Tag 28011 999 |
| 83 | ECACC# 99012901 | Signal Tag 28011 999 |
| 84 | ECACC# 99012901 | Signal Tag 28011 999 |

TABLE VII

| Internal designation | Id | Type of sequence |
|---|---|---|
| 108-002-5-0-B1-FL | 40 | DNA |
| 108-002-5-0-F3-FL | 41 | DNA |
| 108-002-5-0-F4-FL | 42 | DNA |
| 108-003-5-0-A8-FL | 43 | DNA |
| 108-003-5-0-D2-FL | 44 | DNA |
| 108-003-5-0-E5-FL | 45 | DNA |
| 108-003-5-0-H2-FL | 46 | DNA |
| 108-004-5-0-B7-FL | 47 | DNA |
| 108-004-5-0-C8-FL | 48 | DNA |
| 108-004-5-0-D10-FL | 49 | DNA |
| 108-004-5-0-E8-FL | 50 | DNA |
| 108-004-5-0-F5-FL | 51 | DNA |
| 108-004-5-0-G6-FL | 52 | DNA |
| 108-005-5-0-B11-FL | 53 | DNA |
| 108-005-5-0-C1-FL | 54 | DNA |
| 108-005-5-0-F11-FL | 55 | DNA |
| 108-005-5-0-F6-FL | 56 | DNA |
| 108-006-5-0-C2-FL | 57 | DNA |
| 108-006-5-0-E6-FL | 58 | DNA |
| 108-006-5-0-G2-FL | 59 | DNA |
| 108-006-5-0-G4-FL | 60 | DNA |
| 108-008-5-0-A6-FL | 61 | DNA |
| 108-008-5-0-A8-FL | 62 | DNA |
| 108-008-5-0-C10-FL | 63 | DNA |
| 108-008-5-0-E6-FL | 64 | DNA |
| 108-008-5-0-F6-FL | 65 | DNA |
| 108-008-5-0-G12-FL | 66 | DNA |
| 108-008-5-0-G4-FL | 67 | DNA |
| 108-009-5-0-A2-FL | 68 | DNA |
| 108-013-5-0-C12-FL | 69 | DNA |
| 108-013-5-0-G11-FL | 70 | DNA |
| 108-003-5-0-E4-FL | 71 | DNA |
| 108-005-5-0-D6-FL | 72 | DNA |
| 108-008-5-0-G3-FL | 73 | DNA |
| 108-013-5-0-B5-FL | 74 | DNA |
| 26-44-1-B5-CL3_1 | 75 | DNA |
| 47-4-4-C6-CL2_3 | 76 | DNA |
| 47-40-4-G9-CL1_1 | 77 | DNA |
| 48-25-4-D8-CL1_7 | 78 | DNA |
| 48-28-3-A9-CL0_1 | 79 | DNA |
| 51-25-1-A2-CL3_1 | 80 | DNA |
| 55-10-3-F5-CL0_3 | 81 | DNA |
| 57-19-2-G8-CL1_3 | 82 | DNA |
| 58-34-2-H8-CL1_3 | 83 | DNA |
| 76-13-3-A9-CL1_1 | 84 | DNA |
| 78-7-2-B8-FL1 | 130 | DNA |
| 77-8-4-F9-FL1 | 131 | DNA |
| 58-8-1-F2-FL2 | 132 | DNA |
| 77-13-1-A7-FL2 | 133 | DNA |
| 47-2-3-G9-FL1 | 134 | DNA |
| 33-75-4-R7-FL1 | 135 | DNA |
| 51-41-1-F10-FL1 | 136 | DNA |
| 48-51-4-C11-FL1 | 137 | DNA |
| 33-58-3-C8-FL1 | 138 | DNA |
| 76-20-4-C11-FL1 | 139 | DNA |
| 76-28-3-A12-FL1 | 140 | DNA |
| 76-25-4-F11-FL1 | 141 | DNA |
| 58-20-4-G7-FL1 | 142 | DNA |
| 33-54-1-B9-FL1 | 143 | DNA |
| 76-20-3-R1-FL1 | 144 | DNA |
| 47-20-2-G3-FL1 | 145 | DNA |
| 78-25-1-R11-FL1 | 146 | DNA |
| 78-6-2-B10-FL1 | 147 | DNA |
| 58-49-3-G10-FL1 | 148 | DNA |
| 78-21-1-B7-FL1 | 149 | DNA |
| 57-28-4-B12-FL1 | 150 | DNA |
| 33-77-4-E2-FL1 | 151 | DNA |
| 58-19-3-D3-FL2 | 152 | DNA |
| 37-7-4-E7-FL1 | 153 | DNA |
| 60-14-2-H10-FL1 | 154 | DNA |
| 108-002-5-0-B1-FL | 85 | PRT |
| 108-002-5-0-F3-FL | 86 | PRT |
| 108-002-5-0-F4-FL | 87 | PRT |
| 108-003-5-0-A8-FL | 88 | PRT |
| 108-003-5-0-D2-FL | 89 | PRT |
| 108-003-5-0-F5-FL | 90 | PRT |
| 108-003-5-0-R2-FL | 91 | PRT |
| 108-004-5-0-B7-FL | 92 | PRT |
| 108-004-5-0-C8-FL | 93 | PRT |
| 108-004-5-0-D10-FL | 94 | PRT |
| 108-004-5-0-E8-FL | 95 | PRT |
| 108-004-5-0-F5-FL | 96 | PRT |
| 108-004-5-0-G6-FL | 97 | PRT |
| 108-005-5-0-B11-FL | 98 | PRT |

TABLE VII-continued

| Internal designation | Id | Type of sequence |
| --- | --- | --- |
| 108-005-5-0-C1-FL | 99 | PRT |
| 108-005-5-0-F11-FL | 100 | PRT |
| 108-005-5-0-F6-FL | 101 | PRT |
| 108-006-5-0-C2-FL | 102 | PRT |
| 108-006-5-0-E6-FL | 103 | PRT |
| 108-006-5-0-G2-FL | 104 | PRT |
| 108-006-5-0-G4-FL | 105 | PRT |
| 108-008-5-0-A6-FL | 106 | PRT |
| 108-008-5-0-A8-FL | 107 | PRT |
| 108-008-5-0-C10-FL | 108 | PRT |
| 108-008-5-0-E6-FL | 109 | PRT |
| 108-008-5-0-F6-FL | 110 | PRT |
| 108-008-5-0-G12-FL | 111 | PRT |
| 108-008-5-0-G4-FL | 112 | PRT |
| 108-009-5-0-A2-FL | 113 | PRT |
| 108-013-5-0-C12-FL | 114 | PRT |
| 108-013-5-0-G11-FL | 115 | PRT |
| 108-003-5-0-E4-FL | 116 | PRT |
| 108-005-5-0-D6-FL | 117 | PRT |
| 108-008-5-0-G3-FL | 118 | PRT |
| 108-013-5-0-B5-FL | 119 | PRT |
| 26-44-1-B5-CL3_1 | 120 | PRT |
| 47-4-4-C6-CL2_3 | 121 | PRT |
| 47-40-4-G9-CL1_1 | 122 | PRT |
| 48-25-4-D8-CL1_7 | 123 | PRT |
| 48-28-3-A9-CL0_1 | 124 | PRT |
| 51-25-1-A2-CL3_1 | 125 | PRT |
| 55-10-3-F5-CL0_3 | 126 | PRT |
| 57-19-2-G8-CL1_3 | 127 | PRT |
| 58-34-2-R8-CL1_3 | 128 | PRT |
| 76-13-3-A9-CL1_1 | 129 | PRT |
| 78-7-2-B8-FL1 | 155 | PRT |
| 77-8-4-F9-FL1 | 156 | PRT |
| 58-8-1-F2-FL2 | 157 | PRT |
| 77-13-1-A7-FL2 | 158 | PRT |
| 47-2-3-G9-FL1 | 159 | PRT |

TABLE VII-continued

| Internal designation | Id | Type of sequence |
| --- | --- | --- |
| 33-75-4-H7-FL1 | 160 | PRT |
| 51-41-1-F10-FL1 | 161 | PRT |
| 48-51-4-C11-FL1 | 162 | PRT |
| 33-58-3-C8-FL1 | 163 | PRT |
| 76-20-4-C11-FL1 | 164 | PRT |
| 76-28-3-A12-FL1 | 165 | PRT |
| 76-25-4-F11-FL1 | 166 | PRT |
| 58-20-4-G7-FL1 | 167 | PRT |
| 33-54-1-B9-FL1 | 168 | PRT |
| 76-20-3-R1-FL1 | 169 | PRT |
| 47-20-2-G3-FL1 | 170 | PRT |
| 78-25-1-R11-FL1 | 171 | PRT |
| 78-6-2-B10-FL1 | 172 | PRT |
| 58-49-3-G10-FL1 | 173 | PRT |
| 78-21-1-B7-FL1 | 174 | PRT |
| 57-28-4-B12-FL1 | 175 | PRT |
| 33-77-4-E2-FL1 | 176 | PRT |
| 58-19-3-D3-FL2 | 177 | PRT |
| 37-7-4-E7-FL1 | 178 | PRT |
| 60-14-2-R10-FL1 | 179 | PRT |

TABLE VIII

| Id | Locations | PROSITE signature Name |
| --- | --- | --- |
| 89 | 205–226 | Leucine zipper |
| 95 | 5–66 | Amino acid permease |
| 103 | 46–67 | Leucine zipper |
| 113 | 259–280 | Leucine zipper |
| 120 | 27–40 | MAT8 family |
| 122 | 123–125 | Cell attachment sequence |

What is claimed is:

1. A composition comprising: a purified or isolated nucleic acid comprising the sequence of SEQ ID NO: 49 or a sequence complementary thereto.

2. A composition comprising: a purified or isolated nucleic acid comprising a fragment of SEQ ID NO: 49, wherein said fragment encodes a peptide, which exhibits galactosyltransferase activity.

3. A composition comprising: a purified or isolated nucleic acid comprising a sequence that encodes SEQ ID NO: 94 or a sequence complementary thereto.

4. A composition comprising: a purified or isolated nucleic acid, wherein said nucleic acid encodes a fragment of SEQ ID NO: 94 and wherein said fragment exhibits galactosyltransferase activity.

5. A composition comprising: a purified or isolated nucleic acid comprising a nucleotide sequence comprising nucleotides 24 through 1004 of SEQ ID NO: 49.

6. A composition comprising: a purified or isolated nucleic acid comprising a nucleotide sequence encoding a full-length polypeptide comprising the full-length polypeptide encoded by a human cDNA of clone 108-004-5-0-D10-FL, deposit name SignalTag 145-165, of ATCC deposit number 98919.

7. A composition comprising: a purified or isolated nucleic acid comprising a nucleotide sequence comprising nucleotides 24 through 170 of SEQ ID NO: 49.

8. A composition comprising: a purified or isolated nucleic acid comprising a nucleotide sequence encoding a signal peptide comprising the signal peptide encoded by a huinan cDNA of clone 108-004-5-0-D10-FL, deposit name SignalTag 145-165, of ATCC deposit number 98919.

9. A composition comprising: a purified or isolated nucleic acid comprising a nucleotide sequence comprising nucleotides 171 through 1004 of SEQ ID NO: 49.

10. A composition comprising: a purified or isolated nucleic acid comprising a nucleotide sequence encoding a mature polypeptide comprising the mature polypeptide encoded by a human cDNA of clone 108-004-5-0-D10-FL, deposit name SignalTag 145-165, of ATCC deposit number 98919.

11. A composition comprising: a host cell recombinant for a nucleic acid comprising a nucleotide sequence of SEQ ID NO: 49 or a complement thereto.

12. A composition comprising: a host cell recombinant for a nucleic acid comprising a nucleotide sequence encoding a full-length polypeptide comprising the full-length polypeptide encoded by a human cDNA of clone 108-004-5-0-D10-FL, deposit name SignalTag 145-165, of ATCC deposit number 98919.

13. A composition comprising: a host cell recombinant for a nucleic acid comprising a nucleotide sequence encoding a signal peptide comprising the signal peptide encoded by a human cDNA of clone 108-004-5-0-D10-FL, deposit name SignalTag 145-165 of ATCC deposit number 98919.

14. A composition comprising: a host cell recombinant for a nucleic acid comprising a nucleotide sequence encoding a mature polypeptide comprising the mature polypeptide encoded by a human cDNA of clone 108-004-5-0-D10-FL, deposit name SignalTag 145-165 of ATCC deposit number 98919.

15. A composition comprising: a host cell recombinant for a nucleic acid comprising a nucleotide sequence encoding a polypeptide comprising amino acid residues −49 through 278 of SEQ ID NO: 94.

16. A composition comprising: a host cell recombinant for a nucleic acid comprising a nucleotide sequence encoding a polypeptide comprising amino acid residues −49 through −1 of SEQ ID NO: 94.

17. A composition comprising; a host cell recombinant for a nucleic acid comprising a nucleotide sequence encoding a polypeptide comprising amino acid residues 1 through 278 of SEQ ID NO: 94.

18. A composition comprising: a purified or isolated recombinant vector comprising a nucleotide sequence of SEQ ID NO: 49 or a complement thereto.

19. A composition comprising: a purified or isolated recombinant vector comprising a nucleotide sequence encoding a full-length polypeptide comprising the full-length polypeptide encoded by a human cDNA of clone 108-004-5-0-D10-FL, deposit name SignalTag 145-165 of ATCC deposit number 98919.

20. A composition comprising: a purified or isolated recombinant vector comprising a nucleotide sequence encoding a signal peptide comprising the signal peptide encoded by a human cDNA of clone 108-004-5-0-D10-FL, deposit name SignalTag 145-165 of ATCC deposit number 98919.

21. A composition comprising: a purified or isolated recombinant vector comprising a nucleotide sequence encoding a mature polypeptide comprising the mature polypeptide encoded by a human cDNA of clone 108-004-5-0-D10-FL, deposit name SignalTag 145-165 of ATCC deposit number 98919.

22. A composition comprising: a host cell recombinant for a nucleic acid comprising a nucleotide sequence encoding a polypeptide comprising amino acid residues −49 through 278 of SEQ ID NO: 94.

23. A composition comprising: a purified or isolated recombinant vector comprising a nucleotide sequence encoding a polypeptide comprising amino acid residues −49 through −1 of SEQ ID NO: 94.

24. A composition comprising: a purified or isolated recombinant vector comprising a nucleotide sequence encoding a polypeptide comprising amino acid residues 1 through 278 of SEQ ID NO: 94.

25. A purified or isolated nucleic acid capable of hybridizing under stringent conditions to a nucleic acid comprising the nucleotide sequence of SEQ ID NO 49 or a fragment thereof, wherein said purified or isolated nucleic acid encodes a peptide that exhibits galactosyltransferase activity.

26. A composition comprising: a purified or isolated nucleic acid comprising a nucleotide sequence encoding a polypeptide comprising residues −49 through 278 of SEQ ID NO: 94.

27. A composition comprising: a purified or isolated nucleic acid comprising a nucleotide sequence encoding a polypeptide comprising residues −49 through −1 of SEQ ID NO: 94.

28. A composition comprising: a purified or isolated nucleic acid comprising a nucleotide sequence encoding a polypeptide comprising residues 1 through 278 of SEQ ID NO: 94.

29. A composition comprising: a host cell recombinant for a nucleic acid comprising a nucleotide sequence encoding an amino acid sequence comprising the amino acid sequence of SEQ ID NO: 94 or a complement thereof.

30. A composition comprising: a purified or isolated recombinant vector comprising a nucleotide sequence encoding an amino acid sequence of comprising the amino acid sequence of SEQ ID NO: 94 or a complement thereof.

31. A purified or isolated nucleic acid capable of hybridizing under stringent conditions to a nucleic acid comprising a nucleotide sequence that encodes the amino acid sequence of SEQ ID NO: 94 or a fragment thereof, wherein said purified or isolated nucleic acid encodes a polypeptide that exhibits galactosyltransferase activity.

32. A method of making a polypeptide comprising the mature amino acid sequence of SEQ ID NO: 94, wherein said method comprises the steps of:

(i) obtaining a cell capable of expressing said polypeptide, (ii) growing said cell under conditions suitable to produce said polypeptide; and (iii) isolating said polypeptide.

33. A method of making a polypeptide comprising a contiguous portion of amino acid sequence of SEQ ID NO: 94 having galactosyltransferase activity, wherein said method comprises the steps of:

(i) obtaining a cell capable of expressing said polypeptide;

(ii) growing said cell under conditions suitable to produce said polypeptide; and (iii) isolating said polypeptide.

* * * * *

SEQUENCE LISTING

<160> NUMBER OF SEQ ID NOS: 182

<210> SEQ ID NO 1
<211> LENGTH: 47
<212> TYPE: RNA
<213> ORGANISM: Artificial Sequence
<220> FEATURE:
<223> OTHER INFORMATION: in vitro transcription product
<220> FEATURE:
<221> NAME/KEY: modified_base
<222> LOCATION: 1
<223> OTHER INFORMATION: m7g

<400> SEQUENCE: 1
ggcauccuac ucccauccaa uuccacccua acuccuccca ucuccac         47

<210> SEQ ID NO 2
<211> LENGTH: 46
<212> TYPE: RNA
<213> ORGANISM: Artificial Sequence
<220> FEATURE:
<223> OTHER INFORMATION: in vitro transcription product

<400> SEQUENCE: 2
gcauccuacu cccauccaau uccacccuaa cuccucccau cuccac          46

<210> SEQ ID NO 3
<211> LENGTH: 25

```
<212> TYPE: DNA
<213> ORGANISM: Artificial Sequence
<220> FEATURE:
<223> OTHER INFORMATION: oligonucleotide

<400> SEQUENCE: 3
atcaagaatt cgcacgagac catta                                              25

<210> SEQ ID NO 4
<211> LENGTH: 25
<212> TYPE: DNA
<213> ORGANISM: Artificial Sequence
<220> FEATURE:
<223> OTHER INFORMATION: oligonucleotide

<400> SEQUENCE: 4
taatggtctc gtgcgaattc ttgat                                              25

<210> SEQ ID NO 5
<211> LENGTH: 25
<212> TYPE: DNA
<213> ORGANISM: Artificial Sequence
<220> FEATURE:
<223> OTHER INFORMATION: oligonucleotide

<400> SEQUENCE: 5
ccgacaagac caacgtcaag gccgc                                              25

<210> SEQ ID NO 6
<211> LENGTH: 25
<212> TYPE: DNA
<213> ORGANISM: Artificial Sequence
<220> FEATURE:
<223> OTHER INFORMATION: oligonucleotide

<400> SEQUENCE: 6
tcaccagcag gcagtggctt aggag                                              25

<210> SEQ ID NO 7
<211> LENGTH: 25
<212> TYPE: DNA
<213> ORGANISM: Artificial Sequence
<220> FEATURE:
<223> OTHER INFORMATION: oligonucleotide

<400> SEQUENCE: 7
agtgattcct gctactttgg atggc                                              25

<210> SEQ ID NO 8
<211> LENGTH: 25
<212> TYPE: DNA
<213> ORGANISM: Artificial Sequence
<220> FEATURE:
<223> OTHER INFORMATION: oligonucleotide

<400> SEQUENCE: 8
gcttggtctt gttctggagt ttaga                                              25

<210> SEQ ID NO 9
<211> LENGTH: 25
<212> TYPE: DNA
<213> ORGANISM: Artificial Sequence
<220> FEATURE:
<223> OTHER INFORMATION: oligonucleotide

<400> SEQUENCE: 9
```

-continued tccagaatgg gagacaagcc aattt                                       25

<210> SEQ ID NO 10
<211> LENGTH: 25
<212> TYPE: DNA
<213> ORGANISM: Artificial Sequence
<220> FEATURE:
<223> OTHER INFORMATION: oligonucleotide

<400> SEQUENCE: 10
agggaggagg aaacagcgtg agtcc                                       25

<210> SEQ ID NO 11
<211> LENGTH: 25
<212> TYPE: DNA
<213> ORGANISM: Artificial Sequence
<220> FEATURE:
<223> OTHER INFORMATION: oligonucleotide

<400> SEQUENCE: 11
atgggaaagg aaaagactca tatca                                       25

<210> SEQ ID NO 12
<211> LENGTH: 25
<212> TYPE: DNA
<213> ORGANISM: Artificial Sequence
<220> FEATURE:
<223> OTHER INFORMATION: oligonucleotide

<400> SEQUENCE: 12
agcagcaaca atcaggacag cacag                                       25

<210> SEQ ID NO 13
<211> LENGTH: 25
<212> TYPE: DNA
<213> ORGANISM: Artificial Sequence
<220> FEATURE:
<223> OTHER INFORMATION: oligonucleotide

<400> SEQUENCE: 13
atcaagaatt cgcacgagac catta                                       25

<210> SEQ ID NO 14
<211> LENGTH: 67
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: 67
<223> OTHER INFORMATION: n=a, g, c or t

<400> SEQUENCE: 14
atcgttgaga ctcgtaccag cagagtcacg agagagacta cacggtactg gttttttttt    60 tttttvn                                                           67

<210> SEQ ID NO 15
<211> LENGTH: 29
<212> TYPE: DNA
<213> ORGANISM: Artificial Sequence
<220> FEATURE:
<223> OTHER INFORMATION: oligonucleotide

<400> SEQUENCE: 15
ccagcagagt cacgagagag actacacgg                                   29

<210> SEQ ID NO 16
<211> LENGTH: 25
<212> TYPE: DNA
<213> ORGANISM: Artificial Sequence
<220> FEATURE:
<223> OTHER INFORMATION: oligonucleotide

<400> SEQUENCE: 16
cacgagagag actacacggt actgg    25

<210> SEQ ID NO 17
<211> LENGTH: 526
<212> TYPE: DNA
<213> ORGANISM: Homo Sapiens
<220> FEATURE:
<221> NAME/KEY: misc_feature
<222> LOCATION: complement(261..376)
<223> OTHER INFORMATION: blastn
<220> FEATURE:
<221> NAME/KEY: misc_feature
<222> LOCATION: complement(380..486)
<223> OTHER INFORMATION: blastn
<220> FEATURE:
<221> NAME/KEY: misc_feature
<222> LOCATION: complement(110..145)
<223> OTHER INFORMATION: blastn
<220> FEATURE:
<221> NAME/KEY: misc_feature
<222> LOCATION: complement(196..229)
<223> OTHER INFORMATION: blastn
<220> FEATURE:
<221> NAME/KEY: sig_peptide
<222> LOCATION: 90..140
<223> OTHER INFORMATION: Von Heijne matrix
<220> FEATURE:
<221> NAME/KEY: misc_feature
<222> LOCATION: 290
<223> OTHER INFORMATION: n=a, g, c or t

<400> SEQUENCE: 17
aatatrarac agctacaata ttccagggcc artcacttgc catttctcat aacagcgtca    60
gagagaaaga actgactgar acgtttgag atg aag aaa gtt ctc ctc ctg atc    113
                                Met Lys Lys Val Leu Leu Leu Ile
                                    -15              -10 aca gcc atc ttg gca gtg gct gtw ggt ttc cca gtc tct caa gac cag    161
Thr Ala Ile Leu Ala Val Ala Val Gly Phe Pro Val Ser Gln Asp Gln
            -5                  1               5 gaa cga gaa aaa aga agt atc agt gac agc gat gaa tta gct tca ggr    209
Glu Arg Glu Lys Arg Ser Ile Ser Asp Ser Asp Glu Leu Ala Ser Gly
        10                  15                  20 wtt ttt gtg ttc cct tac cca tat cca ttt cgc cca ctt cca cca att    257
Xaa Phe Val Phe Pro Tyr Pro Tyr Pro Phe Arg Pro Leu Pro Pro Ile
    25                  30                  35 cca ttt cca aga ttt cca tgg ttt aga cgt aan ttt cct att cca ata    305
Pro Phe Pro Arg Phe Pro Trp Phe Arg Arg Xaa Phe Pro Ile Pro Ile
40                  45                  50                  55 cct gaa tct gcc cct aca act ccc ctt cct agc gaa aag taaacaaraa    354
Pro Glu Ser Ala Pro Thr Thr Pro Leu Pro Ser Glu Lys
                60                  65 ggaaaagtca crataaacct ggtcacctga aattgaaatt gagccacttc cttgaaraat    414
caaaattcct gttaataaaa raaaaacaaa tgtaattgaa atagcacaca gcattctcta    474
gtcaatatct ttagtgatct tctttaataa acatgaaagc aaaaaaaaaa aa    526

<210> SEQ ID NO 18

```
<211> LENGTH: 17
<212> TYPE: PRT
<213> ORGANISM: Homo Sapiens
<220> FEATURE:
<221> NAME/KEY: SIGNAL
<222> LOCATION: 1..17
<223> OTHER INFORMATION: Von Heijne matrix
      score 8.2
      seq LLLITAILAVAVG/FP

<400> SEQUENCE: 18

Met Lys Lys Val Leu Leu Leu Ile Thr Ala Ile Leu Ala Val Ala Val
1               5                   10                  15
Gly

<210> SEQ ID NO 19
<211> LENGTH: 822
<212> TYPE: DNA
<213> ORGANISM: Homo Sapiens
<220> FEATURE:
<221> NAME/KEY: misc_feature
<222> LOCATION: 260..464
<223> OTHER INFORMATION: blastn
<220> FEATURE:
<221> NAME/KEY: misc_feature
<222> LOCATION: 118..184
<223> OTHER INFORMATION: blastn
<220> FEATURE:
<221> NAME/KEY: misc_feature
<222> LOCATION: 56..113
<223> OTHER INFORMATION: blastn
<220> FEATURE:
<221> NAME/KEY: misc_feature
<222> LOCATION: 454..485
<223> OTHER INFORMATION: blastn
<220> FEATURE:
<221> NAME/KEY: misc_feature
<222> LOCATION: 118..545
<223> OTHER INFORMATION: blastn
<220> FEATURE:
<221> NAME/KEY: misc_feature
<222> LOCATION: 65..369
<223> OTHER INFORMATION: blastn
<220> FEATURE:
<221> NAME/KEY: misc_feature
<222> LOCATION: 61..399
<223> OTHER INFORMATION: blastn
<220> FEATURE:
<221> NAME/KEY: misc_feature
<222> LOCATION: 408..458
<223> OTHER INFORMATION: blastn
<220> FEATURE:
<221> NAME/KEY: misc_feature
<222> LOCATION: 60..399
<223> OTHER INFORMATION: blastn
<220> FEATURE:
<221> NAME/KEY: misc_feature
<222> LOCATION: 393..432
<223> OTHER INFORMATION: blastn
<220> FEATURE:
<221> NAME/KEY: sig_peptide
<222> LOCATION: 346..408
<223> OTHER INFORMATION: Von Heijne matrix
<220> FEATURE:
<221> NAME/KEY: misc_feature
<222> LOCATION: 115
<223> OTHER INFORMATION: n=a, g, c or t

<400> SEQUENCE: 19 actccttta  gcatagggc   ttcggcgcca  gcggccagcg  ctagtcggtc  tggtaagtgc    60
ctgatgccga  gttccgtctc  tcgcgtcttt  tcctggtccc  aggcaaagcg  gasgnagatc  120
ctcaaacggc  ctagtgcttc  gcgcttccgg  agaaaatcag  cggtctaatt  aattcctctg  180
```

```
gtttgttgaa gcagttacca agaatcttca acccctttccc acaaaagcta attgagtaca       240
cgttcctgtt gagtacacgt tcctgttgat ttacaaaagg tgcaggtatg agcaggtctg       300
aagactaaca ttttgtgaag ttgtaaaaca gaaaacctgt agaa atg tgg tgg ttt       357
                                              Met Trp Trp Phe
                                                  -20 cag caa ggc ctc agt ttc ctt cct tca gcc ctt gta att tgg aca tct       405
Gln Gln Gly Leu Ser Phe Leu Pro Ser Ala Leu Val Ile Trp Thr Ser
        -15              -10                  -5 gct gct ttc ata ttt tca tac att act gca gta aca ctc cac cat ata       453
Ala Ala Phe Ile Phe Ser Tyr Ile Thr Ala Val Thr Leu His His Ile
  1           5                      10                      15 gac ccg gct tta cct tat atc agt gac act ggt aca gta gct cca raa       501
Asp Pro Ala Leu Pro Tyr Ile Ser Asp Thr Gly Thr Val Ala Pro Xaa
              20                  25                  30 aaa tgc tta ttt ggg gca atg cta aat att gcg gca gtt tta tgt caa       549
Lys Cys Leu Phe Gly Ala Met Leu Asn Ile Ala Ala Val Leu Cys Gln
              35                  40                  45 aaa tagaaatcag gaarataatt caacttaaag aakttcattt catgaccaaa              602
Lys ctcttcaraa acatgtcttt acaagcatat ctcttgtatt gctttctaca ctgttgaatt       662
gtctggcaat atttctgcag tggaaaattt gatttarmta gttcttgact gataaatatg       722
gtaaggtggg ctttttccccc tgtgtaattg gctactatgt cttactgagc caagttgtaw       782
tttgaaataa aatgatatga gagtgacaca aaaaaaaaaa                             822

<210> SEQ ID NO 20
<211> LENGTH: 21
<212> TYPE: PRT
<213> ORGANISM: Homo Sapiens
<220> FEATURE:
<221> NAME/KEY: SIGNAL
<222> LOCATION: 1..21
<223> OTHER INFORMATION: Von Heijne matrix
      score 5.5
      seq SFLPSALVIWTSA/AF

<400> SEQUENCE: 20

Met Trp Trp Phe Gln Gln Gly Leu Ser Phe Leu Pro Ser Ala Leu Val
1               5                   10                  15

Ile Trp Thr Ser Ala
            20

<210> SEQ ID NO 21
<211> LENGTH: 405
<212> TYPE: DNA
<213> ORGANISM: Homo Sapiens
<220> FEATURE:
<221> NAME/KEY: misc_feature
<222> LOCATION: complement(103..398)
<223> OTHER INFORMATION: blastn
<220> FEATURE:
<221> NAME/KEY: sig_peptide
<222> LOCATION: 185..295
<223> OTHER INFORMATION: Von Heijne matrix

<400> SEQUENCE: 21
atcaccttct tctccatcct tstctgggcc agtccccarc ccagtccctc tcctgacctg        60
cccagcccaa gtcagccttc agcacgcgct tttctgcaca cagatattcc aggcctacct       120
ggcattccag gacctccgma atgatgctcc agtcccttac aagcgcttcc tggatgaggg       180 tggc atg gtg ctg acc acc ctc ccc ttg ccc tct gcc aac agc cct gtg       229
     Met Val Leu Thr Thr Leu Pro Leu Pro Ser Ala Asn Ser Pro Val
```

|  |  |  |  |  |  |  |  |  |  |  |  |  |  |
|---|---|---|---|---|---|---|---|---|---|---|---|---|---|
|  |  | −35 |  |  |  | −30 |  |  |  | −25 |  |  |  |
| aac | atg | ccc | acc | act | ggc | ccc | aac | agc | ctg | agt | tat | gct | agc tct gcc |
| Asn | Met | Pro | Thr | Thr | Gly | Pro | Asn | Ser | Leu | Ser | Tyr | Ala | Ser Ser Ala |
|  | −20 |  |  |  |  | −15 |  |  |  | −10 |  |  |  |

277 ctg tcc ccc tgt ctg acc gct cca aak tcc ccc cgg ctt gct atg atg        325
Leu Ser Pro Cys Leu Thr Ala Pro Xaa Ser Pro Arg Leu Ala Met Met
    −5              1              5                      10 cct gac aac taaatatcct tatccaaatc aataaarwra raatcctccc                 374
Pro Asp Asn tccaraaggg tttctaaaaa caaaaaaaaa a                                      405

<210> SEQ ID NO 22
<211> LENGTH: 37
<212> TYPE: PRT
<213> ORGANISM: Homo Sapiens
<220> FEATURE:
<221> NAME/KEY: SIGNAL
<222> LOCATION: 1..37
<223> OTHER INFORMATION: Von Heijne matrix
      score 5.9
      seq LSYASSALSPCLT/AP

<400> SEQUENCE: 22

Met Val Leu Thr Thr Leu Pro Leu Pro Ser Ala Asn Ser Pro Val Asn
1               5                   10                  15

Met Pro Thr Thr Gly Pro Asn Ser Leu Ser Tyr Ala Ser Ser Ala Leu
            20                  25                  30

Ser Pro Cys Leu Thr
        35

<210> SEQ ID NO 23
<211> LENGTH: 496
<212> TYPE: DNA
<213> ORGANISM: Homo Sapiens
<220> FEATURE:
<221> NAME/KEY: misc_feature
<222> LOCATION: 149..331
<223> OTHER INFORMATION: blastn
<220> FEATURE:
<221> NAME/KEY: misc_feature
<222> LOCATION: 328..485
<223> OTHER INFORMATION: blastn
<220> FEATURE:
<221> NAME/KEY: misc_feature
<222> LOCATION: complement(182..496)
<223> OTHER INFORMATION: blastn
<220> FEATURE:
<221> NAME/KEY: sig_peptide
<222> LOCATION: 196..240
<223> OTHER INFORMATION: Von Heijne matrix
<220> FEATURE:
<221> NAME/KEY: misc_feature
<222> LOCATION: 101
<223> OTHER INFORMATION: n=a, g, c or t

<400> SEQUENCE: 23
aaaaaattgg tcccagtttt caccctgccg cagggctggc tggggagggc agcggtttag       60
attagccgtg gcctaggccg tttaacgggg tgacacgagc ntgcagggcc gagtccaagg      120
cccggagata ggaccaaccg tcaggaatgc gaggaatgtt tttcttcgga ctctatcgag      180
gcacacagac agacc atg ggg att ctg tct aca gtg aca gcc tta aca ttt       231
                Met Gly Ile Leu Ser Thr Val Thr Ala Leu Thr Phe
                    −15              −10                 −5 gcc ara gcc ctg gac ggc tgc aga aat ggc att gcc cac cct gca agt        279
Ala Xaa Ala Leu Asp Gly Cys Arg Asn Gly Ile Ala His Pro Ala Ser
        1               5                   10

```
gag aag cac aga ctc gag aaa tgt agg gaa ctc gag asc asc cac tcg       327
Glu Lys His Arg Leu Glu Lys Cys Arg Glu Leu Glu Xaa Xaa His Ser
     15                  20                  25 gcc cca gga tca acc cas cac cga aga aaa aca acc aga aga aat tat       375
Ala Pro Gly Ser Thr Xaa His Arg Arg Lys Thr Thr Arg Arg Asn Tyr
 30                  35                  40                  45 tct tca gcc tgaaatgaak ccgggatcaa atggttgctg atcaragccc                424
Ser Ser Ala atatttaaat tggaaaagtc aaattgasca ttattaaata aagcttgttt aatatgtctc      484
aaacaaaaaa aa                                                          496

<210> SEQ ID NO 24
<211> LENGTH: 15
<212> TYPE: PRT
<213> ORGANISM: Homo Sapiens
<220> FEATURE:
<221> NAME/KEY: SIGNAL
<222> LOCATION: 1..15
<223> OTHER INFORMATION: Von Heijne matrix
      score 5.5
      seq ILSTVTALTFAXA/LD
<220> FEATURE:
<221> NAME/KEY: UNSURE
<222> LOCATION: 14
<223> OTHER INFORMATION: Xaa = any one of the twenty amino acids

<400> SEQUENCE: 24

Met Gly Ile Leu Ser Thr Val Thr Ala Leu Thr Phe Ala Xaa Ala
 1               5                  10                  15

<210> SEQ ID NO 25
<211> LENGTH: 623
<212> TYPE: DNA
<213> ORGANISM: Homo Sapiens
<220> FEATURE:
<221> NAME/KEY: sig_peptide
<222> LOCATION: 49..96
<223> OTHER INFORMATION: Von Heijne matrix

<400> SEQUENCE: 25
aaagatccct gcagcccggc aggagagaag gctgagcctt ctggcgtc atg gag agg       57
                                                     Met Glu Arg
                                                         -15 ctc gtc cta acc ctg tgc acc ctc ccg ctg gct gtg gcg tct gct ggc       105
Leu Val Leu Thr Leu Cys Thr Leu Pro Leu Ala Val Ala Ser Ala Gly
         -10                  -5                   1 tgc gcc acg acg cca gct cgc aac ctg agc tgc tac cag tgc ttc aag       153
Cys Ala Thr Thr Pro Ala Arg Asn Leu Ser Cys Tyr Gln Cys Phe Lys
      5                  10                  15 gtc agc agc tgg acg gag tgc ccg ccc acc tgg tgc agc ccg ctg gac       201
Val Ser Ser Trp Thr Glu Cys Pro Pro Thr Trp Cys Ser Pro Leu Asp
 20                  25                  30                  35 caa gtc tgc atc tcc aac gag gtg gtc gtc tct ttt aaa tgg agt gta       249
Gln Val Cys Ile Ser Asn Glu Val Val Val Ser Phe Lys Trp Ser Val
                  40                  45                  50 cgc gtc ctg ctc agc aaa cgc tgt gct ccc aga tgt ccc aac gac aac       297
Arg Val Leu Leu Ser Lys Arg Cys Ala Pro Arg Cys Pro Asn Asp Asn
             55                  60                  65 atg aak ttc gaa tgg tcg ccg gcc ccc atg gtg caa ggc gtg atc acc       345
Met Xaa Phe Glu Trp Ser Pro Ala Pro Met Val Gln Gly Val Ile Thr
         70                  75                  80 agg cgc tgc tgt tcc tgg gct ctc tgc aac agg gca ctg acc cca cag       393
Arg Arg Cys Cys Ser Trp Ala Leu Cys Asn Arg Ala Leu Thr Pro Gln
```

-continued

```
                    85                      90                      95
gag  ggg  cgc  tgg  gcc  ctg  cra  ggg  ggg  ctc  ctg  ctc  cag  gac  cct  tcg       441
Glu  Gly  Arg  Trp  Ala  Leu  Xaa  Gly  Gly  Leu  Leu  Leu  Gln  Asp  Pro  Ser
100                      105                     110                     115 agg  ggc  ara  aaa  acc  tgg  gtg  cgg  cca  cag  ctg  ggg  ctc  cca  ctc  tgc       489
Arg  Gly  Xaa  Lys  Thr  Trp  Val  Arg  Pro  Gln  Leu  Gly  Leu  Pro  Leu  Cys
                    120                     125                     130 ctt  ccc  awt  tcc  aac  ccc  ctc  tgc  cca  rgg  gaa  acc  cag  gaa  gga            534
Leu  Pro  Xaa  Ser  Asn  Pro  Leu  Cys  Pro  Xaa  Glu  Thr  Gln  Glu  Gly
               135                      140                     145 taacactgtg ggtgccccca cctgtgcatt gggaccacra cttcaccctc ttggaracaa                    594
taaactctca tgcccccaaa aaaaaaaaa                                                      623
```

<210> SEQ ID NO 26
<211> LENGTH: 16
<212> TYPE: PRT
<213> ORGANISM: Homo Sapiens
<220> FEATURE:
<221> NAME/KEY: SIGNAL
<222> LOCATION: 1..16
<223> OTHER INFORMATION: Von Heijne matrix
      score 10.1
      seq LVLTLCTLPLAVA/SA

<400> SEQUENCE: 26

```
Met Glu Arg Leu Val Leu Thr Leu Cys Thr Leu Pro Leu Ala Val Ala
1               5                   10                  15
```

<210> SEQ ID NO 27
<211> LENGTH: 848
<212> TYPE: DNA
<213> ORGANISM: Homo Sapiens
<220> FEATURE:
<221> NAME/KEY: sig_peptide
<222> LOCATION: 32..73
<223> OTHER INFORMATION: Von Heijne matrix

<400> SEQUENCE: 27

```
aactttgcct tgtgttttcc accctgaaag a atg ttg tgg ctg ctc ttt ttt                       52
                                 Met Leu Trp Leu Leu Phe Phe
                                                    -10 ctg  gtg  act  gcc  att  cat  gct  gaa  ctc  tgt  caa  cca  ggt  gca  gaa  aat       100
Leu  Val  Thr  Ala  Ile  His  Ala  Glu  Leu  Cys  Gln  Pro  Gly  Ala  Glu  Asn
          -5                       1                    5 gct  ttt  aaa  gtg  aga  ctt  agt  atc  aga  aca  gct  ctg  gga  gat  aaa  gca       148
Ala  Phe  Lys  Val  Arg  Leu  Ser  Ile  Arg  Thr  Ala  Leu  Gly  Asp  Lys  Ala
10                       15                      20                      25 tat  gcc  tgg  gat  acc  aat  gaa  gaa  tac  ctc  ttc  aaa  gcg  atg  gta  gct       196
Tyr  Ala  Trp  Asp  Thr  Asn  Glu  Glu  Tyr  Leu  Phe  Lys  Ala  Met  Val  Ala
                    30                      35                      40 ttc  tcc  atg  aga  aaa  gtt  ccc  aac  aga  gaa  gca  aca  gaa  att  tcc  cat       244
Phe  Ser  Met  Arg  Lys  Val  Pro  Asn  Arg  Glu  Ala  Thr  Glu  Ile  Ser  His
               45                       50                      55 gtc  cta  ctt  tgc  aat  gta  acc  cag  agg  gta  tca  ttc  tgg  ttt  gtg  gtt       292
Val  Leu  Leu  Cys  Asn  Val  Thr  Gln  Arg  Val  Ser  Phe  Trp  Phe  Val  Val
               60                       65                      70 aca  gac  cct  tca  aaa  aat  cac  acc  ctt  cct  gct  gtt  gag  gtg  caa  tca       340
Thr  Asp  Pro  Ser  Lys  Asn  His  Thr  Leu  Pro  Ala  Val  Glu  Val  Gln  Ser
     75                       80                      85 gcc  ata  aga  atg  aac  aag  aac  cgg  atc  aac  aat  gcc  ttc  ttt  cta  aat       388
Ala  Ile  Arg  Met  Asn  Lys  Asn  Arg  Ile  Asn  Asn  Ala  Phe  Phe  Leu  Asn
90                       95                     100                      105
```

```
gac caa act ctg gaa ttt tta aaa atc cct tcc aca ctt gca cca ccc      436
Asp Gln Thr Leu Glu Phe Leu Lys Ile Pro Ser Thr Leu Ala Pro Pro
            110                 115                 120 atg gac cca tct gtg ccc atc tgg att att ata ttt ggt gtg ata ttt      484
Met Asp Pro Ser Val Pro Ile Trp Ile Ile Ile Phe Gly Val Ile Phe
            125                 130                 135 tgc atc atc ata gtt gca att gca cta ctg att tta tca ggg atc tgg      532
Cys Ile Ile Ile Val Ala Ile Ala Leu Leu Ile Leu Ser Gly Ile Trp
            140                 145                 150 caa cgt ada ara aag aac aaa gaa cca tct gaa gtg gat gac gct gaa      580
Gln Arg Xaa Xaa Lys Asn Lys Glu Pro Ser Glu Val Asp Asp Ala Glu
            155                 160                 165 rat aak tgt gaa aac atg atc aca att gaa aat ggc atc ccc tct gat      628
Xaa Xaa Cys Glu Asn Met Ile Thr Ile Glu Asn Gly Ile Pro Ser Asp
170             175                 180                 185 ccc ctg gac atg aag gga ggg cat att aat gat gcc ttc atg aca gag      676
Pro Leu Asp Met Lys Gly Gly His Ile Asn Asp Ala Phe Met Thr Glu
            190                 195                 200 gat gag agg ctc acc cct ctc tgaagggctg ttgttctgct tcctcaaraa         727
Asp Glu Arg Leu Thr Pro Leu
            205 attaaacatt tgtttctgtg tgactgctga gcatcctgaa ataccaagag cagatcatat    787 wttttgtttc accattcttc ttttgtaata aattttgaat gtgcttgaaa aaaaaaaaa     847 c                                                                    848

<210> SEQ ID NO 28
<211> LENGTH: 14
<212> TYPE: PRT
<213> ORGANISM: Homo Sapiens
<220> FEATURE:
<221> NAME/KEY: SIGNAL
<222> LOCATION: 1..14
<223> OTHER INFORMATION: Von Heijne matrix
      score 10.7
      seq LWLLFFLVTAIHA/EL

<400> SEQUENCE: 28

Met Leu Trp Leu Leu Phe Phe Leu Val Thr Ala Ile His Ala
1               5                   10

<210> SEQ ID NO 29
<211> LENGTH: 25
<212> TYPE: DNA
<213> ORGANISM: Artificial Sequence
<220> FEATURE:
<223> OTHER INFORMATION: oligonucleotide

<400> SEQUENCE: 29
gggaagatgg agatagtatt gcctg                                        25

<210> SEQ ID NO 30
<211> LENGTH: 26
<212> TYPE: DNA
<213> ORGANISM: Artificial Sequence
<220> FEATURE:
<223> OTHER INFORMATION: oligonucleotide

<400> SEQUENCE: 30
ctgccatgta catgatagag agattc                                          26

<210> SEQ ID NO 31
<211> LENGTH: 546
<212> TYPE: DNA
```

```
<213> ORGANISM: Homo Sapiens
<220> FEATURE:
<221> NAME/KEY: promoter
<222> LOCATION: 1..517
<220> FEATURE:
<223> OTHER INFORMATION: codon_start="518"
<220> FEATURE:
<221> NAME/KEY: protein_bind
<222> LOCATION: 17..25
<223> OTHER INFORMATION: matinspector prediction
      name CMYB_01
      score 0.983
      sequence tgtcagttg
<220> FEATURE:
<221> NAME/KEY: protein_bind
<222> LOCATION: complement(18..27)
<223> OTHER INFORMATION: matinspector prediction
      name MYOD_Q6
      score 0.961
      sequence cccaactgac
<220> FEATURE:
<221> NAME/KEY: protein_bind
<222> LOCATION: complement(75..85)
<223> OTHER INFORMATION: matinspector prediction
      name S8_01
      score 0.960
      sequence aatagaattag
<220> FEATURE:
<221> NAME/KEY: protein_bind
<222> LOCATION: 94..104
<223> OTHER INFORMATION: matinspector prediction
      name S8_01
      score 0.966
      sequence aactaaattag
<220> FEATURE:
<221> NAME/KEY: protein_bind
<222> LOCATION: complement(129..139)
<223> OTHER INFORMATION: matinspector prediction
      name DELTAEF1_01
      score 0.960
      sequence gcacacctcag
<220> FEATURE:
<221> NAME/KEY: protein_bind
<222> LOCATION: complement(155..165)
<223> OTHER INFORMATION: matinspector prediction
      name GATA_C
      score 0.964
      sequence agataaatcca
<220> FEATURE:
<221> NAME/KEY: protein_bind
<222> LOCATION: 170..178
<223> OTHER INFORMATION: matinspector prediction
      name CMYB_01
      score 0.958
      sequence cttcagttg
<220> FEATURE:
<221> NAME/KEY: protein_bind
<222> LOCATION: 176..189
<223> OTHER INFORMATION: matinspector prediction
      name GATA1_02
      score 0.959
      sequence ttgtagataggaca
<220> FEATURE:
<221> NAME/KEY: protein_bind
<222> LOCATION: 180..190
<223> OTHER INFORMATION: matinspector prediction
      name GATA_C
      score 0.953
      sequence agataggacat
<220> FEATURE:
<221> NAME/KEY: protein_bind
<222> LOCATION: 284..299
<223> OTHER INFORMATION: matinspector prediction
      name TAL1ALPHAE47_01
      score 0.973
      sequence cataacagatggtaag
<220> FEATURE:
<221> NAME/KEY: protein_bind
<222> LOCATION: 284..299
```

```
<223> OTHER INFORMATION: matinspector prediction
      name TAL1BETAE47_01
      score 0.983
      sequence cataacagatggtaag
<220> FEATURE:
<221> NAME/KEY: protein_bind
<222> LOCATION: 284..299
<223> OTHER INFORMATION: matinspector prediction
      name TAL1BETAITF2_01
      score 0.978
      sequence cataacagatggtaag
<220> FEATURE:
<221> NAME/KEY: protein_bind
<222> LOCATION: complement(287..296)
<223> OTHER INFORMATION: matinspector prediction
      name MYOD_Q6
      score 0.954
      sequence accatctgtt
<220> FEATURE:
<221> NAME/KEY: protein_bind
<222> LOCATION: complement(302..314)
<223> OTHER INFORMATION: matinspector prediction
      name GATA1_04
      score 0.953
      sequence tcaagataaagta
<220> FEATURE:
<221> NAME/KEY: protein_bind
<222> LOCATION: 393..405
<223> OTHER INFORMATION: matinspector prediction
      name IK1_01
      score 0.963
      sequence agttgggaattcc
<220> FEATURE:
<221> NAME/KEY: protein_bind
<222> LOCATION: 393..404
<223> OTHER INFORMATION: matinspector prediction
      name IK2_01
      score 0.985
      sequence agttgggaattc
<220> FEATURE:
<221> NAME/KEY: protein_bind
<222> LOCATION: 396..405
<223> OTHER INFORMATION: matinspector prediction
      name CREL_01
      score 0.962
      sequence tgggaattcc
<220> FEATURE:
<221> NAME/KEY: protein_bind
<222> LOCATION: 423..436
<223> OTHER INFORMATION: matinspector prediction
      name GATA1_02
      score 0.950
      sequence tcagtgatatggca
<220> FEATURE:
<221> NAME/KEY: protein_bind
<222> LOCATION: complement(478..489)
<223> OTHER INFORMATION: matinspector prediction
      name SRY_02
      score 0.951
      sequence taaaacaaaaca
<220> FEATURE:
<221> NAME/KEY: protein_bind
<222> LOCATION: 486..493
<223> OTHER INFORMATION: matinspector prediction
      name E2F_02
      score 0.957
      sequence tttagcgc
<220> FEATURE:
<221> NAME/KEY: protein_bind
<222> LOCATION: complement(514..521)
<223> OTHER INFORMATION: matinspector prediction
      name MZF1_01
      score 0.975
      sequence tgagggga

<400> SEQUENCE: 31
tgagtgcagt gttacatgtc agttgggtta agtttgttaa tgtcattcaa atcttctatg    60
```

```
tcttgatttg cctgctaatt ctattatttc tggaactaaa ttagtttgat ggttctatta    120
gttattgact gaggtgtgct aatctcccat tatgtggatt tatctatttc ttcagttgta    180
gataggacat tgatagatac ataagtacca ggacaaaagc agggagatct tttttccaaa    240
atcaggagaa aaaaatgaca tctggaaaac ctatagggaa aggcataaca gatggtaagg    300
atactttatc ttgagtagga gagccttcct gtggcaacgt ggagaaggga agaggtcgta    360
gaattgagga gtcagctcag ttagaagcag ggagttggga attccgttca tgtgatttag    420
catcagtgat atggcaaatg tgggactaag ggtagtgatc agagggttaa aattgtgtgt    480
tttgttttag cgctgctggg gcatcgcctt gggtcccctc aaacagattc ccatgaatct    540
cttcat                                                              546
```

```
<210> SEQ ID NO 32
<211> LENGTH: 23
<212> TYPE: DNA
<213> ORGANISM: Artificial Sequence
<220> FEATURE:
<223> OTHER INFORMATION: oligonucleotide

<400> SEQUENCE: 32
gtaccaggga ctgtgaccat tgc                                            23

<210> SEQ ID NO 33
<211> LENGTH: 24
<212> TYPE: DNA
<213> ORGANISM: Artificial Sequence
<220> FEATURE:
<223> OTHER INFORMATION: oligonucleotide

<400> SEQUENCE: 33
ctgtgaccat tgctcccaag agag                                           24

<210> SEQ ID NO 34
<211> LENGTH: 861
<212> TYPE: DNA
<213> ORGANISM: Homo Sapiens
<220> FEATURE:
<221> NAME/KEY: promoter
<222> LOCATION: 1..806
<220> FEATURE:
<223> OTHER INFORMATION: codon_start="807"
<220> FEATURE:
<221> NAME/KEY: protein_bind
<222> LOCATION: complement(60..70)
<223> OTHER INFORMATION: matinspector prediction
      name NFY_Q6
      score 0.956
      sequence ggaccaatcat
<220> FEATURE:
<221> NAME/KEY: protein_bind
<222> LOCATION: 70..77
<223> OTHER INFORMATION: matinspector prediction
      name MZF1_01
      score 0.962
      sequence cctggga
<220> FEATURE:
<221> NAME/KEY: protein_bind
<222> LOCATION: 124..132
<223> OTHER INFORMATION: matinspector prediction
      name CMYB_01
      score 0.994
      sequence tgaccgttg
<220> FEATURE:
<221> NAME/KEY: protein_bind
<222> LOCATION: complement(126..134)
<223> OTHER INFORMATION: matinspector prediction
      name VMYB_02
      score 0.985
```

```
      sequence tccaacggt
<220> FEATURE:
<221> NAME/KEY: protein_bind
<222> LOCATION: 135..143
<223> OTHER INFORMATION: matinspector prediction
      name STAT_01
      score 0.968
      sequence ttcctggaa
<220> FEATURE:
<221> NAME/KEY: protein_bind
<222> LOCATION: complement(135..143)
<223> OTHER INFORMATION: matinspector prediction
      name STAT_01
      score 0.951
      sequence ttccaggaa
<220> FEATURE:
<221> NAME/KEY: protein_bind
<222> LOCATION: complement(252..259)
<223> OTHER INFORMATION: matinspector prediction
      name MZF1_01
      score 0.956
      sequence ttggggga
<220> FEATURE:
<221> NAME/KEY: protein_bind
<222> LOCATION: 357..368
<223> OTHER INFORMATION: matinspector prediction
      name IK2_01
      score 0.965
      sequence gaatgggatttc
<220> FEATURE:
<221> NAME/KEY: protein_bind
<222> LOCATION: 384..391
<223> OTHER INFORMATION: matinspector prediction
      name MZF1_01
      score 0.986
      sequence agagggga
<220> FEATURE:
<221> NAME/KEY: protein_bind
<222> LOCATION: complement(410..421)
<223> OTHER INFORMATION: matinspector prediction
      name SRY_02
      score 0.955
      sequence gaaaacaaaaca
<220> FEATURE:
<221> NAME/KEY: protein_bind
<222> LOCATION: 592..599
<223> OTHER INFORMATION: matinspector prediction
      name MZF1_01
      score 0.960
      sequence gaagggga
<220> FEATURE:
<221> NAME/KEY: protein_bind
<222> LOCATION: 618..627
<223> OTHER INFORMATION: matinspector prediction
      name MYOD_Q6
      score 0.981
      sequence agcatctgcc
<220> FEATURE:
<221> NAME/KEY: protein_bind
<222> LOCATION: 632..642
<223> OTHER INFORMATION: matinspector prediction
      name DELTAEF1_01
      score 0.958
      sequence tcccaccttcc
<220> FEATURE:
<221> NAME/KEY: protein_bind
<222> LOCATION: complement(813..823)
<223> OTHER INFORMATION: matinspector prediction
      name S8_01
      score 0.992
      sequence gaggcaattat
<220> FEATURE:
<221> NAME/KEY: protein_bind
<222> LOCATION: complement(824..831)
<223> OTHER INFORMATION: matinspector prediction
      name MZF1_01
      score 0.986
      sequence agagggga
<220> FEATURE:
```

<221> NAME/KEY: misc_feature
<222> LOCATION: 335,376
<223> OTHER INFORMATION: n=a, g, c or t

<400> SEQUENCE: 34

```
tactataggg cacgcgtggt cgacggccgg gctgttctgg agcagagggc atgtcagtaa      60
tgattggtcc ctggggaagg tctggctggc tccagcacag tgaggcattt aggtatctct    120
cggtgaccgt tggattcctg aagcagtag ctgttctgtt tggatctggt agggacaggg    180
ctcagagggc taggcacgag ggaaggtcag aggagaaggs aggsarggcc cagtgagarg    240
ggagcatgcc ttcccccaac cctggcttsc ycttggymam agggcgktty tgggmacttr    300
aaytcagggc ccaascagaa scacaggccc aktcntggct smaagcacaa tagcctgaat    360
gggatttcag gttagncagg gtgagagggg aggctctctg gcttagtttt gttttgtttt    420
ccaaatcaag gtaacttgct cccttctgct acgggccttg gtcttggctt gtcctcaccc    480
agtcggaact ccctaccact ttcaggagag tggttttagg cccgtggggc tgttctgttc    540
caagcagtgt gagaacatgg ctggtagagg ctctagctgt gtgcggggcc tgaaggggag    600
tgggttctcg cccaaagagc atctgcccat ttcccacctt cccttctccc accagaagct    660
tgcctgagct gtttggacaa aaatccaaac cccacttggc tactctggcc tggcttcagc    720
ttggaaccca atacctaggc ttacaggcca tcctgagcca ggggcctctg gaaattctct    780
tcctgatggt cctttaggtt tgggcacaaa atataattgc ctctcccctc tcccatttc    840
tctcttggga gcaatggtca c                                             861
```

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35

```
ctgggatgga aggcacggta                                                 20
```

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36

```
gagaccacac agctagacaa                                                 20
```

<210> SEQ ID NO 37
<211> LENGTH: 555
<212> TYPE: DNA
<213> ORGANISM: Homo Sapiens
<220> FEATURE:
<221> NAME/KEY: promoter
<222> LOCATION: 1..500
<220> FEATURE:
<223> OTHER INFORMATION: codon_start="501"
<220> FEATURE:
<221> NAME/KEY: protein_bind
<222> LOCATION: 191..206
<223> OTHER INFORMATION: matinspector prediction
     name ARNT_01
     score 0.964
     sequence ggactcacgtgctgct
<220> FEATURE:
<221> NAME/KEY: protein_bind

```
<222> LOCATION: 193..204
<223> OTHER INFORMATION: matinspector prediction
      name NMYC_01
      score 0.965
      sequence actcacgtgctg
<220> FEATURE:
<221> NAME/KEY: protein_bind
<222> LOCATION: 193..204
<223> OTHER INFORMATION: matinspector prediction
      name USF_01
      score 0.985
      sequence actcacgtgctg
<220> FEATURE:
<221> NAME/KEY: protein_bind
<222> LOCATION: complement(193..204)
<223> OTHER INFORMATION: matinspector prediction
      name USF_01
      score 0.985
      sequence cagcacgtgagt
<220> FEATURE:
<221> NAME/KEY: protein_bind
<222> LOCATION: complement(193..204)
<223> OTHER INFORMATION: matinspector prediction
      name NMYC_01
      score 0.956
      sequence cagcacgtgagt
<220> FEATURE:
<221> NAME/KEY: protein_bind
<222> LOCATION: complement(193..204)
<223> OTHER INFORMATION: matinspector prediction
      name MYCMAX_02
      score 0.972
      sequence cagcacgtgagt
<220> FEATURE:
<221> NAME/KEY: protein_bind
<222> LOCATION: 195..202
<223> OTHER INFORMATION: matinspector prediction
      name USF_C
      score 0.997
      sequence tcacgtgc
<220> FEATURE:
<221> NAME/KEY: protein_bind
<222> LOCATION: complement(195..202)
<223> OTHER INFORMATION: matinspector prediction
      name USF_C
      score 0.991
      sequence gcacgtga
<220> FEATURE:
<221> NAME/KEY: protein_bind
<222> LOCATION: complement(210..217)
<223> OTHER INFORMATION: matinspector prediction
      name MZF1_01
      score 0.968
      sequence catggga
<220> FEATURE:
<221> NAME/KEY: protein_bind
<222> LOCATION: 397..410
<223> OTHER INFORMATION: matinspector prediction
      name ELK1_02
      score 0.963
      sequence ctctccggaagcct
<220> FEATURE:
<221> NAME/KEY: protein_bind
<222> LOCATION: 400..409
<223> OTHER INFORMATION: matinspector prediction
      name CETS1P54_01
      score 0.974
      sequence tccggaagcc
<220> FEATURE:
<221> NAME/KEY: protein_bind
<222> LOCATION: complement(460..470)
<223> OTHER INFORMATION: matinspector prediction
      name AP1_Q4
      score 0.963
      sequence agtgactgaac
<220> FEATURE:
<221> NAME/KEY: protein_bind
<222> LOCATION: complement(460..470)
<223> OTHER INFORMATION: matinspector prediction
```

```
      name AP1FJ_Q2
      score 0.961
      sequence agtgactgaac
<220> FEATURE:
<221> NAME/KEY: protein_bind
<222> LOCATION: 547..555
<223> OTHER INFORMATION: matinspector prediction
      name PADS_C
      score 1.000
      sequence tgtggtctc

<400> SEQUENCE: 37
ctatagggca cgcktggtcg acggcccggg ctggtctggt ctgtkgtgga gtcgggttga       60
aggacagcat ttgtkacatc tggtctactg caccttccct ctgccgtgca cttggccttt      120
kawaagctca gcaccggtgc ccatcacagg gccggcagca cacacatccc attactcaga      180
aggaactgac ggactcacgt gctgctccgt ccccatgagc tcagtggacc tgtctatgta      240
gagcagtcag acagtgcctg ggatagagtg agagttcagc cagtaaatcc aagtgattgt      300
cattcctgtc tgcattagta actcccaacc tagatgtgaa aacttagttc tttctcatag      360
gttgctctgc ccatggtccc actgcagacc caggcactct ccggaagcct ggaaatcacc      420
cgtgtcttct gcctgctccc gctcacatcc cacacttgtg ttcagtcact gagttacaga      480
ttttgcctcc tcaatttctc ttgtcttagt cccatcctct gttcccctgg ccagtttgtc      540
tagctgtgtg gtctc                                                       555

<210> SEQ ID NO 38
<211> LENGTH: 19
<212> TYPE: DNA
<213> ORGANISM: Artificial Sequence
<220> FEATURE:
<223> OTHER INFORMATION: oligonucleotide

<400> SEQUENCE: 38
ggccatacac ttgagtgac                                                    19

<210> SEQ ID NO 39
<211> LENGTH: 19
<212> TYPE: DNA
<213> ORGANISM: Artificial Sequence
<220> FEATURE:
<223> OTHER INFORMATION: oligonucleotide

<400> SEQUENCE: 39
atatagacaa acgcacacc                                                    19

<210> SEQ ID NO 40
<211> LENGTH: 699
<212> TYPE: DNA
<213> ORGANISM: Homo sapiens
<220> FEATURE:
<221> NAME/KEY: CDS
<222> LOCATION: 35..568
<220> FEATURE:
<221> NAME/KEY: sig_peptide
<222> LOCATION: 35..100
<223> OTHER INFORMATION: Von Heijne matrix
      score 10.7
      seq LLTLALLGGPTWA/GK
<220> FEATURE:
<221> NAME/KEY: polyA_signal
<222> LOCATION: 667..672
<220> FEATURE:
<221> NAME/KEY: polyA_site
<222> LOCATION: 685..699

<400> SEQUENCE: 40
```

```
aaccagacgc ccagtcacag gcgagagccc tggg atg cac cgg cca gag gcc atg        55
                                     Met His Arg Pro Glu Ala Met
                                                         -20 ctg ctg ctg ctc acg ctt gcc ctc ctg ggg ggc ccc acc tgg gca ggg          103
Leu Leu Leu Leu Thr Leu Ala Leu Leu Gly Gly Pro Thr Trp Ala Gly
-15                 -10                 -5                   1 aag atg tat ggc cct gga gga ggc aag tat ttc agc acc act gaa gac          151
Lys Met Tyr Gly Pro Gly Gly Gly Lys Tyr Phe Ser Thr Thr Glu Asp
         5                   10                  15 tac gac cat gaa atc aca ggg ctg cgg gtg tct gta ggt ctt ctc ctg          199
Tyr Asp His Glu Ile Thr Gly Leu Arg Val Ser Val Gly Leu Leu Leu
             20                  25                  30 gtg aaa agt gtc cag gtg aaa ctt gga gac tcc tgg gac gtg aaa ctg          247
Val Lys Ser Val Gln Val Lys Leu Gly Asp Ser Trp Asp Val Lys Leu
         35                  40                  45 gga gcc tta ggt ggg aat acc cag gaa gtc acc ctg cag cca ggc gaa          295
Gly Ala Leu Gly Gly Asn Thr Gln Glu Val Thr Leu Gln Pro Gly Glu
 50                  55                  60                  65 tac atc aca aaa gtc ttt gtc gcc ttc caa act ttc ctc cgg ggt atg          343
Tyr Ile Thr Lys Val Phe Val Ala Phe Gln Thr Phe Leu Arg Gly Met
             70                  75                  80 gtc atg tac acc agc aag gac cgc tat ttc tat ttt ggg aag ctt gat          391
Val Met Tyr Thr Ser Lys Asp Arg Tyr Phe Tyr Phe Gly Lys Leu Asp
         85                  90                  95 ggc cag atc tcc tct gcc tac ccc agc caa gag ggg cag gtg ctg gtg          439
Gly Gln Ile Ser Ser Ala Tyr Pro Ser Gln Glu Gly Gln Val Leu Val
             100                 105                 110 ggc atc tat ggc cag tat caa ctc ctt ggc atc aag agc att ggc ttt          487
Gly Ile Tyr Gly Gln Tyr Gln Leu Leu Gly Ile Lys Ser Ile Gly Phe
 115                 120                 125 gaa tgg aat tat cca cta gag gag ccg acc act gag cca cca gtt aat          535
Glu Trp Asn Tyr Pro Leu Glu Glu Pro Thr Thr Glu Pro Pro Val Asn
130                 135                 140                 145 ctc aca tac tca gca aac tca ccc gtg ggt cgc tagggtgggg tatggggcca        588
Leu Thr Tyr Ser Ala Asn Ser Pro Val Gly Arg
                150                 155 tccgagctga ggccatctgg gtggtggtgg ctgatggtac tggagtaact gagtcgggac        648
gctgaatctg aatccaccaa taaataaagg ttctgcaaaa aaaaaaaaa a                  699

<210> SEQ ID NO 41
<211> LENGTH: 497
<212> TYPE: DNA
<213> ORGANISM: Homo sapiens
<220> FEATURE:
<221> NAME/KEY: CDS
<222> LOCATION: 68..337
<220> FEATURE:
<221> NAME/KEY: sig_peptide
<222> LOCATION: 68..124
<223> OTHER INFORMATION: Von Heijne matrix
      score 10
      seq LVLLGVSIFLVSA/QN
<220> FEATURE:
<221> NAME/KEY: polyA_signal
<222> LOCATION: 462..467
<220> FEATURE:
<221> NAME/KEY: polyA_site
<222> LOCATION: 482..497

<400> SEQUENCE: 41
agcgccttgc cttctcttag gctttgaagc attttttgtct gtgctccctg atcttcaggt       60 caccacc atg aag ttc tta gca gtc ctg gta ctc ttg gga gtt tcc atc          109
```

```
        Met Lys Phe Leu Ala Val Leu Val Leu Leu Gly Val Ser Ile
                    -15                  -10 ttt ctg gtc tct gcc cag aat ccg aca aca gct gct cca gct gac acg      157
Phe Leu Val Ser Ala Gln Asn Pro Thr Thr Ala Ala Pro Ala Asp Thr
-5              1               5                       10 tat cca gct act ggt cct gct gat gat gaa gcc cct gat gct gaa acc      205
Tyr Pro Ala Thr Gly Pro Ala Asp Asp Glu Ala Pro Asp Ala Glu Thr
        15                  20                  25 act gct gct gca acc act gcg acc act gct gct cct acc act gca acc      253
Thr Ala Ala Ala Thr Thr Ala Thr Thr Ala Ala Pro Thr Thr Ala Thr
        30                  35                  40 acc gct gct tct acc act gct cgt aaa gac att cca gtt tta ccc aaa      301
Thr Ala Ala Ser Thr Thr Ala Arg Lys Asp Ile Pro Val Leu Pro Lys
        45                  50                  55 tgg gtt ggg gat ctc ccg aat ggt aga gtg tgt ccc tgagatggaa           347
Trp Val Gly Asp Leu Pro Asn Gly Arg Val Cys Pro
60              65                  70 tcagcttgag tcttctgcaa ttggtcacaa ctattcatgc ttcctgtgat ttcatccaac    407
tacttacctt gcctacgata tcccctttat ctctaatcag tttatttcct ttcaaataaa    467
aaataactat gagcaaaaaa aaaaaaaaaa                                     497

<210> SEQ ID NO 42
<211> LENGTH: 598
<212> TYPE: DNA
<213> ORGANISM: Homo sapiens
<220> FEATURE:
<221> NAME/KEY: CDS
<222> LOCATION: 39..413
<220> FEATURE:
<221> NAME/KEY: sig_peptide
<222> LOCATION: 39..83
<223> OTHER INFORMATION: Von Heijne matrix
      score 4.6
      seq LLTHNLLSSHVRG/VG
<220> FEATURE:
<221> NAME/KEY: polyA_signal
<222> LOCATION: 566..571
<220> FEATURE:
<221> NAME/KEY: polyA_site
<222> LOCATION: 583..598

<400> SEQUENCE: 42
ttttccggtt ccggcctggc gagagtttgt gcggcgac atg aaa ctg ctt acc cac    56
                                          Met Lys Leu Leu Thr His
                                              -15             -10 aat ctg ctg agc tcg cat gtg cgg ggg gtg ggg tcc cgt ggc ttc ccc      104
Asn Leu Leu Ser Ser His Val Arg Gly Val Gly Ser Arg Gly Phe Pro
            -5              1               5 ctg cgc ctc cag gcc acc gag gtc cgt atc tgc cct gtg gaa ttc aac      152
Leu Arg Leu Gln Ala Thr Glu Val Arg Ile Cys Pro Val Glu Phe Asn
        10                  15                  20 ccc aac ttc gtg gcg cgt atg ata cct aaa gtg gag tgg tcg gcg ttc      200
Pro Asn Phe Val Ala Arg Met Ile Pro Lys Val Glu Trp Ser Ala Phe
        25                  30                  35 ctg gag gcg gcc gat aac ttg cgt ctg atc cag gtg ccg aaa ggg ccg      248
Leu Glu Ala Ala Asp Asn Leu Arg Leu Ile Gln Val Pro Lys Gly Pro
40              45                  50                  55 gtt gag gga tat gag gag aat gag gag ttt ctg agg acc atg cac cac      296
Val Glu Gly Tyr Glu Glu Asn Glu Glu Phe Leu Arg Thr Met His His
                    60                  65                  70 ctg ctg ctg gag gtg gaa gtg ata gag ggc acc ctg cag tgc ccg gaa      344
Leu Leu Leu Glu Val Glu Val Ile Glu Gly Thr Leu Gln Cys Pro Glu
            75                  80                  85
```

```
tct gga cgt atg ttc ccc atc agc cgc ggg atc ccc aac atg ctg ctg    392
Ser Gly Arg Met Phe Pro Ile Ser Arg Gly Ile Pro Asn Met Leu Leu
            90              95                 100 agt gaa gag gaa act gag agt tgattgtgcc aggcgccagt ttttcttgtt       443
Ser Glu Glu Glu Thr Glu Ser
        105             110 atgactgtgt attttgttg atctataccc tgtttccgaa ttctgccgtg tgtatcccca   503
acccttgacc caatgacacc aaacacagtg tttttgagct cggtattata tatttttttc  563
tcattaaagg tttaaaacca aaaaaaaaaa aaaaa                             598

<210> SEQ ID NO 43
<211> LENGTH: 1579
<212> TYPE: DNA
<213> ORGANISM: Homo sapiens
<220> FEATURE:
<221> NAME/KEY: CDS
<222> LOCATION: 235..642
<220> FEATURE:
<221> NAME/KEY: sig_peptide
<222> LOCATION: 235..336
<223> OTHER INFORMATION: Von Heijne matrix
      score 8.7
      seq HLLALLVFSVLLA/LR
<220> FEATURE:
<221> NAME/KEY: polyA_signal
<222> LOCATION: 1540..1545
<220> FEATURE:
<221> NAME/KEY: polyA_site
<222> LOCATION: 1564..1579

<400> SEQUENCE: 43
gtgggggcat ggcgtccgat cgaggcgggc gttcacgggc ggccagggtt gagtcccggg   60
tcggggccgg gggattgccg gcgcatcagg gccgagggct ggggctggcg gggccgctcg  120
ctgcctctcg ctcgcagcag cggcggcagg cgcgggcgag ggccacgggg agaggagacg  180
cagccccgcg ggtggcacgc tcggccgggc cccggcccgc gctcaacggg cgcg atg    237
                                                             Met ctc ttc tcg ctc cgg gag ctg gtg cag tgg cta ggc ttc gcc acc ttc    285
Leu Phe Ser Leu Arg Glu Leu Val Gln Trp Leu Gly Phe Ala Thr Phe
            -30             -25                 -20 gag atc ttc gtg cac ctg ctg gcc ctg ttg gtg ttc tct gtg ctg ctg    333
Glu Ile Phe Val His Leu Leu Ala Leu Leu Val Phe Ser Val Leu Leu
            -15             -10                  -5 gca ctg cgt gtg gat ggc ctg gtc ccg ggc ctc tcc tgg tgg aac gtg    381
Ala Leu Arg Val Asp Gly Leu Val Pro Gly Leu Ser Trp Trp Asn Val
 1               5                  10                  15 ttc gtg cct ttc ttc gcc gct gac ggg ctc agc acc tac ttc acc acc    429
Phe Val Pro Phe Phe Ala Ala Asp Gly Leu Ser Thr Tyr Phe Thr Thr
                20                  25                  30 atc gtg tcc gtg cgc ctc ttc cag gat gga gag aag cgg ctg gcg gtg    477
Ile Val Ser Val Arg Leu Phe Gln Asp Gly Glu Lys Arg Leu Ala Val
                35                  40                  45 ctc cgc ctt ttc tgg gta ctt acg gtc ctg agt ctc aag ttc gtc ttc    525
Leu Arg Leu Phe Trp Val Leu Thr Val Leu Ser Leu Lys Phe Val Phe
                50                  55                  60 gag atg ctg ttg tgc cag aag ctg gcg gag cag act cgg gag ctc tgg    573
Glu Met Leu Leu Cys Gln Lys Leu Ala Glu Gln Thr Arg Glu Leu Trp
                65                  70                  75 ttc ggc ctc att acg tcc ccg ctc ttc att ctg cag ctg ctc atg        621
Phe Gly Leu Ile Thr Ser Pro Leu Phe Ile Leu Gln Leu Leu Met
 80                  85                  90                  95
```

-continued

| | |
|---|---|
| atc cgc gcc tgt cgg gtc aac tagcctcacc gaggtgccgg agagggagcg<br>Ile Arg Ala Cys Arg Val Asn<br>                     100 | 672 |
| ctggacaact agaatgttga cctcgagccg aggccctact tgcagcgcac cggaggagag | 732 |
| gctctctagt ctgaaggcac cgccggcttg cgccgagctg agtgccgggt ttccctattc | 792 |
| caatcctgtt tgaaatggtt tcttcagcag ggcttaaaag agcagccttc atcctgaaaa | 852 |
| tgtatttcct tttgtttaat gctttgagta gataatcctg aattgaggtc atgaggaggc | 912 |
| cccccaggcc agacagtcct gaacccctct gacacttgga aactgaatat aagtaaaatg | 972 |
| tccaggtgga ctctgagtat ttcctgtgga tcctgggaaa gtactgttgc acaaaggctg | 1032 |
| caaagctgga ctcaggaatg tcctccaacc agcagcgcta acctaagagc tccctgtgcc | 1092 |
| gtctatccag accagacttc ggtagatgcc tttgttagat ctatcacatg taaacgagct | 1152 |
| tgtatctcct tccctgtgcc acgagagaga ttggcttttt attccagtct aggcagagac | 1212 |
| agaagaatgt tgaataagag cacgattaga gtcctgtctg gttatctgtt gcccaagaaa | 1272 |
| agaactctgc tgtccaggca ctgcttggct tactatccca gcaaagactg cagttttgtg | 1332 |
| gacttttgac caccttgggc tggcactctt agcacacctg agacagattt aagcctccct | 1392 |
| aagagactga agagaggaac aggtgtcaga tactcatagg cactgagatc tacaaatggg | 1452 |
| aagcttgtga gtggcccatc tttgttggcc tacgaacttt ggtttgatgc cagtcaggtg | 1512 |
| ccacatgaga acctttgctg agatgcaaat aaagtaagag aatgttttcc caaaaaaaa | 1572 |
| aaaaaaa | 1579 |

<210> SEQ ID NO 44
<211> LENGTH: 893
<212> TYPE: DNA
<213> ORGANISM: Homo sapiens
<220> FEATURE:
<221> NAME/KEY: CDS
<222> LOCATION: 42..755
<220> FEATURE:
<221> NAME/KEY: sig_peptide
<222> LOCATION: 42..200
<223> OTHER INFORMATION: Von Heijne matrix
     score 5.8
     seq ILSLQVLLTTVTS/TV
<220> FEATURE:
<221> NAME/KEY: polyA_signal
<222> LOCATION: 860..865
<220> FEATURE:
<221> NAME/KEY: polyA_site
<222> LOCATION: 878..893

<400> SEQUENCE: 44

| | |
|---|---|
| gcggttagtg gaccgggacc ggtaggggtg ctgttgccat c atg gct gac ccc gac<br>                                                      Met Ala Asp Pro Asp<br>                                                                  -50 | 56 |
| ccc cgg tac cct cgc tcc tcg atc gag gac gac ttc aac tat ggc agc<br>Pro Arg Tyr Pro Arg Ser Ser Ile Glu Asp Asp Phe Asn Tyr Gly Ser<br>        -45                    -40                       -35 | 104 |
| agc gtg gcc tcc gcc acc gtg cac atc cga atg gcc ttt ctg aga aaa<br>Ser Val Ala Ser Ala Thr Val His Ile Arg Met Ala Phe Leu Arg Lys<br>    -30                    -25                      -20 | 152 |
| gtc tac agc att ctt tct ctg cag gtt ctc tta act aca gtg act tca<br>Val Tyr Ser Ile Leu Ser Leu Gln Val Leu Leu Thr Thr Val Thr Ser<br>    -15                    -10                      -5 | 200 |
| aca gtt ttt tta tac ttt gag tct gta cgg aca ttt gta cat gag agt<br>Thr Val Phe Leu Tyr Phe Glu Ser Val Arg Thr Phe Val His Glu Ser<br>1             5                    10                   15 | 248 |

-continued

| | | | | | | | | | | | | | | | |
|---|---|---|---|---|---|---|---|---|---|---|---|---|---|---|---|
| cct | gcc | tta | att | ttg | ctg | ttt | gcc | ctc | gga | tct | ctg | ggt | ttg | att | ttt | 296
| Pro | Ala | Leu | Ile | Leu | Leu | Phe | Ala | Leu | Gly | Ser | Leu | Gly | Leu | Ile | Phe |
| | | | 20 | | | | | 25 | | | | | 30 | | |

```
cct gcc tta att ttg ctg ttt gcc ctc gga tct ctg ggt ttg att ttt      296
Pro Ala Leu Ile Leu Leu Phe Ala Leu Gly Ser Leu Gly Leu Ile Phe
             20                  25                  30 gcg ttg att tta aac aga cat aag tat ccc ctt aac ctg tac cta ctt      344
Ala Leu Ile Leu Asn Arg His Lys Tyr Pro Leu Asn Leu Tyr Leu Leu
         35                  40                  45 ttt gga ttt acg ctg ttg gaa gct ctg act gtg gca gtt gtt gtt act      392
Phe Gly Phe Thr Leu Leu Glu Ala Leu Thr Val Ala Val Val Val Thr
 50                  55                  60 ttc tat gat gta tat att att ctg caa gct ttc ata ctg act act aca      440
Phe Tyr Asp Val Tyr Ile Ile Leu Gln Ala Phe Ile Leu Thr Thr Thr
 65                  70                  75                  80 gta ttt ttt ggt ttg act gtg tat act cta caa tct aag aag gat ttc      488
Val Phe Phe Gly Leu Thr Val Tyr Thr Leu Gln Ser Lys Lys Asp Phe
                 85                  90                  95 agc aaa ttt gga gca ggg ctg ttt gct ctt ttg tgg ata ttg tgc ctg      536
Ser Lys Phe Gly Ala Gly Leu Phe Ala Leu Leu Trp Ile Leu Cys Leu
             100                 105                 110 tca gga ttc ttg aag ttt ttt tta tat agt gag ata atg gag ttg gtc      584
Ser Gly Phe Leu Lys Phe Phe Leu Tyr Ser Glu Ile Met Glu Leu Val
             115                 120                 125 tta gcc gct gca gga gcc ctt ctt ttc tgt gga ttc atc atc tat gac      632
Leu Ala Ala Ala Gly Ala Leu Leu Phe Cys Gly Phe Ile Ile Tyr Asp
 130                 135                 140 aca cac tca ctg atg cat aaa ctg tca cct gaa gag tac gta tta gct      680
Thr His Ser Leu Met His Lys Leu Ser Pro Glu Glu Tyr Val Leu Ala
145                 150                 155                 160 gcc atc agc ctc tac ttg gat atc atc aat cta ttc ctg cac ctg tta      728
Ala Ile Ser Leu Tyr Leu Asp Ile Ile Asn Leu Phe Leu His Leu Leu
                 165                 170                 175 cgg ttt ctg gaa gca gtt aat aaa aag taattaaaag tatctcagct            775
Arg Phe Leu Glu Ala Val Asn Lys Lys
             180                 185 caactgaaga acaacaaaaa aaatttaacg agaaaaaagg attaaagtaa ttggaagcag    835
tatatagaaa ctgtttcatt aagtaataaa gtttgaacca ataaaaaaaa aaaaaaa       893

<210> SEQ ID NO 45
<211> LENGTH: 644
<212> TYPE: DNA
<213> ORGANISM: Homo sapiens
<220> FEATURE:
<221> NAME/KEY: CDS
<222> LOCATION: 23..340
<220> FEATURE:
<221> NAME/KEY: sig_peptide
<222> LOCATION: 23..235
<223> OTHER INFORMATION: Von Heijne matrix
      score 3.9
      seq VAVYCSFISFANS/RS
<220> FEATURE:
<221> NAME/KEY: polyA_signal
<222> LOCATION: 611..616
<220> FEATURE:
<221> NAME/KEY: polyA_site
<222> LOCATION: 629..644

<400> SEQUENCE: 45
gtgatctggc cttcgactcg ct atg tcc act aac aat atg tcg gac cca cgg    52
                         Met Ser Thr Asn Asn Met Ser Asp Pro Arg
                                 -70                 -65 agg ccg aac aaa gtg ctg agg tac aag ccc ccg ccg agc gaa tgt aac    100
Arg Pro Asn Lys Val Leu Arg Tyr Lys Pro Pro Pro Ser Glu Cys Asn
     -60                 -55                 -50
```

```
ccg gcc ttg gac gac ccg acg ccg gac tac atg aac ctg ctg ggc atg      148
Pro Ala Leu Asp Asp Pro Thr Pro Asp Tyr Met Asn Leu Leu Gly Met
-45             -40             -35             -30 atc ttc agc atg tgc ggc ctc atg ctt aag ctg aag tgg tgt gct tgg      196
Ile Phe Ser Met Cys Gly Leu Met Leu Lys Leu Lys Trp Cys Ala Trp
            -25             -20             -15 gtc gct gtc tac tgc tcc ttc atc agc ttt gcc aac tct cgg agc tcg      244
Val Ala Val Tyr Cys Ser Phe Ile Ser Phe Ala Asn Ser Arg Ser Ser
        -10              -5               1 gag gac acg aag caa atg atg agt agc ttc atg ctg tcc atc tct gcc      292
Glu Asp Thr Lys Gln Met Met Ser Ser Phe Met Leu Ser Ile Ser Ala
    5               10              15 gtg gtg atg tcc tat ctg cag aat cct cag ccc atg acg ccc cca tgg      340
Val Val Met Ser Tyr Leu Gln Asn Pro Gln Pro Met Thr Pro Pro Trp
20              25              30              35 tgataccagc ctagaagggt cacattttgg accctgtcta tccactaggc ctgggctttg     400
gctgctaaac ctgctgcctt cagctgccat cctggacttc cctgaatgag gccgtctcgg     460
tgcccccagc tggatagagg gaacctggcc ctttcctagg gaacacccta ggcttacccc     520
tcctgcctcc cttcccctgc ctgctgctgg gggagatgct gtccatgttt ctaggggtat     580
tcatttgctt tctcgttgaa acctgttgtt aataaagttt ttcactctaa aaaaaaaaa      640 aaaa                                                                  644

<210> SEQ ID NO 46
<211> LENGTH: 538
<212> TYPE: DNA
<213> ORGANISM: Homo sapiens
<220> FEATURE:
<221> NAME/KEY: CDS
<222> LOCATION: 12..380
<220> FEATURE:
<221> NAME/KEY: sig_peptide
<222> LOCATION: 12..263
<223> OTHER INFORMATION: Von Heijne matrix
      score 6.2
      seq GLFRAAWLPGSRP/SP
<220> FEATURE:
<221> NAME/KEY: polyA_site
<222> LOCATION: 523..538

<400> SEQUENCE: 46
ctgaattcct t atg tcc ggt ggg cca gaa gcc cgt cct cct atg ctg gtg      50
             Met Ser Gly Gly Pro Glu Ala Arg Pro Pro Met Leu Val
                     -80                 -75 gaa ggc gga gga ccg gag tcc ctg cag aag gcc ccg tgc act cgg ggg       98
Glu Gly Gly Gly Pro Glu Ser Leu Gln Lys Ala Pro Cys Thr Arg Gly
    -70             -65             -60 cct ccc tca cat ccc gtg ccc cct gcg ctg gcc ttc aca gta ggt aat      146
Pro Pro Ser His Pro Val Pro Pro Ala Leu Ala Phe Thr Val Gly Asn
-55             -50             -45             -40 ggc tcc ggc ccg ggt gtt cgc tgt cca cgg aac atg gca gag ggg cac      194
Gly Ser Gly Pro Gly Val Arg Cys Pro Arg Asn Met Ala Glu Gly His
            -35             -30             -25 ccc ggc ccg gaa aga cgc cag agc cag cag ggg ctg ttt cgg gcc gcg      242
Pro Gly Pro Glu Arg Arg Gln Ser Gln Gln Gly Leu Phe Arg Ala Ala
        -20             -15             -10 tgg ctc ccc ggg tct cgg ccg tct ccc ctc ttc tgc gtc tgt tcc gtg      290
Trp Leu Pro Gly Ser Arg Pro Ser Pro Leu Phe Cys Val Cys Ser Val
    -5               1               5 act tcg cct ggg tgg gat gta ccg cag gtg cat cgc gtc gag gtg ggg      338
Thr Ser Pro Gly Trp Asp Val Pro Gln Val His Arg Val Glu Val Gly
10              15              20              25
```

```
cac ggc cgc cgg caa gaa acc cac cct gtc cgg agg cgg gcg        380
His Gly Arg Arg Gln Glu Thr His Pro Val Arg Arg Ala
            30                  35 tgagacaagc ccagcccgca cgcgctcatc tttcttcgtt ttttgatcag tttattcaga  440
attgctctat aatttaccaa ttgtatgtat ttaacctatt cttgtggaaa aaaaaggtct  500
ttcattatat ctttatttct gcaaaaaaaa aaaaaaaa                         538

<210> SEQ ID NO 47
<211> LENGTH: 752
<212> TYPE: DNA
<213> ORGANISM: Homo sapiens
<220> FEATURE:
<221> NAME/KEY: CDS
<222> LOCATION: 8..232
<220> FEATURE:
<221> NAME/KEY: sig_peptide
<222> LOCATION: 8..154
<223> OTHER INFORMATION: Von Heijne matrix
      score 4.7
      seq DTFLLSFLSTTWL/KT
<220> FEATURE:
<221> NAME/KEY: polyA_site
<222> LOCATION: 737..752

<400> SEQUENCE: 47 gggggtg atg ccg cgc ggt cgc agg ctt ggg atg gtg ttc gcg cct ccg   49
        Met Pro Arg Gly Arg Arg Leu Gly Met Val Phe Ala Pro Pro
                    -45                 -40 aga ccc gga cag agg caa gca ggg gcg ccg tgg gtg cca gag agg cgg   97
Arg Pro Gly Gln Arg Gln Ala Gly Ala Pro Trp Val Pro Glu Arg Arg
-35             -30                  -25                 -20 aag agg agg cct gat ggg gat acc ttc ctg ctg tcc ttc ctg agc aca  145
Lys Arg Arg Pro Asp Gly Asp Thr Phe Leu Leu Ser Phe Leu Ser Thr
                -15                 -10                 -5 acc tgg ctg aaa acc tgg agg tca caa cag tac aaa gaa tca aag tca  193
Thr Trp Leu Lys Thr Trp Arg Ser Gln Gln Tyr Lys Glu Ser Lys Ser
            1               5                   10 aga tct tgt gcc aga gag caa atg aac tct tcc tct tgc tgagaaaacc  242
Arg Ser Cys Ala Arg Glu Gln Met Asn Ser Ser Ser Cys
    15                  20                  25 caccctgctc acctaaaccc tggccttgcc tggtaattcc atccatgcgc ctggaaggcc  302
ccagacatca aggctctgag gggccaggca cggggagaac ccagcagtgc cctgccctgc  362
agtctgagct accagattcc ttgtgaagat aatttgagga ccatgactca cccaaccaca  422
tttcctgggg cctcaaattg aaaattcagg atgggctttt ctatatgact ggctgatatc  482
caactatgcc atggtcttta catgccatga acattctttc ctgccagagt tctaagaatc  542
tgtgttctct gccttagacc ttctgcagat gagcccacag gaagctccac gtgtagctga  602
gctacatgca ccaggcctca gtttgcccca agtcccctgt gtactctctc atggcctgtg  662
gccaagaaat gtattctctc actttggact taggagtcca aagagaagcc cagaaacaaa  722
attgcttgaa cttgaaaaaa aaaaaaaaaa                                   752

<210> SEQ ID NO 48
<211> LENGTH: 537
<212> TYPE: DNA
<213> ORGANISM: Homo sapiens
<220> FEATURE:
<221> NAME/KEY: CDS
<222> LOCATION: 183..422
<220> FEATURE:
<221> NAME/KEY: sig_peptide
```

```
<222> LOCATION: 183..302
<223> OTHER INFORMATION: Von Heijne matrix
      score 5.8
      seq VLFALFVAFLLRG/KL
<220> FEATURE:
<221> NAME/KEY: polyA_signal
<222> LOCATION: 505..510
<220> FEATURE:
<221> NAME/KEY: polyA_site
<222> LOCATION: 523..537

<400> SEQUENCE: 48
agtatctcac catttctttc tctttctgaa ccacattggg tgccaacaga acttgctctc    60
tgttctcttt caaaattacc aacatggacc ccacccaatt cttcccttgg aactaaggaa   120
cgcctgactg atcatctgat acagcagttc ctgagcagaa caaaacaaca aaaacaggac   180 ag atg gat gga ata ccc atg tca atg aag aat gaa atg ccc atc tcc      227
   Met Asp Gly Ile Pro Met Ser Met Lys Asn Glu Met Pro Ile Ser
   -40             -35             -30 caa cta ctg atg atc atc gcc ccc tcc ttg gga ttt gtg ctc ttc gca    275
Gln Leu Leu Met Ile Ile Ala Pro Ser Leu Gly Phe Val Leu Phe Ala
-25             -20             -15             -10 ttg ttt gtg gcg ttt ctc ctg aga ggg aaa ctc atg gaa acc tat tgt   323
Leu Phe Val Ala Phe Leu Leu Arg Gly Lys Leu Met Glu Thr Tyr Cys
                -5              1               5 tcg cag aaa cac aca agg cta gac tac att gga gat agt aaa aat gtc   371
Ser Gln Lys His Thr Arg Leu Asp Tyr Ile Gly Asp Ser Lys Asn Val
        10              15              20 ctc aat gac gtg cag cat gga agg gaa gac gaa gac ggc ctt ttt acc   419
Leu Asn Asp Val Gln His Gly Arg Glu Asp Glu Asp Gly Leu Phe Thr
    25              30              35 ctc taacaacgca gtagcatgtt agattgagga tgggggcatg acactccagt        472
Leu
40 gtcaaaataa gtcttagtag atttccttgt ttcataaaaa agactcactc aaaaaaaaaa    532 aaaaa                                                                537

<210> SEQ ID NO 49
<211> LENGTH: 1602
<212> TYPE: DNA
<213> ORGANISM: Homo sapiens
<220> FEATURE:
<221> NAME/KEY: CDS
<222> LOCATION: 24..1004
<220> FEATURE:
<221> NAME/KEY: sig_peptide
<222> LOCATION: 24..170
<223> OTHER INFORMATION: Von Heijne matrix
      score 5.6
      seq ACLSLGFFSLLWL/QL
<220> FEATURE:
<221> NAME/KEY: polyA_site
<222> LOCATION: 1586..1602

<400> SEQUENCE: 49
atgcgccgcc gcctctccgc acg atg ttc ccc tcg cgg agg aaa gcg gcg cag    53
                         Met Phe Pro Ser Arg Arg Lys Ala Ala Gln
                                         -45             -40 ctg ccc tgg gag gac ggc agg tcc ggg ttg ctc tcc ggc ggc ctc cct    101
Leu Pro Trp Glu Asp Gly Arg Ser Gly Leu Leu Ser Gly Gly Leu Pro
            -35             -30             -25 cgg aag tgt tcc gtc ttc cac ctg ttc gtg gcc tgc ctc tcg ctg ggc    149
Arg Lys Cys Ser Val Phe His Leu Phe Val Ala Cys Leu Ser Leu Gly
    -20             -15             -10
```

-continued

| | | |
|---|---|---|
| ttc ttc tcc cta ctc tgg ctg cag ctc agc tgc tct ggg gac gtg gcc<br>Phe Phe Ser Leu Leu Trp Leu Gln Leu Ser Cys Ser Gly Asp Val Ala<br>     -5                        1                      5 | 197 | | cgg gca gtc agg gga caa ggg cag gag acc tcg ggc cct ccc cgt gcc    245
Arg Ala Val Arg Gly Gln Gly Gln Glu Thr Ser Gly Pro Pro Arg Ala
 10              15                  20                  25 tgc ccc cca gag ccg ccc cct gag cac tgg gaa gaa gac gca tcc tgg    293
Cys Pro Pro Glu Pro Pro Pro Glu His Trp Glu Glu Asp Ala Ser Trp
                     30                  35                  40 ggc ccc cac cgc ctg gca gtg ctg gtg ccc ttc cgc gaa cgc ttc gag    341
Gly Pro His Arg Leu Ala Val Leu Val Pro Phe Arg Glu Arg Phe Glu
             45                  50                  55 gag ctc ctg gtc ttc gtg ccc cac atg cgc cgc ttc ctg agc agg aag    389
Glu Leu Leu Val Phe Val Pro His Met Arg Arg Phe Leu Ser Arg Lys
         60                  65                  70 aag atc cgg cac cac atc tac gtg ctc aac cag gtg gac cac ttc agg    437
Lys Ile Arg His His Ile Tyr Val Leu Asn Gln Val Asp His Phe Arg
 75                  80                  85 ttc aac cgg gca gcg ctc atc aac gtg ggc ttc ctg gag agc agc aac    485
Phe Asn Arg Ala Ala Leu Ile Asn Val Gly Phe Leu Glu Ser Ser Asn
 90                  95                 100                 105 agc acg gac tac att gcc atg cac gac gtt gac ctg ctc cct ctc aac    533
Ser Thr Asp Tyr Ile Ala Met His Asp Val Asp Leu Leu Pro Leu Asn
                    110                 115                 120 gag gag ctg gac tat ggc ttt cct gag gct ggg ccc ttc cac gtg gcc    581
Glu Glu Leu Asp Tyr Gly Phe Pro Glu Ala Gly Pro Phe His Val Ala
             125                 130                 135 tcc ccg gag ctc cac cct ctc tac cac tac aag acc tat gtc ggc ggc    629
Ser Pro Glu Leu His Pro Leu Tyr His Tyr Lys Thr Tyr Val Gly Gly
         140                 145                 150 atc ctg ctg ctc tcc aag cag cac tac cgg ctg tgc aat ggg atg tcc    677
Ile Leu Leu Leu Ser Lys Gln His Tyr Arg Leu Cys Asn Gly Met Ser
 155                 160                 165 aac cgc ttc tgg ggc tgg ggc cgc gag gac gac gag ttc tac cgg cgc    725
Asn Arg Phe Trp Gly Trp Gly Arg Glu Asp Asp Glu Phe Tyr Arg Arg
170                 175                 180                 185 att aag gga gct ggg ctc cag ctt ttc cgc ccc tcg gga atc aca act    773
Ile Lys Gly Ala Gly Leu Gln Leu Phe Arg Pro Ser Gly Ile Thr Thr
                    190                 195                 200 ggg tac aag aca ttt cgc cac ctg cat gac cca gcc tgg cgg aag agg    821
Gly Tyr Lys Thr Phe Arg His Leu His Asp Pro Ala Trp Arg Lys Arg
             205                 210                 215 gac cag aag cgc atc gca gct caa aaa cag gag cag ttc aag gtg gac    869
Asp Gln Lys Arg Ile Ala Ala Gln Lys Gln Glu Gln Phe Lys Val Asp
         220                 225                 230 agg gag gga ggc ctg aac act gtg aag tac cat gtg gct tcc cgc act    917
Arg Glu Gly Gly Leu Asn Thr Val Lys Tyr His Val Ala Ser Arg Thr
 235                 240                 245 gcc ctg tct gtg ggc ggg gcc ccc tgc act gtc ctc aac atc atg ttg    965
Ala Leu Ser Val Gly Gly Ala Pro Cys Thr Val Leu Asn Ile Met Leu
250                 255                 260                 265 gac tgt gac aag acc gcc aca ccc tgg tgc aca ttc agc tgagctggat   1014
Asp Cys Asp Lys Thr Ala Thr Pro Trp Cys Thr Phe Ser
                    270                 275 ggacagtgag gaagcctgta cctacaggcc atattgctca ggctcaggac aaggcctcag   1074
gtcgtgggcc cagctctgac aggatgtgga gtggccagga ccaagacagc aagctacgca   1134
attgcagcca cccggccgcc aaggcaggct gggctgggca caggacacgt ggggtgcctg   1194
ggacgctgct tgccatgcac agtgatcaga gagaggctgg ggtgtgtcct gtccgggacc   1254

```
cccctgcct tcctgctcac cctactctga cctccttcac gtgcccaggc ctgtgggtag      1314
tggggagggc tgaacaggac aacctctcat caccccact tttgttcctt cctgctgggc      1374
tgcctcgtgc agagacacag tgtaggggcc atgcagctgg cgtaggtggc agttgggcct     1434
ggtgagggtt aggacttcag aaaccagagc acaagcccca cagaggggga acagccagca     1494
ccgctctagc tggttgttgc catgccgaa tgtgggccta gtgttgccag atcttctgat      1554
ttttcgaaag aaactagaat gctggattct caaaaaaaaa aaaaaaaa                  1602

<210> SEQ ID NO 50
<211> LENGTH: 948
<212> TYPE: DNA
<213> ORGANISM: Homo sapiens
<220> FEATURE:
<221> NAME/KEY: CDS
<222> LOCATION: 80..784
<220> FEATURE:
<221> NAME/KEY: sig_peptide
<222> LOCATION: 80..139
<223> OTHER INFORMATION: Von Heijne matrix
      score 4
      seq LLKVVFVVFASLC/AW
<220> FEATURE:
<221> NAME/KEY: polyA_signal
<222> LOCATION: 910..915
<220> FEATURE:
<221> NAME/KEY: polyA_site
<222> LOCATION: 933..948

<400> SEQUENCE: 50
cttcctgacc cagggctcc gctggctgcg gtcgcctggg agctgccgcc agggccagga      60
ggggagcggc acctggaag atg cgc cca ttg gct ggt ggc ctg ctc aag gtg     112
                     Met Arg Pro Leu Ala Gly Gly Leu Leu Lys Val
                         -20             -15                 -10 gtg ttc gtg gtc ttc gcc tcc ttg tgt gcc tgg tat tcg ggg tac ctg     160
Val Phe Val Val Phe Ala Ser Leu Cys Ala Trp Tyr Ser Gly Tyr Leu
            -5                  1               5 ctc gca gag ctc att cca gat gca ccc ctg tcc agt gct gcc tat agc     208
Leu Ala Glu Leu Ile Pro Asp Ala Pro Leu Ser Ser Ala Ala Tyr Ser
        10                  15                  20 atc cgc agc atc ggg gag agg cct gtc ctc aaa gct cca gtc ccc aaa     256
Ile Arg Ser Ile Gly Glu Arg Pro Val Leu Lys Ala Pro Val Pro Lys
    25                  30                  35 agg caa aaa tgt gac cac tgg act ccc tgc cca tct gac acc tat gcc     304
Arg Gln Lys Cys Asp His Trp Thr Pro Cys Pro Ser Asp Thr Tyr Ala
40                  45                  50                  55 tac agg tta ctc agc gga ggt ggc aga agc aag tac gcc aaa atc tgc     352
Tyr Arg Leu Leu Ser Gly Gly Gly Arg Ser Lys Tyr Ala Lys Ile Cys
                60                  65                  70 ttt gag gat aac cta ctt atg gga gaa cag ctg gga aat gtt gcc aga     400
Phe Glu Asp Asn Leu Leu Met Gly Glu Gln Leu Gly Asn Val Ala Arg
            75                  80                  85 gga ata aac att gcc att gtc aac tat gta act ggg aat gtg aca gca     448
Gly Ile Asn Ile Ala Ile Val Asn Tyr Val Thr Gly Asn Val Thr Ala
        90                  95                  100 aca cga tgt ttt gat atg tat gaa ggc gat aac tct gga ccg atg aca     496
Thr Arg Cys Phe Asp Met Tyr Glu Gly Asp Asn Ser Gly Pro Met Thr
    105                 110                 115 aag ttt att cag agt gct gct cca aaa tcc ctg ctc ttc atg gtg acc     544
Lys Phe Ile Gln Ser Ala Ala Pro Lys Ser Leu Leu Phe Met Val Thr
120                 125                 130                 135 tat gac gac gga agc aca aga ctg aat aac gat gcc aag aat gcc ata     592
```

-continued

```
                Tyr Asp Asp Gly Ser Thr Arg Leu Asn Asn Asp Ala Lys Asn Ala Ile
                                140                 145                 150 gaa gca ctt gga agt aaa gaa atc agg aac atg aaa ttc agg tct agc           640
Glu Ala Leu Gly Ser Lys Glu Ile Arg Asn Met Lys Phe Arg Ser Ser
            155                 160                 165 tgg gta ttt att gca gca aaa ggc ttg gaa ctc cct tcc gaa att cag           688
Trp Val Phe Ile Ala Ala Lys Gly Leu Glu Leu Pro Ser Glu Ile Gln
        170                 175                 180 aga gaa aag atc aac cac tct gat gct aag aac aac aga tat tct ggc           736
Arg Glu Lys Ile Asn His Ser Asp Ala Lys Asn Asn Arg Tyr Ser Gly
    185                 190                 195 tgg cct gca gag atc cag ata gaa ggc tgc ata ccc aaa gaa cga agc           784
Trp Pro Ala Glu Ile Gln Ile Glu Gly Cys Ile Pro Lys Glu Arg Ser
200                 205                 210                 215 tgacactgca gggtcctgag taaatgtgtt ctgtataaac aaatgcagct ggaatcgctc          844
aagaatctta ttttctaaa tccaacagcc catatttgat gagtattttg ggtttgttgt           904
aaaccaatga acatttgcta gttgtaccaa aaaaaaaaaa aaaa                           948

<210> SEQ ID NO 51
<211> LENGTH: 687
<212> TYPE: DNA
<213> ORGANISM: Homo sapiens
<220> FEATURE:
<221> NAME/KEY: CDS
<222> LOCATION: 67..222
<220> FEATURE:
<221> NAME/KEY: sig_peptide
<222> LOCATION: 67..159
<223> OTHER INFORMATION: Von Heijne matrix
      score 5.8
      seq VLFSASSFPSISG/NI
<220> FEATURE:
<221> NAME/KEY: polyA_site
<222> LOCATION: 673..687

<400> SEQUENCE: 51
tacaattgga aaatctttat acattgaaaa aagcaacttt tcctccccct ctcaataggt           60 acaaga atg cgg gtt tat aaa agg aca cag ttg agg caa gag acc gga           108
        Met Arg Val Tyr Lys Arg Thr Gln Leu Arg Gln Glu Thr Gly
            -30                 -25                 -20 ccc aaa agt tat gtg ctc ttt agt gcc tca agt ttt cca agc atc tct           156
Pro Lys Ser Tyr Val Leu Phe Ser Ala Ser Ser Phe Pro Ser Ile Ser
        -15                 -10                 -5 ggt aac ata agg agt aga aat tat ttt caa aaa caa aat aat cac tgg           204
Gly Asn Ile Arg Ser Arg Asn Tyr Phe Gln Lys Gln Asn Asn His Trp
1               5                   10                  15 ttc cag acc agt gat tat taacccttttt tgaattatga acccctttaa               252
Phe Gln Thr Ser Asp Tyr
                20 aacctaatga aatttaagga ccctctcccc caaatatac atataaaaaa acaaggcagt           312 ctatggacct actgagtaac tctcaagata gtaagtaagg agagaaagat ctatgtttcc         372 ctctttgata agtatgaaat atttggagga gatgctaatt tttgcacgtt tatgatattt         432 gcaatctttc atttttgtag cagattatac tcaaaaattt gatccagaac ttggccccta         492 ttcttttatc agcactttaa cttgtaaact gaaaagttta ccatcatctg tatgacatcc         552 taatgaggtt aaaagataa aatgcagtta tgattatgat aggtataact gtatccaggt         612 ttccacagca aaaacaaaac aaaacataca ccatgttctg gggttattga cagcctcctc         672 aaaaaaaaaa aaaa                                                           687
```

```
<210> SEQ ID NO 52
<211> LENGTH: 821
<212> TYPE: DNA
<213> ORGANISM: Homo sapiens
<220> FEATURE:
<221> NAME/KEY: CDS
<222> LOCATION: 46..732
<220> FEATURE:
<221> NAME/KEY: sig_peptide
<222> LOCATION: 46..186
<223> OTHER INFORMATION: Von Heijne matrix
      score 9.4
      seq LILLILCVGMVVG/LV
<220> FEATURE:
<221> NAME/KEY: polyA_signal
<222> LOCATION: 781..786
<220> FEATURE:
<221> NAME/KEY: polyA_site
<222> LOCATION: 806..821

<400> SEQUENCE: 52
gcaaagtcat tgaactctga gctcagttgc agtactcggg aagcc atg cag gat gaa      57
                                                  Met Gln Asp Glu
                                                      -45 gat gga tac atc acc tta aat att aaa act cgg aaa cca gct ctc gtc      105
Asp Gly Tyr Ile Thr Leu Asn Ile Lys Thr Arg Lys Pro Ala Leu Val
            -40                 -35                 -30 tcc gtt ggc cct gca tcc tcc ttc tgg tgg cgt gtg atg gct ttg att      153
Ser Val Gly Pro Ala Ser Ser Phe Trp Trp Arg Val Met Ala Leu Ile
        -25                 -20                 -15 ctg ctg atc ctg tgc gtg ggg atg gtt gtc ggg ctg gtg gct ctg ggg      201
Leu Leu Ile Leu Cys Val Gly Met Val Val Gly Leu Val Ala Leu Gly
    -10                  -5                  1                   5 att tgg tct gtc atg cag cgc aat tac cta caa gat gag aat gaa aat      249
Ile Trp Ser Val Met Gln Arg Asn Tyr Leu Gln Asp Glu Asn Glu Asn
                 10                  15                  20 cgc aca gga act ctg caa caa tta gca aag cgc ttc tgt caa tat gtg      297
Arg Thr Gly Thr Leu Gln Gln Leu Ala Lys Arg Phe Cys Gln Tyr Val
             25                  30                  35 gta aaa caa tca gaa cta aag ggc act ttc aaa ggt cat aaa tgc agc      345
Val Lys Gln Ser Glu Leu Lys Gly Thr Phe Lys Gly His Lys Cys Ser
         40                  45                  50 ccc tgt gac aca aac tgg aga tat tat gga gat agc tgc tat ggg ttc      393
Pro Cys Asp Thr Asn Trp Arg Tyr Tyr Gly Asp Ser Cys Tyr Gly Phe
 55                  60                  65 ttc agg cac aac tta aca tgg gaa gag agt aag cag tac tgc act gac      441
Phe Arg His Asn Leu Thr Trp Glu Glu Ser Lys Gln Tyr Cys Thr Asp
 70                  75                  80                  85 atg aat gct act ctc ctg aag att gac aac cgg aac att gtg gag tac      489
Met Asn Ala Thr Leu Leu Lys Ile Asp Asn Arg Asn Ile Val Glu Tyr
                 90                  95                 100 atc aaa gcc agg act cat tta att cgt tgg gtc gga tta tct cgc cag      537
Ile Lys Ala Arg Thr His Leu Ile Arg Trp Val Gly Leu Ser Arg Gln
            105                 110                 115 aag tcg aat gag gtc tgg aag tgg gag gat ggc tcg gtt atc tca gaa      585
Lys Ser Asn Glu Val Trp Lys Trp Glu Asp Gly Ser Val Ile Ser Glu
        120                 125                 130 aat atg ttt gag ttt ttg gaa gat gga aaa gga aat atg aat tgt gct      633
Asn Met Phe Glu Phe Leu Glu Asp Gly Lys Gly Asn Met Asn Cys Ala
    135                 140                 145 tat ttt cat aat ggg aaa atg cac cct acc ttc tgt gag aac aaa cat      681
Tyr Phe His Asn Gly Lys Met His Pro Thr Phe Cys Glu Asn Lys His
150                 155                 160                 165
```

```
tat tta atg tgt gag agg aag gct ggc atg acc aag gtg gac caa cta      729
Tyr Leu Met Cys Glu Arg Lys Ala Gly Met Thr Lys Val Asp Gln Leu
                170                 175                 180 cct taatgcaaag aggtggacag gataacacag ataagggctt tattgtacaa           782
Pro taaaagatat gtatgaatgc aacaaaaaaa aaaaaaaa                            821

<210> SEQ ID NO 53
<211> LENGTH: 445
<212> TYPE: DNA
<213> ORGANISM: Homo sapiens
<220> FEATURE:
<221> NAME/KEY: CDS
<222> LOCATION: 81..356
<220> FEATURE:
<221> NAME/KEY: sig_peptide
<222> LOCATION: 81..152
<223> OTHER INFORMATION: Von Heijne matrix
      score 6.2
      seq AILGSTWVALTTG/AL
<220> FEATURE:
<221> NAME/KEY: polyA_signal
<222> LOCATION: 406..411
<220> FEATURE:
<221> NAME/KEY: polyA_site
<222> LOCATION: 429..445
<220> FEATURE:
<221> NAME/KEY: misc_feature
<222> LOCATION: 1
<223> OTHER INFORMATION: n=a, g, c or t

<400> SEQUENCE: 53
ngaaaaaaaa catccgggcc gcgcggggaa ggggagacgt ggggtagagg ggagcattgc     60
ttccttctct cgcagtgacc atg acg aaa tta gcg cag tgg ctt tgg gga cta   113
                      Met Thr Lys Leu Ala Gln Trp Leu Trp Gly Leu
                                      -20                 -15 gcg atc ctg ggc tcc acc tgg gtg gcc ctg acc acg gga gcc ttg ggc      161
Ala Ile Leu Gly Ser Thr Trp Val Ala Leu Thr Thr Gly Ala Leu Gly
            -10                  -5                   1 ctg gag ctg ccc ttg tcc tgc cag gaa gtc ctg tgg cca ctg ccc gcc      209
Leu Glu Leu Pro Leu Ser Cys Gln Glu Val Leu Trp Pro Leu Pro Ala
        5                   10                  15 tac ttg ctg gtg tcc gcc ggc tgc tat gcc ctg ggc act gtg ggc tat      257
Tyr Leu Leu Val Ser Ala Gly Cys Tyr Ala Leu Gly Thr Val Gly Tyr
20                  25                  30                  35 cgt gtg gcc act ttt cat gac tgc gag gac gcc gca cgc gag ctg cag      305
Arg Val Ala Thr Phe His Asp Cys Glu Asp Ala Ala Arg Glu Leu Gln
                40                  45                  50 agc cag ata cag gag gcc cga gcc gac tta gcc cgc agg ggg ctg cgc      353
Ser Gln Ile Gln Glu Ala Arg Ala Asp Leu Ala Arg Arg Gly Leu Arg
            55                  60                  65 ttc tgacagccta acccattcc tgtgcggaca gcccttcctc ccatttccca            406
Phe ttaaagagcc agtttatttt ctaaaaaaaa aaaaaaaa                            445

<210> SEQ ID NO 54
<211> LENGTH: 1517
<212> TYPE: DNA
<213> ORGANISM: Homo sapiens
<220> FEATURE:
<221> NAME/KEY: CDS
<222> LOCATION: 72..1346
<220> FEATURE:
<221> NAME/KEY: sig_peptide
<222> LOCATION: 72..140
<223> OTHER INFORMATION: Von Heijne matrix
```

-continued

```
       score 5.9
       seq SCDCFVSVPPASA/IP
<220> FEATURE:
<221> NAME/KEY: polyA_signal
<222> LOCATION: 1482..1487
<220> FEATURE:
<221> NAME/KEY: polyA_site
<222> LOCATION: 1502..1517

<400> SEQUENCE: 54
```

| | | | |
|---|---|---|---|
| atgggcggc cctggccaga agcggaggag gtggcacccg ggaccgagct ggggtcttgg | | | 60 |

| aggaagagag | g atg gcg tcg tcg agc cct gac tcc cca tgt tcc tgc gac | 110 |
|---|---|---|
| | Met Ala Ser Ser Ser Pro Asp Ser Pro Cys Ser Cys Asp | |
| |       -20             -15 | |

| tgc ttt gtc tcc gtg ccc ccg gcc tca gcc atc ccg gct gtg atc ttt | 158 |
|---|---|
| Cys Phe Val Ser Val Pro Pro Ala Ser Ala Ile Pro Ala Val Ile Phe | |
| -10          -5               1            5 | |

| gcc aag aac tcg gac cga ccc cgg gac gag gtg cag gag gtg gtg ttt | 206 |
|---|---|
| Ala Lys Asn Ser Asp Arg Pro Arg Asp Glu Val Gln Glu Val Val Phe | |
|         10                 15               20 | |

| gtc ccc gca ggc act cac act cct ggg agc cgg ctc cag tgc acc tac | 254 |
|---|---|
| Val Pro Ala Gly Thr His Thr Pro Gly Ser Arg Leu Gln Cys Thr Tyr | |
|            25               30              35 | |

| att gaa gtg gaa cag gtg tcg aag acg cac gct gtg att ctg agc cgt | 302 |
|---|---|
| Ile Glu Val Glu Gln Val Ser Lys Thr His Ala Val Ile Leu Ser Arg | |
|   40                    45              50 | |

| cct tct tgg cta tgg ggg gct gag atg ggc gcc aac gag cat ggt gtc | 350 |
|---|---|
| Pro Ser Trp Leu Trp Gly Ala Glu Met Gly Ala Asn Glu His Gly Val | |
| 55                  60              65              70 | |

| tgc att ggc aac gag gct gtg tgg acg aag gag cca gtt ggg gag ggg | 398 |
|---|---|
| Cys Ile Gly Asn Glu Ala Val Trp Thr Lys Glu Pro Val Gly Glu Gly | |
|         75                 80               85 | |

| gaa gcc ctg ctg ggc atg gac cta ctc agg ctg gct ttg gaa cgg agc | 446 |
|---|---|
| Glu Ala Leu Leu Gly Met Asp Leu Leu Arg Leu Ala Leu Glu Arg Ser | |
|           90                95              100 | |

| agc tct gcc cag gag gcc ttg cat gtg atc aca ggg tta ctg gag cac | 494 |
|---|---|
| Ser Ser Ala Gln Glu Ala Leu His Val Ile Thr Gly Leu Leu Glu His | |
|          105                 110             115 | |

| tat ggg cag ggg ggc aac tgc ctg gag gat gct gcg cca ttc tcc tac | 542 |
|---|---|
| Tyr Gly Gln Gly Gly Asn Cys Leu Glu Asp Ala Ala Pro Phe Ser Tyr | |
| 120                   125             130 | |

| cat agc acc ttc ctg ctg gct gac cgc act gag gcg tgg gtg ctg gag | 590 |
|---|---|
| His Ser Thr Phe Leu Leu Ala Asp Arg Thr Glu Ala Trp Val Leu Glu | |
| 135                140              145             150 | |

| aca gct ggg agg ctc tgg gct gca cag agg atc cag gag ggg gcc cgc | 638 |
|---|---|
| Thr Ala Gly Arg Leu Trp Ala Ala Gln Arg Ile Gln Glu Gly Ala Arg | |
|              155             160             165 | |

| aac atc tcc aac cag ctg agc att ggc acg gac atc tcg gcc caa cac | 686 |
|---|---|
| Asn Ile Ser Asn Gln Leu Ser Ile Gly Thr Asp Ile Ser Ala Gln His | |
|           170               175             180 | |

| ccg gag ctg cgg act cat gcc cag gcc aag ggc tgg tgg gat ggg cag | 734 |
|---|---|
| Pro Glu Leu Arg Thr His Ala Gln Ala Lys Gly Trp Trp Asp Gly Gln | |
| 185                 190             195 | |

| ggt gcc ttt gac ttt gct cag atc ttc tcc ctg acc cag cag cct gtg | 782 |
|---|---|
| Gly Ala Phe Asp Phe Ala Gln Ile Phe Ser Leu Thr Gln Gln Pro Val | |
| 200                   205             210 | |

| cgc atg gag gct gcc aag gcc cgc ttc cag gca ggg cgg gag ctg ctg | 830 |
|---|---|
| Arg Met Glu Ala Ala Lys Ala Arg Phe Gln Ala Gly Arg Glu Leu Leu | |
| 215                 220             225            230 | |

| cgg caa cgg caa ggg ggc atc acg gca gag gtg atg atg ggc atc ctc | 878 |
|---|---|
| Arg Gln Arg Gln Gly Gly Ile Thr Ala Glu Val Met Met Gly Ile Leu | |

| | | | | | | | | | | | | | | |
|---|---|---|---|---|---|---|---|---|---|---|---|---|---|---|
| | | | | 235 | | | | 240 | | | | 245 | | |
| aga | gac | aag | gag | agt | ggt | atc | tgt | atg | gac | tcg | gga | ggc | ttt cgc acc | 926 |
| Arg | Asp | Lys | Glu | Ser | Gly | Ile | Cys | Met | Asp | Ser | Gly | Gly | Phe Arg Thr | |
| | | | | 250 | | | | 255 | | | | 260 | | |
| acg | gcc | agc | atg | gtg | tct | gtc | ctg | ccc | cag | gat | ccc | acg | cag ccc tgc | 974 |
| Thr | Ala | Ser | Met | Val | Ser | Val | Leu | Pro | Gln | Asp | Pro | Thr | Gln Pro Cys | |
| | | | | 265 | | | | 270 | | | | 275 | | |
| gtg | cac | ttt | ctt | acc | gcc | acg | cca | gac | cca | tcc | agg | tct | gtg ttc aaa | 1022 |
| Val | His | Phe | Leu | Thr | Ala | Thr | Pro | Asp | Pro | Ser | Arg | Ser | Val Phe Lys | |
| | | | | 280 | | | | 285 | | | | 290 | | |
| cct | ttc | atc | ttc | ggg | gtg | ggg | gtg | gcc | cag | gcc | ccc | cag | gtg ctg tcc | 1070 |
| Pro | Phe | Ile | Phe | Gly | Val | Gly | Val | Ala | Gln | Ala | Pro | Gln | Val Leu Ser | |
| 295 | | | | 300 | | | | 305 | | | | | 310 | |
| ccc | act | ttt | gga | gca | caa | gac | cct | gtt | cgg | acc | ctg | ccc | cga ttc cag | 1118 |
| Pro | Thr | Phe | Gly | Ala | Gln | Asp | Pro | Val | Arg | Thr | Leu | Pro | Arg Phe Gln | |
| | | | | 315 | | | | 320 | | | | 325 | | |
| act | cag | gta | gat | cgt | cgg | cat | acc | ctc | tac | cgt | gga | cac | cag gca gcc | 1166 |
| Thr | Gln | Val | Asp | Arg | Arg | His | Thr | Leu | Tyr | Arg | Gly | His | Gln Ala Ala | |
| | | | | 330 | | | | 335 | | | | 340 | | |
| ctg | ggg | ctg | atg | gag | aga | gat | cag | gat | cgg | ggg | cag | cag | ctc cag cag | 1214 |
| Leu | Gly | Leu | Met | Glu | Arg | Asp | Gln | Asp | Arg | Gly | Gln | Gln | Leu Gln Gln | |
| | | | | 345 | | | | 350 | | | | 355 | | |
| aaa | cag | cag | gat | ctg | gag | cag | gaa | ggc | ctc | gag | gcc | aca | cag ggg ctg | 1262 |
| Lys | Gln | Gln | Asp | Leu | Glu | Gln | Glu | Gly | Leu | Glu | Ala | Thr | Gln Gly Leu | |
| | | | | 360 | | | | 365 | | | | 370 | | |
| ctg | gcc | ggc | gag | tgg | gcc | cca | ccc | ctc | tgg | gag | ctg | ggc | agc ctc ttc | 1310 |
| Leu | Ala | Gly | Glu | Trp | Ala | Pro | Pro | Leu | Trp | Glu | Leu | Gly | Ser Leu Phe | |
| 375 | | | | 380 | | | | 385 | | | | | 390 | |
| cag | gcc | ttc | gtg | aag | agg | gag | agc | cag | gct | tat | gcg | taagcttcat | | 1356 |
| Gln | Ala | Phe | Val | Lys | Arg | Glu | Ser | Gln | Ala | Tyr | Ala | | | |
| | | | | 395 | | | | 400 | | | | | | |

```
agcttctgct ggcctggggt ggacccagga cccctgggc ctgggtgccc tgagtggtgg    1416
taaagtggag caatcccttc acgctccttg gccatgttct gagcggccag cttggccttt    1476
gccttaataa atgtgcttta ttttcaaaaa aaaaaaaaa a                         1517
```

<210> SEQ ID NO 55
<211> LENGTH: 1560
<212> TYPE: DNA
<213> ORGANISM: Homo sapiens
<220> FEATURE:
<221> NAME/KEY: CDS
<222> LOCATION: 194..454
<220> FEATURE:
<221> NAME/KEY: sig_peptide
<222> LOCATION: 194..379
<223> OTHER INFORMATION: Von Heijne matrix
      score 4.6
      seq HILTVPLLEPARC/SG
<220> FEATURE:
<221> NAME/KEY: polyA_site
<222> LOCATION: 1545..1560

<400> SEQUENCE: 55

```
cattcataaa tattctctta ccattttact tgacaattat tttaggctta cagaaaagtg    60
gccagagtag tgcagggctc ctatagttgg cttcccctgt tgccatcatc tcgtctgatc   120
gtagggcagg ttagcattgc tacaggcctc ttacccggcc tacagctctt aggcacatct   180
```

| | | | | | | | | | | | | |
|---|---|---|---|---|---|---|---|---|---|---|---|---|
| gtccatttga | cta | atg | gcc | att | ttc | tgg | ata | gtc | cat | gct | cac ttc tgg | 229 |
| | | Met | Ala | Ile | Phe | Trp | Ile | Val | His | Ala | His Phe Trp | |
| | | | | −60 | | | | −55 | | | | |

| | | | | | | | | | | | | |
|---|---|---|---|---|---|---|---|---|---|---|---|---|
| agc | ccc | ctc | cca | ccc | agg | ctc | cca | cat | ggc | cgg | tgc tgt tgc ctg aag | 277 |

```
Ser Pro Leu Pro Pro Arg Leu Pro His Gly Arg Cys Cys Cys Leu Lys
-50                 -45                 -40                 -35 gcc cct ctt cct cct gac gtg gga ccc ctt cag gta gcc ccg cat ctt      325
Ala Pro Leu Pro Pro Asp Val Gly Pro Leu Gln Val Ala Pro His Leu
                -30                 -25                 -20 ttc agc gtg ccc ctt cac att ctg act gtt cct ctt ctg gaa cct gca      373
Phe Ser Val Pro Leu His Ile Leu Thr Val Pro Leu Leu Glu Pro Ala
            -15                 -10                 -5 aga tgc tct ggg atc ctt gta ttt ttc ctg cac cag ccc gtt tca tcc      421
Arg Cys Ser Gly Ile Leu Val Phe Phe Leu His Gln Pro Val Ser Ser
        1                5                   10 ctg agc ttc tgt tat ttt att gga gga tgg tgc tagaaacaca ggtctggatg    474
Leu Ser Phe Cys Tyr Phe Ile Gly Gly Trp Cys
15                  20                  25 caggcaggag acacacgcgt ccacactagc atgcgtgtgt acacacatct acatgtgctt    534
atccccgcg ttcatgttaa aaaccatggg atcataccgg tgtttcagat tcacatccac     594
cccagcaggg tttctcgccc ccattgctta taaccttagc aggtgttgag aaccctggcg    654
ctcactgtcc acagtgagtt tgcttattcg ttgaaaccta gcgtgcctgt agagtgtgga    714
gagttgccgg cccgcacccc tgcgagacac agactttctg accgcagccc tcatgtgtgt    774
ggctcttctt gtccttggcc ttacagtgca gtcggatcgc tgctttccag agttgcctgg    834
gggtaggtcc ctcctcttct gtgctctgcg gcgcagtgag cggcctttgc ctcaggcctc    894
ccgcggcttc cttaagcctc tggcctgccc ggtccctggc gccaggtctg ttttccctgc    954
tcccttctct ctgatcctgc tttggtctga gccgtgcctc tgggcccag cattgctggg    1014
ccgcattgtc gttttatttc tcttgtgtcg ttgcgtctag tgtaagacat tcagtggatc    1074
attgtggatg gtcattagtg gtccagagtg gaaagtgagg tcgttgttgg tggtgtacct   1134
acagtgcctg ttagggagct gttcctggtg ttgcccgtga atattagact tgctcccgag   1194
cctgcgccac agcccatccc tagcgactta gcgacagtgg ctgccaggtg cgggtggctg   1254
tgtcttgtat acactgtgtg ggcagcccag ggccagggc ctcctccttc catggcagcc    1314
tctgtctgca tcacagagat aaggccgcgg ctgccaccag gataaggagc cagcagctgc   1374
tctcggagga gccgccctga ccctccccca tcatgccgcc gtggggtttc catgcagaat   1434
tttccttggg cagagttgct ttttgattct agttttaaa aaaactgttc tttccatcat    1494
gataaaaga aagacatgct catttcaaat agtttaggag atgtggaagc aaaaaaaaaa   1554
aaaaaa                                                              1560

<210> SEQ ID NO 56
<211> LENGTH: 1066
<212> TYPE: DNA
<213> ORGANISM: Homo sapiens
<220> FEATURE:
<221> NAME/KEY: CDS
<222> LOCATION: 48..494
<220> FEATURE:
<221> NAME/KEY: sig_peptide
<222> LOCATION: 48..347
<223> OTHER INFORMATION: Von Heijne matrix
      score 3.7
      seq LASSFLFTMGGLG/FI
<220> FEATURE:
<221> NAME/KEY: polyA_signal
<222> LOCATION: 1031..1036
<220> FEATURE:
<221> NAME/KEY: polyA_site
<222> LOCATION: 1051..1066

<400> SEQUENCE: 56
```

```
gaggcgcgtg gggcttgagg ccgagaacgg cccttgctgc caccaac atg gag act         56
                                                    Met Glu Thr
                                                       -100 ttg tac cgt gtc ccg ttc tta gtg ctc gaa tgt ccc aac ctg aag ctg        104
Leu Tyr Arg Val Pro Phe Leu Val Leu Glu Cys Pro Asn Leu Lys Leu
        -95              -90              -85 aag aag ccg ccc tgg ttg cac atg ccg tcg gcc atg act gtg tat gct        152
Lys Lys Pro Pro Trp Leu His Met Pro Ser Ala Met Thr Val Tyr Ala
    -80              -75              -70 ctg gtg gtg gtg tct tac ttc ctc atc acc gga gga ata att tat gat        200
Leu Val Val Val Ser Tyr Phe Leu Ile Thr Gly Gly Ile Ile Tyr Asp
-65              -60              -55                      -50 gtt att gtt gaa cct cca agt gtc ggt tct atg act gat gaa cat ggg        248
Val Ile Val Glu Pro Pro Ser Val Gly Ser Met Thr Asp Glu His Gly
            -45              -40              -35 cat cag agg cca gta gct ttc ttg gcc tac aga gta aat gga caa tat        296
His Gln Arg Pro Val Ala Phe Leu Ala Tyr Arg Val Asn Gly Gln Tyr
        -30              -25              -20 att atg gaa gga ctt gca tcc agc ttc cta ttt aca atg gga ggt tta        344
Ile Met Glu Gly Leu Ala Ser Ser Phe Leu Phe Thr Met Gly Gly Leu
    -15              -10              -5 ggt ttc ata atc ctg gac cga tcg aat gca cca aat atc cca aaa ctc        392
Gly Phe Ile Ile Leu Asp Arg Ser Asn Ala Pro Asn Ile Pro Lys Leu
 1               5               10              15 aat aga ttc ctt ctt ctg ttc att gga ttc gtc tgt gtc cta ttg agt        440
Asn Arg Phe Leu Leu Leu Phe Ile Gly Phe Val Cys Val Leu Leu Ser
            20              25              30 ttt ttc atg gct aga gta ttc atg aga atg aaa ctg ccg ggc tat ctg        488
Phe Phe Met Ala Arg Val Phe Met Arg Met Lys Leu Pro Gly Tyr Leu
        35              40              45 atg ggt tagagtgcct ttgagaagaa atcagtggat actggatttg ctcctgtcaa        544
Met Gly tgaagtttta aaggctgtac caatcctcta atatgaaatg tggaaaagaa tgaagagcag        604
cagtaaaaga aatatctagt gaaaaaacag gaagcgtatt gaagcttgga ctagaatttc        664
ttcttggtat taaagagaca agtttatcac agaatttttt ttcctgctgg cctattgcta        724
taccaatgat gttgagtggc attttctttt tagttttttca ttaaaatata ttccatatct        784
acaactataa tatcaaataa agtgattatt ttttacaacc ctcttaacat tttttggaga        844
tgacatttct gattttcaga aattaacata aaatccagaa gcaagattcc gtaagctgag        904
aactctggac agttgatcag ctttacctat ggtgctttgc ctttaactag agtgtgtgat        964
ggtagattat ttcagatatg tatgtaaaac tgtttcctga acaataagat gtatgaacgg       1024
agcagaaata aatacttttt ctaattaaaa aaaaaaaaaa aa                          1066

<210> SEQ ID NO 57
<211> LENGTH: 1061
<212> TYPE: DNA
<213> ORGANISM: Homo sapiens
<220> FEATURE:
<221> NAME/KEY: CDS
<222> LOCATION: 111..671
<220> FEATURE:
<221> NAME/KEY: sig_peptide
<222> LOCATION: 111..215
<223> OTHER INFORMATION: Von Heijne matrix
      score 4.5
      seq SFTVSMAIGLVLG/GF
<220> FEATURE:
<221> NAME/KEY: polyA_signal
<222> LOCATION: 990..995
```

```
<220> FEATURE:
<221> NAME/KEY: polyA_site
<222> LOCATION: 1045..1061

<400> SEQUENCE: 57
```

| | | |
|---|---|---|
| attatttttc tcttgctgta ctacaaagag atagaatcaa actgctttt ttcgacatac | | 60 |
| tggtttttct ttctgttttt cttctctttc ttctatttct tgtggatatt atg gct<br>                                                                                  Met Ala<br>                                                                                  -35 | | 116 |

```
aat aac aca aca agt tta ggg agt cca tgg cca gaa aac ttt tgg gag      164
Asn Asn Thr Thr Ser Leu Gly Ser Pro Trp Pro Glu Asn Phe Trp Glu
        -30                 -25                 -20 gac ctt atc atg tcc ttc act gta tcc atg gca atc ggg ctg gta ctt      212
Asp Leu Ile Met Ser Phe Thr Val Ser Met Ala Ile Gly Leu Val Leu
    -15                 -10                  -5 gga gga ttt att tgg gct gtg ttc att tgt ctg tct cga aga aga aga      260
Gly Gly Phe Ile Trp Ala Val Phe Ile Cys Leu Ser Arg Arg Arg Arg
  1               5                  10                  15 gcc agt gct ccc atc tca cag tgg agt tca agc agg aga tct agg tct      308
Ala Ser Ala Pro Ile Ser Gln Trp Ser Ser Ser Arg Arg Ser Arg Ser
             20                  25                  30 tct tac acc cac ggc ctc aac aga act gga ttt tac cgc cac agt ggc      356
Ser Tyr Thr His Gly Leu Asn Arg Thr Gly Phe Tyr Arg His Ser Gly
         35                  40                  45 tgt gaa cgt cga agc aac ctc agc ctg gcc agt ctc acc ttc cag cga      404
Cys Glu Arg Arg Ser Asn Leu Ser Leu Ala Ser Leu Thr Phe Gln Arg
     50                  55                  60 caa gct tcc ctg gaa caa gca aat tcc ttt cca aga aaa tca agt ttc      452
Gln Ala Ser Leu Glu Gln Ala Asn Ser Phe Pro Arg Lys Ser Ser Phe
 65                  70                  75 aga gct tct act ttc cat ccc ttt ctg caa tgt cca cca ctt cct gtg      500
Arg Ala Ser Thr Phe His Pro Phe Leu Gln Cys Pro Pro Leu Pro Val
 80                  85                  90                  95 gaa act gag agt cag ctg gtg act ctc cct tct tcc aat atc tct ccc      548
Glu Thr Glu Ser Gln Leu Val Thr Leu Pro Ser Ser Asn Ile Ser Pro
                100                 105                 110 acc atc agc act tcc cac agt ctg agc cgt cct gac tac tgg tcc agt      596
Thr Ile Ser Thr Ser His Ser Leu Ser Arg Pro Asp Tyr Trp Ser Ser
            115                 120                 125 aac agt ctt cga gtg ggc ctt tca aca ccg ccc cca cct gcc tat gag      644
Asn Ser Leu Arg Val Gly Leu Ser Thr Pro Pro Pro Pro Ala Tyr Glu
        130                 135                 140 tcc atc atc aag gca ttc cca gat tcc tgagtaggg ggcttttggt            691
Ser Ile Ile Lys Ala Phe Pro Asp Ser
    145                 150 ttttgtttct ttcttgtctt gtctttattt gaaaggaaat caaaaatagg ctaaacagaa    751
ttttgagggc atggcccaaa taactcatga gttccaagtt gaaacatggt tgtgcaagtt    811
ggacattaca atgtaaaaca cattttcttc aaacacgttt tcccttttgt ttcaaaaaat    871
gtaatatttt cccccaagcg ttttatattt atgtattttg tattcaatgt gaggcttat    931 aaaaatagtg attctaatgt aagaatcagc taagatgcat tatatatatt ttaattaaaa    991
ttaaaacttc agatatttgt ggattacaat cctcatttac ttccaatgtg actaaaaaaa    1051
aaaaaaaaaa                                                          1061

<210> SEQ ID NO 58
<211> LENGTH: 2025
<212> TYPE: DNA
<213> ORGANISM: Homo sapiens
```

```
<220> FEATURE:
<221> NAME/KEY: CDS
<222> LOCATION: 5..373
<220> FEATURE:
<221> NAME/KEY: sig_peptide
<222> LOCATION: 5..82
<223> OTHER INFORMATION: Von Heijne matrix
      score 4
      seq SLFWFTVITLSFG/YY
<220> FEATURE:
<221> NAME/KEY: polyA_signal
<222> LOCATION: 1986..1991
<220> FEATURE:
<221> NAME/KEY: polyA_site
<222> LOCATION: 2010..2025

<400> SEQUENCE: 58
```

| | | | | | | | | | | | | |
|---|---|---|---|---|---|---|---|---|---|---|---|---|
| agcc | atg | gct | acg | gca | gcc | ggc | gcg | acc | tac | ttt | cag | cga  ggc  agt  ctg |
| | Met | Ala | Thr | Ala | Ala | Gly | Ala | Thr | Tyr | Phe | Gln | Arg  Gly  Ser  Leu |
| | | -25 | | | | -20 | | | | | -15 | |

```
agcc atg gct acg gca gcc ggc gcg acc tac ttt cag cga ggc agt ctg      49
     Met Ala Thr Ala Ala Gly Ala Thr Tyr Phe Gln Arg Gly Ser Leu
         -25             -20                 -15 ttc tgg ttc aca gtc atc acc ctc agc ttt ggc tac tac aca tgg gtt      97
Phe Trp Phe Thr Val Ile Thr Leu Ser Phe Gly Tyr Tyr Thr Trp Val
-10             -5                  1               5 gtc ttc tgg cct cag agt atc cct tat cag aac ctt ggg ccc ctg ggc      145
Val Phe Trp Pro Gln Ser Ile Pro Tyr Gln Asn Leu Gly Pro Leu Gly
                10              15                  20 ccc ttc act cag tac ttg gtg gac cac cat cac acc ctc ctg tgc aat      193
Pro Phe Thr Gln Tyr Leu Val Asp His His Thr Leu Leu Cys Asn
            25                  30                  35 ggg tat tgg ctt gcc tgg ctg att cat gtg gga gag tcc ttg tat gcc      241
Gly Tyr Trp Leu Ala Trp Leu Ile His Val Gly Glu Ser Leu Tyr Ala
        40                  45                  50 ata gta ttg tgc aag cat aaa ggc atc aca agt ggt cgg gct cag cta      289
Ile Val Leu Cys Lys His Lys Gly Ile Thr Ser Gly Arg Ala Gln Leu
    55                  60                  65 ctc tgg ttc cta cag act ttc ttc ttt ggg ata gcg tct ctc acc atc      337
Leu Trp Phe Leu Gln Thr Phe Phe Phe Gly Ile Ala Ser Leu Thr Ile
70              75                  80                  85 ttg att gct tac aaa cgg aag cgc caa aaa caa act tgaagttgtc           383
Leu Ile Ala Tyr Lys Arg Lys Arg Gln Lys Gln Thr
                90                  95 tgaaagcttg ctctacactt ttacattcat cctcacccct ttttttgtgg ggtagaggag    443
gtgcagtaat ttactcagtg atctttctac tttctagaaa ctgtccttca aagctcttta    503
agaccccctc gttagtcagt tttttctctt atatgctctg gttgagcttg aatagaccag    563
ttgttactta agaaagaaac agagaaagat tttagctttt caatcctatt tggcagagga    623
cttcagctac cttcttacag tctttggctg tgttggtacc ctcgtgtgct ctgagctaag    683
ccacatacta aactgacttt ttggtttgta tacccttgct cccgccttct gatgaaaaca    743
ccttaccctc acaaccacca tctttcctct cctttccaaa gctctttcca ccttgctgca    803
ctaagataaa gtgacacttc cactatatgt caattccaca cacatttatt aggtacctgt    863
gaggtaggat cctatcctct caaacttcca tttctcatgc tacagagaaa gataaggaag    923
atgagcaagt gcctggaatg gggcaggctg agcagtcaca caggcataga ggcacgctga    983
gaacctggag gggagactgc agagtgcctt ccctgatgct gcagccggaa gtgatccttc   1043
cctccacctg gcccctggga cactgtgctc tgcagtgtgc agggcctgat ggcactgcta   1103
gattgctcct tcagctcagg gccacagctt aaacagcttt accttccccc tcagcacctg   1163
tcccactatc ttgcacacag gtgctctaac catgtttatt gaacaaagga gggaaactga   1223
tttcactttc acttgttcat tatcattcca attttttatgt gaaaatggca caacccattt   1283
```

-continued

```
ggggtaccct cacccaaaa taaaagccca agtctacctt tgactggtac caccttttt       1343 gtggtttcgt tggtgagaaa cctttatctt tttcatacct ttctattctc aatcacttct       1403
ccaaaagtgt gtctttccag ctctgattta ttcaaaacac aagcatttct gtttagagat       1463
tctagcccat gggttatctg ctagttatt acctctcctg ttcacttagt tatactttat       1523
tattgctcac aggctgggga ggcagaatga ctctgtcacc actaggagcc attagggctt       1583
cttccctgga ggactgcctg cttgctttct ggggacacta gccctcattt cccttctgtg       1643
gtacagtggg gcaaattatt tgtattaagc aaacatttat gggaaacaac ccgctcccga       1703
aaacggagcc cccaagtaaa gcacaaccct gaaagattat gaactatgaa ttgtctctgg       1763
tagagataaa tttctgcaaa catatctcag tcttccctct gtttctctgg tgattaagaa       1823
gttccttttt ggtaaggaaa aggatttta accatagagt taggcatcat ggaaattcaa       1883
accagatttc ttaatacctg gtcttcctca aagagaaata ataacagtaa tagtggtgct       1943
gggaacaata tggcagatta ttgaatgaaa ttgattaact tgaataaat gctgtgaatt       2003 ttctctaaaa aaaaaaaaaa aa                                                2025
```

<210> SEQ ID NO 59
<211> LENGTH: 591
<212> TYPE: DNA
<213> ORGANISM: Homo sapiens
<220> FEATURE:
<221> NAME/KEY: CDS
<222> LOCATION: 14..472
<220> FEATURE:
<221> NAME/KEY: sig_peptide
<222> LOCATION: 14..319
<223> OTHER INFORMATION: Von Heijne matrix
     score 4.9
     seq VFFFGVSIILVLG/ST
<220> FEATURE:
<221> NAME/KEY: polyA_signal
<222> LOCATION: 555..560
<220> FEATURE:
<221> NAME/KEY: polyA_site
<222> LOCATION: 576..591

<400> SEQUENCE: 59

```
agcaccatct gtc atg gcg gct ggg ctg ttt ggt ttg agc gct cgc cgt              49
            Met Ala Ala Gly Leu Phe Gly Leu Ser Ala Arg Arg
                -100                          -95 ctt ttg gcg gca gcg gcg acg cga ggg ctc ccg gcc gcc cgc gtc cgc             97
Leu Leu Ala Ala Ala Ala Thr Arg Gly Leu Pro Ala Ala Arg Val Arg
-90                 -85                 -80                 -75 tgg gaa tct agc ttc tcc agg act gtg gtc gcc ccg tcc gct gtg gcg            145
Trp Glu Ser Ser Phe Ser Arg Thr Val Val Ala Pro Ser Ala Val Ala
                -70                 -65                 -60 gga aag cgg ccc cca gaa ccg acc aca ccg tgg caa gag gac cca gaa            193
Gly Lys Arg Pro Pro Glu Pro Thr Thr Pro Trp Gln Glu Asp Pro Glu
            -55                 -50                 -45 ccc gag gac gaa aac ttg tat gag aag aac cca gac tcc cat ggt tat            241
Pro Glu Asp Glu Asn Leu Tyr Glu Lys Asn Pro Asp Ser His Gly Tyr
        -40                 -35                 -30 gac aag gac ccc gtt ttg gac gtc tgg aac atg cga ctt gtc ttc ttc            289
Asp Lys Asp Pro Val Leu Asp Val Trp Asn Met Arg Leu Val Phe Phe
    -25                 -20                 -15 ttt ggc gtc tcc atc atc ctg gtc ctt ggc agc acc ttt gtg gcc tat            337
Phe Gly Val Ser Ile Ile Leu Val Leu Gly Ser Thr Phe Val Ala Tyr
-10                 -5                   1                   5 ctg cct gac tac agg atg aaa gag tgg tcc cgc cgc gaa gct gag agg            385
```

```
Leu Pro Asp Tyr Arg Met Lys Glu Trp Ser Arg Arg Glu Ala Glu Arg
         10                  15                  20 ctt gtg aaa tac cga gag gcc aat ggc ctt ccc atc atg gaa tcc aac        433
Leu Val Lys Tyr Arg Glu Ala Asn Gly Leu Pro Ile Met Glu Ser Asn
         25                  30                  35 tgc ttc gac ccc agc aag atc cag ctg cca gag gat gag tgaccagttg         482
Cys Phe Asp Pro Ser Lys Ile Gln Leu Pro Glu Asp Glu
         40                  45                  50 ctaagtgggg ctcaagaagc accgccttcc ccaccacctg cctgccattc tgacctcttc      542
tcagagcacc taattaaagg ggctgaaagt ctgaaaaaaa aaaaaaaaa                  591

<210> SEQ ID NO 60
<211> LENGTH: 544
<212> TYPE: DNA
<213> ORGANISM: Homo sapiens
<220> FEATURE:
<221> NAME/KEY: CDS
<222> LOCATION: 2..217
<220> FEATURE:
<221> NAME/KEY: polyA_signal
<222> LOCATION: 489..494
<220> FEATURE:
<221> NAME/KEY: polyA_site
<222> LOCATION: 529..544

<400> SEQUENCE: 60 t cta cct gtg agt act agg atc atc aat cat atc tac agc ttc ccc tca      49
  Leu Pro Val Ser Thr Arg Ile Ile Asn His Ile Tyr Ser Phe Pro Ser
  1               5                  10                  15 gtt gat tta tgg ata gtt tgt att ttc act gta tct gtc tca cac ctt        97
Val Asp Leu Trp Ile Val Cys Ile Phe Thr Val Ser Val Ser His Leu
         20                  25                  30 ttt gaa aag gga aca ttg tat ggc tac ttt tat gtg att aac tcc tcc        145
Phe Glu Lys Gly Thr Leu Tyr Gly Tyr Phe Tyr Val Ile Asn Ser Ser
         35                  40                  45 atc aat tta tgt gtc aat gat tgc ctt cct gta atg gat tca att tct        193
Ile Asn Leu Cys Val Asn Asp Cys Leu Pro Val Met Asp Ser Ile Ser
50                  55                  60 ctg tct cca ttg ttt ctt tct cac tagagaagtt ctttaaaatt ctatgaaaat       247
Leu Ser Pro Leu Phe Leu Ser His
65                  70 gaaactgtgc taaattaaaa atctactcat gataacagga gacactcaaa attatgggtt      307
tcagtttcag gcttctcacc atgtcctcag attgtactcc ctttctagcc cttctgcagc      367
aaataaacct ttgccatcag ttcaccaaaa gcactcatga gaggaaaaat ggcatatcac      427
taaatataga gttctttgtc acttcttgat ttcaaattta caactaatac tcaacacttt      487
aattaaatct ttcttttctc ttcttcctaa acatacatg caaaaaaaaa aaaaaaa        544

<210> SEQ ID NO 61
<211> LENGTH: 1689
<212> TYPE: DNA
<213> ORGANISM: Homo sapiens
<220> FEATURE:
<221> NAME/KEY: CDS
<222> LOCATION: 51..575
<220> FEATURE:
<221> NAME/KEY: sig_peptide
<222> LOCATION: 51..110
<223> OTHER INFORMATION: Von Heijne matrix
      score 11.2
      seq AFLLLVALSYTLA/RD
<220> FEATURE:
<221> NAME/KEY: polyA_signal
<222> LOCATION: 1653..1658
```

-continued

```
<220> FEATURE:
<221> NAME/KEY: polyA_site
<222> LOCATION: 1674..1689

<400> SEQUENCE: 61
```

| | | |
|---|---|---|
| agaagcttgg accgcatcct agccgccgac tcacacaagg cagagttgcc atg gag<br>                                                                                                                                    Met Glu<br>                                                                                                                                   -20 | 56 |

```
aaa att cca gtg tca gca ttc ttg ctc ctt gtg gcc ctc tcc tac act      104
Lys Ile Pro Val Ser Ala Phe Leu Leu Leu Val Ala Leu Ser Tyr Thr
        -15                 -10                  -5 ctg gcc aga gat acc aca gtc aaa cct gga gcc aaa aag gac aca aag      152
Leu Ala Arg Asp Thr Thr Val Lys Pro Gly Ala Lys Lys Asp Thr Lys
         1               5                  10 gac tct cga ccc aaa ctg ccc cag acc ctc tcc aga ggt tgg ggt gac      200
Asp Ser Arg Pro Lys Leu Pro Gln Thr Leu Ser Arg Gly Trp Gly Asp
 15              20                  25                  30 caa ctc atc tgg act cag aca tat gaa gaa gct cta tat aaa tcc aag      248
Gln Leu Ile Trp Thr Gln Thr Tyr Glu Glu Ala Leu Tyr Lys Ser Lys
                 35                  40                  45 aca agc aac aaa ccc ttg atg att att cat cac ttg gat gag tgc cca      296
Thr Ser Asn Lys Pro Leu Met Ile Ile His His Leu Asp Glu Cys Pro
             50                  55                  60 cac agt caa gct tta aag aaa gtg ttt gct gaa aat aaa gaa atc cag      344
His Ser Gln Ala Leu Lys Lys Val Phe Ala Glu Asn Lys Glu Ile Gln
         65                  70                  75 aaa ttg gca gag cag ttt gtc ctc ctc aat ctg gtt tat gaa aca act      392
Lys Leu Ala Glu Gln Phe Val Leu Leu Asn Leu Val Tyr Glu Thr Thr
 80                  85                  90 gac aaa cac ctt tct cct gat ggc cag tat gtc ccc agg att atg ttt      440
Asp Lys His Leu Ser Pro Asp Gly Gln Tyr Val Pro Arg Ile Met Phe
 95                 100                 105                 110 gtt gac cca tct ctg aca gtt aga gcc gat atc act gga aga tat tca      488
Val Asp Pro Ser Leu Thr Val Arg Ala Asp Ile Thr Gly Arg Tyr Ser
                115                 120                 125 aat cgt ctc tat gct tac gaa cct gca gat aca gct ctg ttg ctt gac      536
Asn Arg Leu Tyr Ala Tyr Glu Pro Ala Asp Thr Ala Leu Leu Leu Asp
             130                 135                 140 aac atg aag aaa gct ctc aag ttg ctg aag act gaa ttg taaagaaaaa      585
Asn Met Lys Lys Ala Leu Lys Leu Leu Lys Thr Glu Leu
        145                 150                 155 aaatctccaa gcccttctgt ctgtcaggcc ttgagacttg aaaccagaag aagtgtgaga    645
agactggcta gtgtggaagc atagtgaaca cactgattag gttatggttt aatgttacaa    705
caactatttt ttaagaaaaa caagttttag aaatttggtt tcaagtgtac atgtgtgaaa    765
acaatattgt atactaccat agtgagccat gattttctaa aaaaaaaata aatgttttgg    825
gggtgttctg ttttctccaa cttggtcttt cacagtggtt cgtttaccaa ataggattaa    885
acacacacaa aatgctcaag gaagggacaa gacaaaacca aaactagttc aaatgatgaa    945
gaccaaagac caagttatca tctcaccaca ccacaggttc tcactagatg actgtaagta   1005
gacacgagct taatcaacag aagtatcaag ccatgtgctt tagcataaaa gaatatttag   1065
aaaaacatcc caagaaaatc acatcactac ctagagtcaa ctctggccag gaactctaag   1125
gtacacactt tcatttagta attaaatttt agtcagattt tgcccaacct aatgctctca   1185
gggaaagcct ctggcaagta gctttctcct tcagaggtct aatttagtag aaaggtcatc   1245
caaagaacat ctgcactcct gaacacaccc tgaagaaatc ctgggaattg accttgtaat   1305
cgatttgtct gtcaaggtcc taaagtactg gagtgaaata aattcagcca acatgtgact   1365
```

-continued

```
aattggaaga agagcaaagg gtggtgacgt gttgatgagg cagatggaga tcagaggtta     1425
ctagggttta ggaaacgtga aaggctgtgg catcagggta ggggagcatt ctgcctaaca     1485
gaaattagaa ttgtgtgtta atgtcttcac tctatactta atctcacatt cattaatata     1545
tggaattcct ctactgccca gcccctactg atttctttgg ccctggact atggtgctgt      1605 atataatgct ttgcagtatc tgttgcttgt cttgattaac ttttttggat aaaaccttt      1665 ttgaacagaa aaaaaaaaa aaaa                                             1689

<210> SEQ ID NO 62
<211> LENGTH: 1111
<212> TYPE: DNA
<213> ORGANISM: Homo sapiens
<220> FEATURE:
<221> NAME/KEY: CDS
<222> LOCATION: 69..977
<220> FEATURE:
<221> NAME/KEY: sig_peptide
<222> LOCATION: 69..128
<223> OTHER INFORMATION: Von Heijne matrix
      score 5.3
      seq VLLGSGLTILSQP/LM
<220> FEATURE:
<221> NAME/KEY: polyA_signal
<222> LOCATION: 1076..1081
<220> FEATURE:
<221> NAME/KEY: polyA_site
<222> LOCATION: 1096..1111

<400> SEQUENCE: 62
acctaggacc ggctcaccgg gtcgcttggt ggctccgtct gtctgtccgt ccgcccgcgg      60 gtgccatc atg gcg gac gcg gcc agt cag gtg ctc ctg ggc tcc ggt ctc     110
         Met Ala Asp Ala Ala Ser Gln Val Leu Leu Gly Ser Gly Leu
             -20             -15                 -10 acc atc ctg tcc cag ccg ctc atg tac gtg aaa gtg ctc atc cag gtg     158
Thr Ile Leu Ser Gln Pro Leu Met Tyr Val Lys Val Leu Ile Gln Val
    -5                  1               5                   10 gga tat gag cct ctt cct cca aca ata gga cga aat att ttt ggg cgg     206
Gly Tyr Glu Pro Leu Pro Pro Thr Ile Gly Arg Asn Ile Phe Gly Arg
                15                  20                  25 caa gtg tgt cag ctt cct ggt ctc ttt agt tat gct cag cac att gcc     254
Gln Val Cys Gln Leu Pro Gly Leu Phe Ser Tyr Ala Gln His Ile Ala
            30                  35                  40 agt atc gat ggg agg cgc ggg ttg ttc aca ggc tta act cca aga ctg     302
Ser Ile Asp Gly Arg Arg Gly Leu Phe Thr Gly Leu Thr Pro Arg Leu
        45                  50                  55 tgt tcg gga gtc ctt gga act gtg gtc cat ggt aaa gtt tta cag cat     350
Cys Ser Gly Val Leu Gly Thr Val Val His Gly Lys Val Leu Gln His
    60                  65                  70 tac cag gag agt gac aag ggt gag gag tta gga cct gga aat gta cag     398
Tyr Gln Glu Ser Asp Lys Gly Glu Glu Leu Gly Pro Gly Asn Val Gln
75                  80                  85                  90 aaa gaa gtc tca tct tcc ttt gac cac gtt atc aag gag aca act cga     446
Lys Glu Val Ser Ser Ser Phe Asp His Val Ile Lys Glu Thr Thr Arg
                95                  100                 105 gag atg atc gct cgt tct gct gct acc ctc atc aca cat ccc ttc cat     494
Glu Met Ile Ala Arg Ser Ala Ala Thr Leu Ile Thr His Pro Phe His
            110                 115                 120 gtg atc act ctg aga tct atg gta cag ttc att ggc aga gaa tcc aag     542
Val Ile Thr Leu Arg Ser Met Val Gln Phe Ile Gly Arg Glu Ser Lys
        125                 130                 135 tac tgt gga ctt tgt gat tcc ata ata acc atc tat cgg gaa gag ggc     590
```

```
Tyr Cys Gly Leu Cys Asp Ser Ile Ile Thr Ile Tyr Arg Glu Glu Gly
    140                 145                 150 att cta gga ttt ttc gcg ggt ctt gtt cct cgc ctt cta ggt gac atc      638
Ile Leu Gly Phe Phe Ala Gly Leu Val Pro Arg Leu Leu Gly Asp Ile
155                 160                 165                 170 ctt tct ttg tgg ctg tgt aac tca ctg gcc tac ctc gtc aat acc tat      686
Leu Ser Leu Trp Leu Cys Asn Ser Leu Ala Tyr Leu Val Asn Thr Tyr
                175                 180                 185 gca ctg gac agt ggg gtt tct acc atg aat gaa atg aag agt tat tct      734
Ala Leu Asp Ser Gly Val Ser Thr Met Asn Glu Met Lys Ser Tyr Ser
            190                 195                 200 caa gct gtc aca gga ttt ttt gcg agt atg ttg acc tat ccc ttt gtg      782
Gln Ala Val Thr Gly Phe Phe Ala Ser Met Leu Thr Tyr Pro Phe Val
        205                 210                 215 ctt gtc tcc aat ctt atg gct gtc aac aac tgt ggt ctt gct ggt gga      830
Leu Val Ser Asn Leu Met Ala Val Asn Asn Cys Gly Leu Ala Gly Gly
    220                 225                 230 tgc cct cct tac tcc cca ata tat acg tct tgg ata gac tgt tgg tgc      878
Cys Pro Pro Tyr Ser Pro Ile Tyr Thr Ser Trp Ile Asp Cys Trp Cys
235                 240                 245                 250 atg cta caa aaa gag ggg aat atg agc cga gga aat agc tta ttt ttc      926
Met Leu Gln Lys Glu Gly Asn Met Ser Arg Gly Asn Ser Leu Phe Phe
                255                 260                 265 cgg aag gtc ccc ttt ggg aag act tat tgt tgt gac ctg aaa atg tta      974
Arg Lys Val Pro Phe Gly Lys Thr Tyr Cys Cys Asp Leu Lys Met Leu
            270                 275                 280 att tgaagatgtg gggcagggac agtgacattt ctgtagtccc agatgcacag          1027
Ile aattatggga gagaatgttg atttctatac agtgtggcgc gcttttttaa taatcattta   1087
atcttggcaa aaaaaaaaa aaaa                                           1111

<210> SEQ ID NO 63
<211> LENGTH: 554
<212> TYPE: DNA
<213> ORGANISM: Homo sapiens
<220> FEATURE:
<221> NAME/KEY: CDS
<222> LOCATION: 44..238
<220> FEATURE:
<221> NAME/KEY: sig_peptide
<222> LOCATION: 44..160
<223> OTHER INFORMATION: Von Heijne matrix
      score 3.9
      seq FKTIAFLLLYVSA/GP
<220> FEATURE:
<221> NAME/KEY: polyA_signal
<222> LOCATION: 443..448
<220> FEATURE:
<221> NAME/KEY: polyA_site
<222> LOCATION: 540..554

<400> SEQUENCE: 63
atcctcaaca gaataattgc tgacaaactc tcttgcccag aaa atg tct act gga       55
                                             Met Ser Thr Gly att atg gag tac aaa aaa act aca aaa gca atg aaa aaa aag aag gat      103
Ile Met Glu Tyr Lys Lys Thr Thr Lys Ala Met Lys Lys Lys Lys Asp
-35                 -30                 -25                 -20 gtt tta ttt aca tcc tat ttc aaa acc att gct ttc ttg cta ttg tat      151
Val Leu Phe Thr Ser Tyr Phe Lys Thr Ile Ala Phe Leu Leu Leu Tyr
                -15                 -10                 -5 gtc tct gca ggc cca ata tcg cga atc ttc ata aga agt tta gaa ttg      199
Val Ser Ala Gly Pro Ile Ser Arg Ile Phe Ile Arg Ser Leu Glu Leu
            1                   5                   10
```

```
ttc ctt atg ttt cct tct aac aaa cac tgg tat att tca tgaaagtgta      248
Phe Leu Met Phe Pro Ser Asn Lys His Trp Tyr Ile Ser
     15                  20                  25 tattttattc acttccaaaa cagttagctc ataattcaga acattgaggt ttgcaaaatg    308
actgaaggaa actttaccta aacaatagtt gccagttctg ctgagaatta tcacgggccc    368
acaacggctg tgtgtttttc catacagata ttctaatttt tttattatgc agctaatttt    428
tttttagact cgcgaataaa atagcaagtc agtctgtgca taagcatatg tttaaatcta    488
ccaggagaaa tgtctggaat cttttggtt attaaaatta aaattcagga taaaaaaaaa     548
aaaaaa                                                               554

<210> SEQ ID NO 64
<211> LENGTH: 1773
<212> TYPE: DNA
<213> ORGANISM: Homo sapiens
<220> FEATURE:
<221> NAME/KEY: CDS
<222> LOCATION: 114..524
<220> FEATURE:
<221> NAME/KEY: sig_peptide
<222> LOCATION: 114..164
<223> OTHER INFORMATION: Von Heijne matrix
      score 5.2
      seq ATLAVGLTIFVLS/VV
<220> FEATURE:
<221> NAME/KEY: polyA_signal
<222> LOCATION: 1739..1744
<220> FEATURE:
<221> NAME/KEY: polyA_site
<222> LOCATION: 1758..1773

<400> SEQUENCE: 64
gatttgcttt cttttctcc aaaagggag gaaattgaaa ctgagtggcc cacgatggga      60 agagggaaa gcccagggt acaggaggcc tctgggtgaa ggcagaggct aac atg        116
                                                          Met ggg ttc gga gcg acc ttg gcc gtt ggc ctg acc atc ttt gtg ctg tct     164
Gly Phe Gly Ala Thr Leu Ala Val Gly Leu Thr Ile Phe Val Leu Ser
    -15                 -10                 -5 gtc gtc act atc atc atc tgc ttc acc tgc tcc tgc tgc ctt tac         212
Val Val Thr Ile Ile Ile Cys Phe Thr Cys Ser Cys Cys Leu Tyr
1               5                   10                  15 aag acg tgc cgc cga cca cgt ccg gtt gtc acc acc aca tcc acc         260
Lys Thr Cys Arg Arg Pro Arg Pro Val Val Thr Thr Thr Ser Thr
            20                  25                  30 act gtg gtg cat gcc cct tat cct cag cct cca agt gtg ccg ccc agc     308
Thr Val Val His Ala Pro Tyr Pro Gln Pro Pro Ser Val Pro Pro Ser
            35                  40                  45 tac cct gga cca agc tac cag ggc tac cac acc atg ccg cct cag cca     356
Tyr Pro Gly Pro Ser Tyr Gln Gly Tyr His Thr Met Pro Pro Gln Pro
        50                  55                  60 ggg atg cca gca gca ccc tac cca atg cag tac cca cct tac cca         404
Gly Met Pro Ala Ala Pro Tyr Pro Met Gln Tyr Pro Pro Tyr Pro
65                  70                  75                  80 gcc cag ccc atg ggc cca ccg gcc tac cac gag acc ctg gct gga gga     452
Ala Gln Pro Met Gly Pro Pro Ala Tyr His Glu Thr Leu Ala Gly Gly
                85                  90                  95 gca gcc gcg ccc tac ccc gcc agc cag cct cct tac aac ccg gcc tac     500
Ala Ala Ala Pro Tyr Pro Ala Ser Gln Pro Pro Tyr Asn Pro Ala Tyr
                100                 105                 110 atg gat gcc ccg aag gcg gcc ctc tgagcattcc ctggcctctc tggctgccac    554
Met Asp Ala Pro Lys Ala Ala Leu
```

-continued

```
                115                 120
ttggttatgt tgtgtgtgtg cgtgagtggt gtgcaggcgc ggttccttac gccccatgtg    614
tgctgtgtgt gtccaggcac ggttccttac gccccatgtg tgctgtgtgt gtcctgcctg    674
tatatgtggc ttcctctgat gctgacaagg tggggaacaa tccttgccag agtgggctgg    734
gaccagactt tgttctcttc ctcacctgaa attatgcttc ctaaaatctc aagccaaact    794
caaagaatgg ggtggtgggg ggcaccctgt gaggtggccc ctgagaggtg ggggcctctc    854
cagggcacat ctggagttct tctccagctt accctagggt gaccaagtag ggcctgtcac    914
accagggtgg cgcagctttc tgtgtgatgc agatgtgtcc tggtttcggc agcgtagcca    974
gctgctgctt gaggccatgg ctcgtccccg gagttggggg tacccgttgc agagccaggg   1034
acatgatgca ggcgaagctt gggatctggc caagttggac tttgatcctt tgggcagatg   1094
tcccattgct ccctggagcc tgtcatgcct gttggggatc aggcagcctc ctgatgccag   1154
aacacctcag gcagagccct actcagctgt acctgtctgc ctggactgtc ccctgtcccc   1214
gcatctcccc tgggaccagc tggagggcca catgcacaca cagcctagct gcccccaggg   1274
agctctgctg cccttgctgg ccctgccctt cccacaggtg agcagggctc ctgtccacca   1334
gcacactcag ttctcttccc tgcagtgttt tcattttatt ttagccaaac attttgcctg   1394
ttttctgttt caaacatgat agttgatatg agactgaaac ccctggggttg tggagggaaa   1454 ttggctcaga gatggacaac ctggcaactg tgagtccctg cttcccgaca ccagcctcat   1514
ggaatatgca acaactcctg taccccagtc acggtgttc tggcagcagg gacacctggg    1574
ccaatgggcc atctggacca aaggtggggt gtggggccct ggatggcagc tctggcccag   1634
acatgaatac ctcgtgttcc tcctccctct attactgttt caccagagct gtcttagctc   1694
aaatctgttg tgtttctgag tctagggtct gtacacttgt ttataataaa tgcaatcgtt   1754
tgcaaaaaaa aaaaaaaaa                                                 1773
```

<210> SEQ ID NO 65
<211> LENGTH: 917
<212> TYPE: DNA
<213> ORGANISM: Homo sapiens
<220> FEATURE:
<221> NAME/KEY: CDS
<222> LOCATION: 26..487
<220> FEATURE:
<221> NAME/KEY: sig_peptide
<222> LOCATION: 26..64
<223> OTHER INFORMATION: Von Heijne matrix
score 6.4
seq MALLLSVLRVLLG/GF
<220> FEATURE:
<221> NAME/KEY: polyA_signal
<222> LOCATION: 883..888
<220> FEATURE:
<221> NAME/KEY: polyA_site
<222> LOCATION: 901..917

<400> SEQUENCE: 65

```
aacccacggt gggggagcg cggcc atg gcg ctc ctg ctt tcg gtg ctg cgt      52
                              Met Ala Leu Leu Leu Ser Val Leu Arg
                                      -10                      -5 gta ctg ctg ggc ggc ttc ttc gcg ctc gtg ggg ttg gcc aag ctc tcg     100
Val Leu Leu Gly Gly Phe Phe Ala Leu Val Gly Leu Ala Lys Leu Ser
              1               5                  10 gag gag atc tcg gct cca gtt tcg gag cgg atg aat gcc ctg ttc gtg    148
Glu Glu Ile Ser Ala Pro Val Ser Glu Arg Met Asn Ala Leu Phe Val
         15                  20                  25
```

```
cag ttt gct gag gtg ttc ccg ctg aag gta ttt ggc tac cag cca gat    196
Gln Phe Ala Glu Val Phe Pro Leu Lys Val Phe Gly Tyr Gln Pro Asp
         30                  35                  40 ccc ctg aac tac caa ata gct gtg ggc ttt ctg gaa ctg ctg gct ggg    244
Pro Leu Asn Tyr Gln Ile Ala Val Gly Phe Leu Glu Leu Leu Ala Gly
 45                  50                  55                  60 ttg ctg ctg gtc atg ggc cca ccg atg ctg caa gag atc agt aac ttg    292
Leu Leu Leu Val Met Gly Pro Pro Met Leu Gln Glu Ile Ser Asn Leu
                     65                  70                  75 ttc ttg att ctg ctc atg atg ggg gct atc ttc acc ttg gca gct ctg    340
Phe Leu Ile Leu Leu Met Met Gly Ala Ile Phe Thr Leu Ala Ala Leu
                 80                  85                  90 aaa gag tca cta agc acc tgt atc cca gcc att gtc tgc ctg ggg ttc    388
Lys Glu Ser Leu Ser Thr Cys Ile Pro Ala Ile Val Cys Leu Gly Phe
             95                 100                 105 ctg ctg ctg ctg aat gtc ggc cag ctc tta gcc cag act aag aag gtg    436
Leu Leu Leu Leu Asn Val Gly Gln Leu Leu Ala Gln Thr Lys Lys Val
        110                 115                 120 gtc aga ccc act agg aag aag act cta agt aca ttc aag gaa tcc tgg    484
Val Arg Pro Thr Arg Lys Lys Thr Leu Ser Thr Phe Lys Glu Ser Trp
125                 130                 135                 140 aag tagagcatct ctgtctcttt atgccatgca gctgtcacag caggaacatg          537
Lys gtagaacaca gagtctatca tcttgttacc agtataatat ccagggtcag ccagtgttga   597
aagagacatt ttgtctacct ggcactgctt tctcttttta gctttactac tcttttgtga   657
ggagtacatg ttatgcatat taacattcct catatcatat gaaaatacaa aataagcaga   717
aaagaaattt aaatcaacca aaattctgat gccccaaata accactttta atgccttggt   777
gtaagtatac ctctgaactt ttttctgtgc ctttaaacag atatatattt tttttaaatg   837
aaaataaaac catatatcct attttatttc ctccttttaa aaccttataa actataacac   897
tgcaaaaaaa aaaaaaaaa                                                917

<210> SEQ ID NO 66
<211> LENGTH: 641
<212> TYPE: DNA
<213> ORGANISM: Homo sapiens
<220> FEATURE:
<221> NAME/KEY: CDS
<222> LOCATION: 80..388
<220> FEATURE:
<221> NAME/KEY: sig_peptide
<222> LOCATION: 80..187
<223> OTHER INFORMATION: Von Heijne matrix
      score 3.6
      seq RALSTFLFGSIRG/AA
<220> FEATURE:
<221> NAME/KEY: polyA_signal
<222> LOCATION: 609..614
<220> FEATURE:
<221> NAME/KEY: polyA_site
<222> LOCATION: 627..641

<400> SEQUENCE: 66
gccagtgcgc agacgcaggg gtcggcgccg ggtgagagcg tgcggccggg taagggcgtg    60
tggccggatt caccacaac atg gca aat ctt ttt ata agg aaa atg gtg aac    112
                    Met Ala Asn Leu Phe Ile Arg Lys Met Val Asn
                        -35                 -30 cct ctg ctc tat ctc agt cgt cac acg gtg aag cct cga gcc ctc tcc    160
Pro Leu Leu Tyr Leu Ser Arg His Thr Val Lys Pro Arg Ala Leu Ser
-25                 -20                 -15                 -10 aca ttt cta ttt gga tcc att cga ggt gca gcc ccc gtg gct gtg gaa    208
```

```
Thr Phe Leu Phe Gly Ser Ile Arg Gly Ala Ala Pro Val Ala Val Glu
                -5                   1               5 ccc ggg gca gca gtg cgc tca ctt ctc tca ccc ggc ctc ctg ccc cat         256
Pro Gly Ala Ala Val Arg Ser Leu Leu Ser Pro Gly Leu Leu Pro His
         10                  15                  20 ctg ctg cct gcg ctg ggg ttc aaa aac aag act gtc ctt aat aag cgc         304
Leu Leu Pro Ala Leu Gly Phe Lys Asn Lys Thr Val Leu Asn Lys Arg
 25                  30                  35 tgc aag gac tgt tac ctg gtg aag agg cgg ggt cgg tgg tac gtc tac         352
Cys Lys Asp Cys Tyr Leu Val Lys Arg Arg Gly Arg Trp Tyr Val Tyr
 40                  45                  50                  55 tgt aaa acc cat ccg agg cac aag cag aga cag atg tagacccttt              398
Cys Lys Thr His Pro Arg His Lys Gln Arg Gln Met
                 60                  65 ccctccagac tcacgcacat actcgtcatc gcatcacttg ggagaatggt tgtatcttat       458
ggaaggaatt atcacatcaa ggagtcaggg gaaagtgact ggaagcaaac gccctaaaag       518
ttacccatca cgtttcagtg taaatgagta actatagaag acattgcgtt atcttatttc       578
caaaacgttc caactaaaaa acattttcct attaaaatag accttccgaa aaaaaaaaa        638 aaa                                                                     641

<210> SEQ ID NO 67
<211> LENGTH: 854
<212> TYPE: DNA
<213> ORGANISM: Homo sapiens
<220> FEATURE:
<221> NAME/KEY: CDS
<222> LOCATION: 186..443
<220> FEATURE:
<221> NAME/KEY: sig_peptide
<222> LOCATION: 186..407
<223> OTHER INFORMATION: Von Heijne matrix
      score 3.9
      seq ISCTCLLLYLTHC/IL
<220> FEATURE:
<221> NAME/KEY: polyA_signal
<222> LOCATION: 827..832
<220> FEATURE:
<221> NAME/KEY: polyA_site
<222> LOCATION: 839..854

<400> SEQUENCE: 67
aaatgttaat attagaaaga gtctcatagt gcttatgtga catcattctt tgcctaaagc        60
ctttgtacct actgtaatga agctaaactc cttggcacag gatataaggc tcacgatctg       120
gcctggactc attttcactc ccatcttcag tcatccccta actccccac agtcagtccc        180 caaag atg cca tat gct ttc act tct cca tgc cct tgc tca ttt gtc tca       230
      Met Pro Tyr Ala Phe Thr Ser Pro Cys Pro Cys Ser Phe Val Ser
          -70                  -65                 -60 ttg cct gaa ata tcc ttt tat ttc acc aaa ctg ctg ctc atc ctc aag         278
Leu Pro Glu Ile Ser Phe Tyr Phe Thr Lys Leu Leu Leu Ile Leu Lys
             -55                  -50                  -45 gcc ctg cct gag tca cct ttc ctt ctt gct tcc tcc ccc ttg cct cct         326
Ala Leu Pro Glu Ser Pro Phe Leu Leu Ala Ser Ser Pro Leu Pro Pro
             -40                  -35                  -30 ctc ccc act acc cta aga aaa ttc atc cct ccc cct tca tta ata tca         374
Leu Pro Thr Thr Leu Arg Lys Phe Ile Pro Pro Ser Leu Ile Ser
     -25                  -20                  -15 tgc aca tgc ttg tta tta tat tta aca cat tgt ata tta ggt att tgt         422
Cys Thr Cys Leu Leu Leu Tyr Leu Thr His Cys Ile Leu Gly Ile Cys
 -10                  -5                   1                   5 ttt gct tat cct ttt atc cta tgaaattgtg aacaatttgt tgaataattg            473
```

```
Phe Ala Tyr Pro Phe Ile Leu
             10 aataatcaca tatcaaaatg tagagaggtt atttgtctct tccctgtagg actccatttt      533 caggcagtgt ctgctaagaa tccccttgac ctgggattgg aagttgtttc tcccactgct      593 gagctccttt atattagctc ttcacctctc actcctttgt ttcttctctt ggcactttac      653 gtctttctac ccatttaatt tgataaatgt ctcatgtcat ctttaaaact gaaggtgaca      713 catgtctggt ttatctttat aactcaaaaa tgttgagctt aatgcagaat ggagaatagc      773 tacttagtaa attttaaaa tacatgctac cattttaag gggagaagaa gacaatatac      833 atgacaaaaa aaaaaaaaaa a                                                854

<210> SEQ ID NO 68
<211> LENGTH: 1568
<212> TYPE: DNA
<213> ORGANISM: Homo sapiens
<220> FEATURE:
<221> NAME/KEY: CDS
<222> LOCATION: 75..1259
<220> FEATURE:
<221> NAME/KEY: sig_peptide
<222> LOCATION: 75..1004
<223> OTHER INFORMATION: Von Heijne matrix
      score 4.4
      seq VLILLFSLALIIL/PS
<220> FEATURE:
<221> NAME/KEY: polyA_signal
<222> LOCATION: 1536..1541
<220> FEATURE:
<221> NAME/KEY: polyA_site
<222> LOCATION: 1553..1568

<400> SEQUENCE: 68
agaaaaggtg tagtgtttgg ggcggtcaac gggctatgct ggcttgacag ggctgggctc       60
ttcagaacag aagc atg gat ctc gga atc cct gac ctg ctg gac gcg tgg       110
         Met Asp Leu Gly Ile Pro Asp Leu Leu Asp Ala Trp
         -310               -305               -300 ctg gag ccc cca gag gat atc ttc tcg aca gga tcc gtc ctg gag ctg      158
Leu Glu Pro Pro Glu Asp Ile Phe Ser Thr Gly Ser Val Leu Glu Leu
         -295               -290               -285 gga ctc cac tgc ccc cct cca gag gtt ccg gta act agg cta cag gaa      206
Gly Leu His Cys Pro Pro Pro Glu Val Pro Val Thr Arg Leu Gln Glu
         -280               -275               -270 cag gga ctg caa ggc tgg aag tcc ggt ggg gac cgt ggc tgt ggc ctt      254
Gln Gly Leu Gln Gly Trp Lys Ser Gly Gly Asp Arg Gly Cys Gly Leu
         -265               -260               -255 caa gag agt gag cct gaa gat ttc ttg aag ctt ttc att gat ccc aat      302
Gln Glu Ser Glu Pro Glu Asp Phe Leu Lys Leu Phe Ile Asp Pro Asn
-250               -245               -240               -235 gag gtg tac tgc tca gaa gca tct cct ggc agt gac agt ggc atc tct      350
Glu Val Tyr Cys Ser Glu Ala Ser Pro Gly Ser Asp Ser Gly Ile Ser
         -230               -225               -220 gag gac tcc tgc cat cca gac agt ccc cct gcc ccc agg gca acc agt      398
Glu Asp Ser Cys His Pro Asp Ser Pro Pro Ala Pro Arg Ala Thr Ser
         -215               -210               -205 tct cct atg ctc tat gag gtt gtc tat gag gca ggg gcc ctg gag agg      446
Ser Pro Met Leu Tyr Glu Val Val Tyr Glu Ala Gly Ala Leu Glu Arg
         -200               -195               -190 atg cag ggg gaa act ggg cca aat gta ggc ctt atc tcc atc cag cta      494
Met Gln Gly Glu Thr Gly Pro Asn Val Gly Leu Ile Ser Ile Gln Leu
         -185               -180               -175 gat cag tgg agc cca gca ttt atg gtg cct gat tcc tgc atg gtc agt      542
```

```
Asp Gln Trp Ser Pro Ala Phe Met Val Pro Asp Ser Cys Met Val Ser
-170             -165                 -160                 -155 gag ctg ccc ttt gat gct cat gcc cac atc ctg ccc aga gca ggc acc     590
Glu Leu Pro Phe Asp Ala His Ala His Ile Leu Pro Arg Ala Gly Thr
            -150                 -145                 -140 gta gcc cca gtg ccc tgt aca acc ctg ctg ccc tgt caa acc ctg ttc     638
Val Ala Pro Val Pro Cys Thr Thr Leu Leu Pro Cys Gln Thr Leu Phe
            -135                 -130                 -125 ctg acc gat gag gag aag cgt ctg ctg ggg cag gaa ggg gtt tcc ctg     686
Leu Thr Asp Glu Glu Lys Arg Leu Leu Gly Gln Glu Gly Val Ser Leu
            -120                 -115                 -110 ccc tct cac ctg ccc ctc acc aag gca gag gag agg gtc ctc aag aag     734
Pro Ser His Leu Pro Leu Thr Lys Ala Glu Glu Arg Val Leu Lys Lys
        -105                 -100                  -95 gtc agg agg aaa atc cgt aac aag cag tca gct cag gac agt cgg cgg     782
Val Arg Arg Lys Ile Arg Asn Lys Gln Ser Ala Gln Asp Ser Arg Arg
-90             -85                  -80                  -75 cgg aag aag gag tac att gat ggg ctg gag agc agg gtg gca gcc tgt     830
Arg Lys Lys Glu Tyr Ile Asp Gly Leu Glu Ser Arg Val Ala Ala Cys
                -70                  -65                  -60 tct gca cag aac caa gaa tta cag aaa aaa gtc cag gag ctg gag agg     878
Ser Ala Gln Asn Gln Glu Leu Gln Lys Lys Val Gln Glu Leu Glu Arg
            -55                  -50                  -45 cac aac atc tcc ttg gta gct cag ctc cgc cag ctg cag acg cta att     926
His Asn Ile Ser Leu Val Ala Gln Leu Arg Gln Leu Gln Thr Leu Ile
            -40                  -35                  -30 gct caa act tcc aac aaa gct gcc cag acc agc act tgt gtt tgt att     974
Ala Gln Thr Ser Asn Lys Ala Ala Gln Thr Ser Thr Cys Val Leu Ile
        -25                  -20                  -15 ctt ctt ttt tcc ctg gct ctc atc atc ctg ccc agc ttc agt cca ttc    1022
Leu Leu Phe Ser Leu Ala Leu Ile Ile Leu Pro Ser Phe Ser Pro Phe
-10             -5                    1                    5 cag agt cga cca gaa gct ggg tct gag gat tac cag cct cac gga gtg    1070
Gln Ser Arg Pro Glu Ala Gly Ser Glu Asp Tyr Gln Pro His Gly Val
            10                   15                   20 act tcc aga aat atc ctg acc cac aag gac gta aca gaa aat ctg gag    1118
Thr Ser Arg Asn Ile Leu Thr His Lys Asp Val Thr Glu Asn Leu Glu
        25                   30                   35 acc caa gtg gta gag tcc aga ctg agg gag cca cct gga gcc aag gat    1166
Thr Gln Val Val Glu Ser Arg Leu Arg Glu Pro Pro Gly Ala Lys Asp
        40                   45                   50 gca aat ggc tca aca agg aca ctg ctt gag aag atg gga ggg aag cca    1214
Ala Asn Gly Ser Thr Arg Thr Leu Leu Glu Lys Met Gly Gly Lys Pro
55                   60                   65                   70 aga ccc agt ggg cgc atc cgg tcc gtg ctg cat gca gat gag atg         1259
Arg Pro Ser Gly Arg Ile Arg Ser Val Leu His Ala Asp Glu Met
            75                   80                   85 tgagctggaa cagaccttcc tggcccactt cctgatcaca aggaatcctg ggcttcctta  1319
tggctttctt cccactggga ttcctactta ggtgtctgcc ctcagggtc caaatcactt   1379 caggacaccc caagagatgt cctttagtct ctgcctgagg cctagtctgc atttgtttgc  1439
atatatgaga gggtaccctca aatacttctg ttatgtatct gtgattttat ttcttctttg 1499 ggtatagggt tgaggggaaa taagttttga gtgagaaata aacgttttag ctgaaaaaaa  1559
aaaaaaaaa                                                         1568

<210> SEQ ID NO 69
<211> LENGTH: 506
<212> TYPE: DNA
```

```
<213> ORGANISM: Homo sapiens
<220> FEATURE:
<221> NAME/KEY: CDS
<222> LOCATION: 98..376
<220> FEATURE:
<221> NAME/KEY: sig_peptide
<222> LOCATION: 98..151
<223> OTHER INFORMATION: Von Heijne matrix
      score 12.3
      seq HILFLLLLPVAAA/QT
<220> FEATURE:
<221> NAME/KEY: polyA_signal
<222> LOCATION: 471..476
<220> FEATURE:
<221> NAME/KEY: polyA_site
<222> LOCATION: 491..506

<400> SEQUENCE: 69
gacatccgct attgctactt ctctgctccc ccacagttcc tctggacttc tctggaccac      60
agtcctctgc cagaccctg ccagacccca gtccacc atg atc cat ctg ggt cac      115
                                        Met Ile His Leu Gly His
                                                            -15 atc ctc ttc ctg ctt ttg ctc cca gtg gct gca gct cag acg act cca      163
Ile Leu Phe Leu Leu Leu Leu Pro Val Ala Ala Ala Gln Thr Thr Pro
        -10                  -5                   1 gga gag aga tca tca ctc cct gcc ttt tac cct ggc act tca ggc tct      211
Gly Glu Arg Ser Ser Leu Pro Ala Phe Tyr Pro Gly Thr Ser Gly Ser
 5                  10                 15                  20 tgt tcc gga tgt ggg tcc ctc tct ctg ccg ctc ctg gca ggc ctc gtg      259
Cys Ser Gly Cys Gly Ser Leu Ser Leu Pro Leu Leu Ala Gly Leu Val
                25                  30                  35 gct gct gat gcg gtg gca tcg ctg ctc atc gtg ggg gcg gtg ttc ctg      307
Ala Ala Asp Ala Val Ala Ser Leu Leu Ile Val Gly Ala Val Phe Leu
             40                  45                  50 tgc gca cgc cca cgc cgc agc ccc gcc caa gaa tat ggc aaa gtc tac      355
Cys Ala Arg Pro Arg Arg Ser Pro Ala Gln Glu Tyr Gly Lys Val Tyr
         55                  60                  65 atc aac atg cca ggc agg ggc tgaccctcct gcagcttgga cctttgactt         406
Ile Asn Met Pro Gly Arg Gly
         70                  75 ctgaccctct catcctggat ggtgtgtggt ggcacaggaa ccccgcccc aactttttgga    466 ttgtaataaa acaattgaaa caccaaaaaa aaaaaaaaaa                          506

<210> SEQ ID NO 70
<211> LENGTH: 542
<212> TYPE: DNA
<213> ORGANISM: Homo sapiens
<220> FEATURE:
<221> NAME/KEY: CDS
<222> LOCATION: 72..254
<220> FEATURE:
<221> NAME/KEY: sig_peptide
<222> LOCATION: 72..134
<223> OTHER INFORMATION: Von Heijne matrix
      score 4.2
      seq LINLAASRTLSFC/IS
<220> FEATURE:
<221> NAME/KEY: polyA_signal
<222> LOCATION: 506..511
<220> FEATURE:
<221> NAME/KEY: polyA_site
<222> LOCATION: 528..542

<400> SEQUENCE: 70
gaccttaaga agagctaaac gggctgccac ctgtagctga agagtgcctt aacgccgagg      60
cccacggctc c atg cga gag atg cct gtt cct tct ctg ata aat ttg gca     110
```

```
                Met Arg Glu Met Pro Val Pro Ser Leu Ile Asn Leu Ala
                    -20             -15                 -10 gct tca cgt acc cta agt ttt tgc att tct gac aac cac gtg tcc tca     158
Ala Ser Arg Thr Leu Ser Phe Cys Ile Ser Asp Asn His Val Ser Ser
        -5                   1                   5 cct gga ccc gcc aac cca tcc tgt ggc ctc cac cct cac tgg ctt cgt     206
Pro Gly Pro Ala Asn Pro Ser Cys Gly Leu His Pro His Trp Leu Arg
    10                  15                  20 cca ctt aaa ctt tta acg tac aca tgt aga gag ctg aaa ctc cag ggg     254
Pro Leu Lys Leu Leu Thr Tyr Thr Cys Arg Glu Leu Lys Leu Gln Gly
25                  30                  35                  40 taacatggga caggtcctct tgatttaatg aaaacagaag atcaactgga ccgggtagca   314
agaaataagg cttaagaagc actggtttct ctgcagaaga cagcaagatg ccccagggaa   374
tgtttgtgaa aaaggatgac tggatgggaa gcaagctgaa gaaaaagaag gaaagaaaga   434
gagaaatcag taaatcacca cacaagaggt ggagaagagg acttataaat attgtttcta   494
tgacatttga aaataaatgt tttactccat gctaaaaaaa aaaaaaaa                542

<210> SEQ ID NO 71
<211> LENGTH: 1629
<212> TYPE: DNA
<213> ORGANISM: Homo sapiens
<220> FEATURE:
<221> NAME/KEY: CDS
<222> LOCATION: 148..1140
<220> FEATURE:
<221> NAME/KEY: sig_peptide
<222> LOCATION: 148..240
<223> OTHER INFORMATION: Von Heijne matrix
      score 10
      seq LVLLLVTRSPVNA/CL
<220> FEATURE:
<221> NAME/KEY: polyA_signal
<222> LOCATION: 1590..1595
<220> FEATURE:
<221> NAME/KEY: polyA_site
<222> LOCATION: 1614..1629

<400> SEQUENCE: 71
gtctgctgcc gccattgtgc ggcgctggtc ccctcagagg gttcctgctg ctgccggtgc    60
cttggaccct ccccctcgct tctcgttcta ctgcccagg agcccggcgg gtccgggact    120
cccgtccgtg ccggtgcggg cgccggc atg tgg ctg tgg gag gac cag ggc ggc   174
                                Met Trp Leu Trp Glu Asp Gln Gly Gly
                                    -30                 -25 ctc ctg ggc cct ttc tcc ttc ctg ctg cta gtg ctg ctg ctg gtg acg     222
Leu Leu Gly Pro Phe Ser Phe Leu Leu Leu Val Leu Leu Leu Val Thr
        -20                 -15                 -10 cgg agc ccg gtc aat gcc tgc ctc ctc acc ggc agc ctc ttc gtt cta     270
Arg Ser Pro Val Asn Ala Cys Leu Leu Thr Gly Ser Leu Phe Val Leu
    -5                   1                   5                  10 ctg cgc gtc ttc agc ttt gag ccg gtg ccc tct tgc agg gcc ctg cag     318
Leu Arg Val Phe Ser Phe Glu Pro Val Pro Ser Cys Arg Ala Leu Gln
                15                  20                  25 gtg ctc aag ccc cgg gac cgc att tct gcc atc gcc cac cgt ggc ggc     366
Val Leu Lys Pro Arg Asp Arg Ile Ser Ala Ile Ala His Arg Gly Gly
            30                  35                  40 agc cac gac gcg ccc gag aac acg ctg gcg gcc att cgg cag gca gct     414
Ser His Asp Ala Pro Glu Asn Thr Leu Ala Ala Ile Arg Gln Ala Ala
                45                  50                  55 aag aat gga gca aca ggc gtg gag ttg gac att gag ttt act tct gac     462
Lys Asn Gly Ala Thr Gly Val Glu Leu Asp Ile Glu Phe Thr Ser Asp
60                  65                  70
```

```
ggg att cct gtc tta atg cac gat aac aca gta gat agg acg act gat      510
Gly Ile Pro Val Leu Met His Asp Asn Thr Val Asp Arg Thr Thr Asp
 75              80                  85                  90 ggg act ggg cga ttg tgt gat ttg aca ttt gaa caa att agg aag ctg      558
Gly Thr Gly Arg Leu Cys Asp Leu Thr Phe Glu Gln Ile Arg Lys Leu
                 95                 100                 105 aat cct gca gca aac cac aga ctc agg aat gat ttc cct gat gaa aag      606
Asn Pro Ala Ala Asn His Arg Leu Arg Asn Asp Phe Pro Asp Glu Lys
             110                 115                 120 atc cct acc cta atg gaa gct gtt gca gag tgc cta aac cat aac ctc      654
Ile Pro Thr Leu Met Glu Ala Val Ala Glu Cys Leu Asn His Asn Leu
         125                 130                 135 aca atc ttc ttt gat gtc aaa ggc cat gca cac aag gct act gag gct      702
Thr Ile Phe Phe Asp Val Lys Gly His Ala His Lys Ala Thr Glu Ala
     140                 145                 150 cta aag aaa atg tat atg gaa ttt cct caa ctg tat aat aat agt gtg      750
Leu Lys Lys Met Tyr Met Glu Phe Pro Gln Leu Tyr Asn Asn Ser Val
155                 160                 165                 170 gtc tgt tct ttc ttg cca gaa gtt atc tac aag atg aga caa aca gat      798
Val Cys Ser Phe Leu Pro Glu Val Ile Tyr Lys Met Arg Gln Thr Asp
                175                 180                 185 cgg gat gta ata aca gca tta act cac aga cct tgg agc cta agc cat      846
Arg Asp Val Ile Thr Ala Leu Thr His Arg Pro Trp Ser Leu Ser His
             190                 195                 200 aca gga gat ggg aaa cca cgc tat gat act ttc tgg aaa cat ttt ata      894
Thr Gly Asp Gly Lys Pro Arg Tyr Asp Thr Phe Trp Lys His Phe Ile
         205                 210                 215 ttt gtt atg atg gac att ttg ctc gat tgg agc atg cat aat atc ttg      942
Phe Val Met Met Asp Ile Leu Leu Asp Trp Ser Met His Asn Ile Leu
     220                 225                 230 tgg tac ctg tgt gga att tca gct ttc ctc atg caa aag gat ttt gta      990
Trp Tyr Leu Cys Gly Ile Ser Ala Phe Leu Met Gln Lys Asp Phe Val
235                 240                 245                 250 tcc ccg gcc tac ttg aag aag tgg tca gct aaa gga atc cag gtt gtt     1038
Ser Pro Ala Tyr Leu Lys Lys Trp Ser Ala Lys Gly Ile Gln Val Val
                255                 260                 265 ggt tgg act gtt aat acc ttt gat gaa aag agt tac tac gaa tcc cat     1086
Gly Trp Thr Val Asn Thr Phe Asp Glu Lys Ser Tyr Tyr Glu Ser His
             270                 275                 280 ctt ggt tcc agc tat atc act gac agc atg gta gaa gac tgc gaa cct     1134
Leu Gly Ser Ser Tyr Ile Thr Asp Ser Met Val Glu Asp Cys Glu Pro
         285                 290                 295 cac ttc tagactttca cggtgggacg aaacgggttc agaaactgcc aggggcctca      1190
His Phe
    300 tacagggata tcaaatacc ctttgtgcta gcccaggccc tggggaatca ggtgactcac     1250 acaaatgcaa tagttggtca ctgcattttt acctgaacca aagctaaacc cggtgttgcc    1310 accatgcacc atggcatgcc agagttcaac actgttgctc ttgaaaatct gggtctgaaa    1370 aaacgcacaa gagcccctgc cctgccctag ctgaggcaca cagggagacc cagtgaggat    1430 aagcacagat tgaattgtac aatttgcaga tgcagatgta aatgcatggg acatgcatga    1490 taactcagag ttgacatttt aaaacttgcc acacttattt caaatatttg tactcagcta    1550 tgttaacatg tactgtagac atcaaacttg tggccatact aataaaatta ttaaaaggag    1610 cacaaaaaaa aaaaaaaaa                                                 1629

<210> SEQ ID NO 72
```

```
<211> LENGTH: 1665
<212> TYPE: DNA
<213> ORGANISM: Homo sapiens
<220> FEATURE:
<221> NAME/KEY: CDS
<222> LOCATION: 109..738
<220> FEATURE:
<221> NAME/KEY: sig_peptide
<222> LOCATION: 109..405
<223> OTHER INFORMATION: Von Heijne matrix
      score 4.5
      seq LAPGSFLAAVVDA/LE
<220> FEATURE:
<221> NAME/KEY: polyA_signal
<222> LOCATION: 1633..1638
<220> FEATURE:
<221> NAME/KEY: polyA_site
<222> LOCATION: 1650..1665

<400> SEQUENCE: 72
cccagcgttc ctcctccggc cccaggtcac cgccagcacg cgcctgcttc ccgtctgcgc      60
gagtccacgc agctccccag gcccttcacc agcacagcag cagcaggc atg gca gca     117
                                                   Met Ala Ala agc gtg gag cag cgc gag ggc acc atc cag gtg cag ggc cag gcc ctc     165
Ser Val Glu Gln Arg Glu Gly Thr Ile Gln Val Gln Gly Gln Ala Leu
    -95             -90                 -85 ttc ttc cga gag gcc ctg ccc ggc agt ggg cag gct cgc ttc tct gta     213
Phe Phe Arg Glu Ala Leu Pro Gly Ser Gly Gln Ala Arg Phe Ser Val
-80                 -75                 -70                 -65 ctg ctg ctg cat ggt att cgc ttc tcc tcc gag acc tgg cag aac ctg     261
Leu Leu Leu His Gly Ile Arg Phe Ser Ser Glu Thr Trp Gln Asn Leu
                -60                 -55                 -50 ggt aca ctg cac agg ctg gcc cag gct ggc tac cgg gct gtg gcc att     309
Gly Thr Leu His Arg Leu Ala Gln Ala Gly Tyr Arg Ala Val Ala Ile
            -45                 -40                 -35 gac ctg cca ggt ctg ggg cac tcc aag gaa gca gca gcc cct gcc cct     357
Asp Leu Pro Gly Leu Gly His Ser Lys Glu Ala Ala Ala Pro Ala Pro
        -30                 -25                 -20 att ggg gag ctg gcc cct ggc agc ttc ctg gcg gct gtg gtg gat gcc     405
Ile Gly Glu Leu Ala Pro Gly Ser Phe Leu Ala Ala Val Val Asp Ala
    -15                 -10                 -5 ttg gag ctg ggc ccc ccg gtt gtg atc agt cca tca ctg agt ggc atg     453
Leu Glu Leu Gly Pro Pro Val Val Ile Ser Pro Ser Leu Ser Gly Met
1               5                   10                  15 tac tcc ctg ccc ttc ctc acg gcc cct ggc tcc cag ctc ccg ggc ttt     501
Tyr Ser Leu Pro Phe Leu Thr Ala Pro Gly Ser Gln Leu Pro Gly Phe
            20                  25                  30 gtg cca gtg gcc ccc atc tgc act gac aaa atc aat gct gcc aac tat     549
Val Pro Val Ala Pro Ile Cys Thr Asp Lys Ile Asn Ala Ala Asn Tyr
        35                  40                  45 gcc agt gtg aag act cca gct ctg att gta tat gga gac cag gac ccc     597
Ala Ser Val Lys Thr Pro Ala Leu Ile Val Tyr Gly Asp Gln Asp Pro
    50                  55                  60 atg ggt cag acc agc ttt gag cac ctg aag cag ctg ccc aac cac cgg     645
Met Gly Gln Thr Ser Phe Glu His Leu Lys Gln Leu Pro Asn His Arg
65                  70                  75                  80 gtg ctg atc atg aag ggg gcg ggg cac ccc tgt tac ctg gac aaa cca     693
Val Leu Ile Met Lys Gly Ala Gly His Pro Cys Tyr Leu Asp Lys Pro
                85                  90                  95 gag gag tgg cat aca ggg ctg ctg gac ttc ctg cag ggg ctc cag         738
Glu Glu Trp His Thr Gly Leu Leu Asp Phe Leu Gln Gly Leu Gln
            100                 105                 110 tgaagcccag cactgctgca gggggtgggc tgcctgcctg ctctgagctc tctcttgcac    798
```

-continued

```
gctctctctt ctctcccagg ctctggctca tgcacatgca acaggtgcgt ctgtctatat      858
gtctgggttc ttgtcttttg tggtctgttt gtcttttcta cctctttctc ttgcagtgat      918
agactgaggg ggtaaaatca agagaaaaaa ctctcaggaa tcaaggaaca taatcctgtg      978
gagggtaatc cattacatga gcttctcctg ttcttccact ttcctgcctg gctttcactc     1038 cttccctgc tctgcccagc ctttccctcc cacccactcc tacttctgca aatgccctga     1098
aggccagccc ttaccccaac acccacttcc ccacctcctt aggccccaga tacatacatg     1158
cccacatgca cgcttacatg tttagagcca tccttgtttc caaatatgac ccttcgcttg     1218
agggcaactg cataggtaca tctaactctg gactggcatg cacattgtca tgtgcagctt     1278
tgcatataca cacatgcata catgagcctc cacacaagca cttgcacaca tgtggactcc     1338
taaccatgct aacctcactg gctgggaagg tggggacccc atgggccagc ccttgcagga     1398
ggcccttttg caaggcttag ggtgtggcca gccctgaaag ctacttggac acaggtttca     1458
gctggcccca gcccagaagt gaccccgaga aagggagggc caccgctttg ccccctgctt     1518
ttacccttcc ttctgggtgc tctacacctc aggttaccag gctgaggca tctcagccaa     1578 gcttgtttcc tgctctgagg cttgtggggt gggagccaga gtggaggtcg gtgaaataaa     1638
gtgatgcaat taaaaaaaaa aaaaaaa                                          1665
```

```
<210> SEQ ID NO 73
<211> LENGTH: 425
<212> TYPE: DNA
<213> ORGANISM: Homo sapiens
<220> FEATURE:
<221> NAME/KEY: CDS
<222> LOCATION: 55..291
<220> FEATURE:
<221> NAME/KEY: sig_peptide
<222> LOCATION: 55..255
<223> OTHER INFORMATION: Von Heijne matrix
      score 4.4
      seq LISLVASLFMGFG/VL
<220> FEATURE:
<221> NAME/KEY: polyA_signal
<222> LOCATION: 390..395
<220> FEATURE:
<221> NAME/KEY: polyA_site
<222> LOCATION: 410..425

<400> SEQUENCE: 73
```

```
ctgccgacgt gttcttccgg tggcggagcg gcggattagc cttcgcgggg caaa atg       57
                                                                 Met gag ctc gag gcc atg agc aga tat acc agc cca gtg aac cca gct gtc      105
Glu Leu Glu Ala Met Ser Arg Tyr Thr Ser Pro Val Asn Pro Ala Val
    -65                 -60                 -55 ttc ccc cat ctg acc gtg gtg ctt ttg gcc att ggc atg ttc ttc acc      153
Phe Pro His Leu Thr Val Val Leu Leu Ala Ile Gly Met Phe Phe Thr
-50                 -45                 -40                 -35 gcc tgg ttc ttc gtt tac gag gtc acc tct acc aag tac act cgt gat      201
Ala Trp Phe Phe Val Tyr Glu Val Thr Ser Thr Lys Tyr Thr Arg Asp
                -30                 -25                 -20 atc tat aaa gag ctc ctc atc tcc tta gtg gcc tca ctc ttc atg ggc      249
Ile Tyr Lys Glu Leu Leu Ile Ser Leu Val Ala Ser Leu Phe Met Gly
            -15                 -10                  -5 ttt gga gtc ctc ttc ctg ctg ctc tgg gtt ggc atc tac gtg               291
Phe Gly Val Leu Phe Leu Leu Leu Trp Val Gly Ile Tyr Val
         1               5                  10 tgagcaccca aggtaacaa ccagatggct tcactgaaac ctgcttttgt aaattacttt     351
```

-continued

```
tttttactgt tgctggaaat gtcccacctg ctgctcataa taaatgcaga tgtataacaa      411
aaaaaaaaaa aaaa                                                        425
```

<210> SEQ ID NO 74
<211> LENGTH: 546
<212> TYPE: DNA
<213> ORGANISM: Homo sapiens
<220> FEATURE:
<221> NAME/KEY: CDS
<222> LOCATION: 25..276
<220> FEATURE:
<221> NAME/KEY: polyA_signal
<222> LOCATION: 508..513
<220> FEATURE:
<221> NAME/KEY: polyA_site
<222> LOCATION: 533..546

<400> SEQUENCE: 74

```
gttgcaccag gcgatgcaag acac atg gca gtc tgg cct gaa gtt tcc caa        51
                          Met Ala Val Trp Pro Glu Val Ser Gln
                           1               5 aac agg ctg act agg ggc cta ctg ctt ccc aac tac cag ctg agg ggg        99
Asn Arg Leu Thr Arg Gly Leu Leu Leu Pro Asn Tyr Gln Leu Arg Gly
 10              15                  20                  25 tcc gtc ccg aaa agg gag aag agg cct aag agg aaa cat caa cat ctt       147
Ser Val Pro Lys Arg Glu Lys Arg Pro Lys Arg Lys His Gln His Leu
             30                  35                  40 ttt act cct agc gag cgg cat tct gtc tgc ctt gat tgt ctt ctg gaa       195
Phe Thr Pro Ser Glu Arg His Ser Val Cys Leu Asp Cys Leu Leu Glu
                 45                  50                  55 ata tcg ctt tca ggg aaa caa tgg cga aat gtc atc agt ttc aac tgc       243
Ile Ser Leu Ser Gly Lys Gln Trp Arg Asn Val Ile Ser Phe Asn Cys
             60                  65                  70 ttt tgc act act aag acg ctt ttc tgg gtt aat tagcagcaat acagacaacg     296
Phe Cys Thr Thr Lys Thr Leu Phe Trp Val Asn
     75                  80 atcttttatt caacaacctc tctcgagata ttttaaataa tttctcacac tcgaaaaaca     356
tgcagaagcg actattggca aacctgaaga gggtggaata ccaaatggct gaactggaat     416
attttctagt tagcgagggt ttgagaggtg cgtcaggtct ccagaaattc acctcaaaag     476
cgtacaggat gtaatgccag tggtggaaat cattaaagac actttgagta gattcaaaaa     536
aaaaaaaaaa                                                            546
```

<210> SEQ ID NO 75
<211> LENGTH: 485
<212> TYPE: DNA
<213> ORGANISM: Homo sapiens
<220> FEATURE:
<221> NAME/KEY: CDS
<222> LOCATION: 32..307
<220> FEATURE:
<221> NAME/KEY: sig_peptide
<222> LOCATION: 32..91
<223> OTHER INFORMATION: Von Heijne matrix
      score 7.4
      seq LVFCVGLLTMAKA/ES
<220> FEATURE:
<221> NAME/KEY: polyA_signal
<222> LOCATION: 452..457
<220> FEATURE:
<221> NAME/KEY: polyA_site
<222> LOCATION: 472..485

<400> SEQUENCE: 75

```
ctttcagcag gggacagccc gattggggac a atg gcg tct ctt ggc cac atc         52
```

```
                              Met Ala Ser Leu Gly His Ile
                                  -20                 -15
ttg gtt ttc tgt gtg ggt ctc ctc acc atg gcc aag gca gaa agt cca      100
Leu Val Phe Cys Val Gly Leu Leu Thr Met Ala Lys Ala Glu Ser Pro
            -10             -5                       1 aag gaa cac gac ccg ttc act tac gac tac cag tcc ctg cag atc gga      148
Lys Glu His Asp Pro Phe Thr Tyr Asp Tyr Gln Ser Leu Gln Ile Gly
        5                   10                  15 ggc ctc gtc atc gcc ggg atc ctc ttc atc ctg ggc atc ctc atc gtg      196
Gly Leu Val Ile Ala Gly Ile Leu Phe Ile Leu Gly Ile Leu Ile Val
20                  25                  30                  35 ctg agc aga aga tgc cgg tgc aag ttc aac cag cag cag agg act ggg      244
Leu Ser Arg Arg Cys Arg Cys Lys Phe Asn Gln Gln Gln Arg Thr Gly
                40                  45                  50 gaa ccc gat gaa gag gag gga act ttc cgc agc tcc atc cgc cgt ctg      292
Glu Pro Asp Glu Glu Glu Gly Thr Phe Arg Ser Ser Ile Arg Arg Leu
            55                  60                  65 tcc acc cgc agg cgg tagaaacacc tggagcgatg aatccggcc aggactcccc      347
Ser Thr Arg Arg Arg
            70 tggcacctga catctcccac gctccacctg cgcgccacc gcccctccg ccgccccttc      407 cccagccctg ccccgcaga ctcccccctgc cgccaagact tccaataaaa cgtgcgttcc    467 tctcaaaaaa aaaagaaa                                                  485

<210> SEQ ID NO 76
<211> LENGTH: 1394
<212> TYPE: DNA
<213> ORGANISM: Homo sapiens
<220> FEATURE:
<221> NAME/KEY: CDS
<222> LOCATION: 46..675
<220> FEATURE:
<221> NAME/KEY: sig_peptide
<222> LOCATION: 46..87
<223> OTHER INFORMATION: Von Heijne matrix
      score 5.9
      seq LTLLGLSLILAGL/IV
<220> FEATURE:
<221> NAME/KEY: polyA_signal
<222> LOCATION: 1363..1368
<220> FEATURE:
<221> NAME/KEY: polyA_site
<222> LOCATION: 1382..1394

<400> SEQUENCE: 76
ctccgagttg ccacccagga aaagagggc tcctctggga gatgt atg ctt act ctc    57
                                                Met Leu Thr Leu tta ggc ctt tca ctc atc ttg gca gga ctt att gtt ggt gga gcc tgc    105
Leu Gly Leu Ser Leu Ile Leu Ala Gly Leu Ile Val Gly Gly Ala Cys
-10              -5                  1                   5 att tac aag cac ttc atg ccc aag agc acc att tac cgt gga gag atg    153
Ile Tyr Lys His Phe Met Pro Lys Ser Thr Ile Tyr Arg Gly Glu Met
             10                  15                  20 tgc ttt ttt gat tct gag gat cct gca aat tcc ctt cgt gga gga gag    201
Cys Phe Phe Asp Ser Glu Asp Pro Ala Asn Ser Leu Arg Gly Gly Glu
             25                  30                  35 cct aac ttc ctg cct gtg act gag gag gct gac att cgt gag gat gac    249
Pro Asn Phe Leu Pro Val Thr Glu Glu Ala Asp Ile Arg Glu Asp Asp
         40                  45                  50 aac att gca atc att gat gtg cct gtc ccc agt ttc tct gat agt gac    297
Asn Ile Ala Ile Ile Asp Val Pro Val Pro Ser Phe Ser Asp Ser Asp
55                  60                  65                  70
```

| | | |
|---|---|---|
| cct gca gca att att cat gac ttt gaa aag gga atg act gct tac ctg<br>Pro Ala Ala Ile Ile His Asp Phe Glu Lys Gly Met Thr Ala Tyr Leu<br>75 80 85 | | 345 |
| gac ttg ttg ctg ggg aac tgc tat ctg atg ccc ctc aat act tct att<br>Asp Leu Leu Leu Gly Asn Cys Tyr Leu Met Pro Leu Asn Thr Ser Ile<br>90 95 100 | | 393 |
| gtt atg cct cca gaa aat ctg gta gag ctc ttt ggc aaa ctg gcg agt<br>Val Met Pro Pro Glu Asn Leu Val Glu Leu Phe Gly Lys Leu Ala Ser<br>105 110 115 | | 441 |
| ggc aga tat ctg cct caa act tat gtg gtt cga gaa gac cta gtt gct<br>Gly Arg Tyr Leu Pro Gln Thr Tyr Val Val Arg Glu Asp Leu Val Ala<br>120 125 130 | | 489 |
| gtg gag gaa att cgt gat gtt agt aac ctt ggc atc ttt att tac caa<br>Val Glu Glu Ile Arg Asp Val Ser Asn Leu Gly Ile Phe Ile Tyr Gln<br>135 140 145 150 | | 537 |
| ctt tgc aat aac aga aag tcc ttc cgc ctt cgt cgc aga gac ctc ttg<br>Leu Cys Asn Asn Arg Lys Ser Phe Arg Leu Arg Arg Arg Asp Leu Leu<br>155 160 165 | | 585 |
| ctg ggt ttc aac aaa cgt gcc att gat aaa tgc tgg aag att aga cac<br>Leu Gly Phe Asn Lys Arg Ala Ile Asp Lys Cys Trp Lys Ile Arg His<br>170 175 180 | | 633 |
| ttc ccc aac gaa ttt att gtt gag acc aag atc tgt caa gag<br>Phe Pro Asn Glu Phe Ile Val Glu Thr Lys Ile Cys Gln Glu<br>185 190 195 | | 675 |
| taagaggcaa cagatagagt gtccttggta acaagaagtc agagatttac aatatgactt | | 735 |
| taacattaag gtttatggga tactcaagat atttactcat gcatttactc tattgcttat | | 795 |
| gctttaaaaa aagaaaaaa aaaaactact aaccactgca agctcttgtc aaattttagt | | 855 |
| ttaattggca ttgcttgttt tttgaaactg aaattacctg agtttcattt tttctttgaa | | 915 |
| tttatagggt ttagatttct gaaagcagca tgaatatatc acctaacatc ctgacaataa | | 975 |
| attccatccg ttgttttttt tgtttgtttg ttttttcttt tcctttaagt aagctcttta | | 1035 |
| ttcatcttat ggtgcagcaa ttttaaaatt tgaaatattt taaattgttt ttgaactttt | | 1095 |
| tgtgtaaaat atatcagatc tcaacattgt tggtttcttt tgttttttcat tttgtacaac | | 1155 |
| tttcttgaat ttagaaatta catctttgca gctctgttag gtgctctgta attaacctga | | 1215 |
| cttatatgtg aacaatttc atgagacagt catttttaaa taatgcagtg attctttctc | | 1275 |
| actactatct gtattgtgga atgcacaaaa ttgtgtaggt gctgaatgct gtaaggagtt | | 1335 |
| taggttgtat gaattctaca accctataat aaattttact ctatacaaaa aaaaaaaaa | | 1394 |

<210> SEQ ID NO 77
<211> LENGTH: 1333
<212> TYPE: DNA
<213> ORGANISM: Homo sapiens
<220> FEATURE:
<221> NAME/KEY: CDS
<222> LOCATION: 329..943
<220> FEATURE:
<221> NAME/KEY: sig_peptide
<222> LOCATION: 329..745
<223> OTHER INFORMATION: Von Heijne matrix
score 4.2
seq SLSLALKTGPTSG/LC
<220> FEATURE:
<221> NAME/KEY: polyA_site
<222> LOCATION: 1322..1333

<400> SEQUENCE: 77
cgccagtgtc agtggtgttg gcatcagctt gggcaggtgt gcgggctcag gatggggcgg    60
ccgtggtgag gaaccctgga ctctcagcat cacaagaggc aacaccagga gccaacatga   120

```
gctcgggact gaactgctgt ggcccggagc agcgctgctg gtgctgttgg gggtggcagc      180
cagtctgtgt gtgcgctgct cacgcccagg tgcaaagagg tcagagagaa tctaccagca      240
gagaagtctg cgtgaggacc aacagagctt tacggggtcc cggacctact ccttggtcgg     300
gcaggcatgg ccaggacccc tggcggac atg gca ccc aca agg aag gac aag        352
                                Met Ala Pro Thr Arg Lys Asp Lys
                                                        -135 ctg ttg caa ttc tac ccc agc ctg gag gat cca gca tct tcc agg tac       400
Leu Leu Gln Phe Tyr Pro Ser Leu Glu Asp Pro Ala Ser Ser Arg Tyr
    -130            -125                -120 cag aac ttc agc aaa gga agc aga cac ggg tcg gag gaa gcc tac ata       448
Gln Asn Phe Ser Lys Gly Ser Arg His Gly Ser Glu Glu Ala Tyr Ile
-115            -110                -105                    -100 gac ccc att gcc atg gag tat tac aac tgg ggg cgg ttc tcg aag ccc       496
Asp Pro Ile Ala Met Glu Tyr Tyr Asn Trp Gly Arg Phe Ser Lys Pro
                -95                 -90                 -85 cca gaa ggt gag gcg aag gac aaa gcc gga ggt gga gga agt ggt gtg       544
Pro Glu Gly Glu Ala Lys Asp Lys Ala Gly Gly Gly Gly Ser Gly Val
            -80              -75                 -70 gga gct cag ggc aga agc cat acc tcc agg cag gag agg agg ctg ggc       592
Gly Ala Gln Gly Arg Ser His Thr Ser Arg Gln Glu Arg Arg Leu Gly
        -65              -60                 -55 ctg ggt tcg gat gat gat gcc aat tcc tac gag aat gtg ctc att tgc      640
Leu Gly Ser Asp Asp Asp Ala Asn Ser Tyr Glu Asn Val Leu Ile Cys
    -50                 -45                 -40 aag cag aaa acc aca gag aca ggt gcc cag cag gag gac gta ggt ggc       688
Lys Gln Lys Thr Thr Glu Thr Gly Ala Gln Gln Glu Asp Val Gly Gly
-35             -30                 -25                     -20 ctc tgc aga ggg gac ctc agc ctg tca ctg gcc ctg aag act ggc ccc       736
Leu Cys Arg Gly Asp Leu Ser Leu Ser Leu Ala Leu Lys Thr Gly Pro
                -15             -10                 -5 act tct ggt ctc tgt ccc tct gcc tcc ccg gaa gaa gat ggg gaa tct      784
Thr Ser Gly Leu Cys Pro Ser Ala Ser Pro Glu Glu Asp Gly Glu Ser
            1               5                   10 gag gat tat cag aac tca gca tcc atc cat caa tgg cgc gag tcc agg       832
Glu Asp Tyr Gln Asn Ser Ala Ser Ile His Gln Trp Arg Glu Ser Arg
        15              20                  25 aag gtc atg ggg caa ctc cag aga gaa gca tcc cct ggc ccg gtg gga       880
Lys Val Met Gly Gln Leu Gln Arg Glu Ala Ser Pro Gly Pro Val Gly
30              35                  40                  45 agc cca gac gag gag gac ggg gaa ccg gat tac gtg aat ggg gag gtg       928
Ser Pro Asp Glu Glu Asp Gly Glu Pro Asp Tyr Val Asn Gly Glu Val
                50                  55                  60 gca gcc aca gaa gcc tagggcagac caagaagaaa ggagccaagg caaagagggg      983
Ala Ala Thr Glu Ala
                65 ccactgtgct catggaccca tcgctgcctt ccaaggacca tttcccagag ctactcaact    1043 tttaagcccc tgccatggtt gctcctggaa ggagaaccag ccaccctgag gaccacctgg    1103 ccatgcgtgc acagcctggg aaagacagt tactcacggg agctgcaggc ccgtcaccaa     1163 gccctctccc gacccaggct ttgtggggca ggcacctggt accatgggta acccggctcc    1223 tggtatggac ggatgcgcag gatttaggat aagctgtcac ccagtcccca taacaaaacc    1283 actgtccaac actggtatct gtgttctttt gtgctatgaa aaaaaaaaa                1333

<210> SEQ ID NO 78
<211> LENGTH: 326
<212> TYPE: DNA
```

```
<213> ORGANISM: Homo sapiens
<220> FEATURE:
<221> NAME/KEY: CDS
<222> LOCATION: 27..281
<220> FEATURE:
<221> NAME/KEY: sig_peptide
<222> LOCATION: 27..77
<223> OTHER INFORMATION: Von Heijne matrix
      score 8.2
      seq LLLITAILAVAVG/FP

<400> SEQUENCE: 78
```

| | | | | | | | | | | | | |
|---|---|---|---|---|---|---|---|---|---|---|---|---|
| gaaagaact gactgaaacg tttgag | atg | aag | aaa | gtt | ctc | ctc | ctg | atc | aca | | | 53 |
| | Met | Lys | Lys | Val | Leu | Leu | Leu | Ile | Thr | | | |
| | | -15 | | | | | -10 | | | | | |

| gcc | atc | ttg | gca | gtg | gct | gtt | ggt | ttc | cca | gtc | tct | caa | gac | cag | gaa | 101 |
|---|---|---|---|---|---|---|---|---|---|---|---|---|---|---|---|---|
| Ala | Ile | Leu | Ala | Val | Ala | Val | Gly | Phe | Pro | Val | Ser | Gln | Asp | Gln | Glu | |
| | | -5 | | | | | 1 | | | 5 | | | | | | |

| cga | gaa | aaa | aga | agt | atc | agt | gac | agc | gat | gaa | tta | gct | tca | ggg | ttt | 149 |
|---|---|---|---|---|---|---|---|---|---|---|---|---|---|---|---|---|
| Arg | Glu | Lys | Arg | Ser | Ile | Ser | Asp | Ser | Asp | Glu | Leu | Ala | Ser | Gly | Phe | |
| | 10 | | | | 15 | | | | 20 | | | | | | | |

| ttt | gtg | ttc | cct | tac | cca | tat | cca | ttt | cgc | cca | ctt | cca | cca | att | cca | 197 |
|---|---|---|---|---|---|---|---|---|---|---|---|---|---|---|---|---|
| Phe | Val | Phe | Pro | Tyr | Pro | Tyr | Pro | Phe | Arg | Pro | Leu | Pro | Pro | Ile | Pro | |
| 25 | | | | 30 | | | | 35 | | | | | 40 | | | |

| ttt | cca | aga | ttt | cca | tgg | ttt | aga | cgt | aat | ttt | cct | att | cca | ata | cct | 245 |
|---|---|---|---|---|---|---|---|---|---|---|---|---|---|---|---|---|
| Phe | Pro | Arg | Phe | Pro | Trp | Phe | Arg | Arg | Asn | Phe | Pro | Ile | Pro | Ile | Pro | |
| | | | 45 | | | | | 50 | | | | | 55 | | | |

| gaa | tct | gcc | cct | aca | act | ccc | ctt | cct | agc | gaa | aag | taaacaagaa | 291 |
|---|---|---|---|---|---|---|---|---|---|---|---|---|---|
| Glu | Ser | Ala | Pro | Thr | Thr | Pro | Leu | Pro | Ser | Glu | Lys | | |
| | | 60 | | | | | 65 | | | | | | |

| ggaaaagtca cgataaacct ggtcacctga aattg | 326 |
|---|---|

```
<210> SEQ ID NO 79
<211> LENGTH: 703
<212> TYPE: DNA
<213> ORGANISM: Homo sapiens
<220> FEATURE:
<221> NAME/KEY: CDS
<222> LOCATION: 61..405
<220> FEATURE:
<221> NAME/KEY: sig_peptide
<222> LOCATION: 61..213
<223> OTHER INFORMATION: Von Heijne matrix
      score 8.1
      seq VCLCGTFCFPCLG/CQ
<220> FEATURE:
<221> NAME/KEY: polyA_signal
<222> LOCATION: 675..680
<220> FEATURE:
<221> NAME/KEY: polyA_site
<222> LOCATION: 692..703

<400> SEQUENCE: 79
```

| catttcctgc tcggaacctt gtttactaat ttccactgct tttaaggccc tgcactgaaa | 60 |
|---|---|

| atg | caa | gct | cag | gcg | ccg | gtg | gtc | gtt | gtg | acc | caa | cct | gga | gtc | ggt | 108 |
|---|---|---|---|---|---|---|---|---|---|---|---|---|---|---|---|---|
| Met | Gln | Ala | Gln | Ala | Pro | Val | Val | Val | Val | Thr | Gln | Pro | Gly | Val | Gly | |
| -50 | | | | -45 | | | | | -40 | | | | | | | |

| ccc | ggt | ccg | gcc | ccc | cag | aac | tcc | aac | tgg | cag | aca | ggc | atg | tgt | gac | 156 |
|---|---|---|---|---|---|---|---|---|---|---|---|---|---|---|---|---|
| Pro | Gly | Pro | Ala | Pro | Gln | Asn | Ser | Asn | Trp | Gln | Thr | Gly | Met | Cys | Asp | |
| -35 | | | | | -30 | | | | | -25 | | | | | -20 | |

| tgt | ttc | agc | gac | tgc | gga | gtc | tgt | ctc | tgt | ggc | aca | ttt | tgt | ttc | ccg | 204 |
|---|---|---|---|---|---|---|---|---|---|---|---|---|---|---|---|---|
| Cys | Phe | Ser | Asp | Cys | Gly | Val | Cys | Leu | Cys | Gly | Thr | Phe | Cys | Phe | Pro | |
| | | | | -15 | | | | | -10 | | | | | -5 | | |

| tgc | ctt | ggg | tgt | caa | gtt | gca | gct | gat | atg | aat | gaa | tgc | tgt | ctg | tgt | 252 |
|---|---|---|---|---|---|---|---|---|---|---|---|---|---|---|---|---|
| Cys | Leu | Gly | Cys | Gln | Val | Ala | Ala | Asp | Met | Asn | Glu | Cys | Cys | Leu | Cys | |
| | | | 1 | | | 5 | | | | 10 | | | | | | |

```
gga aca agc gtc gca atg agg act ctc tac agg acc cga tat ggc atc        300
Gly Thr Ser Val Ala Met Arg Thr Leu Tyr Arg Thr Arg Tyr Gly Ile
        15                  20                  25 cct gga cct att tgt gat gac tat atg gca act ctt tgc tgt cct cat        348
Pro Gly Pro Ile Cys Asp Asp Tyr Met Ala Thr Leu Cys Cys Pro His
 30                  35                  40                  45 tgt act ctt tgc caa atc aag aga gat atc aac aga agg aga gcc atg        396
Cys Thr Leu Cys Gln Ile Lys Arg Asp Ile Asn Arg Arg Arg Ala Met
                 50                  55                  60 cgt act ttc taaaaactga tggtgaaaag ctcttaccga agcaacaaaa                 445
Arg Thr Phe ttcagcagac acctctccag cttgagttct tcaccatctt ttgcaactga aatatgatgg       505
atatgcttaa gtacaactga tggcatgaaa aaaatcaaat ttttgattta ttataaatga       565
atgttgtccc tgaacttagc taaatggtgc aacttagttt ctccttgctt tcatattatc       625
gaatttcctg gcttataaac tttttaaatt acatttgaaa tataaaccaa atgaaatatt       685
ttactcaaaa aaaaaaaa                                                     703

<210> SEQ ID NO 80
<211> LENGTH: 768
<212> TYPE: DNA
<213> ORGANISM: Homo sapiens
<220> FEATURE:
<221> NAME/KEY: CDS
<222> LOCATION: 137..379
<220> FEATURE:
<221> NAME/KEY: sig_peptide
<222> LOCATION: 137..229
<223> OTHER INFORMATION: Von Heijne matrix
      score 4.4
      seq TCCHLGLPHPVRA/PR
<220> FEATURE:
<221> NAME/KEY: polyA_signal
<222> LOCATION: 728..733
<220> FEATURE:
<221> NAME/KEY: polyA_site
<222> LOCATION: 755..768

<400> SEQUENCE: 80
tcggagttgg aaagggacgc ctggtttccc cccaagcgaa ccgggatggg aagtgacttc        60
aatgagattg aacttcagct ggattgaaag agaggctaga agttccgctt gccagcagcc       120
cccttagtag agcgga atg agt aat acc cac acg gtg ctt gtc tca ctt ccc       172
               Met Ser Asn Thr His Thr Val Leu Val Ser Leu Pro
                    -30                 -25                 -20 cat ccg cac ccg gcc ctc acc tgc tgt cac ctc ggc ctc cca cac ccg        220
His Pro His Pro Ala Leu Thr Cys Cys His Leu Gly Leu Pro His Pro
             -15                 -10                  -5 gtc cgc gct ccc cgc cct ctt cct cgc gta gaa ccg tgg gat cct agg        268
Val Arg Ala Pro Arg Pro Leu Pro Arg Val Glu Pro Trp Asp Pro Arg
             1                   5                   10 tgg cag gac tca gag cta agg tat cca cag gcc atg aat tcc ttc cta        316
Trp Gln Asp Ser Glu Leu Arg Tyr Pro Gln Ala Met Asn Ser Phe Leu
        15                  20                  25 aat gag cgg tca tcg ccg tgc agg acc tta agg caa gaa gca tcg gct        364
Asn Glu Arg Ser Ser Pro Cys Arg Thr Leu Arg Gln Glu Ala Ser Ala
 30                  35                  40                  45 gac aga tgt gat ctc tgaacctgat agattgctga ttttatctta ttttatcctt        419
Asp Arg Cys Asp Leu
                 50 gacttggtac aagttttggg atttctgaaa agaccatgca gataaccaca aatatcaaga       479
```

```
aagtcgtctt cagtattaag tagaatttag atttaggttt ccttcctgct tcccacctcc        539
ttcgaataag gaaacgtctt tgggaccaac tttatggaat aaataagctg agctgtattt        599
caagtaatat agttataaat taacaatgta gcagttattg atagagaaat tgagaaaact        659
gaaacgtgac cggagtattg gaaataacgt agtacatcac ctagcacaat gacacatagt        719
aggtgctcaa taaatttatg cttataattt ttgtcaaaaa aaaaaataa                    768
```

<210> SEQ ID NO 81
<211> LENGTH: 1007
<212> TYPE: DNA
<213> ORGANISM: Homo sapiens
<220> FEATURE:
<221> NAME/KEY: CDS
<222> LOCATION: 37..741
<220> FEATURE:
<221> NAME/KEY: sig_peptide
<222> LOCATION: 37..153
<223> OTHER INFORMATION: Von Heijne matrix
      score 7.2
      seq SALAKLLLTCCSA/LR
<220> FEATURE:
<221> NAME/KEY: polyA_signal
<222> LOCATION: 969..974
<220> FEATURE:
<221> NAME/KEY: polyA_site
<222> LOCATION: 994..1007

<400> SEQUENCE: 81

```
cgcaggtccc gaggagcgca gactgtgtcc ctgaca atg gga aca gcc gac agt          54
                                        Met Gly Thr Ala Asp Ser
                                                        -35 gat gag atg gcc ccg gag gcc cca cag cac acc cac atc gat gtg cac         102
Asp Glu Met Ala Pro Glu Ala Pro Gln His Thr His Ile Asp Val His
        -30              -25                  -20 atc cac cag gag tct gcc ctg gcc aag ctc ctg ctc acc tgc tgc tct         150
Ile His Gln Glu Ser Ala Leu Ala Lys Leu Leu Leu Thr Cys Cys Ser
            -15              -10                  -5 gcg ctg cgg ccc cgg gcc acc cag gcc agg ggc agc agc cgg ctg ctg         198
Ala Leu Arg Pro Arg Ala Thr Gln Ala Arg Gly Ser Ser Arg Leu Leu
 1               5                  10                  15 gtg gcc tcg tgg gtg atg cag atc gtg ctg ggg atc ttg agt gca gtc         246
Val Ala Ser Trp Val Met Gln Ile Val Leu Gly Ile Leu Ser Ala Val
                20                  25                  30 cta gga gga ttt ttc tac atc cgc gac tac acc ctc ctc gtc acc tcg         294
Leu Gly Gly Phe Phe Tyr Ile Arg Asp Tyr Thr Leu Leu Val Thr Ser
            35                  40                  45 ggg gct gcc atc tgg aca ggg gct gtg gct gtg ctg gct gga gct gct         342
Gly Ala Ala Ile Trp Thr Gly Ala Val Ala Val Leu Ala Gly Ala Ala
        50                  55                  60 gcc ttc att tac gag aaa cgg ggt ggt aca tac tgg gcc ctg ctg agg         390
Ala Phe Ile Tyr Glu Lys Arg Gly Gly Thr Tyr Trp Ala Leu Leu Arg
 65                  70                  75 act ctg cta gcg ctg gca gct ttc tcc aca gcc atc gct gcc ctc aaa         438
Thr Leu Leu Ala Leu Ala Ala Phe Ser Thr Ala Ile Ala Ala Leu Lys
 80                  85                  90                  95 ctt tgg aat gaa gat ttc cga tat ggc tac tct tat tac aac agt gcc         486
Leu Trp Asn Glu Asp Phe Arg Tyr Gly Tyr Ser Tyr Tyr Asn Ser Ala
                100                 105                 110 tgc cgc atc tcc agc tcg agt gac tgg aac act cca gcc ccc act cag         534
Cys Arg Ile Ser Ser Ser Ser Asp Trp Asn Thr Pro Ala Pro Thr Gln
            115                 120                 125 agt cca gaa gaa gtc aga agg cta cac cta tgt acc tcc ttc atg gac         582
Ser Pro Glu Glu Val Arg Arg Leu His Leu Cys Thr Ser Phe Met Asp
```

```
atg ctg aag gcc ttg ttc aga acc ctt cag gcc atg ctc ttg ggt gtc      630
Met Leu Lys Ala Leu Phe Arg Thr Leu Gln Ala Met Leu Leu Gly Val
        145                 150                 155 tgg att ctg ctg ctt ctg gca tct ctg gcc cct ctg tgg ctg tac tgc      678
Trp Ile Leu Leu Leu Leu Ala Ser Leu Ala Pro Leu Trp Leu Tyr Cys
160                 165                 170                 175 tgg aga atg ttc cca acc aaa ggg aaa aga gac cag aag gaa atg ttg      726
Trp Arg Met Phe Pro Thr Lys Gly Lys Arg Asp Gln Lys Glu Met Leu
                180                 185                 190 gaa gtg agt gga atc tagccatgcc tctcctgatt attagtgcct ggtgcttctg      781
Glu Val Ser Gly Ile
            195 caccgggcgt ccctgcatct gactgctgga agaagaacca gactgaggaa aagaggctct    841 tcaacagccc cagttatcct ggccccatga ccgtggccac agccctgctc agcagcact     901 tgcccattcc ttacacccct tccccatcct gctccgcttc atgtcccctc ctgagtagtc    961 atgtgataat aaactctcat gttattgttc ccaaaaaaaa aaaaaa                  1007

<210> SEQ ID NO 82
<211> LENGTH: 527
<212> TYPE: DNA
<213> ORGANISM: Homo sapiens
<220> FEATURE:
<221> NAME/KEY: CDS
<222> LOCATION: 80..265
<220> FEATURE:
<221> NAME/KEY: sig_peptide
<222> LOCATION: 80..142
<223> OTHER INFORMATION: Von Heijne matrix
      score 5.4
      seq TFCLIFGLGAVWG/LG
<220> FEATURE:
<221> NAME/KEY: polyA_signal
<222> LOCATION: 491..496
<220> FEATURE:
<221> NAME/KEY: polyA_site
<222> LOCATION: 517..527

<400> SEQUENCE: 82
cccgcttgat ccaagaaacc tcttcgattt ttatttttat ttttaaagag ggagacgatg     60
gactgagctg atccgcacc atg gag tct cgg gtc tta ctg aga aca ttc tgt     112
                    Met Glu Ser Arg Val Leu Leu Arg Thr Phe Cys
                        -20                 -15 ttg atc ttc ggt ctc gga gca gtt tgg ggg ctt ggt gtg gac cct tcc      160
Leu Ile Phe Gly Leu Gly Ala Val Trp Gly Leu Gly Val Asp Pro Ser
-10                 -5                  1                   5 cta cag att gac gtc tta aca gag tta gaa ctt ggg gag tcc acg acc      208
Leu Gln Ile Asp Val Leu Thr Glu Leu Glu Leu Gly Glu Ser Thr Thr
            10                  15                  20 gga gtg cgt cag gtc ccg ggg ctg cat aat ggg acg aaa gcc ttt ctc      256
Gly Val Arg Gln Val Pro Gly Leu His Asn Gly Thr Lys Ala Phe Leu
        25                  30                  35 ttt caa gcg tgactgaagc agcagcctgc acatgtggat ggtcatcagt              305
Phe Gln Ala
        40 gcctcgccca gagatacctg gccttcatcc aaagggaccc tgctgccaca agtcctccag    365 gcagcacccg cactgtggct ccttcgcact gagtatgttg gactctgcca tagactgacc    425 ctcttgtctg gctgctgcag tttgtctgta atgcccgtgac atgttgcatt ctccccattt   485 ggataaataa aacaaacaa atgcttctgt caaaaaaaaa aa                       527
```

```
<210> SEQ ID NO 83
<211> LENGTH: 861
<212> TYPE: DNA
<213> ORGANISM: Homo sapiens
<220> FEATURE:
<221> NAME/KEY: CDS
<222> LOCATION: 612..644
<220> FEATURE:
<221> NAME/KEY: polyA_signal
<222> LOCATION: 829..834
<220> FEATURE:
<221> NAME/KEY: polyA_site
<222> LOCATION: 850..861

<400> SEQUENCE: 83
```

| | | | | |
|---|---|---|---|---|
| agctctggtg gttctggctg ctctggactg tcctcatcct ctttagctgc tgttgcgcct | | | | 60 |
| tccgccaccg acgagctaaa ctcaggctgc aacaacagca gcggcagcgt gaaatcaact | | | | 120 |
| tgttggccta tcatggggca tgccatgggg ctggtccttt ccctaccggt tcactgcttg | | | | 180 |
| accttcgcct cctcagcacc ttcaagcccc agcctacga ggatgtggtt caccgcccag | | | | 240 |
| gcacaccacc cccccttat actgtggccc caggccgccc cttgactgct tccagtgaac | | | | 300 |
| aaacctgctg ttcctcctca tccagctgcc ctgcccactt tgaaggaaca aatgtggaag | | | | 360 |
| gtgtttcctc ccaccagagt gccccccctc atcaggaggg tgagcccggg gcaggggtga | | | | 420 |
| ccccctgcctc cacaccccc tcctgccgct atcgccgttt aactggcgac tccggtattg | | | | 480 |
| agctctgccc ttgtcctgcc tccggtgagg gtgagccagt caaggaggtg agggttagtg | | | | 540 |
| ccaccctgcc agatctggag gactactccc cgtgtgcact accccagag tctgtaccgc | | | | 600 | agatctttcc c atg ggg ctg tct tcc agt gaa ggg gac atc cca    644
            Met Gly Leu Ser Ser Ser Glu Gly Asp Ile Pro
              1               5                   10

| | | | | |
|---|---|---|---|---|
| taagtagttt tgagagggtg gatgggttac ttgcccacca gaaacagccc tagtcccaac | | | | 704 |
| tccttgcgtt cctttggccc ctccctgcct acctagaatc tgcctgaagg ggctggagag | | | | 764 |
| ggacagtatt gggggactgt gctagcttta ccccgcagg acatacacag gagccttga | | | | 824 |
| tctcattaaa gagatgtaaa ccagcaaaaa aaaaaaa | | | | 861 |

```
<210> SEQ ID NO 84
<211> LENGTH: 239
<212> TYPE: DNA
<213> ORGANISM: Homo sapiens
<220> FEATURE:
<221> NAME/KEY: CDS
<222> LOCATION: 61..228
<220> FEATURE:
<221> NAME/KEY: sig_peptide
<222> LOCATION: 61..162
<223> OTHER INFORMATION: Von Heijne matrix
      score 4
      seq IAVLYLHLYDVFG/DP
<220> FEATURE:
<221> NAME/KEY: polyA_signal
<222> LOCATION: 208..213

<400> SEQUENCE: 84
```
aatctgactc ctgagttctc acaacgcttg accaataaga ttcggaagct tcttcagcaa    60 atg gag aga ggc ctg aaa tca gca gac cct cgg gat ggc acc ggt tac    108
Met Glu Arg Gly Leu Lys Ser Ala Asp Pro Arg Asp Gly Thr Gly Tyr
               -30                 -25                 -20 act ggc tgg gca ggt att gct gtg ctt tac tta cat ctt tat gat gta    156
Thr Gly Trp Ala Gly Ile Ala Val Leu Tyr Leu His Leu Tyr Asp Val
         -15                 -10                  -5

```
ttt ggg gac cct gcc tct atg ttc tgt aaa gta ttt gac tta cta gtt    204
Phe Gly Asp Pro Ala Ser Met Phe Cys Lys Val Phe Asp Leu Leu Val
        1               5                  10 ctc aat aaa att tta tta gga cta taaaaaaaaa a                       239
Leu Asn Lys Ile Leu Leu Gly Leu
15                  20
```

```
<210> SEQ ID NO 85
<211> LENGTH: 178
<212> TYPE: PRT
<213> ORGANISM: Homo sapiens
<220> FEATURE:
<221> NAME/KEY: SIGNAL
<222> LOCATION: -22...-1

<400> SEQUENCE: 85
```

```
Met His Arg Pro Glu Ala Met Leu Leu Leu Thr Leu Ala Leu Leu
        -20             -15                 -10

Gly Gly Pro Thr Trp Ala Gly Lys Met Tyr Gly Pro Gly Gly Lys
    -5              1               5                   10

Tyr Phe Ser Thr Thr Glu Asp Tyr Asp His Glu Ile Thr Gly Leu Arg
            15                  20                  25

Val Ser Val Gly Leu Leu Val Lys Ser Val Gln Val Lys Leu Gly
            30                  35                  40

Asp Ser Trp Asp Val Lys Leu Gly Ala Leu Gly Gly Asn Thr Gln Glu
            45                  50                  55

Val Thr Leu Gln Pro Gly Glu Tyr Ile Thr Lys Val Phe Val Ala Phe
60                  65                  70

Gln Thr Phe Leu Arg Gly Met Val Met Tyr Thr Ser Lys Asp Arg Tyr
75                  80                  85                  90

Phe Tyr Phe Gly Lys Leu Asp Gly Gln Ile Ser Ser Ala Tyr Pro Ser
            95                  100                 105

Gln Glu Gly Gln Val Leu Val Gly Ile Tyr Gly Gln Tyr Gln Leu Leu
                110                 115                 120

Gly Ile Lys Ser Ile Gly Phe Glu Trp Asn Tyr Pro Leu Glu Glu Pro
            125                 130                 135

Thr Thr Glu Pro Pro Val Asn Leu Thr Tyr Ser Ala Asn Ser Pro Val
            140                 145                 150

Gly Arg
155
```

```
<210> SEQ ID NO 86
<211> LENGTH: 90
<212> TYPE: PRT
<213> ORGANISM: Homo sapiens
<220> FEATURE:
<221> NAME/KEY: SIGNAL
<222> LOCATION: -19..-1

<400> SEQUENCE: 86
```

```
Met Lys Phe Leu Ala Val Leu Val Leu Leu Gly Val Ser Ile Phe Leu
                -15                 -10                 -5

Val Ser Ala Gln Asn Pro Thr Thr Ala Ala Pro Ala Asp Thr Tyr Pro
            1               5                   10

Ala Thr Gly Pro Ala Asp Asp Glu Ala Pro Asp Ala Glu Thr Thr Ala
            15                  20                  25

Ala Ala Thr Thr Ala Thr Thr Ala Ala Pro Thr Thr Ala Thr Thr Ala
30                  35                  40                  45

Ala Ser Thr Thr Ala Arg Lys Asp Ile Pro Val Leu Pro Lys Trp Val
```

```
                    50                  55                  60
Gly Asp Leu Pro Asn Gly Arg Val Cys Pro
            65                  70

<210> SEQ ID NO 87
<211> LENGTH: 125
<212> TYPE: PRT
<213> ORGANISM: Homo sapiens
<220> FEATURE:
<221> NAME/KEY: SIGNAL
<222> LOCATION: -15..-1

<400> SEQUENCE: 87

Met Lys Leu Leu Thr His Asn Leu Leu Ser Ser His Val Arg Gly Val
-15                 -10                 -5                   1

Gly Ser Arg Gly Phe Pro Leu Arg Leu Gln Ala Thr Glu Val Arg Ile
                5                  10                  15

Cys Pro Val Glu Phe Asn Pro Asn Phe Val Ala Arg Met Ile Pro Lys
            20                  25                  30

Val Glu Trp Ser Ala Phe Leu Glu Ala Ala Asp Asn Leu Arg Leu Ile
        35                  40                  45

Gln Val Pro Lys Gly Pro Val Glu Gly Tyr Glu Glu Asn Glu Glu Phe
50                  55                  60                  65

Leu Arg Thr Met His His Leu Leu Glu Val Val Ile Glu Gly
            70                  75                  80

Thr Leu Gln Cys Pro Glu Ser Gly Arg Met Phe Pro Ile Ser Arg Gly
            85                  90                  95

Ile Pro Asn Met Leu Leu Ser Glu Glu Glu Thr Glu Ser
            100                 105                 110

<210> SEQ ID NO 88
<211> LENGTH: 136
<212> TYPE: PRT
<213> ORGANISM: Homo sapiens
<220> FEATURE:
<221> NAME/KEY: SIGNAL
<222> LOCATION: -34..-1

<400> SEQUENCE: 88

Met Leu Phe Ser Leu Arg Glu Leu Val Gln Trp Leu Gly Phe Ala Thr
                -30                 -25                 -20

Phe Glu Ile Phe Val His Leu Leu Ala Leu Leu Val Phe Ser Val Leu
            -15                 -10                 -5

Leu Ala Leu Arg Val Asp Gly Leu Val Pro Gly Leu Ser Trp Trp Asn
        1                   5                   10

Val Phe Val Pro Phe Phe Ala Ala Asp Gly Leu Ser Thr Tyr Phe Thr
15                  20                  25                  30

Thr Ile Val Ser Val Arg Leu Phe Gln Asp Gly Glu Lys Arg Leu Ala
            35                  40                  45

Val Leu Arg Leu Phe Trp Val Leu Thr Val Leu Ser Leu Lys Phe Val
        50                  55                  60

Phe Glu Met Leu Leu Cys Gln Lys Leu Ala Glu Gln Thr Arg Glu Leu
            65                  70                  75

Trp Phe Gly Leu Ile Thr Ser Pro Leu Phe Ile Leu Leu Gln Leu Leu
        80                  85                  90

Met Ile Arg Ala Cys Arg Val Asn
95                  100
```

```
<210> SEQ ID NO 89
<211> LENGTH: 238
<212> TYPE: PRT
<213> ORGANISM: Homo sapiens
<220> FEATURE:
<221> NAME/KEY: SIGNAL
<222> LOCATION: -53..-1

<400> SEQUENCE: 89

Met Ala Asp Pro Asp Pro Arg Tyr Pro Arg Ser Ser Ile Glu Asp Asp
            -50                 -45                 -40

Phe Asn Tyr Gly Ser Ser Val Ala Ser Ala Thr Val His Ile Arg Met
        -35                 -30                 -25

Ala Phe Leu Arg Lys Val Tyr Ser Ile Leu Ser Leu Gln Val Leu Leu
    -20                 -15                 -10

Thr Thr Val Thr Ser Thr Val Phe Leu Tyr Phe Glu Ser Val Arg Thr
-5                   1                   5                  10

Phe Val His Glu Ser Pro Ala Leu Ile Leu Leu Phe Ala Leu Gly Ser
                15                  20                  25

Leu Gly Leu Ile Phe Ala Leu Ile Leu Asn Arg His Lys Tyr Pro Leu
            30                  35                  40

Asn Leu Tyr Leu Leu Phe Gly Phe Thr Leu Leu Glu Ala Leu Thr Val
        45                  50                  55

Ala Val Val Val Thr Phe Tyr Asp Val Tyr Ile Ile Leu Gln Ala Phe
60                  65                  70                  75

Ile Leu Thr Thr Thr Val Phe Phe Gly Leu Thr Val Tyr Thr Leu Gln
                80                  85                  90

Ser Lys Lys Asp Phe Ser Lys Phe Gly Ala Gly Leu Phe Ala Leu Leu
            95                 100                 105

Trp Ile Leu Cys Leu Ser Gly Phe Leu Lys Phe Phe Leu Tyr Ser Glu
        110                 115                 120

Ile Met Glu Leu Val Leu Ala Ala Gly Ala Leu Leu Phe Cys Gly
            125                 130                 135       Gly

Phe Ile Ile Tyr Asp Thr His Ser Leu Met His Lys Leu Ser Pro Glu
140                 145                 150                 155

Glu Tyr Val Leu Ala Ala Ile Ser Leu Tyr Leu Asp Ile Ile Asn Leu
                160                 165                 170

Phe Leu His Leu Leu Arg Phe Leu Glu Ala Val Asn Lys Lys
            175                 180                 185

<210> SEQ ID NO 90
<211> LENGTH: 106
<212> TYPE: PRT
<213> ORGANISM: Homo sapiens
<220> FEATURE:
<221> NAME/KEY: SIGNAL
<222> LOCATION: -71..-1

<400> SEQUENCE: 90

Met Ser Thr Asn Asn Met Ser Asp Pro Arg Arg Pro Asn Lys Val Leu
        -70                 -65                 -60

Arg Tyr Lys Pro Pro Pro Ser Glu Cys Asn Pro Ala Leu Asp Asp Pro
-55                 -50                 -45                 -40

Thr Pro Asp Tyr Met Asn Leu Leu Gly Met Ile Phe Ser Met Cys Gly
                -35                 -30                 -25

Leu Met Leu Lys Leu Lys Trp Cys Ala Trp Val Ala Val Tyr Cys Ser
            -20                 -15                 -10

Phe Ile Ser Phe Ala Asn Ser Arg Ser Ser Glu Asp Thr Lys Gln Met
```

```
               -5                  1                  5
Met Ser Ser Phe Met Leu Ser Ile Ser Ala Val Val Met Ser Tyr Leu
10                  15                  20                  25

Gln Asn Pro Gln Pro Met Thr Pro Pro Trp
                    30                  35
```

<210> SEQ ID NO 91
<211> LENGTH: 123
<212> TYPE: PRT
<213> ORGANISM: Homo sapiens
<220> FEATURE:
<221> NAME/KEY: SIGNAL
<222> LOCATION: -84..-1

<400> SEQUENCE: 91

```
Met Ser Gly Gly Pro Glu Ala Arg Pro Pro Met Leu Val Glu Gly Gly
                -80                 -75                 -70

Gly Pro Glu Ser Leu Gln Lys Ala Pro Cys Thr Arg Gly Pro Pro Ser
            -65                 -60                 -55

His Pro Val Pro Pro Ala Leu Ala Phe Thr Val Gly Asn Gly Ser Gly
        -50                 -45                 -40

Pro Gly Val Arg Cys Pro Arg Asn Met Ala Glu Gly His Pro Gly Pro
    -35                 -30                 -25

Glu Arg Arg Gln Ser Gln Gln Gly Leu Phe Arg Ala Ala Trp Leu Pro
-20                 -15                 -10                 -5

Gly Ser Arg Pro Ser Pro Leu Phe Cys Val Cys Ser Val Thr Ser Pro
                1                   5                   10

Gly Trp Asp Val Pro Gln Val His Arg Val Glu Val Gly His Gly Arg
        15                  20                  25

Arg Gln Glu Thr His Pro Val Arg Arg Ala
    30                  35
```

<210> SEQ ID NO 92
<211> LENGTH: 75
<212> TYPE: PRT
<213> ORGANISM: Homo sapiens
<220> FEATURE:
<221> NAME/KEY: SIGNAL
<222> LOCATION: -49..-1

<400> SEQUENCE: 92

```
Met Pro Arg Gly Arg Arg Leu Gly Met Val Phe Ala Pro Pro Arg Pro
                -45                 -40                 -35

Gly Gln Arg Gln Ala Gly Ala Pro Trp Val Pro Glu Arg Arg Lys Arg
            -30                 -25                 -20

Arg Pro Asp Gly Asp Thr Phe Leu Leu Ser Phe Leu Ser Thr Thr Trp
        -15                 -10                 -5

Leu Lys Thr Trp Arg Ser Gln Gln Tyr Lys Glu Ser Lys Ser Arg Ser
1                   5                   10                  15

Cys Ala Arg Glu Gln Met Asn Ser Ser Cys
                20                  25
```

<210> SEQ ID NO 93
<211> LENGTH: 80
<212> TYPE: PRT
<213> ORGANISM: Homo sapiens
<220> FEATURE:
<221> NAME/KEY: SIGNAL
<222> LOCATION: -40..-1

<400> SEQUENCE: 93

```
Met Asp Gly Ile Pro Met Ser Met Lys Asn Glu Met Pro Ile Ser Gln
-40                 -35                 -30                 -25

Leu Leu Met Ile Ile Ala Pro Ser Leu Gly Phe Val Leu Phe Ala Leu
            -20                 -15                 -10

Phe Val Ala Phe Leu Leu Arg Gly Lys Leu Met Glu Thr Tyr Cys Ser
        -5                   1               5

Gln Lys His Thr Arg Leu Asp Tyr Ile Gly Asp Ser Lys Asn Val Leu
        10              15              20

Asn Asp Val Gln His Gly Arg Glu Asp Glu Asp Gly Leu Phe Thr Leu
25              30              35                          40

<210> SEQ ID NO 94
<211> LENGTH: 327
<212> TYPE: PRT
<213> ORGANISM: Homo sapiens
<220> FEATURE:
<221> NAME/KEY: SIGNAL
<222> LOCATION: -49..-1

<400> SEQUENCE: 94

Met Phe Pro Ser Arg Arg Lys Ala Ala Gln Leu Pro Trp Glu Asp Gly
                -45                 -40                 -35

Arg Ser Gly Leu Leu Ser Gly Gly Leu Pro Arg Lys Cys Ser Val Phe
            -30                 -25                 -20

His Leu Phe Val Ala Cys Leu Ser Leu Gly Phe Phe Ser Leu Leu Trp
        -15                 -10                 -5

Leu Gln Leu Ser Cys Ser Gly Asp Val Ala Arg Ala Val Arg Gly Gln
 1               5              10                  15

Gly Gln Glu Thr Ser Gly Pro Pro Arg Ala Cys Pro Pro Glu Pro Pro
            20                  25                  30

Pro Glu His Trp Glu Glu Asp Ala Ser Trp Gly Pro His Arg Leu Ala
            35                  40                  45

Val Leu Val Pro Phe Arg Glu Arg Phe Glu Glu Leu Leu Val Phe Val
            50                  55                  60

Pro His Met Arg Arg Phe Leu Ser Arg Lys Lys Ile Arg His His Ile
    65                  70                  75

Tyr Val Leu Asn Gln Val Asp His Phe Arg Phe Asn Arg Ala Ala Leu
80                  85                  90                  95

Ile Asn Val Gly Phe Leu Glu Ser Ser Asn Ser Thr Asp Tyr Ile Ala
                100                 105                 110

Met His Asp Val Asp Leu Leu Pro Leu Asn Glu Glu Leu Asp Tyr Gly
            115                 120                 125

Phe Pro Glu Ala Gly Pro Phe His Val Ala Ser Pro Glu Leu His Pro
        130                 135                 140

Leu Tyr His Tyr Lys Thr Tyr Val Gly Gly Ile Leu Leu Leu Ser Lys
    145                 150                 155

Gln His Tyr Arg Leu Cys Asn Gly Met Ser Asn Arg Phe Trp Gly Trp
160                 165                 170                 175

Gly Arg Glu Asp Asp Glu Phe Tyr Arg Arg Ile Lys Gly Ala Gly Leu
                180                 185                 190

Gln Leu Phe Arg Pro Ser Gly Ile Thr Thr Gly Tyr Lys Thr Phe Arg
            195                 200                 205

His Leu His Asp Pro Ala Trp Arg Lys Arg Asp Gln Lys Arg Ile Ala
        210                 215                 220

Ala Gln Lys Gln Glu Gln Phe Lys Val Asp Arg Glu Gly Gly Leu Asn
```

```
            225                 230                 235
Thr Val Lys Tyr His Val Ala Ser Arg Thr Ala Leu Ser Val Gly Gly
240                 245                 250                 255

Ala Pro Cys Thr Val Leu Asn Ile Met Leu Asp Cys Asp Lys Thr Ala
                260                 265                 270

Thr Pro Trp Cys Thr Phe Ser
                275

<210> SEQ ID NO 95
<211> LENGTH: 235
<212> TYPE: PRT
<213> ORGANISM: Homo sapiens
<220> FEATURE:
<221> NAME/KEY: SIGNAL
<222> LOCATION: -20..-1

<400> SEQUENCE: 95

Met Arg Pro Leu Ala Gly Gly Leu Leu Lys Val Val Phe Val Val Phe
-20                 -15                 -10                 -5

Ala Ser Leu Cys Ala Trp Tyr Ser Gly Tyr Leu Leu Ala Glu Leu Ile
                1                   5                   10

Pro Asp Ala Pro Leu Ser Ser Ala Ala Tyr Ser Ile Arg Ser Ile Gly
                15                  20                  25

Glu Arg Pro Val Leu Lys Ala Pro Val Pro Lys Arg Gln Lys Cys Asp
    30                  35                  40

His Trp Thr Pro Cys Pro Ser Asp Thr Tyr Ala Tyr Arg Leu Leu Ser
45                  50                  55                  60

Gly Gly Gly Arg Ser Lys Tyr Ala Lys Ile Cys Phe Glu Asp Asn Leu
                65                  70                  75

Leu Met Gly Glu Gln Leu Gly Asn Val Ala Arg Gly Ile Asn Ile Ala
                80                  85                  90

Ile Val Asn Tyr Val Thr Gly Asn Val Thr Ala Thr Arg Cys Phe Asp
                95                  100                 105

Met Tyr Glu Gly Asp Asn Ser Gly Pro Met Thr Lys Phe Ile Gln Ser
        110                 115                 120

Ala Ala Pro Lys Ser Leu Leu Phe Met Val Thr Tyr Asp Asp Gly Ser
125                 130                 135                 140

Thr Arg Leu Asn Asn Asp Ala Lys Asn Ala Ile Glu Ala Leu Gly Ser
                145                 150                 155

Lys Glu Ile Arg Asn Met Lys Phe Arg Ser Ser Trp Val Phe Ile Ala
                160                 165                 170

Ala Lys Gly Leu Glu Leu Pro Ser Glu Ile Gln Arg Glu Lys Ile Asn
        175                 180                 185

His Ser Asp Ala Lys Asn Asn Arg Tyr Ser Gly Trp Pro Ala Glu Ile
        190                 195                 200

Gln Ile Glu Gly Cys Ile Pro Lys Glu Arg Ser
205                 210                 215

<210> SEQ ID NO 96
<211> LENGTH: 52
<212> TYPE: PRT
<213> ORGANISM: Homo sapiens
<220> FEATURE:
<221> NAME/KEY: SIGNAL
<222> LOCATION: -31..-1

<400> SEQUENCE: 96

Met Arg Val Tyr Lys Arg Thr Gln Leu Arg Gln Glu Thr Gly Pro Lys
```

-continued

```
                -30                 -25                 -20
Ser Tyr Val Leu Phe Ser Ala Ser Ser Phe Pro Ser Ile Ser Gly Asn
-15                 -10                 -5                  1

Ile Arg Ser Arg Asn Tyr Phe Gln Lys Gln Asn Asn His Trp Phe Gln
            5                   10                  15

Thr Ser Asp Tyr
            20

<210> SEQ ID NO 97
<211> LENGTH: 229
<212> TYPE: PRT
<213> ORGANISM: Homo sapiens
<220> FEATURE:
<221> NAME/KEY: SIGNAL
<222> LOCATION: -47..-1

<400> SEQUENCE: 97

Met Gln Asp Glu Asp Gly Tyr Ile Thr Leu Asn Ile Lys Thr Arg Lys
            -45                 -40                 -35

Pro Ala Leu Val Ser Val Gly Pro Ala Ser Ser Phe Trp Trp Arg Val
            -30                 -25                 -20

Met Ala Leu Ile Leu Leu Ile Leu Cys Val Gly Met Val Val Gly Leu
-15                 -10                 -5                  1

Val Ala Leu Gly Ile Trp Ser Val Met Gln Arg Asn Tyr Leu Gln Asp
            5                   10                  15

Glu Asn Glu Asn Arg Thr Gly Thr Leu Gln Gln Leu Ala Lys Arg Phe
            20                  25                  30

Cys Gln Tyr Val Val Lys Gln Ser Glu Leu Lys Gly Thr Phe Lys Gly
            35                  40                  45

His Lys Cys Ser Pro Cys Asp Thr Asn Trp Arg Tyr Tyr Gly Asp Ser
50                  55                  60                  65

Cys Tyr Gly Phe Phe Arg His Asn Leu Thr Trp Glu Glu Ser Lys Gln
                70                  75                  80

Tyr Cys Thr Asp Met Asn Ala Thr Leu Leu Lys Ile Asp Asn Arg Asn
                85                  90                  95

Ile Val Glu Tyr Ile Lys Ala Arg Thr His Leu Ile Arg Trp Val Gly
                100                 105                 110

Leu Ser Arg Gln Lys Ser Asn Glu Val Trp Lys Trp Glu Asp Gly Ser
    115                 120                 125

Val Ile Ser Glu Asn Met Phe Glu Phe Leu Glu Asp Gly Lys Gly Asn
130                 135                 140                 145

Met Asn Cys Ala Tyr Phe His Asn Gly Lys Met His Pro Thr Phe Cys
                150                 155                 160

Glu Asn Lys His Tyr Leu Met Cys Glu Arg Lys Ala Gly Met Thr Lys
                165                 170                 175

Val Asp Gln Leu Pro
            180

<210> SEQ ID NO 98
<211> LENGTH: 92
<212> TYPE: PRT
<213> ORGANISM: Homo sapiens
<220> FEATURE:
<221> NAME/KEY: SIGNAL
<222> LOCATION: -24..-1

<400> SEQUENCE: 98

Met Thr Lys Leu Ala Gln Trp Leu Trp Gly Leu Ala Ile Leu Gly Ser
```

```
                    -20                 -15                 -10
Thr Trp Val Ala Leu Thr Thr Gly Ala Leu Gly Leu Glu Leu Pro Leu
                -5                   1                   5

Ser Cys Gln Glu Val Leu Trp Pro Leu Pro Ala Tyr Leu Leu Val Ser
 10                  15                  20

Ala Gly Cys Tyr Ala Leu Gly Thr Val Gly Tyr Arg Val Ala Thr Phe
 25                  30                  35                  40

His Asp Cys Glu Asp Ala Ala Arg Glu Leu Gln Ser Gln Ile Gln Glu
                 45                  50                  55

Ala Arg Ala Asp Leu Ala Arg Arg Gly Leu Arg Phe
                 60                  65

<210> SEQ ID NO 99
<211> LENGTH: 425
<212> TYPE: PRT
<213> ORGANISM: Homo sapiens
<220> FEATURE:
<221> NAME/KEY: SIGNAL
<222> LOCATION: -23..-1

<400> SEQUENCE: 99

Met Ala Ser Ser Pro Asp Ser Pro Cys Ser Cys Asp Cys Phe Val
                -20                 -15                 -10

Ser Val Pro Pro Ala Ser Ala Ile Pro Ala Val Ile Phe Ala Lys Asn
                -5                   1                   5

Ser Asp Arg Pro Arg Asp Glu Val Gln Glu Val Val Phe Val Pro Ala
 10                  15                  20                  25

Gly Thr His Thr Pro Gly Ser Arg Leu Gln Cys Thr Tyr Ile Glu Val
                 30                  35                  40

Glu Gln Val Ser Lys Thr His Ala Val Ile Leu Ser Arg Pro Ser Trp
                 45                  50                  55

Leu Trp Gly Ala Glu Met Gly Ala Asn Glu His Gly Val Cys Ile Gly
                 60                  65                  70

Asn Glu Ala Val Trp Thr Lys Glu Pro Val Gly Glu Gly Ala Leu
 75                  80                  85

Leu Gly Met Asp Leu Leu Arg Leu Ala Leu Glu Arg Ser Ser Ala
 90                  95                 100                 105

Gln Glu Ala Leu His Val Ile Thr Gly Leu Leu Glu His Tyr Gly Gln
                110                 115                 120

Gly Gly Asn Cys Leu Glu Asp Ala Ala Pro Phe Ser Tyr His Ser Thr
                125                 130                 135

Phe Leu Leu Ala Asp Arg Thr Glu Ala Trp Val Leu Glu Thr Ala Gly
                140                 145                 150

Arg Leu Trp Ala Ala Gln Arg Ile Gln Glu Gly Ala Arg Asn Ile Ser
                155                 160                 165

Asn Gln Leu Ser Ile Gly Thr Asp Ile Ser Ala Gln His Pro Glu Leu
170                 175                 180                 185

Arg Thr His Ala Gln Ala Lys Gly Trp Trp Asp Gly Gln Gly Ala Phe
                190                 195                 200

Asp Phe Ala Gln Ile Phe Ser Leu Thr Gln Gln Pro Val Arg Met Glu
                205                 210                 215

Ala Ala Lys Ala Arg Phe Gln Ala Gly Arg Glu Leu Leu Arg Gln Arg
                220                 225                 230

Gln Gly Gly Ile Thr Ala Glu Val Met Met Gly Ile Leu Arg Asp Lys
                235                 240                 245
```

-continued

```
Glu Ser Gly Ile Cys Met Asp Ser Gly Phe Arg Thr Thr Ala Ser
250                 255                 260                 265

Met Val Ser Val Leu Pro Gln Asp Pro Thr Gln Pro Cys Val His Phe
            270                 275                 280

Leu Thr Ala Thr Pro Asp Pro Ser Arg Ser Val Phe Lys Pro Phe Ile
                285                 290                 295

Phe Gly Val Gly Val Ala Gln Ala Pro Gln Val Leu Ser Pro Thr Phe
            300                 305                 310

Gly Ala Gln Asp Pro Val Arg Thr Leu Pro Arg Phe Gln Thr Gln Val
    315                 320                 325

Asp Arg Arg His Thr Leu Tyr Arg Gly His Gln Ala Ala Leu Gly Leu
330                 335                 340                 345

Met Glu Arg Asp Gln Asp Arg Gly Gln Gln Leu Gln Gln Lys Gln Gln
                350                 355                 360

Asp Leu Glu Gln Glu Gly Leu Glu Ala Thr Gln Gly Leu Leu Ala Gly
            365                 370                 375

Glu Trp Ala Pro Pro Leu Trp Glu Leu Gly Ser Leu Phe Gln Ala Phe
                380                 385                 390

Val Lys Arg Glu Ser Gln Ala Tyr Ala
    395                 400
```

<210> SEQ ID NO 100
<211> LENGTH: 87
<212> TYPE: PRT
<213> ORGANISM: Homo sapiens
<220> FEATURE:
<221> NAME/KEY: SIGNAL
<222> LOCATION: -62..-1

<400> SEQUENCE: 100

```
Met Ala Ile Phe Trp Ile Val His Ala His Phe Trp Ser Pro Leu Pro
        -60                 -55                 -50

Pro Arg Leu Pro His Gly Arg Cys Cys Leu Lys Ala Pro Leu Pro
    -45                 -40                 -35

Pro Asp Val Gly Pro Leu Gln Val Ala Pro His Leu Phe Ser Val Pro
-30                 -25                 -20                 -15

Leu His Ile Leu Thr Val Pro Leu Leu Glu Pro Ala Arg Cys Ser Gly
                -10                 -5                   1

Ile Leu Val Phe Phe Leu His Gln Pro Val Ser Ser Leu Ser Phe Cys
        5                   10                  15

Tyr Phe Ile Gly Gly Trp Cys
        20                  25
```

<210> SEQ ID NO 101
<211> LENGTH: 149
<212> TYPE: PRT
<213> ORGANISM: Homo sapiens
<220> FEATURE:
<221> NAME/KEY: SIGNAL
<222> LOCATION: -100..-1

<400> SEQUENCE: 101

```
Met Glu Thr Leu Tyr Arg Val Pro Phe Leu Val Leu Glu Cys Pro Asn
-100                -95                 -90                 -85

Leu Lys Leu Lys Lys Pro Pro Trp Leu His Met Pro Ser Ala Met Thr
                -80                 -75                 -70

Val Tyr Ala Leu Val Val Val Ser Tyr Phe Leu Ile Thr Gly Gly Ile
            -65                 -60                 -55
```

```
Ile Tyr Asp Val Ile Val Glu Pro Pro Ser Val Gly Ser Met Thr Asp
        -50             -45                 -40

Glu His Gly His Gln Arg Pro Val Ala Phe Leu Ala Tyr Arg Val Asn
        -35             -30                 -25

Gly Gln Tyr Ile Met Glu Gly Leu Ala Ser Ser Phe Leu Phe Thr Met
-20             -15              -10                          -5

Gly Gly Leu Gly Phe Ile Ile Leu Asp Arg Ser Asn Ala Pro Asn Ile
             1               5                   10

Pro Lys Leu Asn Arg Phe Leu Leu Leu Phe Ile Gly Phe Val Cys Val
         15              20              25

Leu Leu Ser Phe Phe Met Ala Arg Val Phe Met Arg Met Lys Leu Pro
         30              35              40

Gly Tyr Leu Met Gly
45

<210> SEQ ID NO 102
<211> LENGTH: 187
<212> TYPE: PRT
<213> ORGANISM: Homo sapiens
<220> FEATURE:
<221> NAME/KEY: SIGNAL
<222> LOCATION: -35..-1

<400> SEQUENCE: 102

Met Ala Asn Asn Thr Thr Ser Leu Gly Ser Pro Trp Pro Glu Asn Phe
-35                 -30              -25                  -20

Trp Glu Asp Leu Ile Met Ser Phe Thr Val Ser Met Ala Ile Gly Leu
                -15              -10                  -5

Val Leu Gly Gly Phe Ile Trp Ala Val Phe Ile Cys Leu Ser Arg Arg
             1               5                  10

Arg Arg Ala Ser Ala Pro Ile Ser Gln Trp Ser Ser Arg Arg Ser
         15              20              25

Arg Ser Ser Tyr Thr His Gly Leu Asn Arg Thr Gly Phe Tyr Arg His
30               35              40              45

Ser Gly Cys Glu Arg Arg Ser Asn Leu Ser Leu Ala Ser Leu Thr Phe
             50              55              60

Gln Arg Gln Ala Ser Leu Glu Gln Ala Asn Ser Phe Pro Arg Lys Ser
         65              70              75

Ser Phe Arg Ala Ser Thr Phe His Pro Phe Leu Gln Cys Pro Pro Leu
         80              85              90

Pro Val Glu Thr Glu Ser Gln Leu Val Thr Leu Pro Ser Ser Asn Ile
         95              100             105

Ser Pro Thr Ile Ser Thr Ser His Ser Leu Ser Arg Pro Asp Tyr Trp
110              115             120             125

Ser Ser Asn Ser Leu Arg Val Gly Leu Ser Thr Pro Pro Pro Ala
             130             135             140

Tyr Glu Ser Ile Ile Lys Ala Phe Pro Asp Ser
             145             150

<210> SEQ ID NO 103
<211> LENGTH: 123
<212> TYPE: PRT
<213> ORGANISM: Homo sapiens
<220> FEATURE:
<221> NAME/KEY: SIGNAL
<222> LOCATION: -26..-1

<400> SEQUENCE: 103
```

```
Met Ala Thr Ala Ala Gly Ala Thr Tyr Phe Gln Arg Gly Ser Leu Phe
        -25             -20                 -15

Trp Phe Thr Val Ile Thr Leu Ser Phe Gly Tyr Tyr Thr Trp Val Val
-10              -5                   1                   5

Phe Trp Pro Gln Ser Ile Pro Tyr Gln Asn Leu Gly Pro Leu Gly Pro
             10              15                  20

Phe Thr Gln Tyr Leu Val Asp His His Thr Leu Leu Cys Asn Gly
             25              30              35

Tyr Trp Leu Ala Trp Leu Ile His Val Gly Glu Ser Leu Tyr Ala Ile
        40              45                  50

Val Leu Cys Lys His Lys Gly Ile Thr Ser Gly Arg Ala Gln Leu Leu
55              60              65                          70

Trp Phe Leu Gln Thr Phe Phe Gly Ile Ala Ser Leu Thr Ile Leu
                 75              80              85

Ile Ala Tyr Lys Arg Lys Arg Gln Lys Gln Thr
            90              95
```

<210> SEQ ID NO 104
<211> LENGTH: 153
<212> TYPE: PRT
<213> ORGANISM: Homo sapiens
<220> FEATURE:
<221> NAME/KEY: SIGNAL
<222> LOCATION: -102..-1

<400> SEQUENCE: 104

```
Met Ala Ala Gly Leu Phe Gly Leu Ser Ala Arg Arg Leu Leu Ala Ala
         -100             -95             -90

Ala Ala Thr Arg Gly Leu Pro Ala Ala Arg Val Arg Trp Glu Ser Ser
        -85              -80             -75

Phe Ser Arg Thr Val Val Ala Pro Ser Ala Val Ala Gly Lys Arg Pro
-70              -65             -60                          -55

Pro Glu Pro Thr Thr Pro Trp Gln Glu Asp Pro Glu Pro Glu Asp Glu
             -50             -45             -40

Asn Leu Tyr Glu Lys Asn Pro Asp Ser His Gly Tyr Asp Lys Asp Pro
         -35              -30                  -25

Val Leu Asp Val Trp Asn Met Arg Leu Val Phe Phe Phe Gly Val Ser
         -20              -15                  -10

Ile Ile Leu Val Leu Gly Ser Thr Phe Val Ala Tyr Leu Pro Asp Tyr
 -5              1                5                          10

Arg Met Lys Glu Trp Ser Arg Arg Glu Ala Glu Arg Leu Val Lys Tyr
             15              20                  25

Arg Glu Ala Asn Gly Leu Pro Ile Met Glu Ser Asn Cys Phe Asp Pro
         30              35              40

Ser Lys Ile Gln Leu Pro Glu Asp Glu
             45              50
```

<210> SEQ ID NO 105
<211> LENGTH: 72
<212> TYPE: PRT
<213> ORGANISM: Homo sapiens

<400> SEQUENCE: 105

```
Leu Pro Val Ser Thr Arg Ile Ile Asn His Ile Tyr Ser Phe Pro Ser
1                5                   10                  15

Val Asp Leu Trp Ile Val Cys Ile Phe Thr Val Ser Val Ser His Leu
             20              25              30
```

```
Phe Glu Lys Gly Thr Leu Tyr Gly Tyr Phe Tyr Val Ile Asn Ser Ser
             35                  40                  45

Ile Asn Leu Cys Val Asn Asp Cys Leu Pro Val Met Asp Ser Ile Ser
 50                  55                  60

Leu Ser Pro Leu Phe Leu Ser His
 65                  70
```

<210> SEQ ID NO 106
<211> LENGTH: 175
<212> TYPE: PRT
<213> ORGANISM: Homo sapiens
<220> FEATURE:
<221> NAME/KEY: SIGNAL
<222> LOCATION: -20..-1

<400> SEQUENCE: 106

```
Met Glu Lys Ile Pro Val Ser Ala Phe Leu Leu Leu Val Ala Leu Ser
-20                 -15                 -10                  -5

Tyr Thr Leu Ala Arg Asp Thr Thr Val Lys Pro Gly Ala Lys Lys Asp
                 1                   5                  10

Thr Lys Asp Ser Arg Pro Lys Leu Pro Gln Thr Leu Ser Arg Gly Trp
         15                  20                  25

Gly Asp Gln Leu Ile Trp Thr Gln Thr Tyr Glu Glu Ala Leu Tyr Lys
 30                  35                  40

Ser Lys Thr Ser Asn Lys Pro Leu Met Ile Ile His His Leu Asp Glu
 45                  50                  55                  60

Cys Pro His Ser Gln Ala Leu Lys Lys Val Phe Ala Glu Asn Lys Glu
                 65                  70                  75

Ile Gln Lys Leu Ala Glu Gln Phe Val Leu Leu Asn Leu Val Tyr Glu
                 80                  85                  90

Thr Thr Asp Lys His Leu Ser Pro Asp Gly Gln Tyr Val Pro Arg Ile
             95                 100                 105

Met Phe Val Asp Pro Ser Leu Thr Val Arg Ala Asp Ile Thr Gly Arg
    110                 115                 120

Tyr Ser Asn Arg Leu Tyr Ala Tyr Glu Pro Ala Asp Thr Ala Leu Leu
125                 130                 135                 140

Leu Asp Asn Met Lys Lys Ala Leu Lys Leu Lys Thr Glu Leu
                145                 150                 155
```

<210> SEQ ID NO 107
<211> LENGTH: 303
<212> TYPE: PRT
<213> ORGANISM: Homo sapiens
<220> FEATURE:
<221> NAME/KEY: SIGNAL
<222> LOCATION: -20..-1

<400> SEQUENCE: 107

```
Met Ala Asp Ala Ala Ser Gln Val Leu Leu Gly Ser Gly Leu Thr Ile
-20                 -15                 -10                  -5

Leu Ser Gln Pro Leu Met Tyr Val Lys Val Leu Ile Gln Val Gly Tyr
                 1                   5                  10

Glu Pro Leu Pro Pro Thr Ile Gly Arg Asn Ile Phe Gly Arg Gln Val
         15                  20                  25

Cys Gln Leu Pro Gly Leu Phe Ser Tyr Ala Gln His Ile Ala Ser Ile
 30                  35                  40

Asp Gly Arg Arg Gly Leu Phe Thr Gly Leu Thr Pro Arg Leu Cys Ser
 45                  50                  55                  60
```

```
Gly Val Leu Gly Thr Val Val His Gly Lys Val Leu Gln His Tyr Gln
                65                  70                  75

Glu Ser Asp Lys Gly Glu Glu Leu Gly Pro Gly Asn Val Gln Lys Glu
            80                  85                  90

Val Ser Ser Ser Phe Asp His Val Ile Lys Glu Thr Thr Arg Glu Met
 95                 100                 105

Ile Ala Arg Ser Ala Ala Thr Leu Ile Thr His Pro Phe His Val Ile
        110                 115                 120

Thr Leu Arg Ser Met Val Gln Phe Ile Gly Arg Glu Ser Lys Tyr Cys
125                 130                 135                 140

Gly Leu Cys Asp Ser Ile Ile Thr Ile Tyr Arg Glu Glu Gly Ile Leu
                145                 150                 155

Gly Phe Phe Ala Gly Leu Val Pro Arg Leu Leu Gly Asp Ile Leu Ser
                160                 165                 170

Leu Trp Leu Cys Asn Ser Leu Ala Tyr Leu Val Asn Thr Tyr Ala Leu
        175                 180                 185

Asp Ser Gly Val Ser Thr Met Asn Glu Met Lys Ser Tyr Ser Gln Ala
190                 195                 200

Val Thr Gly Phe Phe Ala Ser Met Leu Thr Tyr Pro Phe Val Leu Val
205                 210                 215                 220

Ser Asn Leu Met Ala Val Asn Asn Cys Gly Leu Ala Gly Gly Cys Pro
                225                 230                 235

Pro Tyr Ser Pro Ile Tyr Thr Ser Trp Ile Asp Cys Trp Cys Met Leu
                240                 245                 250

Gln Lys Glu Gly Asn Met Ser Arg Gly Asn Ser Leu Phe Phe Arg Lys
                255                 260                 265

Val Pro Phe Gly Lys Thr Tyr Cys Cys Asp Leu Lys Met Leu Ile
                270                 275                 280

<210> SEQ ID NO 108
<211> LENGTH: 65
<212> TYPE: PRT
<213> ORGANISM: Homo sapiens
<220> FEATURE:
<221> NAME/KEY: SIGNAL
<222> LOCATION: -39..-1

<400> SEQUENCE: 108

Met Ser Thr Gly Ile Met Glu Tyr Lys Lys Thr Thr Lys Ala Met Lys
                -35                 -30                 -25

Lys Lys Lys Asp Val Leu Phe Thr Ser Tyr Phe Lys Thr Ile Ala Phe
            -20                 -15                 -10

Leu Leu Leu Tyr Val Ser Ala Gly Pro Ile Ser Arg Ile Phe Ile Arg
         -5                   1                  5

Ser Leu Glu Leu Phe Leu Met Phe Pro Ser Asn Lys His Trp Tyr Ile
 10                  15                  20                  25

Ser

<210> SEQ ID NO 109
<211> LENGTH: 137
<212> TYPE: PRT
<213> ORGANISM: Homo sapiens
<220> FEATURE:
<221> NAME/KEY: SIGNAL
<222> LOCATION: -17..-1

<400> SEQUENCE: 109

Met Gly Phe Gly Ala Thr Leu Ala Val Gly Leu Thr Ile Phe Val Leu
```

```
                -15                 -10                 -5
Ser Val Val Thr Ile Ile Cys Phe Thr Cys Ser Cys Cys Cys Leu
 1                   5                  10                  15

Tyr Lys Thr Cys Arg Arg Pro Arg Pro Val Thr Thr Thr Thr Ser
                 20                  25                  30

Thr Thr Val Val His Ala Pro Tyr Pro Gln Pro Pro Ser Val Pro Pro
             35                  40                  45

Ser Tyr Pro Gly Pro Ser Tyr Gln Gly Tyr His Thr Met Pro Pro Gln
             50                  55                  60

Pro Gly Met Pro Ala Ala Pro Tyr Pro Met Gln Tyr Pro Pro Pro Tyr
         65                  70                  75

Pro Ala Gln Pro Met Gly Pro Pro Ala Tyr His Glu Thr Leu Ala Gly
 80              85                  90                  95

Gly Ala Ala Ala Pro Tyr Pro Ala Ser Gln Pro Pro Tyr Asn Pro Ala
                100                 105                 110

Tyr Met Asp Ala Pro Lys Ala Ala Leu
             115                 120

<210> SEQ ID NO 110
<211> LENGTH: 154
<212> TYPE: PRT
<213> ORGANISM: Homo sapiens
<220> FEATURE:
<221> NAME/KEY: SIGNAL
<222> LOCATION: -13..-1

<400> SEQUENCE: 110

Met Ala Leu Leu Leu Ser Val Leu Arg Val Leu Leu Gly Gly Phe Phe
                 -10                 -5                  1

Ala Leu Val Gly Leu Ala Lys Leu Ser Glu Glu Ile Ser Ala Pro Val
  5                  10                 15

Ser Glu Arg Met Asn Ala Leu Phe Val Gln Phe Ala Glu Val Phe Pro
 20                  25                  30                  35

Leu Lys Val Phe Gly Tyr Gln Pro Asp Pro Leu Asn Tyr Gln Ile Ala
                 40                  45                  50

Val Gly Phe Leu Glu Leu Leu Ala Gly Leu Leu Val Met Gly Pro
                 55                  60                  65

Pro Met Leu Gln Glu Ile Ser Asn Leu Phe Leu Ile Leu Leu Met Met
             70                  75                  80

Gly Ala Ile Phe Thr Leu Ala Ala Leu Lys Glu Ser Leu Ser Thr Cys
         85                  90                  95

Ile Pro Ala Ile Val Cys Leu Gly Phe Leu Leu Leu Asn Val Gly
100                 105                 110                 115

Gln Leu Leu Ala Gln Thr Lys Lys Val Val Arg Pro Thr Arg Lys Lys
             120                 125                 130

Thr Leu Ser Thr Phe Lys Glu Ser Trp Lys
             135                 140

<210> SEQ ID NO 111
<211> LENGTH: 103
<212> TYPE: PRT
<213> ORGANISM: Homo sapiens
<220> FEATURE:
<221> NAME/KEY: SIGNAL
<222> LOCATION: -36..-1

<400> SEQUENCE: 111

Met Ala Asn Leu Phe Ile Arg Lys Met Val Asn Pro Leu Leu Tyr Leu
```

```
                -35                -30                -25
Ser Arg His Thr Val Lys Pro Arg Ala Leu Ser Thr Phe Leu Phe Gly
-20             -15                -10                       -5

Ser Ile Arg Gly Ala Ala Pro Val Ala Val Glu Pro Gly Ala Ala Val
                 1               5                  10

Arg Ser Leu Leu Ser Pro Gly Leu Leu Pro His Leu Leu Pro Ala Leu
         15                  20              25

Gly Phe Lys Asn Lys Thr Val Leu Asn Lys Arg Cys Lys Asp Cys Tyr
     30              35              40

Leu Val Lys Arg Arg Gly Arg Trp Tyr Val Tyr Cys Lys Thr His Pro
 45              50              55                      60

Arg His Lys Gln Arg Gln Met
                 65

<210> SEQ ID NO 112
<211> LENGTH: 86
<212> TYPE: PRT
<213> ORGANISM: Homo sapiens
<220> FEATURE:
<221> NAME/KEY: SIGNAL
<222> LOCATION: -74..-1

<400> SEQUENCE: 112

Met Pro Tyr Ala Phe Thr Ser Pro Cys Pro Cys Ser Phe Val Ser Leu
                 -70             -65                 -60

Pro Glu Ile Ser Phe Tyr Phe Thr Lys Leu Leu Leu Ile Leu Lys Ala
             -55             -50                 -45

Leu Pro Glu Ser Pro Phe Leu Leu Ala Ser Ser Pro Leu Pro Pro Leu
         -40                 -35                 -30

Pro Thr Thr Leu Arg Lys Phe Ile Pro Pro Ser Leu Ile Ser Cys
         -25             -20              -15

Thr Cys Leu Leu Leu Tyr Leu Thr His Cys Ile Leu Gly Ile Cys Phe
-10              -5                   1               5

Ala Tyr Pro Phe Ile Leu
             10

<210> SEQ ID NO 113
<211> LENGTH: 395
<212> TYPE: PRT
<213> ORGANISM: Homo sapiens
<220> FEATURE:
<221> NAME/KEY: SIGNAL
<222> LOCATION: -310..-1

<400> SEQUENCE: 113

Met Asp Leu Gly Ile Pro Asp Leu Leu Asp Ala Trp Leu Glu Pro Pro
-310             -305                -300                -295

Glu Asp Ile Phe Ser Thr Gly Ser Val Leu Glu Leu Gly Leu His Cys
             -290                -285                -280

Pro Pro Pro Glu Val Pro Val Thr Arg Leu Gln Glu Gln Gly Leu Gln
             -275                -270                -265

Gly Trp Lys Ser Gly Gly Asp Arg Gly Cys Gly Leu Gln Glu Ser Glu
         -260                -255                -250

Pro Glu Asp Phe Leu Lys Leu Phe Ile Asp Pro Asn Glu Val Tyr Cys
         -245                -240                -235

Ser Glu Ala Ser Pro Gly Ser Asp Ser Gly Ile Ser Glu Asp Ser Cys
-230                 -225                -220                -215

His Pro Asp Ser Pro Pro Ala Pro Arg Ala Thr Ser Ser Pro Met Leu
```

```
                  -210              -205              -200
Tyr Glu Val Val Tyr Glu Ala Gly Ala Leu Glu Arg Met Gln Gly Glu
            -195              -190              -185

Thr Gly Pro Asn Val Gly Leu Ile Ser Ile Gln Leu Asp Gln Trp Ser
        -180              -175              -170

Pro Ala Phe Met Val Pro Asp Ser Cys Met Val Ser Glu Leu Pro Phe
    -165              -160              -155

Asp Ala His Ala His Ile Leu Pro Arg Ala Gly Thr Val Ala Pro Val
-150              -145              -140              -135

Pro Cys Thr Thr Leu Leu Pro Cys Gln Thr Leu Phe Leu Thr Asp Glu
              -130              -125              -120

Glu Lys Arg Leu Leu Gly Gln Glu Gly Val Ser Leu Pro Ser His Leu
          -115              -110              -105

Pro Leu Thr Lys Ala Glu Glu Arg Val Leu Lys Lys Val Arg Arg Lys
        -100               -95               -90

Ile Arg Asn Lys Gln Ser Ala Gln Asp Ser Arg Arg Arg Lys Lys Glu
 -85               -80               -75

Tyr Ile Asp Gly Leu Glu Ser Arg Val Ala Ala Cys Ser Ala Gln Asn
-70                -65               -60                -55

Gln Glu Leu Gln Lys Lys Val Gln Glu Leu Glu Arg His Asn Ile Ser
              -50                -45               -40

Leu Val Ala Gln Leu Arg Gln Leu Gln Thr Leu Ile Ala Gln Thr Ser
             -35               -30               -25

Asn Lys Ala Ala Gln Thr Ser Thr Cys Val Leu Ile Leu Leu Phe Ser
          -20              -15               -10

Leu Ala Leu Ile Ile Leu Pro Ser Phe Ser Pro Phe Gln Ser Arg Pro
  -5                1                 5                 10

Glu Ala Gly Ser Glu Asp Tyr Gln Pro His Gly Val Thr Ser Arg Asn
            15                20                25

Ile Leu Thr His Lys Asp Val Thr Glu Asn Leu Glu Thr Gln Val Val
            30                35                40

Glu Ser Arg Leu Arg Glu Pro Pro Gly Ala Lys Asp Ala Asn Gly Ser
        45                50                55

Thr Arg Thr Leu Leu Glu Lys Met Gly Gly Lys Pro Arg Pro Ser Gly
    60                65                70

Arg Ile Arg Ser Val Leu His Ala Asp Glu Met
75                80                85

<210> SEQ ID NO 114
<211> LENGTH: 93
<212> TYPE: PRT
<213> ORGANISM: Homo sapiens
<220> FEATURE:
<221> NAME/KEY: SIGNAL
<222> LOCATION: -18...-1

<400> SEQUENCE: 114

Met Ile His Leu Gly His Ile Leu Phe Leu Leu Leu Leu Pro Val Ala
              -15               -10                -5

Ala Ala Gln Thr Thr Pro Gly Glu Arg Ser Ser Leu Pro Ala Phe Tyr
  1                 5                 10

Pro Gly Thr Ser Gly Ser Cys Ser Gly Cys Gly Ser Leu Ser Leu Pro
15                20                25                30

Leu Leu Ala Gly Leu Val Ala Ala Asp Ala Val Ala Ser Leu Leu Ile
              35                40                45
```

-continued

```
Val Gly Ala Val Phe Leu Cys Ala Arg Pro Arg Ser Pro Ala Gln
             50                  55                  60

Glu Tyr Gly Lys Val Tyr Ile Asn Met Pro Gly Arg Gly
             65                  70                  75

<210> SEQ ID NO 115
<211> LENGTH: 61
<212> TYPE: PRT
<213> ORGANISM: Homo sapiens
<220> FEATURE:
<221> NAME/KEY: SIGNAL
<222> LOCATION: -21..-1

<400> SEQUENCE: 115

Met Arg Glu Met Pro Val Pro Ser Leu Ile Asn Leu Ala Ala Ser Arg
        -20                 -15                 -10

Thr Leu Ser Phe Cys Ile Ser Asp Asn His Val Ser Ser Pro Gly Pro
-5                   1                   5                  10

Ala Asn Pro Ser Cys Gly Leu His Pro His Trp Leu Arg Pro Leu Lys
             15                  20                  25

Leu Leu Thr Tyr Thr Cys Arg Glu Leu Lys Leu Gln Gly
             30                  35                  40

<210> SEQ ID NO 116
<211> LENGTH: 331
<212> TYPE: PRT
<213> ORGANISM: Homo sapiens
<220> FEATURE:
<221> NAME/KEY: SIGNAL
<222> LOCATION: -31..-1

<400> SEQUENCE: 116

Met Trp Leu Trp Glu Asp Gln Gly Gly Leu Leu Gly Pro Phe Ser Phe
        -30                 -25                 -20

Leu Leu Leu Val Leu Leu Leu Val Thr Arg Ser Pro Val Asn Ala Cys
-15                 -10                  -5                   1

Leu Leu Thr Gly Ser Leu Phe Val Leu Leu Arg Val Phe Ser Phe Glu
             5                   10                  15

Pro Val Pro Ser Cys Arg Ala Leu Gln Val Leu Lys Pro Arg Asp Arg
             20                  25                  30

Ile Ser Ala Ile Ala His Arg Gly Gly Ser His Asp Ala Pro Glu Asn
             35                  40                  45

Thr Leu Ala Ala Ile Arg Gln Ala Lys Asn Gly Ala Thr Gly Val
50                   55                  60                  65

Glu Leu Asp Ile Glu Phe Thr Ser Asp Gly Ile Pro Val Leu Met His
                     70                  75                  80

Asp Asn Thr Val Asp Arg Thr Thr Asp Gly Thr Gly Arg Leu Cys Asp
                     85                  90                  95

Leu Thr Phe Glu Gln Ile Arg Lys Leu Asn Pro Ala Ala Asn His Arg
                     100                 105                 110

Leu Arg Asn Asp Phe Pro Asp Glu Lys Ile Pro Thr Leu Met Glu Ala
                     115                 120                 125

Val Ala Glu Cys Leu Asn His Asn Leu Thr Ile Phe Phe Asp Val Lys
130                  135                 140                 145

Gly His Ala His Lys Ala Thr Glu Ala Leu Lys Lys Met Tyr Met Glu
                     150                 155                 160

Phe Pro Gln Leu Tyr Asn Asn Ser Val Val Cys Ser Phe Leu Pro Glu
                     165                 170                 175
```

```
Val Ile Tyr Lys Met Arg Gln Thr Asp Arg Asp Val Ile Thr Ala Leu
        180                 185                 190

Thr His Arg Pro Trp Ser Leu Ser His Thr Gly Asp Gly Lys Pro Arg
        195                 200                 205

Tyr Asp Thr Phe Trp Lys His Phe Ile Phe Val Met Met Asp Ile Leu
210                 215                 220                 225

Leu Asp Trp Ser Met His Asn Ile Leu Trp Tyr Leu Cys Gly Ile Ser
                230                 235                 240

Ala Phe Leu Met Gln Lys Asp Phe Val Ser Pro Ala Tyr Leu Lys Lys
                245                 250                 255

Trp Ser Ala Lys Gly Ile Gln Val Gly Trp Thr Val Asn Thr Phe
                260                 265                 270

Asp Glu Lys Ser Tyr Tyr Glu Ser His Leu Gly Ser Ser Tyr Ile Thr
        275                 280                 285

Asp Ser Met Val Glu Asp Cys Glu Pro His Phe
290                 295                 300

<210> SEQ ID NO 117
<211> LENGTH: 210
<212> TYPE: PRT
<213> ORGANISM: Homo sapiens
<220> FEATURE:
<221> NAME/KEY: SIGNAL
<222> LOCATION: -99..-1

<400> SEQUENCE: 117

Met Ala Ala Ser Val Glu Gln Arg Glu Gly Thr Ile Gln Val Gln Gly
                -95                 -90                 -85

Gln Ala Leu Phe Phe Arg Glu Ala Leu Pro Gly Ser Gly Gln Ala Arg
                -80                 -75                 -70

Phe Ser Val Leu Leu His Gly Ile Arg Phe Ser Ser Glu Thr Trp
                -65                 -60                 -55

Gln Asn Leu Gly Thr Leu His Arg Leu Ala Gln Ala Gly Tyr Arg Ala
        -50                 -45                 -40

Val Ala Ile Asp Leu Pro Gly Leu Gly His Ser Lys Glu Ala Ala Ala
-35                 -30                 -25                 -20

Pro Ala Pro Ile Gly Glu Leu Ala Pro Gly Ser Phe Leu Ala Ala Val
                -15                 -10                 -5

Val Asp Ala Leu Glu Leu Gly Pro Pro Val Val Ile Ser Pro Ser Leu
                1                   5                   10

Ser Gly Met Tyr Ser Leu Pro Phe Leu Thr Ala Pro Gly Ser Gln Leu
        15                  20                  25

Pro Gly Phe Val Pro Val Ala Pro Ile Cys Thr Asp Lys Ile Asn Ala
30                  35                  40                  45

Ala Asn Tyr Ala Ser Val Lys Thr Pro Ala Leu Ile Val Tyr Gly Asp
                50                  55                  60

Gln Asp Pro Met Gly Gln Thr Ser Phe Glu His Leu Lys Gln Leu Pro
                65                  70                  75

Asn His Arg Val Leu Ile Met Lys Gly Ala Gly His Pro Cys Tyr Leu
                80                  85                  90

Asp Lys Pro Glu Glu Trp His Thr Gly Leu Leu Asp Phe Leu Gln Gly
        95                  100                 105

Leu Gln
110

<210> SEQ ID NO 118
```

```
<211> LENGTH: 79
<212> TYPE: PRT
<213> ORGANISM: Homo sapiens
<220> FEATURE:
<221> NAME/KEY: SIGNAL
<222> LOCATION: -67..-1

<400> SEQUENCE: 118

Met Glu Leu Glu Ala Met Ser Arg Tyr Thr Ser Pro Val Asn Pro Ala
        -65                 -60                 -55

Val Phe Pro His Leu Thr Val Val Leu Leu Ala Ile Gly Met Phe Phe
        -50                 -45                 -40

Thr Ala Trp Phe Phe Val Tyr Glu Val Thr Ser Thr Lys Tyr Thr Arg
-35                 -30                 -25                 -20

Asp Ile Tyr Lys Glu Leu Leu Ile Ser Leu Val Ala Ser Leu Phe Met
                -15                 -10                  -5

Gly Phe Gly Val Leu Phe Leu Leu Leu Trp Val Gly Ile Tyr Val
                 1               5                  10

<210> SEQ ID NO 119
<211> LENGTH: 84
<212> TYPE: PRT
<213> ORGANISM: Homo sapiens

<400> SEQUENCE: 119

Met Ala Val Trp Pro Glu Val Ser Gln Asn Arg Leu Thr Arg Gly Leu
1                5                  10                  15

Leu Leu Pro Asn Tyr Gln Leu Arg Gly Ser Val Pro Lys Arg Glu Lys
                20                  25                  30

Arg Pro Lys Arg Lys His Gln His Leu Phe Thr Pro Ser Glu Arg His
                35                  40                  45

Ser Val Cys Leu Asp Cys Leu Leu Glu Ile Ser Leu Ser Gly Lys Gln
                50                  55                  60

Trp Arg Asn Val Ile Ser Phe Asn Cys Phe Cys Thr Thr Lys Thr Leu
65                  70                  75                  80

Phe Trp Val Asn

<210> SEQ ID NO 120
<211> LENGTH: 92
<212> TYPE: PRT
<213> ORGANISM: Homo sapiens
<220> FEATURE:
<221> NAME/KEY: SIGNAL
<222> LOCATION: -20..-1

<400> SEQUENCE: 120

Met Ala Ser Leu Gly His Ile Leu Val Phe Cys Val Gly Leu Leu Thr
-20                 -15                 -10                  -5

Met Ala Lys Ala Glu Ser Pro Lys Glu His Asp Pro Phe Thr Tyr Asp
                 1               5                  10

Tyr Gln Ser Leu Gln Ile Gly Gly Leu Val Ile Ala Gly Ile Leu Phe
                15                  20                  25

Ile Leu Gly Ile Leu Ile Val Leu Ser Arg Arg Cys Arg Cys Lys Phe
                30                  35                  40

Asn Gln Gln Gln Arg Thr Gly Glu Pro Asp Glu Glu Gly Thr Phe Arg
45                  50                  55                  60

Arg Ser Ser Ile Arg Arg Leu Ser Thr Arg Arg Arg
                65                  70
```

```
<210> SEQ ID NO 121
<211> LENGTH: 210
<212> TYPE: PRT
<213> ORGANISM: Homo sapiens
<220> FEATURE:
<221> NAME/KEY: SIGNAL
<222> LOCATION: -14..-1

<400> SEQUENCE: 121

Met Leu Thr Leu Leu Gly Leu Ser Leu Ile Leu Ala Gly Leu Ile Val
                -10                  -5                   1
Gly Gly Ala Cys Ile Tyr Lys His Phe Met Pro Lys Ser Thr Ile Tyr
             5                  10                  15
Arg Gly Glu Met Cys Phe Phe Asp Ser Glu Asp Pro Ala Asn Ser Leu
         20                  25                  30
Arg Gly Gly Glu Pro Asn Phe Leu Pro Val Thr Glu Glu Ala Asp Ile
 35                  40                  45                  50
Arg Glu Asp Asp Asn Ile Ala Ile Ile Asp Val Pro Val Pro Ser Phe
                 55                  60                  65
Ser Asp Ser Asp Pro Ala Ala Ile Ile His Asp Phe Glu Lys Gly Met
             70                  75                  80
Thr Ala Tyr Leu Asp Leu Leu Leu Gly Asn Cys Tyr Leu Met Pro Leu
         85                  90                  95
Asn Thr Ser Ile Val Met Pro Pro Glu Asn Leu Val Glu Leu Phe Gly
    100                 105                 110
Lys Leu Ala Ser Gly Arg Tyr Leu Pro Gln Thr Tyr Val Val Arg Glu
115                 120                 125                 130
Asp Leu Val Ala Val Glu Glu Ile Arg Asp Val Ser Asn Leu Gly Ile
                135                 140                 145
Phe Ile Tyr Gln Leu Cys Asn Asn Arg Lys Ser Phe Arg Leu Arg Arg
            150                 155                 160
Arg Asp Leu Leu Leu Gly Phe Asn Lys Arg Ala Ile Asp Lys Cys Trp
        165                 170                 175
Lys Ile Arg His Phe Pro Asn Glu Phe Ile Val Glu Thr Lys Ile Cys
    180                 185                 190
Gln Glu
195

<210> SEQ ID NO 122
<211> LENGTH: 205
<212> TYPE: PRT
<213> ORGANISM: Homo sapiens
<220> FEATURE:
<221> NAME/KEY: SIGNAL
<222> LOCATION: -139..-1

<400> SEQUENCE: 122

Met Ala Pro Thr Arg Lys Asp Lys Leu Leu Gln Phe Tyr Pro Ser Leu
                -135                -130                -125
Glu Asp Pro Ala Ser Ser Arg Tyr Gln Asn Phe Ser Lys Gly Ser Arg
            -120                -115                -110
His Gly Ser Glu Glu Ala Tyr Ile Asp Pro Ile Ala Met Glu Tyr Tyr
        -105                -100                 -95
Asn Trp Gly Arg Phe Ser Lys Pro Pro Glu Gly Glu Ala Lys Asp Lys
     -90                 -85                 -80
Ala Gly Gly Gly Ser Gly Val Gly Ala Gln Gly Arg Ser His Thr
 -75                 -70                 -65                 -60
Ser Arg Gln Glu Arg Arg Leu Gly Leu Gly Ser Asp Asp Ala Asn
```

-continued

```
                 -55                 -50                 -45
Ser Tyr Glu Asn Val Leu Ile Cys Lys Gln Lys Thr Thr Glu Thr Gly
                -40                 -35                 -30

Ala Gln Gln Glu Asp Val Gly Gly Leu Cys Arg Gly Asp Leu Ser Leu
        -25                 -20                 -15

Ser Leu Ala Leu Lys Thr Gly Pro Thr Ser Gly Leu Cys Pro Ser Ala
        -10                  -5                  1               5

Ser Pro Glu Glu Asp Gly Glu Ser Glu Asp Tyr Gln Asn Ser Ala Ser
                 10                  15                  20

Ile His Gln Trp Arg Glu Ser Arg Lys Val Met Gly Gln Leu Gln Arg
                 25                  30                  35

Glu Ala Ser Pro Gly Pro Val Gly Ser Pro Asp Glu Glu Asp Gly Glu
        40                  45                  50

Pro Asp Tyr Val Asn Gly Glu Val Ala Ala Thr Glu Ala
    55                  60                  65
```

<210> SEQ ID NO 123
<211> LENGTH: 85
<212> TYPE: PRT
<213> ORGANISM: Homo sapiens
<220> FEATURE:
<221> NAME/KEY: SIGNAL
<222> LOCATION: -17...-1

<400> SEQUENCE: 123

```
Met Lys Lys Val Leu Leu Leu Ile Thr Ala Ile Leu Ala Val Ala Val
        -15                 -10                  -5

Gly Phe Pro Val Ser Gln Asp Gln Glu Arg Glu Lys Arg Ser Ile Ser
 1               5                  10                  15

Asp Ser Asp Glu Leu Ala Ser Gly Phe Phe Val Phe Pro Tyr Pro Tyr
                 20                  25                  30

Pro Phe Arg Pro Leu Pro Pro Ile Pro Phe Pro Arg Phe Pro Trp Phe
             35                  40                  45

Arg Arg Asn Phe Pro Ile Pro Ile Pro Glu Ser Ala Pro Thr Thr Pro
             50                  55                  60

Leu Pro Ser Glu Lys
     65
```

<210> SEQ ID NO 124
<211> LENGTH: 115
<212> TYPE: PRT
<213> ORGANISM: Homo sapiens
<220> FEATURE:
<221> NAME/KEY: SIGNAL
<222> LOCATION: -51...-1

<400> SEQUENCE: 124

```
Met Gln Ala Gln Ala Pro Val Val Val Thr Gln Pro Gly Val Gly
        -50                 -45                 -40

Pro Gly Pro Ala Pro Gln Asn Ser Asn Trp Gln Thr Gly Met Cys Asp
-35                 -30                  -25                 -20

Cys Phe Ser Asp Cys Gly Val Cys Leu Cys Gly Thr Phe Cys Phe Pro
            -15                 -10                  -5

Cys Leu Gly Cys Gln Val Ala Ala Asp Met Asn Glu Cys Cys Leu Cys
             1                   5                  10

Gly Thr Ser Val Ala Met Arg Thr Leu Tyr Arg Thr Arg Tyr Gly Ile
    15                  20                  25

Pro Gly Pro Ile Cys Asp Asp Tyr Met Ala Thr Leu Cys Cys Pro His
```

-continued

```
              30                  35                  40                  45
Cys Thr Leu Cys Gln Ile Lys Arg Asp Ile Asn Arg Arg Ala Met
                    50                  55                  60
Arg Thr Phe

<210> SEQ ID NO 125
<211> LENGTH: 81
<212> TYPE: PRT
<213> ORGANISM: Homo sapiens
<220> FEATURE:
<221> NAME/KEY: SIGNAL
<222> LOCATION: -31..-1

<400> SEQUENCE: 125

Met Ser Asn Thr His Thr Val Leu Val Ser Leu Pro His Pro
    -30                 -25                 -20
Ala Leu Thr Cys Cys His Leu Gly Leu Pro His Pro Val Arg Ala Pro
-15                 -10                  -5                   1
Arg Pro Leu Pro Arg Val Glu Pro Trp Asp Pro Arg Trp Gln Asp Ser
                5                   10                  15
Glu Leu Arg Tyr Pro Gln Ala Met Asn Ser Phe Leu Asn Glu Arg Ser
            20                  25                  30
Ser Pro Cys Arg Thr Leu Arg Gln Glu Ala Ser Ala Asp Arg Cys Asp
        35                  40                  45
Leu
50

<210> SEQ ID NO 126
<211> LENGTH: 235
<212> TYPE: PRT
<213> ORGANISM: Homo sapiens
<220> FEATURE:
<221> NAME/KEY: SIGNAL
<222> LOCATION: -39..-1

<400> SEQUENCE: 126

Met Gly Thr Ala Asp Ser Asp Glu Met Ala Pro Glu Ala Pro Gln His
                -35                 -30                 -25
Thr His Ile Asp Val His Ile His Gln Glu Ser Ala Leu Ala Lys Leu
            -20                 -15                 -10
Leu Leu Thr Cys Cys Ser Ala Leu Arg Pro Arg Ala Thr Gln Ala Arg
         -5                   1                   5
Gly Ser Ser Arg Leu Leu Val Ala Ser Trp Val Met Gln Ile Val Leu
10                  15                  20                  25
Gly Ile Leu Ser Ala Val Leu Gly Gly Phe Phe Tyr Ile Arg Asp Tyr
                30                  35                  40
Thr Leu Leu Val Thr Ser Gly Ala Ala Ile Trp Thr Gly Ala Val Ala
            45                  50                  55
Val Leu Ala Gly Ala Ala Ala Phe Ile Tyr Glu Lys Arg Gly Gly Thr
            60                  65                  70
Tyr Trp Ala Leu Leu Arg Thr Leu Leu Ala Leu Ala Phe Ser Thr
        75                  80                  85
Ala Ile Ala Ala Leu Lys Leu Trp Asn Glu Asp Phe Arg Tyr Gly Tyr
90                  95                  100                 105
Ser Tyr Tyr Asn Ser Ala Cys Arg Ile Ser Ser Ser Asp Trp Asn
                110                 115                 120
Thr Pro Ala Pro Thr Gln Ser Pro Glu Glu Val Arg Arg Leu His Leu
            125                 130                 135
```

```
Cys Thr Ser Phe Met Asp Met Leu Lys Ala Leu Phe Arg Thr Leu Gln
        140                 145                 150

Ala Met Leu Leu Gly Val Trp Ile Leu Leu Leu Ala Ser Leu Ala
        155                 160                 165

Pro Leu Trp Leu Tyr Cys Trp Arg Met Phe Pro Thr Lys Gly Lys Arg
170                 175                 180                 185

Asp Gln Lys Glu Met Leu Glu Val Ser Gly Ile
                190                 195

<210> SEQ ID NO 127
<211> LENGTH: 62
<212> TYPE: PRT
<213> ORGANISM: Homo sapiens
<220> FEATURE:
<221> NAME/KEY: SIGNAL
<222> LOCATION: -21..-1

<400> SEQUENCE: 127

Met Glu Ser Arg Val Leu Leu Arg Thr Phe Cys Leu Ile Phe Gly Leu
        -20                 -15                 -10

Gly Ala Val Trp Gly Leu Gly Val Asp Pro Ser Leu Gln Ile Asp Val
-5                   1                   5                  10

Leu Thr Glu Leu Glu Leu Gly Glu Ser Thr Thr Gly Val Arg Gln Val
                15                  20                  25

Pro Gly Leu His Asn Gly Thr Lys Ala Phe Leu Phe Gln Ala
            30                  35                  40

<210> SEQ ID NO 128
<211> LENGTH: 11
<212> TYPE: PRT
<213> ORGANISM: Homo sapiens

<400> SEQUENCE: 128

Met Gly Leu Ser Ser Ser Glu Gly Asp Ile Pro
1                   5                  10

<210> SEQ ID NO 129
<211> LENGTH: 56
<212> TYPE: PRT
<213> ORGANISM: Homo sapiens
<220> FEATURE:
<221> NAME/KEY: SIGNAL
<222> LOCATION: -34..-1

<400> SEQUENCE: 129

Met Glu Arg Gly Leu Lys Ser Ala Asp Pro Arg Asp Gly Thr Gly Tyr
            -30                 -25                 -20

Thr Gly Trp Ala Gly Ile Ala Val Leu Tyr Leu His Leu Tyr Asp Val
            -15                 -10                  -5

Phe Gly Asp Pro Ala Ser Met Phe Cys Lys Val Phe Asp Leu Leu Val
             1                   5                  10

Leu Asn Lys Ile Leu Leu Gly Leu
15                  20

<210> SEQ ID NO 130
<211> LENGTH: 542
<212> TYPE: DNA
<213> ORGANISM: Homo sapiens
<220> FEATURE:
<221> NAME/KEY: CDS
<222> LOCATION: 15..311
<220> FEATURE:
```

```
<221> NAME/KEY: sig_peptide
<222> LOCATION: 15..110
<223> OTHER INFORMATION: Von Heijne matrix
      score 3.5
      seq RIHLCQRSXGSQG/VR
<220> FEATURE:
<221> NAME/KEY: polyA_signal
<222> LOCATION: 507..512
<220> FEATURE:
<221> NAME/KEY: polyA_site
<222> LOCATION: 531..542

<400> SEQUENCE: 130
```

| | | | | | | | | | | | | | | |
|---|---|---|---|---|---|---|---|---|---|---|---|---|---|---|
| agatattaac | aagg | atg | gcg | gcg | gcc | gca | gca | agt | cga | gga | gtc | ggg | gca | 50 |
| | | Met | Ala | Ala | Ala | Ala | Ala | Ser | Arg | Gly | Val | Gly | Ala | |
| | | | -30 | | | | | -25 | | | | | | |

```
aag ctg ggc ctg cgt gag att cgc atc cac tta tgt cag cgc tcg scc        98
Lys Leu Gly Leu Arg Glu Ile Arg Ile His Leu Cys Gln Arg Ser Xaa
-20             -15             -10              -5 ggc agc cag ggc gtc agg gac ttc att gag aaa cgc tac gtg gag ctg       146
Gly Ser Gln Gly Val Arg Asp Phe Ile Glu Lys Arg Tyr Val Glu Leu
             1               5              10 aag aag gcg aat ccc gac cta ccc atc cta atc cgc gaa tgc tcc gat       194
Lys Lys Ala Asn Pro Asp Leu Pro Ile Leu Ile Arg Glu Cys Ser Asp
         15              20              25 gtg cag ccc aag ctc tgg gcc cgc tac gca ttt ggc caa rag acg aat       242
Val Gln Pro Lys Leu Trp Ala Arg Tyr Ala Phe Gly Gln Xaa Thr Asn
     30              35              40 gtc cct ttg aac aac ttc agt gct gat cag gta acc aga rcc ctg gag       290
Val Pro Leu Asn Asn Phe Ser Ala Asp Gln Val Thr Arg Xaa Leu Glu
45              50              55              60 aac gtt cta agt ggt aaa gcc tgaagcctcc actgaggatt aagagcaaca         341
Asn Val Leu Ser Gly Lys Ala
                65 gccccagagc ctgggctctg ctggacttar tataatgtga aaaaaatgtg ttctcctatt    401 cctcataaag cttgtgctgt aaaatacttt ctcagggtgt tcttgtcctc atctaccctc    461 tacccettac tgtgcaacca ctgaggcaaa gtagcttaat ataaaaataa aactttattc    521 tgtctcatca aaaaaaaaaa a                                              542

<210> SEQ ID NO 131
<211> LENGTH: 909
<212> TYPE: DNA
<213> ORGANISM: Homo sapiens
<220> FEATURE:
<221> NAME/KEY: CDS
<222> LOCATION: 50..529
<220> FEATURE:
<221> NAME/KEY: sig_peptide
<222> LOCATION: 50..130
<223> OTHER INFORMATION: Von Heijne matrix
      score 7.19999980926514
      seq VLWLSGLSEPGAA/RQ
<220> FEATURE:
<221> NAME/KEY: polyA_signal
<222> LOCATION: 877..882
<220> FEATURE:
<221> NAME/KEY: polyA_site
<222> LOCATION: 899..909

<400> SEQUENCE: 131
aagacggtgg cgcgattggg acagtcgcca gggatggctg agcgtgaag atg cag cgg     58
                                                    Met Gln Arg
                                                            -25 gtg tcc ggg ctg ctc tcc tgg acg ctg agc aga gtc ctg tgg ctc tcc      106
Val Ser Gly Leu Leu Ser Trp Thr Leu Ser Arg Val Leu Trp Leu Ser
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     | -20 |     |     |     | -15 |     |     |     | -10 |     |     |     |     |     |
| ggc | ctc | tct | gag | ccg | gga | gct | gcc | cgg | cag | ccc | cgg | atc | atg | gaa | gag | 154 |
| Gly | Leu | Ser | Glu | Pro | Gly | Ala | Ala | Arg | Gln | Pro | Arg | Ile | Met | Glu | Glu |
|     |     | -5  |     |     |     | 1   |     |     |     | 5   |     |     |     |     |     |
| aaa | gcg | cta | gag | gtt | tat | gat | ttg | att | aga | act | atc | cgg | gac | cca | gaa | 202 |
| Lys | Ala | Leu | Glu | Val | Tyr | Asp | Leu | Ile | Arg | Thr | Ile | Arg | Asp | Pro | Glu |
|     | 10  |     |     |     | 15  |     |     |     | 20  |     |     |     |     |     |     |
| aag | ccc | aat | act | tta | gaa | gaa | ctg | gaa | gtg | gtc | tcg | gaa | agt | tgt | gtg | 250 |
| Lys | Pro | Asn | Thr | Leu | Glu | Glu | Leu | Glu | Val | Val | Ser | Glu | Ser | Cys | Val |
| 25  |     |     |     | 30  |     |     |     | 35  |     |     |     |     | 40  |     |     |
| gaa | gtt | cag | gag | ata | aat | gaa | gaa | raa | tat | ctg | gtt | att | atc | agg | ttc | 298 |
| Glu | Val | Gln | Glu | Ile | Asn | Glu | Glu | Xaa | Tyr | Leu | Val | Ile | Ile | Arg | Phe |
|     |     |     | 45  |     |     |     | 50  |     |     |     |     |     | 55  |     |     |
| acg | cca | aca | gta | cct | cat | tgc | tct | ttg | gcg | act | ctt | att | ggg | ctg | tgc | 346 |
| Thr | Pro | Thr | Val | Pro | His | Cys | Ser | Leu | Ala | Thr | Leu | Ile | Gly | Leu | Cys |
|     |     |     | 60  |     |     |     | 65  |     |     |     | 70  |     |     |     |     |
| yta | arw | kta | aaa | ctt | cag | cga | tgt | tta | cca | ttt | aaa | cat | aag | ttg | gma | 394 |
| Leu | Xaa | Xaa | Lys | Leu | Gln | Arg | Cys | Leu | Pro | Phe | Lys | His | Lys | Leu | Xaa |
|     |     | 75  |     |     |     | 80  |     |     |     |     | 85  |     |     |     |     |
| atc | tac | att | tct | gaa | gga | acc | cac | tca | rsa | gar | gaa | gac | atc | aat | wwk | 442 |
| Ile | Tyr | Ile | Ser | Glu | Gly | Thr | His | Ser | Xaa | Glu | Glu | Asp | Ile | Asn | Xaa |
|     | 90  |     |     |     |     | 95  |     |     |     | 100 |     |     |     |     |     |
| cag | ata | aat | gac | aaa | gag | cgw | ktg | gca | kct | gca | atg | gaa | aac | ccc | awc | 490 |
| Gln | Ile | Asn | Asp | Lys | Glu | Arg | Xaa | Ala | Xaa | Ala | Met | Glu | Asn | Pro | Xaa |
| 105 |     |     |     | 110 |     |     |     |     | 115 |     |     |     |     | 120 |     |
| tta | cgg | gaa | att | gtg | gaa | cag | tgt | gtc | ctt | gaa | cct | gac | tgawakctgt |     |     | 539 |
| Leu | Arg | Glu | Ile | Val | Glu | Gln | Cys | Val | Leu | Glu | Pro | Asp |     |     |     |
|     |     | 125 |     |     |     |     | 130 |     |     |     |     |     |     |     |     | tttaaragcc actggcctgt aattgtttga tatatttgtt taaactctt gtataatgtc 599 agaggactca tgtttaatac ataggtgatt tgtacctcag agcatttttt aaaggattct 659 ttccaagcga gatttaatta taggtagta cctaatttgt tcaatgtata acattctcag 719 gatttgtaac acttaaatga tcagacagaa taatattttc tagttattat gtgtaagatg 779 agttgctatt tttctgatgc tcattctgat acaactattt ttcgtgtcaa atatctactg 839 tgcccaaatg tactcaattt aaatcattac tctgtaaaat aaataagcag atgattctta 899 aaaaaaaaaa 909

```
<210> SEQ ID NO 132
<211> LENGTH: 1149
<212> TYPE: DNA
<213> ORGANISM: Homo sapiens
<220> FEATURE:
<221> NAME/KEY: CDS
<222> LOCATION: 240..416
<220> FEATURE:
<221> NAME/KEY: sig_peptide
<222> LOCATION: 240..305
<223> OTHER INFORMATION: Von Heijne matrix
      score 3.70000004768372
      seq AVLDCAFYDPTHA/WS
<220> FEATURE:
<221> NAME/KEY: polyA_signal
<222> LOCATION: 1117..1122
<220> FEATURE:
<221> NAME/KEY: polyA_site
<222> LOCATION: 1139..1149

<400> SEQUENCE: 132
```
actagcctgc gagtgttctg agggaagcaa ggaggcggcg gcggccgcag cgagtggcga 60
gtagtggaaa cgttgcttct gagggggtgtc caagatgacc ggttctaacg gagttcaagc 120

-continued

```
tgaaccagcc acccgaggat ggcatctcct ccgtgaagtt cagccccaac acctcccagt      180
tcctgcttgt ctcctcctgg gacacgtccg tgcgtctcta cgatgtgccg gccaactcc      239 atg cgg ctc aag tac cag cac acc ggc gcc gtc ctg gac tgc gcc ttc      287
Met Arg Leu Lys Tyr Gln His Thr Gly Ala Val Leu Asp Cys Ala Phe
        -20                 -15                 -10 tac gat cca acg cat gcc tgg agt gga gga cta gat cat caa ttg aaa      335
Tyr Asp Pro Thr His Ala Trp Ser Gly Gly Leu Asp His Gln Leu Lys
    -5                   1               5                    10 atg cat gat ttg aac act gat caa gaa aat ctt gtt ggg acc atg atg      383
Met His Asp Leu Asn Thr Asp Gln Glu Asn Leu Val Gly Thr Met Met
            15                  20                  25 ccc cta tca gat gtg ttg aat act gtc cac aaa tgaatgtgat ggtcmctgga    436
Pro Leu Ser Asp Val Leu Asn Thr Val His Lys
            30                  35 akttgggatc aaacagttaa actgtgggat cccamaactc cttgtaatgc tgggaccttc      496
tctcmkcctg aaaaggtata taccctctca gtgtctggag accggctgat tgtgggaaca      556
gcaggccgca gagtgttggt gtgggactta cggaacatgg gttacgtgca gcagcgcagg      616
gagtccagcc tgaaatacca gactcgctgc atacgagcgt ttccaaacaa gcagggttat      676
gtattaagct ctattgaagg ccgagtggca gttgagtatt tggacccaag ccctgaggta      736
cagaagaaga agtatgcctt caaatgtcac agactaaaag aaaataatat tgagcagatt      796
tacccagtca atgccatttc ttttcacaat atccacaata catttgccac aggtggttct      856
gatggctttg taaatatttg ggatccattt aacaaaaagc gactgtgcca attccatcgg      916
taccccacga gcatcgcatc acttgccttc agtaatgatg ggactacgct tgcaatagcg      976
tcatcatata tgtatgaaat ggatgacaca gaacatcctg aagatggtat cttcattcgc     1036
caagtgacag atgcagaaac aaaacccaag tcaccatgta cttgacaaga tttcatttac     1096
ttaagtgcca tgttgatgat aataaaacaa ttcgtactcc ccaaaaaaaa aaa            1149
```

<210> SEQ ID NO 133
<211> LENGTH: 921
<212> TYPE: DNA
<213> ORGANISM: Homo sapiens
<220> FEATURE:
<221> NAME/KEY: CDS
<222> LOCATION: 111..446
<220> FEATURE:
<221> NAME/KEY: sig_peptide
<222> LOCATION: 111..254
<223> OTHER INFORMATION: Von Heijne matrix
    score 4.90000009536743
    seq PSLAAGLLFGSLA/GL
<220> FEATURE:
<221> NAME/KEY: polyA_signal
<222> LOCATION: 890..895
<220> FEATURE:
<221> NAME/KEY: polyA_site
<222> LOCATION: 909..921

<400> SEQUENCE: 133

```
agacacctcg cagtcattcc tgcggcttgc gcgcccttgt agacagccgg ggccttcgtg       60
agaccggtgc aggcctgggg tagtctccag tctggacaga aagagaaaa atg cag        116
                                                        Met Gln gac act ggc tca gta gtg cct ttg cat tgg ttt ggc ttt ggc tac gca      164
Asp Thr Gly Ser Val Val Pro Leu His Trp Phe Gly Phe Gly Tyr Ala
    -45                 -40                 -35 gca ctg gtt gct tct ggt ggg atc att ggc tat gta aaa gca ggb agc      212
Ala Leu Val Ala Ser Gly Gly Ile Ile Gly Tyr Val Lys Ala Gly Ser
-30                 -25                 -20                 -15
```

```
gtg ccg tcc ctg gct gca ggg ctg ctc ttt ggc agt cta gcc ggc ctg         260
Val Pro Ser Leu Ala Ala Gly Leu Leu Phe Gly Ser Leu Ala Gly Leu
            -10                 -5                           1 ggt gct tac cag ctg tct cag gat cca agg aac gtt tgg gtt ttc cta         308
Gly Ala Tyr Gln Leu Ser Gln Asp Pro Arg Asn Val Trp Val Phe Leu
        5                   10                  15 gct aca tct ggt acc ttg gct ggc att atg gga atg agg ttc tac cac         356
Ala Thr Ser Gly Thr Leu Ala Gly Ile Met Gly Met Arg Phe Tyr His
        20                  25                  30 tct gga aaa ttc atg cct gca ggt tta att gca ggt gcc akt ttg ctg         404
Ser Gly Lys Phe Met Pro Ala Gly Leu Ile Ala Gly Ala Xaa Leu Leu
35                  40                  45                  50 atg gtc gcc aaa att gga gtt agt atg ttc aac aga ccc cat                 446
Met Val Ala Lys Ile Gly Val Ser Met Phe Asn Arg Pro His
                55                  60 tagcagaakt catgttccag cttagactga tgaagaatta aaaatctgca tcttccacta       506
ttttcaatat attaagagaa ataagtgcag catttttgca tctgacattt tacctaaaaa       566
aaaagacacc aaacttggma raraggtgga aaatcagtca tgattacaaa cctacagagg       626
tggcgagtat gtaacacaag agcttaataa gaccctcata ragcttgatt cttgtawatt       686
gatgttgtct tttcttt ckg tatctgtagg taaatctcaa gggtaaaatg ttaggtgtca      746
gctttcaggg ctctgaaacc chattccctg ctctgaggaa cagtgtgaaa aaaagtcttt       806
taggagattt acaatatctg ttcttttgct catcttagac cacagactga ctttgaaatt       866
atgttaagtg aaatatcaat gaaataaag tttactataa ataataaaaa aaaaa            921

<210> SEQ ID NO 134
<211> LENGTH: 916
<212> TYPE: DNA
<213> ORGANISM: Homo sapiens
<220> FEATURE:
<221> NAME/KEY: CDS
<222> LOCATION: 123..455
<220> FEATURE:
<221> NAME/KEY: sig_peptide
<222> LOCATION: 123..290
<223> OTHER INFORMATION: Von Heijne matrix
      score 4.5
      seq FCAGVLLTLLLIA/FI
<220> FEATURE:
<221> NAME/KEY: polyA_signal
<222> LOCATION: 886..891
<220> FEATURE:
<221> NAME/KEY: polyA_site
<222> LOCATION: 904..916

<400> SEQUENCE: 134
aaagtaatct ttatttcgtc attttttgara catagaagcc gtaacggaag caagtgaaat       60
gctcagtctt agacgactgc gtcgtgctat gaccggactt tttcttgaaa ggggatgaca      120 gc atg gga ggc aat ggc tcc aca tgt aaa ccc gac act gaa aga caa         167
   Met Gly Gly Asn Gly Ser Thr Cys Lys Pro Asp Thr Glu Arg Gln
       -55                 -50                 -45 ggc act ctc tcc aca gca gcc cca aca act agc cct gca ccc tgt ctc        215
Gly Thr Leu Ser Thr Ala Ala Pro Thr Thr Ser Pro Ala Pro Cys Leu
    -40                 -35                 -30 tct aac cac cac aac aaa aaa cat tta atc ctt gcc ttt tgt gct ggg        263
Ser Asn His His Asn Lys Lys His Leu Ile Leu Ala Phe Cys Ala Gly
-25             -20                 -15                  -10 gtt cta ctg aca ctg ctg ctg ata gcc ttt atc ttc ctc atc ata aag        311
Val Leu Leu Thr Leu Leu Leu Ile Ala Phe Ile Phe Leu Ile Ile Lys
        -5                   1                   5
```

```
agc tac aga aaa tat cac tcc aag ccc cag gcc cca gat cct cac tca      359
Ser Tyr Arg Lys Tyr His Ser Lys Pro Gln Ala Pro Asp Pro His Ser
        10              15                  20 gat cct cca kcc rrg ctt tca tcc atc cca ggg gaa tca ctt acc tat      407
Asp Pro Pro Xaa Xaa Leu Ser Ser Ile Pro Gly Glu Ser Leu Thr Tyr
25              30                  35 gcc agc aca ags ktt caa act ctc aga aka ama gag cam yca ctt ggc      455
Ala Ser Thr Xaa Xaa Gln Thr Leu Arg Xaa Xaa Glu Xaa Xaa Leu Gly
40              45                  50                  55 tgagaaccat tctgcagact ttgaccccak kgtctatgct caaattaaag taacaaacta    515
actcagcttt tccaatgagg cttgaatcca tttcctcksa tctcagccct atcttcacas    575
atcactttca ctttttaca watttttggac caccacctgt gtgaaactgc agtcggagtt    635
gtttasatgt gatctggcaa tgctatccag catctttgga gaccaatggt cagtcttttc    695
ctggccakag gaaasattga tggccctccc asttggaact gacagcctgt gagcccttg     755 ggggcataga ctgccttcct tggacccttc caaagtgtgt ggtacrgagc tcagtgcaca    815
gagtattcac ccagcatcat gaatcaactt gggaggagtc aaccaaatga acaatctacc    875
aaaaatttca aataaagtca aacccccac aaaaaaaaaa a                         916

<210> SEQ ID NO 135
<211> LENGTH: 520
<212> TYPE: DNA
<213> ORGANISM: Homo sapiens
<220> FEATURE:
<221> NAME/KEY: CDS
<222> LOCATION: 2..433
<220> FEATURE:
<221> NAME/KEY: sig_peptide
<222> LOCATION: 2..232
<223> OTHER INFORMATION: Von Heijne matrix
      score 4.40000009536743
      seq FEARIALLPLLQA/ET
<220> FEATURE:
<221> NAME/KEY: polyA_signal
<222> LOCATION: 488..493
<220> FEATURE:
<221> NAME/KEY: polyA_site
<222> LOCATION: 510..520

<400> SEQUENCE: 135 a atg gcg gcg tca aag gtg aag cag gac atg cct ccr mcg ggg ggc tat   49
  Met Ala Ala Ser Lys Val Lys Gln Asp Met Pro Pro Xaa Gly Gly Tyr
          -75                 -70                 -65 ggg ccc atc gac tac aaa cgg aac ttg ccg cgt cga gga ctg tcg ggc     97
Gly Pro Ile Asp Tyr Lys Arg Asn Leu Pro Arg Arg Gly Leu Ser Gly
    -60             -55                 -50 tac agc atg ctg gcc ata ggg att gga acc ctg atc tac ggg cac tgg    145
Tyr Ser Met Leu Ala Ile Gly Ile Gly Thr Leu Ile Tyr Gly His Trp
-45             -40              -35                 -30 agc ata atg aag tgg aac cgt gag cgc agg cgc cta caa atc gag gac    193
Ser Ile Met Lys Trp Asn Arg Glu Arg Arg Arg Leu Gln Ile Glu Asp
            -25                 -20                 -15 ttc gag gct cgc atc gcg ctg ttg cca ctg tta cag gca gaa acc gac    241
Phe Glu Ala Arg Ile Ala Leu Leu Pro Leu Leu Gln Ala Glu Thr Asp
        -10                 -5                  1 cgg agg acc ttg cag atg ctt cgg gag aac ctg gag gag gag gcc atc    289
Arg Arg Thr Leu Gln Met Leu Arg Glu Asn Leu Glu Glu Glu Ala Ile
    5                   10                  15 atc atg aag gac gtg ccc gac tgg aag gtg ggg gak tct gtg tyc cac    337
Ile Met Lys Asp Val Pro Asp Trp Lys Val Gly Xaa Ser Val Xaa His
20                  25                  30                  35
```

```
aca acc cgc tgg gtg ccc ccc ttg atc ggg gag ctg tac ggg ctg cgc        385
Thr Thr Arg Trp Val Pro Pro Leu Ile Gly Glu Leu Tyr Gly Leu Arg
             40                  45                  50 acc aca aag gag gct ctc cat gcc agc cac ggc ttc atg tgg tac acg        433
Thr Thr Lys Glu Ala Leu His Ala Ser His Gly Phe Met Trp Tyr Thr
             55                  60                  65 taggccctgt gccctccggc cacctggatc cctgcccctc cccactgggg acgaataaa        493 tgctctgcag acctggaaaa aaaaaaa                                          520

<210> SEQ ID NO 136
<211> LENGTH: 568
<212> TYPE: DNA
<213> ORGANISM: Homo sapiens
<220> FEATURE:
<221> NAME/KEY: CDS
<222> LOCATION: 34..363
<220> FEATURE:
<221> NAME/KEY: sig_peptide
<222> LOCATION: 34..87
<223> OTHER INFORMATION: Von Heijne matrix
      score 8.30000019073486
      seq LLSLSSLPLVLLG/WE
<220> FEATURE:
<221> NAME/KEY: polyA_signal
<222> LOCATION: 536..541
<220> FEATURE:
<221> NAME/KEY: polyA_site
<222> LOCATION: 558..568

<400> SEQUENCE: 136
aaccagactt ctgacccctt gggcaacagc cag atg gag act ggt cgc ctt ttg         54
                                    Met Glu Thr Gly Arg Leu Leu
                                                    -15 agc ctc agc tct ctt cct ctt gtt ctc cta ggg tgg gag tac agc agc        102
Ser Leu Ser Ser Leu Pro Leu Val Leu Leu Gly Trp Glu Tyr Ser Ser
    -10                  -5                   1                   5 caa acg ctg aac tta gtc cca tcc act tcc atc tta tcc ttt gtg ccc        150
Gln Thr Leu Asn Leu Val Pro Ser Thr Ser Ile Leu Ser Phe Val Pro
                 10                  15                  20 ttc atc ccc ctg cat ctt gtc ctt ttt gcc ctc tgg tac ctc cca gtg        198
Phe Ile Pro Leu His Leu Val Leu Phe Ala Leu Trp Tyr Leu Pro Val
             25                  30                  35 ccc cat cat ctc tac ccc cag gga ctc gga rat cat gca gca raa gca        246
Pro His His Leu Tyr Pro Gln Gly Leu Gly Xaa His Ala Ala Xaa Ala
             40                  45                  50 gaa raa ggc aaa cga raa gaa gga gga acc caa kta gct ttg tgg ctt        294
Glu Xaa Gly Lys Arg Xaa Glu Gly Gly Thr Gln Xaa Ala Leu Trp Leu
             55                  60                  65 cgt gtc caa ccc tct tgc cct tcg cct gtg tgc ctg gag cca gtc cca        342
Arg Val Gln Pro Ser Cys Pro Ser Pro Val Cys Leu Glu Pro Val Pro
70                  75                  80                  85 cca cgc tcg cgt ttc ctc ctg tagtgctcac aggtcccagc accgatggca           393
Pro Arg Ser Arg Phe Leu Leu
                 90 ttcctttgc cctgagtctg carcgggtcc cttttgtgct tccttcccct caggtagcct        453
ctctccccct gggccactcc cggggtgag ggggtttacc ccttcccagt gttttttatt        513 cctgtgggc tcaccccaaa gtattaaaag tagctttgta attcaaaaaa aaaaa            568

<210> SEQ ID NO 137
<211> LENGTH: 419
<212> TYPE: DNA
<213> ORGANISM: Homo sapiens
```

```
<220> FEATURE:
<221> NAME/KEY: CDS
<222> LOCATION: 50..286
<220> FEATURE:
<221> NAME/KEY: sig_peptide
<222> LOCATION: 50..157
<223> OTHER INFORMATION: Von Heijne matrix
      score 4.80000019073486
      seq VLLAIGMFFTAWF/FV
<220> FEATURE:
<221> NAME/KEY: polyA_signal
<222> LOCATION: 385..390
<220> FEATURE:
<221> NAME/KEY: polyA_site
<222> LOCATION: 405..416

<400> SEQUENCE: 137
agacgtgttc ttccggtggc ggasggcgga ttagccttcg cggggcaaa atg gag ctc        58
                                                       Met Glu Leu
                                                           -35 gag gcc atg agc aga tat acc agc cca gtg aac cca gct gtc ttc ccc         106
Glu Ala Met Ser Arg Tyr Thr Ser Pro Val Asn Pro Ala Val Phe Pro
        -30                 -25                 -20 cat ctg acc gtg gtg ctt ttg gcc att ggc atg ttc ttc acc gcc tgg         154
His Leu Thr Val Val Leu Leu Ala Ile Gly Met Phe Phe Thr Ala Trp
    -15                 -10                  -5 ttc ttc gtt tac gag gtc acc tct acc aag tac act cgt gat atc tat         202
Phe Phe Val Tyr Glu Val Thr Ser Thr Lys Tyr Thr Arg Asp Ile Tyr
 1               5                  10                  15 aaa gag ctc ctc atc tcc tta gtg gcc tca ctc ttc atg ggc ttt gga         250
Lys Glu Leu Leu Ile Ser Leu Val Ala Ser Leu Phe Met Gly Phe Gly
                20                  25                  30 gtc ctc ttc ctg ctg ctc tgg gtt ggc atc tac gtg tgagcaccca              296
Val Leu Phe Leu Leu Leu Trp Val Gly Ile Tyr Val
                35                  40 agggtaacaa ccagatggct tcactgaaac ctgcttttgt aaattactt ttttttactgt       356 tgctggaagt gtcccacctg ctgctcataa taaatgcaga agtatagcaa aaaaaaaaa        416 ccc                                                                     419

<210> SEQ ID NO 138
<211> LENGTH: 1289
<212> TYPE: DNA
<213> ORGANISM: Homo sapiens
<220> FEATURE:
<221> NAME/KEY: CDS
<222> LOCATION: 50..637
<220> FEATURE:
<221> NAME/KEY: sig_peptide
<222> LOCATION: 50..151
<223> OTHER INFORMATION: Von Heijne matrix
      score 5.90000009536743
      seq LGAAALALLLANT/DV
<220> FEATURE:
<221> NAME/KEY: polyA_site
<222> LOCATION: 1277..1289

<400> SEQUENCE: 138
aatatacttc tttgtcaaga gaagcagagg tgtggacgct gtgtatgaa atg tct ttc        58
                                                     Met Ser Phe ctc cag gac cca agt ttc ttc acc atg ggg atg tgg tcc att ggt gca         106
Leu Gln Asp Pro Ser Phe Phe Thr Met Gly Met Trp Ser Ile Gly Ala
        -30                 -25                 -20 gga gcc ctg ggg gct gct gcc ttg gca ttg ctg ctt gcc aac aca gac         154
Gly Ala Leu Gly Ala Ala Ala Leu Ala Leu Leu Leu Ala Asn Thr Asp
    -15                 -10                  -5                  1
```

| | | | | | | | | | | | | | | | | |
|---|---|---|---|---|---|---|---|---|---|---|---|---|---|---|---|---|
| gtg | ttt | ctg | tcc | aag | ccc | cag | aaa | gcg | gcc | ctg | gag | tac | ctg | gag | gat | 202 |
| Val | Phe | Leu | Ser | Lys | Pro | Gln | Lys | Ala | Ala | Leu | Glu | Tyr | Leu | Glu | Asp | |
| | | | 5 | | | | 10 | | | | | 15 | | | | |
| ata | gac | ctg | aaa | aca | ctg | gag | aag | gaa | cca | agg | act | ttc | aaa | gca | aag | 250 |
| Ile | Asp | Leu | Lys | Thr | Leu | Glu | Lys | Glu | Pro | Arg | Thr | Phe | Lys | Ala | Lys | |
| | | 20 | | | | | 25 | | | | 30 | | | | | |
| gag | cta | tgg | gaa | aaa | aat | gga | gct | gtg | att | atg | gcc | gtg | cgg | agg | cca | 298 |
| Glu | Leu | Trp | Glu | Lys | Asn | Gly | Ala | Val | Ile | Met | Ala | Val | Arg | Arg | Pro | |
| | 35 | | | | | 40 | | | | 45 | | | | | | |
| ggc | tgt | ttc | ctc | tgt | cga | gag | gaa | gct | gcg | gat | ctg | tcc | tcc | ctg | aaa | 346 |
| Gly | Cys | Phe | Leu | Cys | Arg | Glu | Glu | Ala | Ala | Asp | Leu | Ser | Ser | Leu | Lys | |
| 50 | | | | | 55 | | | | 60 | | | | | 65 | | |
| agc | atg | ttg | gac | cag | ctg | ggc | gtc | ccc | ctc | tat | gca | gtg | gta | aag | gas | 394 |
| Ser | Met | Leu | Asp | Gln | Leu | Gly | Val | Pro | Leu | Tyr | Ala | Val | Val | Lys | Xaa | |
| | | | 70 | | | | 75 | | | | 80 | | | | | |
| cac | atc | rgg | act | gaa | ktg | aag | gat | ttc | cag | cct | tat | ttc | aaa | gga | gaa | 442 |
| His | Ile | Xaa | Thr | Glu | Xaa | Lys | Asp | Phe | Gln | Pro | Tyr | Phe | Lys | Gly | Glu | |
| | | | 85 | | | | 90 | | | | 95 | | | | | |
| atc | ttc | ctg | gat | gaa | aar | aaa | aag | ttc | tat | ggt | cca | caa | agg | cgg | aag | 490 |
| Ile | Phe | Leu | Asp | Glu | Lys | Lys | Lys | Phe | Tyr | Gly | Pro | Gln | Arg | Arg | Lys | |
| | | 100 | | | | | 105 | | | | 110 | | | | | |
| atg | atg | ttt | atg | gga | ttt | atc | cgt | ctg | gga | atg | tgg | tac | aac | ttc | ttc | 538 |
| Met | Met | Phe | Met | Gly | Phe | Ile | Arg | Leu | Gly | Met | Trp | Tyr | Asn | Phe | Phe | |
| | 115 | | | | | 120 | | | | 125 | | | | | | |
| cga | rcc | tgg | aac | gga | rgc | ttc | tct | gga | aac | ctg | gaa | gga | raa | ggc | ttc | 586 |
| Arg | Xaa | Trp | Asn | Gly | Xaa | Phe | Ser | Gly | Asn | Leu | Glu | Gly | Xaa | Gly | Phe | |
| 130 | | | | | 135 | | | | 140 | | | | | 145 | | |
| atc | ctt | ggg | gga | att | ttc | gtg | gtg | gga | tca | asg | aaa | gca | ggg | cat | tct | 634 |
| Ile | Leu | Gly | Gly | Ile | Phe | Val | Val | Gly | Ser | Xaa | Lys | Ala | Gly | His | Ser | |
| | | | | 150 | | | | 155 | | | | | 160 | | | |
| tct tgarcmccga gaaaagaat tggagacaa agtaaaccta ctttctgttc<br>Ser | 687 |
|---|---|
| tggaagctgc taagatgatc aaaccacaga ctttggcctc agagaaaaaa tgattgtgtg | 747 |
| aaactgccca gctcagggat aaccagggac attcacctgt gttcatggga tgtattgttt | 807 |
| ccactcgtgt ccctaaggag tgagaaaccc atttatactc tactctcagt atggattatt | 867 |
| aatgtatttt aatattctgt ttaggccac taaggcaaaa tacccccaaa acaagactga | 927 |
| caaaaatctg aaaaactaat gaggattatt aagctaaaac ctgggaaata ggaggcttaa | 987 |
| aattgactgc caggctgggt gcagtggctc acacctgtaa tcccagcact ttgggaggcc | 1047 |
| aaggtgagca agtcacttga ggtcgggagt tcgagaccag cctgagcaac atggcgaaac | 1107 |
| cccgtctcta ckaaaaatac araaatcacc cgggtgtggt ggcaggcacc tgtagtccca | 1167 |
| gctacccggg aggctgaggc aggagaatca cttgaacctg ggaggtggag gttgcggtga | 1227 |
| gctgagatca caccactgta ttccagcctg ggtgactgag actctaacca aaaaaaaaaa | 1287 |
| aa | 1289 |

<210> SEQ ID NO 139
<211> LENGTH: 715
<212> TYPE: DNA
<213> ORGANISM: Homo sapiens
<220> FEATURE:
<221> NAME/KEY: CDS
<222> LOCATION: 72..602
<220> FEATURE:
<221> NAME/KEY: sig_peptide
<222> LOCATION: 72..125
<223> OTHER INFORMATION: Von Heijne matrix
score 5.59999990463257
seq LTPLFFMFPTGFS/SP

```
<220> FEATURE:
<221> NAME/KEY: polyA_site
<222> LOCATION: 704..715

<400> SEQUENCE: 139
acttcccttc ccctctagc attgctacct tctctcctac acgcacgcag gcatataaac      60
gtaggttttt g atg ctc ctc tgc ctg ttg acc ccg cta ttt ttc atg ttt    110
            Met Leu Leu Cys Leu Leu Thr Pro Leu Phe Phe Met Phe
                -15                     -10 cca aca ggt ttt tct tcc ccc agt ccc tca gct gct gct gct gct cag    158
Pro Thr Gly Phe Ser Ser Pro Ser Pro Ser Ala Ala Ala Ala Ala Gln
-5              1               5                       10 gag gtc aga tct gcc act gat ggt aat acc agc acc act ccg ccc acc    206
Glu Val Arg Ser Ala Thr Asp Gly Asn Thr Ser Thr Thr Pro Pro Thr
            15              20              25 tct gcc aar aar aka aag tta aac agc agc agc agt agc agc agt aac    254
Ser Ala Lys Lys Xaa Lys Leu Asn Ser Ser Ser Ser Ser Ser Ser Asn
            30              35              40 agt agt aac gag aga gaa gac ttt gat tcs acc tct tcc tcc tct tcc    302
Ser Ser Asn Glu Arg Glu Asp Phe Asp Ser Thr Ser Ser Ser Ser Ser
45              50              55 act cct cct tta caa ccc agg gat tcg gca tcc cct tca acc tcg tcc    350
Thr Pro Pro Leu Gln Pro Arg Asp Ser Ala Ser Pro Ser Thr Ser Ser
60              65              70              75 ttc tgc ctg ggg gtt tca gtg gct gct tcc agc cac gta ccg ata swg    398
Phe Cys Leu Gly Val Ser Val Ala Ala Ser Ser His Val Pro Ile Xaa
                80              85              90 aar aag ctg cgt ttt gaa rac acc ctg gag ttt gta ggg ttt gat gcg    446
Lys Lys Leu Arg Phe Glu Xaa Thr Leu Glu Phe Val Gly Phe Asp Ala
            95              100             105 aar atg gct gar gaa tcc tcc tcc tcc tcc tca tct tca cca ack        494
Lys Met Ala Glu Glu Ser Ser Ser Ser Ser Ser Ser Pro Thr
            110             115             120 gct gca aca tct cag cag cag caa ctt aaa aat aag agt ata ttg aat    542
Ala Ala Thr Ser Gln Gln Gln Gln Leu Lys Asn Lys Ser Ile Leu Asn
125             130             135 ctc ttc tgt ggc ttc ggt gca tca tgc aaa cgg cct agc caa atc ttc    590
Leu Phe Cys Gly Phe Gly Ala Ser Cys Lys Arg Pro Ser Gln Ile Phe
140             145             150             155 tac cac cgt ctc tagctttgct aacagcaaac ctggctctgc taagaagtta        642
Tyr His Arg Leu gtgatcaaga actttaaaga taagcctaaa ttaccagaaa actacacaga tgaaacctgg   702
caaaaaaaaa aaa                                                     715

<210> SEQ ID NO 140
<211> LENGTH: 931
<212> TYPE: DNA
<213> ORGANISM: Homo sapiens
<220> FEATURE:
<221> NAME/KEY: CDS
<222> LOCATION: 120..434
<220> FEATURE:
<221> NAME/KEY: sig_peptide
<222> LOCATION: 120..185
<223> OTHER INFORMATION: Von Heijne matrix
      score 6.30000019073486
      seq FALVWLWLRSTGC/FW
<220> FEATURE:
<221> NAME/KEY: polyA_signal
<222> LOCATION: 899..904
<220> FEATURE:
<221> NAME/KEY: polyA_site
<222> LOCATION: 918..931
```

<400> SEQUENCE: 140

```
aatttccggc gacacctcgc agtcattcct gcggcttgcg cgcccttgta gacagccggg      60
gccttcgtga gaccggtgca ggcctggggt agtctcctgt ctggacagag aagagaaaa     119 atg cag gga cac tgg ctc agt agt gcc ttt gca ttg gtt tgg ctt tgg      167
Met Gln Gly His Trp Leu Ser Ser Ala Phe Ala Leu Val Trp Leu Trp
    -20             -15                 -10 cta cgc agc act ggt tgc ttc tgg tgg gat cat tgg cta tgt aaa agc      215
Leu Arg Ser Thr Gly Cys Phe Trp Trp Asp His Trp Leu Cys Lys Ser
 -5              1                   5                      10 agg cag cgt gcc gtc cct ggc tgc agg gct gct ctt tgg cag tct agc      263
Arg Gln Arg Ala Val Pro Gly Cys Arg Ala Ala Leu Trp Gln Ser Ser
                15                  20                  25 cgg cct ggg tgc tta cca gct gtc tca gga tcc aag gaa cgt ttg ggt      311
Arg Pro Gly Cys Leu Pro Ala Val Ser Gly Ser Lys Glu Arg Leu Gly
            30                  35                  40 ttt cct agc tac atc tgg tac ctt ggc tgg cat tat ggg aat gag gtt      359
Phe Pro Ser Tyr Ile Trp Tyr Leu Gly Trp His Tyr Gly Asn Glu Val
        45                  50                  55 cta cca ctc tgg aaa att cat gcc tgc agg ttt aat tgc agg tgc cag      407
Leu Pro Leu Trp Lys Ile His Ala Cys Arg Phe Asn Cys Arg Cys Gln
    60                  65                  70 ttt gct gat ggt cgc caa agt tgg agt tagtatgtkc aacagacccc             454
Phe Ala Asp Gly Arg Gln Ser Trp Ser
75              80 attagcagaa gtcatgttcc agcttagatg atgaaraatt aaaaatctgc atcttccact     514
attttcaata tattaagaga ataagtgcat gcattttttgc atctgacatt ttacctaaaa    574
aaaaaaacmc caaacttggc aaaaaggtgg aaaatcagtc atgattacaa acctacagag    634
gtggcgagta tgtaacacaa gagcttaata agaccctcat agagcttgat tcttgtatat    694
tgatgttgtc ttttcttttct gtatctgtag gtaaatctca agggtaaaat gttaggtgtc    754
agctttcagg gctctgaaac cchattccct gctctgagga acagtgtgaa aaaaagtctt    814
ttaggaratt tacaatatct gttctttttgc tcatcttara ccacagactg actttgaaat   874
takgttaagt gaaatatcaa tgaaaataaa gtttactata aataawaaaa aaaaaaa       931
```

<210> SEQ ID NO 141
<211> LENGTH: 891
<212> TYPE: DNA
<213> ORGANISM: Homo sapiens
<220> FEATURE:
<221> NAME/KEY: CDS
<222> LOCATION: 4..447
<220> FEATURE:
<221> NAME/KEY: sig_peptide
<222> LOCATION: 4..147
<223> OTHER INFORMATION: Von Heijne matrix
      score 5.69999980926514
      seq LLLFFGKLLVVGG/VG
<220> FEATURE:
<221> NAME/KEY: polyA_signal
<222> LOCATION: 858..863
<220> FEATURE:
<221> NAME/KEY: polyA_site
<222> LOCATION: 880..891

<400> SEQUENCE: 141

```
atc atg atc gcc atc tac ggg aag aat ttc tgt gtc tca gcc aaa aat       48
    Met Ile Ala Ile Tyr Gly Lys Asn Phe Cys Val Ser Ala Lys Asn
        -45                 -40                 -35 gcg ttc atg cta ctc atg cga aac att gtc agg gtg gtc gtc ctg gac       96
```

```
Ala Phe Met Leu Leu Met Arg Asn Ile Val Arg Val Val Leu Asp
        -30              -25               -20 aaa gtc aca gac ctg ctg ctg ttc ttt ggg aag ctg ctg gtg gtc gga    144
Lys Val Thr Asp Leu Leu Leu Phe Phe Gly Lys Leu Leu Val Val Gly
        -15              -10               -5 ggc gtg ggg gtc ctg tcc ttc ttt ttt ttc tcc ggt cgc atc ccg ggg    192
Gly Val Gly Val Leu Ser Phe Phe Phe Phe Ser Gly Arg Ile Pro Gly
1               5               10              15 ctg ggt aaa gac ttt aag agc ccc cac ctc aac tat tac tgg ctg ccc    240
Leu Gly Lys Asp Phe Lys Ser Pro His Leu Asn Tyr Tyr Trp Leu Pro
                20              25              30 ayc atg acc tcc atc ctg ggg gcc tat gtc atc gcc agy ggc ttc ttc    288
Xaa Met Thr Ser Ile Leu Gly Ala Tyr Val Ile Ala Ser Gly Phe Phe
            35              40              45 agc gtt ttc ggc atg tgt gtg gac acg ctc ttc ctc tgc ttc ctg gaa    336
Ser Val Phe Gly Met Cys Val Asp Thr Leu Phe Leu Cys Phe Leu Glu
        50              55              60 gac ctg gag cgg aca acg gct ccc tgg acg gcc cta cta cat gtc caa    384
Asp Leu Glu Arg Thr Thr Ala Pro Trp Thr Ala Leu Leu His Val Gln
    65              70              75 gag ctt cta aag att ctg ggc aag aag aac gag gcg ccc ccg gac aac    432
Glu Leu Leu Lys Ile Leu Gly Lys Lys Asn Glu Ala Pro Pro Asp Asn
80              85              90              95 aag aaa agg aaa aak tgacagctcc ggccctgatc caggactgca ccccaccccc    487
Lys Lys Arg Lys Xaa
            100 accgtccagc catccaacct cacttcgcct tacaggtctc cattttgtgg taaaaaagg    547 ttttaggcca ggcgccgtgg ctcacgcctg twatccaaca ctttgaragg ctgaggcggg    607 cggatcacct kaktcaggak tycgagacca kcctggccaa catggtgaaa cctccgtctc    667 tattaaaaat acaaaaatta gccgagagtg gtggcatgca cctgtcatcc cagctactcg    727 ggaggctgag gcaggagaat cgcttgaacc cgggaggcag aggttgcagt gagccgagat    787 cgcgccactg cactccaacc tgggtgacag actctgtctc caaacaaaa caaacaaaca    847 aaaagatttt attaaagata ttttgttaac tcaraaaaaa aaaa                   891

<210> SEQ ID NO 142
<211> LENGTH: 817
<212> TYPE: DNA
<213> ORGANISM: Homo sapiens
<220> FEATURE:
<221> NAME/KEY: CDS
<222> LOCATION: 28..804
<220> FEATURE:
<221> NAME/KEY: sig_peptide
<222> LOCATION: 28..96
<223> OTHER INFORMATION: Von Heijne matrix
      score 10
      seq PLLGLLLSLPAGA/DV
<220> FEATURE:
<221> NAME/KEY: polyA_site
<222> LOCATION: 806..817

<400> SEQUENCE: 142
aaccgagctg gatttgtatg ttgcacc atg cct tct tgg atc ggg gct gtg att   54
                              Met Pro Ser Trp Ile Gly Ala Val Ile
                                  -20                     -15 ctt ccc ctc ttg ggg ctg ctg ctc tcc ctc ccc gcc ggg gcg gat gtg   102
Leu Pro Leu Leu Gly Leu Leu Leu Ser Leu Pro Ala Gly Ala Asp Val
            -10              -5                      1 aag gct cgg agc tgc gga gag gtc cgc cag gcg tac ggt gcc aag gga   150
Lys Ala Arg Ser Cys Gly Glu Val Arg Gln Ala Tyr Gly Ala Lys Gly
```

```
                5                   10                  15
ttc agc ctg gcg gac atc ccc tac cag gag atc gca kgg gaa cac tta    198
Phe Ser Leu Ala Asp Ile Pro Tyr Gln Glu Ile Ala Xaa Glu His Leu
        20                  25                  30 aga atc tgt cct cag gaa tat aca tgc tgc acc aca gaa atg gar gac    246
Arg Ile Cys Pro Gln Glu Tyr Thr Cys Cys Thr Thr Glu Met Glu Asp
35                  40                  45                  50 aag tta agc caa caa agc aaa ctc gaa ttt gaa aac ctt gtg gaa gag    294
Lys Leu Ser Gln Gln Ser Lys Leu Glu Phe Glu Asn Leu Val Glu Glu
                55                  60                  65 aca agc cat ttt gtg cgc acc act ttt gtg tcc agg cat aag aaa ttt    342
Thr Ser His Phe Val Arg Thr Thr Phe Val Ser Arg His Lys Lys Phe
            70                  75                  80 gac gaw ttt ttc cga rag ctc ckg gag aat gca raa aag tca cta aat    390
Asp Xaa Phe Phe Arg Xaa Leu Xaa Glu Asn Ala Xaa Lys Ser Leu Asn
        85                  90                  95 gat rtg ttt gtm cgg acc tat ggc atg ctg tac wtg car aat kca gaa    438
Asp Xaa Phe Val Arg Thr Tyr Gly Met Leu Tyr Xaa Gln Asn Xaa Glu
    100                 105                 110 gtc ttc crg gac ctc ttc aca rag ctg aaa agg tac tac act ggg ggt    486
Val Phe Xaa Asp Leu Phe Thr Xaa Leu Lys Arg Tyr Tyr Thr Gly Gly
115                 120                 125                 130 aat gtg aat ctg gag gaa atg ctc aat gac ttt tgg gct cgg ctc ctg    534
Asn Val Asn Leu Glu Glu Met Leu Asn Asp Phe Trp Ala Arg Leu Leu
                135                 140                 145 gaa cgg atg ttt cag cwr awa aac cct cag tat cac ttc agt gaa gac    582
Glu Arg Met Phe Gln Xaa Xaa Asn Pro Gln Tyr His Phe Ser Glu Asp
            150                 155                 160 tac ctg gaa tgt gtg agc aaa tac act gac cak ctc aag cca ttt gga    630
Tyr Leu Glu Cys Val Ser Lys Tyr Thr Asp Xaa Leu Lys Pro Phe Gly
        165                 170                 175 gac gtg ccc cgg aaa ctg aag att cag gtk acc cgc gcc ttc atk gsk    678
Asp Val Pro Arg Lys Leu Lys Ile Gln Val Thr Arg Ala Phe Xaa Xaa
    180                 185                 190 gcc agg acc ttt gtc cag ggg ctg act gtg ggc aga gaa gtt gca aac    726
Ala Arg Thr Phe Val Gln Gly Leu Thr Val Gly Arg Glu Val Ala Asn
195                 200                 205                 210 cga gtt tcc aag gta att gaa aac gtg ctt tct ttc tca ttg gtg ttc    774
Arg Val Ser Lys Val Ile Glu Asn Val Leu Ser Phe Ser Leu Val Phe
                215                 220                 225 ctt gtt tat tct gtt ttt aaa acc aat gtt taaaaaaaaa aaa            817
Leu Val Tyr Ser Val Phe Lys Thr Asn Val
            230                 235

<210> SEQ ID NO 143
<211> LENGTH: 1020
<212> TYPE: DNA
<213> ORGANISM: Homo sapiens
<220> FEATURE:
<221> NAME/KEY: CDS
<222> LOCATION: 27..359
<220> FEATURE:
<221> NAME/KEY: sig_peptide
<222> LOCATION: 27..212
<223> OTHER INFORMATION: Von Heijne matrix
      score 3.59999990463257
      seq SWLSLLAALAHLA/AA
<220> FEATURE:
<221> NAME/KEY: polyA_signal
<222> LOCATION: 988..993
<220> FEATURE:
<221> NAME/KEY: polyA_site
<222> LOCATION: 1009..1020
```

<400> SEQUENCE: 143

```
agtgggtcga kctggggcgc agtcgc atg ggg gag tct atc ccg ctg gcc gcc        53
                             Met Gly Glu Ser Ile Pro Leu Ala Ala
                                 -60                 -55 ccg gtc ccg gtg gaa cag gcg gtg ctg gag acg ttc ttc tct cac ctg        101
Pro Val Pro Val Glu Gln Ala Val Leu Glu Thr Phe Phe Ser His Leu
            -50                 -45                 -40 ggt atc ttc tct tac gac aag gct aag gac aat gtg gag aag gaa cga        149
Gly Ile Phe Ser Tyr Asp Lys Ala Lys Asp Asn Val Glu Lys Glu Arg
        -35                 -30                 -25 gag gcc aac aag agc gcg ggg ggc agc tgg ctg tcg ctg ctg gcg gcc        197
Glu Ala Asn Lys Ser Ala Gly Gly Ser Trp Leu Ser Leu Leu Ala Ala
    -20                 -15                 -10 ttg gcg cac ctg gcc gcg gcc gag aag gtc tat cac agc ctc acc tac        245
Leu Ala His Leu Ala Ala Ala Glu Lys Val Tyr His Ser Leu Thr Tyr
-5                   1               5                  10 ctg ggg cag aaa cta ggt acc tcc gcc ccg ccc ccc gag ccc ctt gag        293
Leu Gly Gln Lys Leu Gly Thr Ser Ala Pro Pro Pro Glu Pro Leu Glu
             15                  20                  25 gag gaa gta aag ggg gta tat tcc cca dtc ggc agt ggc ttg ggt btc        341
Glu Glu Val Lys Gly Val Tyr Ser Pro Xaa Gly Ser Gly Leu Gly Xaa
         30                  35                  40 ccg tct ctg tgt cac ttc tagtcgcagg ctcgactcgg cattcccaga               389
Pro Ser Leu Cys His Phe
         45 tctcctccca ccgttccttt ccttccctgg gcttccacaa gccccgccca ccrgcctgcr      449 ctgctgatag attggcgaac tgggtagatg ctctttgcaa ggctgtgacc caaaccgaaw      509 ggtttgccct tttgcctcgt gcatggattg atgccataaa tgagaagtta accaaaaaaa      569 aaaaacmcwd tycckktttm cccccccgg grmcagaaga gcaaactttt gcaaacaac       629 ctagttctat tactgaacac tgttgtgtgg cctcttaagg ttaaggcccg agagtcacat      689 ttagagtcct accccgtctt catagtcccc caatacatat ttaatgacta aagtwataaa      749 tgaatattgg gcaggaaagg caagaaatat gcctaacact agcaagaaga gacttaaggg     809 gaaaatggta aacactctta gcacttcatg tacatcttgc ctctgaaata agattcaaga     869 gctgattcaa ctgatttttta ctagtagaag caataagtat aagtagatga gaaggaaata     929 atagatgtaa aaggcatgga atatgcatac aaaataatat tactgcttaa ttatgacaaa     989 taaatatatt ttgaatccta aaaaaaaaaa a                                   1020
```

<210> SEQ ID NO 144
<211> LENGTH: 1399
<212> TYPE: DNA
<213> ORGANISM: Homo sapiens
<220> FEATURE:
<221> NAME/KEY: CDS
<222> LOCATION: 25..957
<220> FEATURE:
<221> NAME/KEY: sig_peptide
<222> LOCATION: 25..93
<223> OTHER INFORMATION: Von Heijne matrix
      score 4.09999990463257
      seq LEAFSQAISAIQA/LR
<220> FEATURE:
<221> NAME/KEY: polyA_signal
<222> LOCATION: 1368..1373
<220> FEATURE:
<221> NAME/KEY: polyA_site
<222> LOCATION: 1388..1399

<400> SEQUENCE: 144

-continued

| | | |
|---|---|---|
| aakagctgct gtggcggcgg caac atg gcg gac gtg ata aat gtc agt gtg<br>                                          Met Ala Asp Val Ile Asn Val Ser Val<br>                                                   -20                  -15 | | 51 |
| aac ctg gag gcc ttt tcc cag gcc att agt gcc atc cag gcg ctg cga<br>Asn Leu Glu Ala Phe Ser Gln Ala Ile Ser Ala Ile Gln Ala Leu Arg<br>         -10                 -5                                 1 | | 99 |
| tcc agc gtg agc agg gtg ttc gac tgc ctg aag gat ggg atg cgg aac<br>Ser Ser Val Ser Arg Val Phe Asp Cys Leu Lys Asp Gly Met Arg Asn<br>          5                       10                       15 | | 147 |
| aag gag acg ctg gag ggc cgg gag aag gcc ttt att gcg cac ttc cag<br>Lys Glu Thr Leu Glu Gly Arg Glu Lys Ala Phe Ile Ala His Phe Gln<br>     20                     25                     30 | | 195 |
| gac aac tta cat tcg gtc aac cgg gac ctc aat gag ctg gaa cgt ctg<br>Asp Asn Leu His Ser Val Asn Arg Asp Leu Asn Glu Leu Glu Arg Leu<br>35                   40                     45                     50 | | 243 |
| agc aat ctg gta ggc arg cca tct gar aac cat cct ctt cat aac agt<br>Ser Asn Leu Val Gly Xaa Pro Ser Glu Asn His Pro Leu His Asn Ser<br>                  55                     60                     65 | | 291 |
| ggg ctg tta asc ctg gat cct gtg car gac aaa act cct ctc tat agt<br>Gly Leu Leu Xaa Leu Asp Pro Val Gln Asp Lys Thr Pro Leu Tyr Ser<br>            70                     75                     80 | | 339 |
| caa ctc ctt caa gca tat aag tgg tca aac aag ttg cag tac cat gca<br>Gln Leu Leu Gln Ala Tyr Lys Trp Ser Asn Lys Leu Gln Tyr His Ala<br>                85                     90                     95 | | 387 |
| gga cta gca tct ggc ctt tta aat cas car tca ktg aag cgt ycc gct<br>Gly Leu Ala Ser Gly Leu Leu Asn Xaa Gln Ser Xaa Lys Arg Xaa Ala<br>     100                    105                    110 | | 435 |
| aat cag atg gga gta tct gcc aaa cgt aga cca aag gct cag ccc aca<br>Asn Gln Met Gly Val Ser Ala Lys Arg Arg Pro Lys Ala Gln Pro Thr<br>115                   120                     125                   130 | | 483 |
| act ctt gtc cta cca cct caa tat gtt gat gat gtg atc agc cgc att<br>Thr Leu Val Leu Pro Pro Gln Tyr Val Asp Asp Val Ile Ser Arg Ile<br>                 135                     140                    145 | | 531 |
| gac agg atg ttt cct gaa atg tcc atc cac tta tcc aga ccc aat gga<br>Asp Arg Met Phe Pro Glu Met Ser Ile His Leu Ser Arg Pro Asn Gly<br>               150                     155                     160 | | 579 |
| aca tca gca atg ctt ctg gtg acc ttg gga aar gtg ttg aaa gtg awc<br>Thr Ser Ala Met Leu Leu Val Thr Leu Gly Lys Val Leu Lys Val Xaa<br>           165                     170                    175 | | 627 |
| gtc gtc rtr cgg arm ctg ttc att gat cga aca ata gtw aag gga tat<br>Val Val Xaa Arg Xaa Leu Phe Ile Asp Arg Thr Ile Val Lys Gly Tyr<br>     180                    185                    190 | | 675 |
| wac gag aat gtc tac rca gaa kat ggc mag ctt gat ata tgg tcc aaa<br>Xaa Glu Asn Val Tyr Xaa Glu Xaa Gly Xaa Leu Asp Ile Trp Ser Lys<br>195                   200                     205                   210 | | 723 |
| tcc aac tat caa gta ttc cag aag gtg aca gac cat gcc acc act gcc<br>Ser Asn Tyr Gln Val Phe Gln Lys Val Thr Asp His Ala Thr Thr Ala<br>               215                     220                    225 | | 771 |
| ctg ctc cac taw mag ctg ccc cag atg ccg gat gtc gtg gtc cga tcc<br>Leu Leu His Xaa Xaa Leu Pro Gln Met Pro Asp Val Val Val Arg Ser<br>               230                     235                    240 | | 819 |
| ttc awg acc tgg tta aga agt tac ata aag ctg ttc cag gcc ccg tgc<br>Phe Xaa Thr Trp Leu Arg Ser Tyr Ile Lys Leu Phe Gln Ala Pro Cys<br>     245                    250                    255 | | 867 |
| cag cgc tgc ggg aag ttt ctg cag gac ggc ctt ccc ccg aca tgg agg<br>Gln Arg Cys Gly Lys Phe Leu Gln Asp Gly Leu Pro Pro Thr Trp Arg<br>     260                    265                    270 | | 915 |
| gat ttc cga acc ctc gaa gcc ttc cat gac acc tgc cgg cag<br>Asp Phe Arg Thr Leu Glu Ala Phe His Asp Thr Cys Arg Gln<br>275                   280                     285 | | 957 |

```
tagcccccac gctggcccca gcctcagacc ccacccagca ccttcccaga cacgcaggaa    1017
gcccacagaa ggctcagctg gttcctcact gcccagatgt gtacagctgc tcctcccttt    1077
cataaagcag cgccatgtgt gcagaggcca ctcttgaaga gcagactccc tctgtggctg    1137
atgggactaa ttattcccac tagccagcgg actgaaggca agaagacct ttctagaacc     1197 tggtagaagg aagctgtgca gcatgctcct cgtccatgtg tgtcggcagt gctggtgtct    1257
gtcgtctccg cgagctgtta ctggaatgag cccttgtgtt catgggtatc gtcatgcggg    1317
gttcttgtgt tttgtggggc ttgggttttg gttaacttat ttttataagc aataaaccttt  1377 ttgtatcctg aaaaaaaaaa aa                                             1399

<210> SEQ ID NO 145
<211> LENGTH: 666
<212> TYPE: DNA
<213> ORGANISM: Homo sapiens
<220> FEATURE:
<221> NAME/KEY: CDS
<222> LOCATION: 47..319
<220> FEATURE:
<221> NAME/KEY: sig_peptide
<222> LOCATION: 47..226
<223> OTHER INFORMATION: Von Heijne matrix
      score 3.90000009536743
      seq SSLVPFFLFTCFG/HF
<220> FEATURE:
<221> NAME/KEY: polyA_site
<222> LOCATION: 656..666

<400> SEQUENCE: 145
acttttgcct agcatttgac tttggtgttt taagttctgt agttcc atg aca tca          55
                                                    Met Thr Ser
                                                       -60 ttg ttt gct gtt gtg tta cag aga gag aag gaa cct cac ctg tgg ctc       103
Leu Phe Ala Val Val Leu Gln Arg Glu Lys Glu Pro His Leu Trp Leu
        -55                 -50                 -45 agc tca ccc cac atc cgt ttc tca tta cgt gta aat aaa ctg tca gag       151
Ser Ser Pro His Ile Arg Phe Ser Leu Arg Val Asn Lys Leu Ser Glu
    -40                 -35                 -30 ctg atg tta cag ctt tta cag ttt aaa gca ttc ccc tcg tct cta gtt       199
Leu Met Leu Gln Leu Leu Gln Phe Lys Ala Phe Pro Ser Ser Leu Val
-25                 -20                 -15                 -10 cct ttt ttc ttg ttt aca tgt ttt ggg cac ttt ccc tca ttc acc acc       247
Pro Phe Phe Leu Phe Thr Cys Phe Gly His Phe Pro Ser Phe Thr Thr
                -5                   1                   5 ttc cag ggc ttc ata gaa aat aac ttg tta caa aat cag ttc aat tct       295
Phe Gln Gly Phe Ile Glu Asn Asn Leu Leu Gln Asn Gln Phe Asn Ser
        10                  15                  20 aat gtg gac ata gtg gca tgt tca taattagacc catataggg acactgagct       349
Asn Val Asp Ile Val Ala Cys Ser
    25                  30 ttaaatcgtt gattctaaac tctatacatt aaaaaaattc agcccaggcc cctcaaagcc    409
tgaraaaatt taatttgctc ttaatttaat gttccaaaac tcactcttgg aaaaatgcct    469
gttggaaaac tacaggtggg tcacatgtkg gggctgtctc cgtgacactc aggattccag    529
tcaraaccta atcctcatat ctattgccta caaaaataga ccaagaatgt tgctgctctt    589
ttataatcct ttaaatattt aacattcaag ttttctttgt cttaaattca gcctcttcct    649
aaaagcaaaa aaaaaa                                                    666

<210> SEQ ID NO 146
```

```
<211> LENGTH: 1131
<212> TYPE: DNA
<213> ORGANISM: Homo sapiens
<220> FEATURE:
<221> NAME/KEY: CDS
<222> LOCATION: 80..940
<220> FEATURE:
<221> NAME/KEY: sig_peptide
<222> LOCATION: 80..130
<223> OTHER INFORMATION: Von Heijne matrix
      score 3.70000004768372
      seq RIVSAALLAFVQT/HL
<220> FEATURE:
<221> NAME/KEY: polyA_signal
<222> LOCATION: 1101..1106
<220> FEATURE:
<221> NAME/KEY: polyA_site
<222> LOCATION: 1119..1130

<400> SEQUENCE: 146
agttggtggg gctgggggat gagagctgca ccgcgcggga yaagtcgccg gcggcgcccg      60
amggagcaga acagagagc atg gag ctg gag agg atc gtc agt gca gcc ctc     112
                     Met Glu Leu Glu Arg Ile Val Ser Ala Ala Leu
                             -15             -10 ctt gcc ttt gtc cag aca cac ctc ccg gag gcc gac ctc agt ggc ttg     160
Leu Ala Phe Val Gln Thr His Leu Pro Glu Ala Asp Leu Ser Gly Leu
    -5               1               5                      10 gat gag gtc atc ttc tcc tat gtg ctt ggg gtc ctg gag gac ctg ggc     208
Asp Glu Val Ile Phe Ser Tyr Val Leu Gly Val Leu Glu Asp Leu Gly
                 15                  20                  25 ccc tcg ggc cca tca gag gag aac ttc gat atg gag gct ttc act gag     256
Pro Ser Gly Pro Ser Glu Glu Asn Phe Asp Met Glu Ala Phe Thr Glu
         30                  35                  40 atg atg gag gcc tat gtg cct ggc ttc gcc cac atc ccc agg ggc aca     304
Met Met Glu Ala Tyr Val Pro Gly Phe Ala His Ile Pro Arg Gly Thr
             45                  50                  55 ata ggg gac atg atg cag aar ctc tca ggg cag ctg agc gat gcc vgg     352
Ile Gly Asp Met Met Gln Lys Leu Ser Gly Gln Leu Ser Asp Ala Xaa
         60                  65                  70 aac aaa gag aac ctg caa ccg cag aac tct ggt gtc caa ggt cag gtg     400
Asn Lys Glu Asn Leu Gln Pro Gln Asn Ser Gly Val Gln Gly Gln Val
75                   80                  85                  90 ccc atc tcc cca gag ccc ctg cag cgg ccc gaa atg ctc aaa gaa gag     448
Pro Ile Ser Pro Glu Pro Leu Gln Arg Pro Glu Met Leu Lys Glu Glu
                 95                 100                 105 act agg tct tcg gct gct gct gct gca gac acc caa gat gag gca act     496
Thr Arg Ser Ser Ala Ala Ala Ala Ala Asp Thr Gln Asp Glu Ala Thr
            110                 115                 120 ggc gct gag gag gag ctt ctg cca ggg gtg gat gta ctc ctg gag gtg     544
Gly Ala Glu Glu Glu Leu Leu Pro Gly Val Asp Val Leu Leu Glu Val
        125                 130                 135 ttc cct acc tgt tcg gtg gag cag gcc cag tgg gtg ctg gcc aaa gct     592
Phe Pro Thr Cys Ser Val Glu Gln Ala Gln Trp Val Leu Ala Lys Ala
140                 145                 150 cgg ggg gac ttg gaa gaa gct gtg cag atg ctg gta gag gga aag gaa     640
Arg Gly Asp Leu Glu Glu Ala Val Gln Met Leu Val Glu Gly Lys Glu
155                 160                 165                 170 gag ggg cct gca gcc tgg gag ggc ccc aac cag gac ctg ccc aga cgc     688
Glu Gly Pro Ala Ala Trp Glu Gly Pro Asn Gln Asp Leu Pro Arg Arg
                175                 180                 185 ctc aga ggc ccc caa aag gat gag ctg aag tcc ttc atc ctg cag aag     736
Leu Arg Gly Pro Gln Lys Asp Glu Leu Lys Ser Phe Ile Leu Gln Lys
            190                 195                 200
```

```
tac atg atg gtg gat agc gca gag gat cag aag att cac cgg ccc atg      784
Tyr Met Met Val Asp Ser Ala Glu Asp Gln Lys Ile His Arg Pro Met
        205                 210                 215 gct ccc aag gag gcc ccc aag aag ctg atc cga tac atc gac aac cag      832
Ala Pro Lys Glu Ala Pro Lys Lys Leu Ile Arg Tyr Ile Asp Asn Gln
    220                 225                 230 gta gtg agc acc aaa ggg gag cga ttc aaa gat gtg cgg aac cct gag      880
Val Val Ser Thr Lys Gly Glu Arg Phe Lys Asp Val Arg Asn Pro Glu
235                 240                 245                 250 gcc gag gag atg aag gcc aca tac atc aac ctc aag cca gcc aga aag      928
Ala Glu Glu Met Lys Ala Thr Tyr Ile Asn Leu Lys Pro Ala Arg Lys
                255                 260                 265 tac cgc ttc cat tgaggcactc gccggactct gcccgagcct tctaggctca          980
Tyr Arg Phe His
            270 gatcccagag ggatgcagga gccctatacc cctacacagg ggcccctaa ctcctgtccc    1040 ccttctctac tcctttgctc catagtgtta acctactctc ggagctgcct ccatgggcac   1100 agtaaaggtg gcccaaggaa aaaaaaaaw t                                   1131

<210> SEQ ID NO 147
<211> LENGTH: 475
<212> TYPE: DNA
<213> ORGANISM: Homo sapiens
<220> FEATURE:
<221> NAME/KEY: CDS
<222> LOCATION: 146..457
<220> FEATURE:
<221> NAME/KEY: sig_peptide
<222> LOCATION: 146..292
<223> OTHER INFORMATION: Von Heijne matrix
      score 5.19999980926514
      seq CFLCLYPIPLCTS/HP
<220> FEATURE:
<221> NAME/KEY: polyA_signal
<222> LOCATION: 442..447
<220> FEATURE:
<221> NAME/KEY: polyA_site
<222> LOCATION: 465..475

<400> SEQUENCE: 147
attgtaacaa acagtaccaa tttattttgg ccgtgggttt ttgcttttttt tccagttgat    60 gactttgtga acattcccag gtattggagc ctctgtggcc ttaaatgtgg ctcagtggag   120
ggagacccag catagccagg ccagt atg gag cac ctc acg cac agc tct cag     172
                            Met Glu His Leu Thr His Ser Ser Gln
                                                        -45 aag ctg cag gcg gac gaa cat ctg acc aaa gag gtg tgg tcg agg ctc     220
Lys Leu Gln Ala Asp Glu His Leu Thr Lys Glu Val Trp Ser Arg Leu
-40                 -35                 -30                 -25 ctg aaa gag aaa ggg cct gct ggt ctc atc ctc tgc ttc ctt tgc ctt     268
Leu Lys Glu Lys Gly Pro Ala Gly Leu Ile Leu Cys Phe Leu Cys Leu
                -20                 -15                 -10 tac cct ata cct ctc tgc acg tcc cac ccc gtt tkg ctg tgt gcy cac     316
Tyr Pro Ile Pro Leu Cys Thr Ser His Pro Val Xaa Leu Cys Ala His
            -5                  1                   5 ccc cag gat gtg tac ccg gtt gta gta aga gct gaa atc cat gct gag     364
Pro Gln Asp Val Tyr Pro Val Val Val Arg Ala Glu Ile His Ala Glu
        10                  15                  20 ctg tac cag gaa ctt gca tat cta aaa aca gaa act gag tca ctg gcc     412
Leu Tyr Gln Glu Leu Ala Tyr Leu Lys Thr Glu Thr Glu Ser Leu Ala
25                  30                  35                  40 cat ctc ttt gct ctt gtg ccc cag gcc aaa ata aag aat aga gtg         457
His Leu Phe Ala Leu Val Pro Gln Ala Lys Ile Lys Asn Arg Val
```

```
                           45              50              55
taragtgaaa aaaaaaaa                                                 475

<210> SEQ ID NO 148
<211> LENGTH: 949
<212> TYPE: DNA
<213> ORGANISM: Homo sapiens
<220> FEATURE:
<221> NAME/KEY: CDS
<222> LOCATION: 100..351
<220> FEATURE:
<221> NAME/KEY: sig_peptide
<222> LOCATION: 100..207
<223> OTHER INFORMATION: Von Heijne matrix
      score 4.19999980926514
      seq CLAVSWEAAGCHG/AG
<220> FEATURE:
<221> NAME/KEY: polyA_site
<222> LOCATION: 940..949
<220> FEATURE:
<221> NAME/KEY: misc_feature
<222> LOCATION: 745
<223> OTHER INFORMATION: n=a, g, c or t

<400> SEQUENCE: 148
aaaggaatac tgacagataa ggccggaaac aaaactgatg gcttgaaaaa catttttatg      60
gaatgtattt actatcattt tgttttacta tagaggtag atg gga ctc tta act       114
                                         Met Gly Leu Leu Thr
                                             -35 ttt ggg tac att gaa amc akg ckg aaa act gaa cac aat cct gat cat      162
Phe Gly Tyr Ile Glu Xaa Xaa Xaa Lys Thr Glu His Asn Pro Asp His
    -30                 -25                 -20 cac tcc tgc ctg gct gtc tcc tgg gag gct gcc ggg tgc cac gga gct      210
His Ser Cys Leu Ala Val Ser Trp Glu Ala Ala Gly Cys His Gly Ala
-15                 -10                  -5                   1 ggg aca cag cag agc ccg cta ggt gtt gca ggg ccc tgg agg cca agg      258
Gly Thr Gln Gln Ser Pro Leu Gly Val Ala Gly Pro Trp Arg Pro Arg
                5                  10                  15 cca ccc tgt gtg ggg tcc ctg ttg gca gcc agg tcc cta cac aaa caa      306
Pro Pro Cys Val Gly Ser Leu Leu Ala Ala Arg Ser Leu His Lys Gln
            20                  25                  30 gta atc ctg ttt ggc ctc cta ggt ttt gca tat gac cac gca gcc          351
Val Ile Leu Phe Gly Leu Leu Gly Phe Ala Tyr Asp His Ala Ala
        35                  40                  45 taatttgggg tgtaggggaa cctctgctgg cccttgctcc tttgtatgtt gggtgacttt    411
aatggctggc cacataccc tttctcccag ctactcattc actgacttgg gtaagttcta     471
gcacaatgcg cacttagaaa cagaatgtga cacatcaaca ttaacttttc ctgaaaagaa    531
cagtttgcct aacatggacc cmaaagaagc ttggaattta taagactttc ctttataaga    591
tatagtgggg gttttttttgg gtggaggggg gttgttttt gttttttgtt ttcaagacag    651
agtctcgctc agttgtccag gctggartgt aktggcatga tctcggctca ctgcarcctc    711
tgcctcccag gttcatgcca ttctcctgcc tcancctccc gagtagctgg gactacaggt    771
gtctgccgcc acgcctggct aattttttg tattttagt agagacgggg tttcaccatg      831
ttggtcagga tggtctcgat ttcctgacct cgtgatccgc ctgtctcggc ctcccaaagt    891
gctgggatta caggcgtgag ccaccacgcc tggcctataa gatacggyaa aaaaaaa      949

<210> SEQ ID NO 149
<211> LENGTH: 940
<212> TYPE: DNA
<213> ORGANISM: Homo sapiens
```

<220> FEATURE:
<221> NAME/KEY: CDS
<222> LOCATION: 177..569
<220> FEATURE:
<221> NAME/KEY: sig_peptide
<222> LOCATION: 177..236
<223> OTHER INFORMATION: Von Heijne matrix
    score 11.1999998092651
    seq AFLLLVALSYTLA/RD
<220> FEATURE:
<221> NAME/KEY: polyA_site
<222> LOCATION: 931..939
<220> FEATURE:
<221> NAME/KEY: misc_feature
<222> LOCATION: 482
<223> OTHER INFORMATION: n=a, g, c or t

<400> SEQUENCE: 149

| | |
|---|---|
| agaagataat cacttgggga aaggaaggtt cgtttctgag ttagcaacaa gtaaatgcag | 60 |
| cactagtggg tgggattgag gtatgccctg gtgcataaat agagactcag ctgtgctggc | 120 |
| acactcagaa gcttggaccg catcctagcc gccgactcac acaaggcaga gttgcc atg | 179 |
|                                                                                       Met<br>                                                                                      -20 | |
| gaa aaa att cca gtg tca gca ttc ttg ctc ctt gtg gcc ctc tcc tac<br>Glu Lys Ile Pro Val Ser Ala Phe Leu Leu Leu Val Ala Leu Ser Tyr<br>         -15                        -10                       -5 | 227 |
| act ctg gcc aga gat acc aca gtc aaa cct gga gcc aaa aag gac aca<br>Thr Leu Ala Arg Asp Thr Thr Val Lys Pro Gly Ala Lys Lys Asp Thr<br>          1                       5                              10 | 275 |
| aag gac tct cga ccc aaa ctg ccc cag acc ctc tcc aga ggt tgg ggt<br>Lys Asp Ser Arg Pro Lys Leu Pro Gln Thr Leu Ser Arg Gly Trp Gly<br> 15                    20                        25 | 323 |
| gac caa ctc atc tgg aca car aca tat gaa raa rct cta twt aaa tcc<br>Asp Gln Leu Ile Trp Thr Gln Thr Tyr Glu Xaa Xaa Leu Xaa Lys Ser<br>30               35                       40                   45 | 371 |
| aar aca agc aac aaa ccc ttg atg att att cat cac ttg gat gad tgc<br>Lys Thr Ser Asn Lys Pro Leu Met Ile Ile His His Leu Asp Xaa Cys<br>              50                       55                       60 | 419 |
| cca cac agt caa gct tta aaa aaa ktg ttt gct gaa aat aaa raa atc<br>Pro His Ser Gln Ala Leu Lys Lys Xaa Phe Ala Glu Asn Lys Xaa Ile<br>             65                       70                       75 | 467 |
| cag aaa ttg gca ran cag ttt gtc cyc ctc aat ctg gtt tat gaa aca<br>Gln Lys Leu Ala Xaa Gln Phe Val Xaa Leu Asn Leu Val Tyr Glu Thr<br>        80                       85                       90 | 515 |
| act gac aaa cac ctt tct cct gat ggc caa tat ktc ccc cmg gat tat<br>Thr Asp Lys His Leu Ser Pro Asp Gly Gln Tyr Xaa Pro Xaa Asp Tyr<br> 95                    100                        105 | 563 |
| gtt tgt tgacccatct ctgacagtta gagccgatat cactggaaga tattcaaayc<br>Val Cys<br>110 | 619 |
| gtctctatgc ttacgaacct gcagatacag ctctgttgct tgacaacatg aagaaagctc | 679 |
| tcaagttgct gaagactgaa ttgtaaagaa aaaaatctc caagcccttc tgtctgtcag | 739 |
| gccttgagac ttgaaaccag aagaagtgtg agaagactgg ctagtgtgga agcatagtga | 799 |
| acacactgat taggttatgg tttaatgtta caacaactat tttttaagaa aaacaagttt | 859 |
| tagaaatttg gttcaagtg tacatgtgtg aaaacaatat tgtatactac catagtgagc | 919 |
| catgattttc taaaaaaaaa a | 940 |

<210> SEQ ID NO 150
<211> LENGTH: 887
<212> TYPE: DNA

```
<213> ORGANISM: Homo sapiens
<220> FEATURE:
<221> NAME/KEY: CDS
<222> LOCATION: 67..459
<220> FEATURE:
<221> NAME/KEY: sig_peptide
<222> LOCATION: 67..135
<223> OTHER INFORMATION: Von Heijne matrix
      score 5.19999980926514
      seq IGVGLYLLASAAA/FY
<220> FEATURE:
<221> NAME/KEY: polyA_signal
<222> LOCATION: 856..861
<220> FEATURE:
<221> NAME/KEY: polyA_site
<222> LOCATION: 875..887

<400> SEQUENCE: 150
agcggcggca tccgggacgg cgggcgggct ggccaccacg ggacaggaag gcacagagca       60 tggaga atg atg aac ttc cgt cag cgg atg gga tgg att gga gtg gga         108
       Met Met Asn Phe Arg Gln Arg Met Gly Trp Ile Gly Val Gly
           -20             -15                 -10 ttg tat ctg tta gcc agt gca gca gca ttt tac tat gtt ttt gaa atc        156
Leu Tyr Leu Leu Ala Ser Ala Ala Ala Phe Tyr Tyr Val Phe Glu Ile
            -5                  1                   5 agt gag act tac aac agg ctg gcc ttg gaa cac att caa cag cac cct        204
Ser Glu Thr Tyr Asn Arg Leu Ala Leu Glu His Ile Gln Gln His Pro
        10                  15                  20 ggg gag ccc ctt gaa gga acc aca tgg aca cac tcc ttg aaa gct caa        252
Gly Glu Pro Leu Glu Gly Thr Thr Trp Thr His Ser Leu Lys Ala Gln
    25                  30                  35 tta ctc tcc ttg cct ttt tgg gtg tgg aca gtt att ttt ctg gta cct        300
Leu Leu Ser Leu Pro Phe Trp Val Trp Thr Val Ile Phe Leu Val Pro
40                  45                  50                  55 tac tta car atk ttt ttg ttc cta tac tct tgt aca aaa vct gat ccc        348
Tyr Leu Gln Xaa Phe Leu Phe Leu Tyr Ser Cys Thr Lys Xaa Asp Pro
                60                  65                  70 aaa aca gtg ggc tac tgt wtc atc cct ata tgc ttg gca rtt att tsc        396
Lys Thr Val Gly Tyr Cys Xaa Ile Pro Ile Cys Leu Ala Xaa Ile Xaa
            75                  80                  85 aat cgc cac cag gat ttt gtc aag gct tct aat caa atc agc aaa cta        444
Asn Arg His Gln Asp Phe Val Lys Ala Ser Asn Gln Ile Ser Lys Leu
        90                  95                  100 caa ctg att gac acg taaaatcagt caccgttttt tccctacgat tacaaaactg       499
Gln Leu Ile Asp Thr
    105 ccagtcctat atggagtctg atcacaagac tgcagtttct tcacagatct caggaagttg      559 tcgtggggca gaggcttttt aaaaacatgt gattagggag ctatctttat ctgaataata      619 acgaattttt aggtaaaacc tgagatagag tactacaaaa tcatgttgat gacttcagat      679 tttggaagtt aaatcatgtc tgttatttgc attcttttaga aacttgacta agtacctgaa     739 ttcatatttc tattctactg tgcaacatag tgatgattca gaattttttc ctttggggaa      799 aaaaatgaat atgaacattt ccattgtgtt aagtgtaaaa aggtccagka catgatcata      859 aaatttaaat tttatacaaa aaaaaaaa                                         887

<210> SEQ ID NO 151
<211> LENGTH: 2010
<212> TYPE: DNA
<213> ORGANISM: Homo sapiens
<220> FEATURE:
<221> NAME/KEY: CDS
<222> LOCATION: 65..1069
```

```
<220> FEATURE:
<221> NAME/KEY: sig_peptide
<222> LOCATION: 65..112
<223> OTHER INFORMATION: Von Heijne matrix
      score 12.5
      seq FVVLLALVAGVLG/NE
<220> FEATURE:
<221> NAME/KEY: polyA_signal
<222> LOCATION: 1978..1983
<220> FEATURE:
<221> NAME/KEY: polyA_site
<222> LOCATION: 1999..2010

<400> SEQUENCE: 151
atgtcgcccg tgtcccgccg gcccgttccg tgtcgccccg cagtgytgcg gccgccgckk        60 cacc atg gct gtg ttt gtc gtg ctc ctg gcg ttg gtg gcg ggt gtt ttg       109
     Met Ala Val Phe Val Val Leu Leu Ala Leu Val Ala Gly Val Leu
         -15             -10                 -5 ggg aac gag ttt agt ata tta aaa tca cca ggg tct gtt gtt ttc cga       157
Gly Asn Glu Phe Ser Ile Leu Lys Ser Pro Gly Ser Val Val Phe Arg
  1               5                  10                  15 aat gga aat tgg cct ata cca gga gag cgg atc cca gac gtg gct gca       205
Asn Gly Asn Trp Pro Ile Pro Gly Glu Arg Ile Pro Asp Val Ala Ala
             20                  25                  30 ttg tcc atg ggc ttc tct gtg aaa gaa gac ctt tct tgg cca gga ctc       253
Leu Ser Met Gly Phe Ser Val Lys Glu Asp Leu Ser Trp Pro Gly Leu
         35                  40                  45 gca gtg ggt aac ctg ttt cat cgt cct cgg gct agc gtc atg gtg atg       301
Ala Val Gly Asn Leu Phe His Arg Pro Arg Ala Ser Val Met Val Met
     50                  55                  60 gtg aag gga gtt aac aac tmc cct cta ccc cca ggc tgt gtc att tcg       349
Val Lys Gly Val Asn Asn Xaa Pro Leu Pro Pro Gly Cys Val Ile Ser
 65                  70                  75 tac cct ttg gag aat gca gtt cct ttt agt ctt gac agt gtt gca aat       397
Tyr Pro Leu Glu Asn Ala Val Pro Phe Ser Leu Asp Ser Val Ala Asn
 80                  85                  90                  95 tcc att cac tcc tta ttt tct gag gaa act cct gtt gtt ttg cag ttg       445
Ser Ile His Ser Leu Phe Ser Glu Glu Thr Pro Val Val Leu Gln Leu
                100                 105                 110 gct ccc agt gag gaa aga gtg tat atg gta ggg aag gcm aac tca gtg       493
Ala Pro Ser Glu Glu Arg Val Tyr Met Val Gly Lys Ala Asn Ser Val
            115                 120                 125 tgg aar acc ttt cag tca ctt gcg cca gct ccg kta atc rcc tgt ttc       541
Trp Lys Thr Phe Gln Ser Leu Ala Pro Ala Pro Xaa Ile Xaa Cys Phe
        130                 135                 140 aag aaa act ctg ttc tca gtt cac tcc ccc ycc att cma ctg agt agg       589
Lys Lys Thr Leu Phe Ser Val His Ser Pro Xaa Ile Xaa Leu Ser Arg
    145                 150                 155 aac aat gaa gtt gac cyg ctc ttt ctt tct gaa ctg caa gtg cta cat       637
Asn Asn Glu Val Asp Xaa Leu Phe Leu Ser Glu Leu Gln Val Leu His
160                 165                 170                 175 gat att tca agc ttg ctg tct cgt cat aag cat cta gcc aag gat cat       685
Asp Ile Ser Ser Leu Leu Ser Arg His Lys His Leu Ala Lys Asp His
                180                 185                 190 tct cct gat tta tat tca ctg gag ctg gca ggt ttg gat gaa att ggg       733
Ser Pro Asp Leu Tyr Ser Leu Glu Leu Ala Gly Leu Asp Glu Ile Gly
            195                 200                 205 aag cgt tat ggg gaa gac tct gaa caa ttc aga gat gct tct aag atc       781
Lys Arg Tyr Gly Glu Asp Ser Glu Gln Phe Arg Asp Ala Ser Lys Ile
        210                 215                 220 ctt gtt gac gct ctg caa aag ttt gca gat gac atg tac agt ctt tat       829
Leu Val Asp Ala Leu Gln Lys Phe Ala Asp Asp Met Tyr Ser Leu Tyr
```

|  |  |  |  |  |  |  |  |  |  |  |  |  |  |  |  |
|---|---|---|---|---|---|---|---|---|---|---|---|---|---|---|---|
|  |  | 225 |  |  |  | 230 |  |  |  |  | 235 |  |  |  |  |
| ggt | ggg | aat | gca | gtg | gta | gag | tta | gtc | act | gtc | aag | tca | ttt | gac | acc |
| Gly | Gly | Asn | Ala | Val | Val | Glu | Leu | Val | Thr | Val | Lys | Ser | Phe | Asp | Thr |
| 240 |  |  |  |  | 245 |  |  |  |  | 250 |  |  |  |  | 255 |

877 tcc ctc att agg aag aca agg act atc ctt gag gca aaa caa gcg aag    925
Ser Leu Ile Arg Lys Thr Arg Thr Ile Leu Glu Ala Lys Gln Ala Lys
            260                 265                 270 aac cca gca agt ccc tat aac ctt gca tat aag tat aat ttt gaa tat    973
Asn Pro Ala Ser Pro Tyr Asn Leu Ala Tyr Lys Tyr Asn Phe Glu Tyr
        275                 280                 285 tcc gtg gtt ttc aac atg gta ctt tgg ata atg atc gcc ttg gcc ttg   1021
Ser Val Val Phe Asn Met Val Leu Trp Ile Met Ile Ala Leu Ala Leu
        290                 295                 300 gct gtg att atc acc tct tac aat att tgg aac atg gaa tcc tgg ata   1069
Ala Val Ile Ile Thr Ser Tyr Asn Ile Trp Asn Met Glu Ser Trp Ile
    305                 310                 315 tgatagcatc atttatagga tgacaaacca gaagattcgg aatggattga atgttacctg   1129
tgccagaatt akaaaagggg gttggaaatt ggctgttttg ttaaaatata tcttttagtg   1189
tgctttaaag tagatagtat actttacatt tataaaaaaa aatcaaattt tgttctttat   1249
tttgtgtgtg cctgtgatgt ttttctagag tgaattatag tattgacgtg aatcccactg   1309
tggtatagat tccataatat gcttgaatat tatgatatag ccatttaata acattgattt   1369
cattctgttt aatgaatttg gaaatatgca ctgaaagaaa tgtaaaacat ttagaatagc   1429
tcgtgttatg gaaaaagtg cactgaattt attagacaaa cttacgaatg cttaacttct   1489
ttacacagca taggtgaaaa tcatatttgg gctattgtat actatgaaca atttgtaaat   1549
gtcttaattt gatgtaaata actctgaaac aagagaaaag gtttttaact tagagtagcc   1609
ctaaaatatg gatgtgctta tataatcgct tagttttgga actgtatctg agtaacagag   1669
gacagctgtt ttttaacccct cttctgcaag tttgttgacc tacatgggct aatatggata   1729
ctaaaaatac tacattgatc taagaagaaa ctagccttgt ggagtatata gatgcttttc   1789
attatacaca caaaaatccc tgagggacat tttgaggcat gaatataaaa catttttatt   1849
tcagtaactt ttcccectgt gtaagttact atggtttgtg gtacaacttc attctataga   1909
atattaagtg gaagtgggtg aattctactt tttatgttgg agtggaccaa tgtctatcaa   1969
gagtgacaaa taaagttaat gatgattcca aaaaaaaaa a                        2010

<210> SEQ ID NO 152
<211> LENGTH: 387
<212> TYPE: DNA
<213> ORGANISM: Homo sapiens
<220> FEATURE:
<221> NAME/KEY: CDS
<222> LOCATION: 70..321
<220> FEATURE:
<221> NAME/KEY: sig_peptide
<222> LOCATION: 70..234
<223> OTHER INFORMATION: Von Heijne matrix
    score 4.09999990463257
    seq AVCAALLASHPTA/EV
<220> FEATURE:
<221> NAME/KEY: polyA_signal
<222> LOCATION: 364..369
<220> FEATURE:
<221> NAME/KEY: polyA_site
<222> LOCATION: 375..387

<400> SEQUENCE: 152
agaaatcgta ggacttccga aagcagcggc ggcgtttgct tcactgcttg gaagtgtgag      60

-continued

```
tgcgcgaag atg cga aag gtg gtt ttr att acc ggg gct agc agt ggc att        111
         Met Arg Lys Val Val Leu Ile Thr Gly Ala Ser Ser Gly Ile
         -55                 -50                 -45 ggc ctg gcc ctc tgc aag cgg ctg ctg gcg gaa gat gat gag ctt cat          159
Gly Leu Ala Leu Cys Lys Arg Leu Leu Ala Glu Asp Asp Glu Leu His
    -40             -35                 -30 ctg tgt ttg gcg tgc agg aat atg agc aag gca gaa gct gtc tgt gct          207
Leu Cys Leu Ala Cys Arg Asn Met Ser Lys Ala Glu Ala Val Cys Ala
-25             -20                 -15                 -10 gct ctg ctg gcc tct cac ccc act gct gag gtc acc att gtc cag gtg          255
Ala Leu Leu Ala Ser His Pro Thr Ala Glu Val Thr Ile Val Gln Val
                -5                  1                   5 gat gtc agc aac ctg cag tca ttc ttc cgg gcc tcc aag gaa ctt aag          303
Asp Val Ser Asn Leu Gln Ser Phe Phe Arg Ala Ser Lys Glu Leu Lys
        10                  15                  20 caa agg atg atc tct tgc tgatggattt tttttctcat gtgattgtgc                 351
Gln Arg Met Ile Ser Cys
        25 ascataacac ttaataaaat aagaaaaaaa aaaaaa                                  387

<210> SEQ ID NO 153
<211> LENGTH: 983
<212> TYPE: DNA
<213> ORGANISM: Homo sapiens
<220> FEATURE:
<221> NAME/KEY: CDS
<222> LOCATION: 38..877
<220> FEATURE:
<221> NAME/KEY: sig_peptide
<222> LOCATION: 38..91
<223> OTHER INFORMATION: Von Heijne matrix
      score 7.40000009536743
      seq GWLVLCVLAISLA/SM
<220> FEATURE:
<221> NAME/KEY: polyA_signal
<222> LOCATION: 947..952
<220> FEATURE:
<221> NAME/KEY: polyA_site
<222> LOCATION: 974..983

<400> SEQUENCE: 153
aatccagtyg gasttgacaa caggaggcag aggcatc atg gag ggt ccc cgg gga         55
                                        Met Glu Gly Pro Arg Gly
                                                    -15 tgg ctg gtg ctc tgt gtg ctg gcc ata tcg ctg gcc tct atg gtg acc          103
Trp Leu Val Leu Cys Val Leu Ala Ile Ser Leu Ala Ser Met Val Thr
        -10                 -5                  1 gag gac ttg tgc cga gca cca gac ggg aag aaa ggg gag gca gga aga          151
Glu Asp Leu Cys Arg Ala Pro Asp Gly Lys Lys Gly Glu Ala Gly Arg
5                   10                  15                  20 cct ggc aga cgg ggg cgg cca ggc ctc aag ggg gag caa ggg gag ccg          199
Pro Gly Arg Arg Gly Arg Pro Gly Leu Lys Gly Glu Gln Gly Glu Pro
            25                  30                  35 ggg gcc cct ggc atc cgg aca ggc atc caa ggc ctt aaa gga gac cag          247
Gly Ala Pro Gly Ile Arg Thr Gly Ile Gln Gly Leu Lys Gly Asp Gln
        40                  45                  50 ggg gaa cct ggg ccc tct gga aac ccc ggc aag gtg ggc tac cca ggg          295
Gly Glu Pro Gly Pro Ser Gly Asn Pro Gly Lys Val Gly Tyr Pro Gly
    55                  60                  65 ccc agc ggc ccc ctc gga gcc cgt ggc atc ccg gga att aaa ggc acc          343
Pro Ser Gly Pro Leu Gly Ala Arg Gly Ile Pro Gly Ile Lys Gly Thr
70                  75                  80 aag ggc agc cca gga aac atc aag gac cag ccg agg cca gcc ttc tcc          391
Lys Gly Ser Pro Gly Asn Ile Lys Asp Gln Pro Arg Pro Ala Phe Ser
```

```
85                90                95               100
gcc att cgg cgg aac ccc cca atg ggg ggc aac gtg gtc atc ttc gac    439
Ala Ile Arg Arg Asn Pro Pro Met Gly Gly Asn Val Val Ile Phe Asp
                105                110                115 acg gtc atc acc aac cag gaa gaa ccg tac cag aac cac tcc ggc cga    487
Thr Val Ile Thr Asn Gln Glu Glu Pro Tyr Gln Asn His Ser Gly Arg
        120                125                130 ttc gtc tgc act gta ccc gct act act act tca cct tcc agg tgc tgt    535
Phe Val Cys Thr Val Pro Ala Thr Thr Thr Ser Pro Ser Arg Cys Cys
            135                140                145 ccc agt ggg aaa tct gcc tgt cca tcg tct cct cct caa ggg gcc agg    583
Pro Ser Gly Lys Ser Ala Cys Pro Ser Ser Pro Gln Gly Ala Arg
        150                155                160 tcc gac gct ccc tgg gct tct gtg aca cca cca aca agg ggc tct tcc    631
Ser Asp Ala Pro Trp Ala Ser Val Thr Pro Pro Thr Arg Gly Ser Ser
165                170                175                180 agg tgg tgt cag ggg gca tgg tgc ttc agc tgc agc agg gtg acc agg    679
Arg Trp Cys Gln Gly Ala Trp Cys Phe Ser Cys Ser Arg Val Thr Arg
            185                190                195 tct ggg ttg aaa aag acc cca aaa agg gtc aca ttt acc agg gct ctg    727
Ser Gly Leu Lys Lys Thr Pro Lys Arg Val Thr Phe Thr Arg Ala Leu
        200                205                210 agg ccg aca gcg tct tca gcg gct tcc tca tct tcc cat ctg cct gag    775
Arg Pro Thr Ala Ser Ser Ala Ala Ser Ser Ser His Leu Pro Glu
        215                220                225 cca ggg aag gac ccc ctc ccc cac cca cct ctc tgg ctt cca tgc tcc    823
Pro Gly Lys Asp Pro Leu Pro His Pro Pro Leu Trp Leu Pro Cys Ser
        230                235                240 gcc tgt aaa atg ggg gcg cta ttg ctt cag ctg ctg aag gga ggg ggc    871
Ala Cys Lys Met Gly Ala Leu Leu Leu Gln Leu Leu Lys Gly Gly Gly
245                250                255                260 tgg ctc tgagagcccc aggactggct gccccgtgac acatgctcta agaagctcgt    927
Trp Leu ttcttagacc tcttcctgga ataaacatct gtgtctgtgt ctgctgaaaa aaaaaa      983

<210> SEQ ID NO 154
<211> LENGTH: 1614
<212> TYPE: DNA
<213> ORGANISM: Homo sapiens
<220> FEATURE:
<221> NAME/KEY: CDS
<222> LOCATION: 51..470
<220> FEATURE:
<221> NAME/KEY: sig_peptide
<222> LOCATION: 51..203
<223> OTHER INFORMATION: Von Heijne matrix
      score 5.80000019073486
      seq AVGLFPAPTECFA/RV
<220> FEATURE:
<221> NAME/KEY: polyA_signal
<222> LOCATION: 1585..1590
<220> FEATURE:
<221> NAME/KEY: polyA_site
<222> LOCATION: 1604..1614

<400> SEQUENCE: 154
ataagcctgt ggttgatgga aattcacaaa gtgaggcatt atcactggaa atg aga       56
                                                         Met Arg
                                                             -50 aag gat ccg agc ggg gct ggc ctc tgg ctt cac agt ggc ggc cca gtg    104
Lys Asp Pro Ser Gly Ala Gly Leu Trp Leu His Ser Gly Gly Pro Val
        -45                -40                -35 ctt cca tat gtg aga gaa tca gta aga aga aat cca gcc tca gca gcc    152
```

-continued

```
Leu Pro Tyr Val Arg Glu Ser Val Arg Arg Asn Pro Ala Ser Ala Ala
        -30              -25              -20 act ccg agc aca gcc gtg ggt ttg ttc cct gct cca aca gag tgt ttt       200
Thr Pro Ser Thr Ala Val Gly Leu Phe Pro Ala Pro Thr Glu Cys Phe
        -15              -10               -5 gct cgg gtg tcc tgc agt ggt gtt gaa gct ctg ggg cgg cga gac tgg       248
Ala Arg Val Ser Cys Ser Gly Val Glu Ala Leu Gly Arg Arg Asp Trp
  1               5              10                  15 ctg gga gga ggg ccc agg gcc cac tgr msg gcv aca gag gmc agt gcc       296
Leu Gly Gly Gly Pro Arg Ala His Xaa Xaa Ala Thr Glu Xaa Ser Ala
                20              25                  30 cca aag gag agc ctc ggg tgt cac gac tgc cac gcc atc aaa aag tgc       344
Pro Lys Glu Ser Leu Gly Cys His Asp Cys His Ala Ile Lys Lys Cys
             35              40              45 cgg aaa tgg gaa gtt ttc agg atg acc cac caa gtg ctt ttc cca agg       392
Arg Lys Trp Glu Val Phe Arg Met Thr His Gln Val Leu Phe Pro Arg
          50              55              60 gtc tgg gct ctg agt tgg aac ccg ctt gcc tgc act cca tcc tgt ctg       440
Val Trp Ala Leu Ser Trp Asn Pro Leu Ala Cys Thr Pro Ser Cys Leu
       65              70              75 caa cgc tgc aca tgt atc ccg aak tgc tcc tgagtgagga racaaaacgc         490
Gln Arg Cys Thr Cys Ile Pro Xaa Cys Ser
80                   85 atktyccttg accgtytaaa gcccatgttt ycaaagcaaa caatavaatt caaraarrtg     550
cttaaaagca cctcaratgg tckgcaaata acactgggt tactggctct gcaaccttt       610 gaattavcaa atacattatg ccatagttaa ggtacaagca gaacaatacc aatagattaa     670
ttttaagagt tgtcttagaa tgatttcttt cgcataaagt ctggatgcaa actgtgcagc    730
ccttaggtmc ctgctgtagt tttgtacgac ctggcagact taaagtaaat tgagtttaaa    790
ttcaaagcca gttgatgcgg aaggaacttt tttggcatgt gttaaattgt gctttaaaag    850
acatataaag aattgggaaa catttcagga gacgatcata gcctgtataa ataccagatt    910
agaacatacg gatttaccat gaagttctgt cttcaacatc cattctaaag ggctactgtc    970
ccaaatcctg tgtgtccttt tgacttgtct gatcacccaa tggaagtgga tacttgtaaa   1030
gtctacacca ctgtacttgg cgttaaatct tgctgaattc gtggtaagct gttaccatgt    1090
ctacattttg tagaatgatt ttggtctgca gcaaaattcg atttcacttc tcatacccct    1150
ttccttccac ttgaaatgca atttagacag akgccctgtg gtgaaagttg caatattaag   1210
tttaccttta gaagatccct tctcaaactc agaaccctag cagtgttacc ttaaacaaaa   1270
atgakctcga gaaaaagta gctcagttac agagaagcaa atcgagttat ttcccacata    1330
aaaagtttcc cagattctaa gaattgcagt atcctgtacc ctaaaatttt tcaaggtgac   1390
tcctgttgtc gtctgttgat aactttaata aaggtcattt aaggacataa gtttttaaag   1450
actcccaaag tgaaacttaa acattttcgg gattatcgat tgcatatatc agtttatgct    1510
gtgtgctgaa ttactatgcc atgtgctatt ttagtgtttg gggaaatga aaaataaaat    1570 ttgttcttta gcttaataaa tawgtcttat tttaaaaaaa aaaa                    1614
```

<210> SEQ ID NO 155
<211> LENGTH: 99
<212> TYPE: PRT
<213> ORGANISM: Homo sapiens
<220> FEATURE:
<221> NAME/KEY: SIGNAL
<222> LOCATION: -32...-1
<220> FEATURE:
<221> NAME/KEY: UNSURE
<222> LOCATION: -5,42,58
<223> OTHER INFORMATION: Xaa = any one of the twenty amino acids

<400> SEQUENCE: 155

Met Ala Ala Ala Ala Ser Arg Gly Val Gly Ala Lys Leu Gly Leu
        -30                 -25                 -20

Arg Glu Ile Arg Ile His Leu Cys Gln Arg Ser Xaa Gly Ser Gln Gly
    -15                 -10                  -5

Val Arg Asp Phe Ile Glu Lys Arg Tyr Val Glu Leu Lys Lys Ala Asn
1                5                  10                  15

Pro Asp Leu Pro Ile Leu Ile Arg Glu Cys Ser Asp Val Gln Pro Lys
            20                  25                  30

Leu Trp Ala Arg Tyr Ala Phe Gly Gln Xaa Thr Asn Val Pro Leu Asn
        35                  40                  45

Asn Phe Ser Ala Asp Gln Val Thr Arg Xaa Leu Glu Asn Val Leu Ser
    50                  55                  60

Gly Lys Ala
65

<210> SEQ ID NO 156
<211> LENGTH: 160
<212> TYPE: PRT
<213> ORGANISM: Homo sapiens
<220> FEATURE:
<221> NAME/KEY: SIGNAL
<222> LOCATION: -27..-1
<220> FEATURE:
<221> NAME/KEY: UNSURE
<222> LOCATION: 49,74,75,88,98,104,112,114,120
<223> OTHER INFORMATION: Xaa = any one of the twenty amino acids

<400> SEQUENCE: 156

Met Gln Arg Val Ser Gly Leu Leu Ser Trp Thr Leu Ser Arg Val Leu
        -25                 -20                 -15

Trp Leu Ser Gly Leu Ser Glu Pro Gly Ala Ala Arg Gln Pro Arg Ile
    -10                  -5                   1                   5

Met Glu Glu Lys Ala Leu Glu Val Tyr Asp Leu Ile Arg Thr Ile Arg
                10                  15                  20

Asp Pro Glu Lys Pro Asn Thr Leu Glu Glu Leu Glu Val Val Ser Glu
            25                  30                  35

Ser Cys Val Glu Val Gln Glu Ile Asn Glu Glu Xaa Tyr Leu Val Ile
            40                  45                  50

Ile Arg Phe Thr Pro Thr Val Pro His Cys Ser Leu Ala Thr Leu Ile
    55                  60                  65

Gly Leu Cys Leu Xaa Xaa Lys Leu Gln Arg Cys Leu Pro Phe Lys His
70                  75                  80                  85

Lys Leu Xaa Ile Tyr Ile Ser Glu Gly Thr His Ser Xaa Glu Glu Asp
                90                  95                  100

Ile Asn Xaa Gln Ile Asn Asp Lys Glu Arg Xaa Ala Xaa Ala Met Glu
            105                 110                 115

Asn Pro Xaa Leu Arg Glu Ile Val Glu Gln Cys Val Leu Glu Pro Asp
            120                 125                 130

<210> SEQ ID NO 157
<211> LENGTH: 59
<212> TYPE: PRT
<213> ORGANISM: Homo sapiens
<220> FEATURE:
<221> NAME/KEY: SIGNAL
<222> LOCATION: -22...-1

-continued

```
<400> SEQUENCE: 157

Met Arg Leu Lys Tyr Gln His Thr Gly Ala Val Leu Asp Cys Ala Phe
        -20                 -15                 -10

Tyr Asp Pro Thr His Ala Trp Ser Gly Gly Leu Asp His Gln Leu Lys
     -5                   1                 5                  10

Met His Asp Leu Asn Thr Asp Gln Glu Asn Leu Val Gly Thr Met Met
             15                  20                  25

Pro Leu Ser Asp Val Leu Asn Thr Val His Lys
             30                  35

<210> SEQ ID NO 158
<211> LENGTH: 112
<212> TYPE: PRT
<213> ORGANISM: Homo sapiens
<220> FEATURE:
<221> NAME/KEY: SIGNAL
<222> LOCATION: -48..-1
<220> FEATURE:
<221> NAME/KEY: UNSURE
<222> LOCATION: 48
<223> OTHER INFORMATION: Xaa = any one of the twenty amino acids

<400> SEQUENCE: 158

Met Gln Asp Thr Gly Ser Val Val Pro Leu His Trp Phe Gly Phe Gly
        -45                 -40                 -35

Tyr Ala Ala Leu Val Ala Ser Gly Gly Ile Ile Gly Tyr Val Lys Ala
        -30                 -25                 -20

Gly Ser Val Pro Ser Leu Ala Ala Gly Leu Leu Phe Gly Ser Leu Ala
        -15                 -10                  -5

Gly Leu Gly Ala Tyr Gln Leu Ser Gln Asp Pro Arg Asn Val Trp Val
 1               5                  10                  15

Phe Leu Ala Thr Ser Gly Thr Leu Ala Gly Ile Met Gly Met Arg Phe
             20                  25                  30

Tyr His Ser Gly Lys Phe Met Pro Ala Gly Leu Ile Ala Gly Ala Xaa
             35                  40                  45

Leu Leu Met Val Ala Lys Ile Gly Val Ser Met Phe Asn Arg Pro His
     50                  55                  60

<210> SEQ ID NO 159
<211> LENGTH: 111
<212> TYPE: PRT
<213> ORGANISM: Homo sapiens
<220> FEATURE:
<221> NAME/KEY: SIGNAL
<222> LOCATION: -56..-1
<220> FEATURE:
<221> NAME/KEY: UNSURE
<222> LOCATION: 27,28,43,44,49,50,52,53
<223> OTHER INFORMATION: Xaa = any one of the twenty amino acids

<400> SEQUENCE: 159

Met Gly Gly Asn Gly Ser Thr Cys Lys Pro Asp Thr Glu Arg Gln Gly
    -55                 -50                 -45

Thr Leu Ser Thr Ala Ala Pro Thr Thr Ser Pro Ala Pro Cys Leu Ser
-40                 -35                 -30                 -25

Asn His His Asn Lys Lys His Leu Ile Leu Ala Phe Cys Ala Gly Val
                -20                 -15                 -10

Leu Leu Thr Leu Leu Leu Ile Ala Phe Ile Phe Leu Ile Ile Lys Ser
         -5                   1                   5

Tyr Arg Lys Tyr His Ser Lys Pro Gln Ala Pro Asp Pro His Ser Asp
```

```
              10                  15                  20
Pro Pro Xaa Xaa Leu Ser Ser Ile Pro Gly Glu Ser Leu Thr Tyr Ala
 25                  30                  35                  40

Ser Thr Xaa Xaa Gln Thr Leu Arg Xaa Xaa Glu Xaa Xaa Leu Gly
             45                  50                  55

<210> SEQ ID NO 160
<211> LENGTH: 144
<212> TYPE: PRT
<213> ORGANISM: Homo sapiens
<220> FEATURE:
<221> NAME/KEY: SIGNAL
<222> LOCATION: -77..-1
<220> FEATURE:
<221> NAME/KEY: UNSURE
<222> LOCATION: -65,31,34
<223> OTHER INFORMATION: Xaa = any one of the twenty amino acids

<400> SEQUENCE: 160

Met Ala Ala Ser Lys Val Lys Gln Asp Met Pro Pro Xaa Gly Gly Tyr
        -75                 -70                 -65

Gly Pro Ile Asp Tyr Lys Arg Asn Leu Pro Arg Arg Gly Leu Ser Gly
    -60                 -55                 -50

Tyr Ser Met Leu Ala Ile Gly Ile Gly Thr Leu Ile Tyr Gly His Trp
-45                 -40                 -35                 -30

Ser Ile Met Lys Trp Asn Arg Glu Arg Arg Arg Leu Gln Ile Glu Asp
                -25                 -20                 -15

Phe Glu Ala Arg Ile Ala Leu Leu Pro Leu Leu Gln Ala Glu Thr Asp
            -10                  -5                   1

Arg Arg Thr Leu Gln Met Leu Arg Glu Asn Leu Glu Glu Glu Ala Ile
  5                  10                  15

Ile Met Lys Asp Val Pro Asp Trp Lys Val Gly Xaa Ser Val Xaa His
 20                  25                  30                  35

Thr Thr Arg Trp Val Pro Pro Leu Ile Gly Glu Leu Tyr Gly Leu Arg
                 40                  45                  50

Thr Thr Lys Glu Ala Leu His Ala Ser His Gly Phe Met Trp Tyr Thr
                 55                  60                  65

<210> SEQ ID NO 161
<211> LENGTH: 110
<212> TYPE: PRT
<213> ORGANISM: Homo sapiens
<220> FEATURE:
<221> NAME/KEY: SIGNAL
<222> LOCATION: -18..-1
<220> FEATURE:
<221> NAME/KEY: UNSURE
<222> LOCATION: 48,52,55,59,65
<223> OTHER INFORMATION: Xaa = any one of the twenty amino acids

<400> SEQUENCE: 161

Met Glu Thr Gly Arg Leu Leu Ser Leu Ser Ser Leu Pro Leu Val Leu
            -15                 -10                  -5

Leu Gly Trp Glu Tyr Ser Ser Gln Thr Leu Asn Leu Val Pro Ser Thr
             1                   5                  10

Ser Ile Leu Ser Phe Val Pro Phe Ile Pro Leu His Leu Val Leu Phe
 15                  20                  25                  30

Ala Leu Trp Tyr Leu Pro Val Pro His His Leu Tyr Pro Gln Gly Leu
                 35                  40                  45

Gly Xaa His Ala Ala Xaa Ala Glu Xaa Gly Lys Arg Xaa Glu Gly Gly
                 50                  55                  60
```

```
Thr Gln Xaa Ala Leu Trp Leu Arg Val Gln Pro Ser Cys Pro Ser Pro
        65                  70                  75
Val Cys Leu Glu Pro Val Pro Pro Arg Ser Arg Phe Leu Leu
    80                  85                  90

<210> SEQ ID NO 162
<211> LENGTH: 79
<212> TYPE: PRT
<213> ORGANISM: Homo sapiens
<220> FEATURE:
<221> NAME/KEY: SIGNAL
<222> LOCATION: -36..-1

<400> SEQUENCE: 162

Met Glu Leu Glu Ala Met Ser Arg Tyr Thr Ser Pro Val Asn Pro Ala
    -35                 -30                 -25
Val Phe Pro His Leu Thr Val Val Leu Leu Ala Ile Gly Met Phe Phe
-20                 -15                 -10                  -5
Thr Ala Trp Phe Phe Val Tyr Glu Val Thr Ser Thr Lys Tyr Thr Arg
                 1                   5                  10
Asp Ile Tyr Lys Glu Leu Leu Ile Ser Leu Val Ala Ser Leu Phe Met
            15                  20                  25
Gly Phe Gly Val Leu Phe Leu Leu Trp Val Gly Ile Tyr Val
        30                  35                  40

<210> SEQ ID NO 163
<211> LENGTH: 196
<212> TYPE: PRT
<213> ORGANISM: Homo sapiens
<220> FEATURE:
<221> NAME/KEY: SIGNAL
<222> LOCATION: -34..-1
<220> FEATURE:
<221> NAME/KEY: UNSURE
<222> LOCATION: 81,84,87,131,135,143,156
<223> OTHER INFORMATION: Xaa = any one of the twenty amino acids

<400> SEQUENCE: 163

Met Ser Phe Leu Gln Asp Pro Ser Phe Phe Thr Met Gly Met Trp Ser
                -30                 -25                 -20
Ile Gly Ala Gly Ala Leu Gly Ala Ala Leu Ala Leu Leu Leu Ala
            -15                 -10                  -5
Asn Thr Asp Val Phe Leu Ser Lys Pro Gln Lys Ala Ala Leu Glu Tyr
 1                   5                  10
Leu Glu Asp Ile Asp Leu Lys Thr Leu Glu Lys Glu Pro Arg Thr Phe
15                  20                  25                  30
Lys Ala Lys Glu Leu Trp Glu Lys Asn Gly Ala Val Ile Met Ala Val
                35                  40                  45
Arg Arg Pro Gly Cys Phe Leu Cys Arg Glu Glu Ala Ala Asp Leu Ser
            50                  55                  60
Ser Leu Lys Ser Met Leu Asp Gln Leu Gly Val Pro Leu Tyr Ala Val
            65                  70                  75
Val Lys Xaa His Ile Xaa Thr Glu Xaa Lys Asp Phe Gln Pro Tyr Phe
        80                  85                  90
Lys Gly Glu Ile Phe Leu Asp Gly Lys Lys Phe Tyr Gly Pro Gln
95                  100                 105                 110
Arg Arg Lys Met Met Phe Met Gly Phe Ile Arg Leu Gly Met Trp Tyr
                115                 120                 125
Asn Phe Phe Arg Xaa Trp Asn Gly Xaa Phe Ser Gly Asn Leu Glu Gly
```

```
                    130             135             140
Xaa Gly Phe Ile Leu Gly Gly Ile Phe Val Val Gly Ser Xaa Lys Ala
            145             150             155
Gly His Ser Ser
    160

<210> SEQ ID NO 164
<211> LENGTH: 177
<212> TYPE: PRT
<213> ORGANISM: Homo sapiens
<220> FEATURE:
<221> NAME/KEY: SIGNAL
<222> LOCATION: -18...-1
<220> FEATURE:
<221> NAME/KEY: UNSURE
<222> LOCATION: 32,91,98
<223> OTHER INFORMATION: Xaa = any one of the twenty amino acids

<400> SEQUENCE: 164

Met Leu Leu Cys Leu Leu Thr Pro Leu Phe Phe Met Phe Pro Thr Gly
            -15             -10              -5

Phe Ser Ser Pro Ser Pro Ser Ala Ala Ala Ala Gln Glu Val Arg
        1               5              10

Ser Ala Thr Asp Gly Asn Thr Ser Thr Thr Pro Pro Thr Ser Ala Lys
15              20              25              30

Lys Xaa Lys Leu Asn Ser Ser Ser Ser Ser Ser Asn Ser Ser Asn
            35              40              45

Glu Arg Glu Asp Phe Asp Ser Thr Ser Ser Ser Ser Thr Pro Pro
            50              55              60

Leu Gln Pro Arg Asp Ser Ala Ser Pro Ser Thr Ser Ser Phe Cys Leu
            65              70              75

Gly Val Ser Val Ala Ala Ser Ser His Val Pro Ile Xaa Lys Lys Leu
80              85              90

Arg Phe Glu Xaa Thr Leu Glu Phe Val Gly Phe Asp Ala Lys Met Ala
95              100             105             110

Glu Glu Ser Ser Ser Ser Ser Ser Ser Ser Pro Thr Ala Ala Thr
            115             120             125

Ser Gln Gln Gln Gln Leu Lys Asn Lys Ser Ile Leu Asn Leu Phe Cys
            130             135             140

Gly Phe Gly Ala Ser Cys Lys Arg Pro Ser Gln Ile Phe Tyr His Arg
            145             150             155
Leu

<210> SEQ ID NO 165
<211> LENGTH: 105
<212> TYPE: PRT
<213> ORGANISM: Homo sapiens
<220> FEATURE:
<221> NAME/KEY: SIGNAL
<222> LOCATION: -22...-1

<400> SEQUENCE: 165

Met Gln Gly His Trp Leu Ser Ser Ala Phe Ala Leu Val Trp Leu Trp
        -20             -15             -10

Leu Arg Ser Thr Gly Cys Phe Trp Trp Asp His Trp Leu Cys Lys Ser
    -5              1               5              10

Arg Gln Arg Ala Val Pro Gly Cys Arg Ala Ala Leu Trp Gln Ser Ser
            15              20              25

Arg Pro Gly Cys Leu Pro Ala Val Ser Gly Ser Lys Glu Arg Leu Gly
```

-continued

```
                30              35              40
Phe Pro Ser Tyr Ile Trp Tyr Leu Gly Trp His Tyr Gly Asn Glu Val
        45                  50                  55

Leu Pro Leu Trp Lys Ile His Ala Cys Arg Phe Asn Cys Arg Cys Gln
        60                  65                  70

Phe Ala Asp Gly Arg Gln Ser Trp Ser
75                  80
```

<210> SEQ ID NO 166
<211> LENGTH: 148
<212> TYPE: PRT
<213> ORGANISM: Homo sapiens
<220> FEATURE:
<221> NAME/KEY: SIGNAL
<222> LOCATION: -48..-1
<220> FEATURE:
<221> NAME/KEY: UNSURE
<222> LOCATION: 32,100
<223> OTHER INFORMATION: Xaa = any one of the twenty amino acids

<400> SEQUENCE: 166

```
Met Ile Ala Ile Tyr Gly Lys Asn Phe Cys Val Ser Ala Lys Asn Ala
            -45                 -40                 -35

Phe Met Leu Leu Met Arg Asn Ile Val Arg Val Val Leu Asp Lys
        -30                 -25                 -20

Val Thr Asp Leu Leu Leu Phe Phe Gly Lys Leu Leu Val Val Gly Gly
        -15                 -10                 -5

Val Gly Val Leu Ser Phe Phe Phe Ser Gly Arg Ile Pro Gly Leu
1                5                   10                  15

Gly Lys Asp Phe Lys Ser Pro His Leu Asn Tyr Tyr Trp Leu Pro Xaa
            20                  25                  30

Met Thr Ser Ile Leu Gly Ala Tyr Val Ile Ala Ser Gly Phe Phe Ser
            35                  40                  45

Val Phe Gly Met Cys Val Asp Thr Leu Phe Leu Cys Phe Leu Glu Asp
        50                  55                  60

Leu Glu Arg Thr Thr Ala Pro Trp Thr Ala Leu His Val Gln Glu
65                  70                  75                  80

Leu Leu Lys Ile Leu Gly Lys Lys Asn Glu Ala Pro Pro Asp Asn Lys
                85                  90                  95

Lys Arg Lys Xaa
            100
```

<210> SEQ ID NO 167
<211> LENGTH: 259
<212> TYPE: PRT
<213> ORGANISM: Homo sapiens
<220> FEATURE:
<221> NAME/KEY: SIGNAL
<222> LOCATION: -23..-1
<220> FEATURE:
<221> NAME/KEY: UNSURE
<222> LOCATION: 31,84,88,90,94,100,110,113,117,122,152,153,173,193,194
<223> OTHER INFORMATION: Xaa = any one of the twenty amino acids

<400> SEQUENCE: 167

```
Met Pro Ser Trp Ile Gly Ala Val Ile Leu Pro Leu Gly Leu Leu
            -20                 -15                 -10

Leu Ser Leu Pro Ala Gly Ala Asp Val Lys Ala Arg Ser Cys Gly Glu
        -5                  1                   5

Val Arg Gln Ala Tyr Gly Ala Lys Gly Phe Ser Leu Ala Asp Ile Pro
10                  15                  20                  25
```

```
Tyr Gln Glu Ile Ala Xaa Glu His Leu Arg Ile Cys Pro Gln Glu Tyr
                30                  35                  40

Thr Cys Cys Thr Thr Glu Met Glu Asp Lys Leu Ser Gln Gln Ser Lys
            45                  50                  55

Leu Glu Phe Glu Asn Leu Val Glu Glu Thr Ser His Phe Val Arg Thr
        60                  65                  70

Thr Phe Val Ser Arg His Lys Lys Phe Asp Xaa Phe Phe Arg Xaa Leu
    75                  80                  85

Xaa Glu Asn Ala Xaa Lys Ser Leu Asn Asp Xaa Phe Val Arg Thr Tyr
90                  95                  100                 105

Gly Met Leu Tyr Xaa Gln Asn Xaa Glu Val Phe Xaa Asp Leu Phe Thr
                110                 115                 120

Xaa Leu Lys Arg Tyr Tyr Thr Gly Gly Asn Val Asn Leu Glu Glu Met
            125                 130                 135

Leu Asn Asp Phe Trp Ala Arg Leu Leu Glu Arg Met Phe Gln Xaa Xaa
            140                 145                 150

Asn Pro Gln Tyr His Phe Ser Glu Asp Tyr Leu Glu Cys Val Ser Lys
        155                 160                 165

Tyr Thr Asp Xaa Leu Lys Pro Phe Gly Asp Val Pro Arg Lys Leu Lys
170                 175                 180                 185

Ile Gln Val Thr Arg Ala Phe Xaa Xaa Ala Arg Thr Phe Val Gln Gly
                190                 195                 200

Leu Thr Val Gly Arg Glu Val Ala Asn Arg Val Ser Lys Val Ile Glu
            205                 210                 215

Asn Val Leu Ser Phe Ser Leu Val Phe Leu Val Tyr Ser Val Phe Lys
        220                 225                 230

Thr Asn Val
    235

<210> SEQ ID NO 168
<211> LENGTH: 111
<212> TYPE: PRT
<213> ORGANISM: Homo sapiens
<220> FEATURE:
<221> NAME/KEY: SIGNAL
<222> LOCATION: -62..-1
<220> FEATURE:
<221> NAME/KEY: UNSURE
<222> LOCATION: 37,43
<223> OTHER INFORMATION: Xaa = any one of the twenty amino acids

<400> SEQUENCE: 168

Met Gly Glu Ser Ile Pro Leu Ala Ala Pro Val Pro Val Gln Ala
        -60                 -55                 -50

Val Leu Glu Thr Phe Phe Ser His Leu Gly Ile Phe Ser Tyr Asp Lys
    -45                 -40                 -35

Ala Lys Asp Asn Val Glu Lys Glu Arg Glu Ala Asn Lys Ser Ala Gly
-30                 -25                 -20                 -15

Gly Ser Trp Leu Ser Leu Leu Ala Ala Leu Ala His Leu Ala Ala Ala
            -10                 -5                   1

Glu Lys Val Tyr His Ser Leu Thr Tyr Leu Gly Gln Lys Leu Gly Thr
        5                   10                  15

Ser Ala Pro Pro Glu Pro Leu Glu Glu Val Lys Gly Val Tyr
    20                  25                  30

Ser Pro Xaa Gly Ser Gly Leu Gly Xaa Pro Ser Leu Cys His Phe
35                  40                  45
```

```
<210> SEQ ID NO 169
<211> LENGTH: 311
<212> TYPE: PRT
<213> ORGANISM: Homo sapiens
<220> FEATURE:
<221> NAME/KEY: SIGNAL
<222> LOCATION: -23...-1
<220> FEATURE:
<221> NAME/KEY: UNSURE
<222> LOCATION: 56,70,107,110,113,178,181,183,195,200,202,204,230,231,
                244
<223> OTHER INFORMATION: Xaa = any one of the twenty amino acids

<400> SEQUENCE: 169

Met Ala Asp Val Ile Asn Val Ser Val Asn Leu Glu Ala Phe Ser Gln
            -20                 -15                 -10

Ala Ile Ser Ala Ile Gln Ala Leu Arg Ser Ser Val Ser Arg Val Phe
          -5                   1                   5

Asp Cys Leu Lys Asp Gly Met Arg Asn Lys Glu Thr Leu Glu Gly Arg
 10                  15                  20                  25

Glu Lys Ala Phe Ile Ala His Phe Gln Asp Asn Leu His Ser Val Asn
                 30                  35                  40

Arg Asp Leu Asn Glu Leu Glu Arg Leu Ser Asn Leu Val Gly Xaa Pro
             45                  50                  55

Ser Glu Asn His Pro Leu His Asn Ser Gly Leu Leu Xaa Leu Asp Pro
         60                  65                  70

Val Gln Asp Lys Thr Pro Leu Tyr Ser Gln Leu Leu Gln Ala Tyr Lys
     75                  80                  85

Trp Ser Asn Lys Leu Gln Tyr His Ala Gly Leu Ala Ser Gly Leu Leu
 90                  95                 100                 105

Asn Xaa Gln Ser Xaa Lys Arg Xaa Ala Asn Gln Met Gly Val Ser Ala
                110                 115                 120

Lys Arg Arg Pro Lys Ala Gln Pro Thr Thr Leu Val Leu Pro Pro Gln
             125                 130                 135

Tyr Val Asp Asp Val Ile Ser Arg Ile Asp Arg Met Phe Pro Glu Met
         140                 145                 150

Ser Ile His Leu Ser Arg Pro Asn Gly Thr Ser Ala Met Leu Leu Val
     155                 160                 165

Thr Leu Gly Lys Val Leu Lys Val Xaa Val Val Xaa Arg Xaa Leu Phe
170                 175                 180                 185

Ile Asp Arg Thr Ile Val Lys Gly Tyr Xaa Glu Asn Val Tyr Xaa Glu
                190                 195                 200

Xaa Gly Xaa Leu Asp Ile Trp Ser Lys Ser Asn Tyr Gln Val Phe Gln
             205                 210                 215

Lys Val Thr Asp His Ala Thr Thr Ala Leu Leu His Xaa Xaa Leu Pro
         220                 225                 230

Gln Met Pro Asp Val Val Val Arg Ser Phe Xaa Thr Trp Leu Arg Ser
     235                 240                 245

Tyr Ile Lys Leu Phe Gln Ala Pro Cys Gln Arg Cys Gly Lys Phe Leu
250                 255                 260                 265

Gln Asp Gly Leu Pro Pro Thr Trp Arg Asp Phe Arg Thr Leu Glu Ala
             270                 275                 280

Phe His Asp Thr Cys Arg Gln
             285

<210> SEQ ID NO 170
<211> LENGTH: 91
```

```
<212> TYPE: PRT
<213> ORGANISM: Homo sapiens
<220> FEATURE:
<221> NAME/KEY: SIGNAL
<222> LOCATION: -60..-1

<400> SEQUENCE: 170

Met Thr Ser Leu Phe Ala Val Val Leu Gln Arg Glu Lys Glu Pro His
-60                 -55                 -50                 -45

Leu Trp Leu Ser Ser Pro His Ile Arg Phe Ser Leu Arg Val Asn Lys
                -40                 -35                 -30

Leu Ser Glu Leu Met Leu Gln Leu Leu Gln Phe Lys Ala Phe Pro Ser
            -25                 -20                 -15

Ser Leu Val Pro Phe Phe Leu Phe Thr Cys Phe Gly His Phe Pro Ser
        -10                  -5                  1

Phe Thr Thr Phe Gln Gly Phe Ile Glu Asn Asn Leu Leu Gln Asn Gln
 5               10                  15                  20

Phe Asn Ser Asn Val Asp Ile Val Ala Cys Ser
                 25                  30

<210> SEQ ID NO 171
<211> LENGTH: 287
<212> TYPE: PRT
<213> ORGANISM: Homo sapiens
<220> FEATURE:
<221> NAME/KEY: SIGNAL
<222> LOCATION: -17..-1
<220> FEATURE:
<221> NAME/KEY: UNSURE
<222> LOCATION: 74
<223> OTHER INFORMATION: Xaa = any one of the twenty amino acids

<400> SEQUENCE: 171

Met Glu Leu Glu Arg Ile Val Ser Ala Ala Leu Leu Ala Phe Val Gln
        -15                 -10                  -5

Thr His Leu Pro Glu Ala Asp Leu Ser Gly Leu Asp Glu Val Ile Phe
 1               5                   10                  15

Ser Tyr Val Leu Gly Val Leu Glu Asp Leu Pro Ser Gly Pro Ser
                 20                  25                  30

Glu Glu Asn Phe Asp Met Glu Ala Phe Thr Glu Met Met Glu Ala Tyr
            35                  40                  45

Val Pro Gly Phe Ala His Ile Pro Arg Gly Thr Ile Gly Asp Met Met
         50                  55                  60

Gln Lys Leu Ser Gly Gln Leu Ser Asp Ala Xaa Asn Lys Glu Asn Leu
 65                  70                  75

Gln Pro Gln Asn Ser Gly Val Gln Gly Gln Val Pro Ile Ser Pro Glu
 80                  85                  90                  95

Pro Leu Gln Arg Pro Glu Met Leu Lys Glu Glu Thr Arg Ser Ser Ala
                 100                 105                 110

Ala Ala Ala Ala Asp Thr Gln Asp Glu Ala Thr Gly Ala Glu Glu Glu
                 115                 120                 125

Leu Leu Pro Gly Val Asp Val Leu Glu Val Phe Pro Thr Cys Ser
                 130                 135                 140

Val Glu Gln Ala Gln Trp Val Leu Ala Lys Ala Arg Gly Asp Leu Glu
145                 150                 155

Glu Ala Val Gln Met Leu Val Glu Gly Lys Glu Glu Gly Pro Ala Ala
160                 165                 170                 175

Trp Glu Gly Pro Asn Gln Asp Leu Pro Arg Arg Leu Arg Gly Pro Gln
                 180                 185                 190
```

```
Lys Asp Glu Leu Lys Ser Phe Ile Leu Gln Lys Tyr Met Met Val Asp
            195                 200                 205

Ser Ala Glu Asp Gln Lys Ile His Arg Pro Met Ala Pro Lys Glu Ala
            210                 215                 220

Pro Lys Lys Leu Ile Arg Tyr Ile Asp Asn Gln Val Val Ser Thr Lys
            225                 230                 235

Gly Glu Arg Phe Lys Asp Val Arg Asn Pro Glu Ala Glu Met Lys
240             245                 250                 255

Ala Thr Tyr Ile Asn Leu Lys Pro Ala Arg Lys Tyr Arg Phe His
            260                 265                 270

<210> SEQ ID NO 172
<211> LENGTH: 104
<212> TYPE: PRT
<213> ORGANISM: Homo sapiens
<220> FEATURE:
<221> NAME/KEY: SIGNAL
<222> LOCATION: -49..-1
<220> FEATURE:
<221> NAME/KEY: UNSURE
<222> LOCATION: 4
<223> OTHER INFORMATION: Xaa = any one of the twenty amino acids

<400> SEQUENCE: 172

Met Glu His Leu Thr His Ser Ser Gln Lys Leu Gln Ala Asp Glu His
            -45                 -40                 -35

Leu Thr Lys Glu Val Trp Ser Arg Leu Leu Lys Glu Lys Gly Pro Ala
            -30                 -25                 -20

Gly Leu Ile Leu Cys Phe Leu Cys Leu Tyr Pro Ile Pro Leu Cys Thr
            -15                 -10                 -5

Ser His Pro Val Xaa Leu Cys Ala His Pro Gln Asp Val Tyr Pro Val
  1              5                 10                  15

Val Val Arg Ala Glu Ile His Ala Glu Leu Tyr Gln Glu Leu Ala Tyr
            20                  25                  30

Leu Lys Thr Glu Thr Glu Ser Leu Ala His Leu Phe Ala Leu Val Pro
            35                  40                  45

Gln Ala Lys Ile Lys Asn Arg Val
            50                  55

<210> SEQ ID NO 173
<211> LENGTH: 84
<212> TYPE: PRT
<213> ORGANISM: Homo sapiens
<220> FEATURE:
<221> NAME/KEY: SIGNAL
<222> LOCATION: -36..-1
<220> FEATURE:
<221> NAME/KEY: UNSURE
<222> LOCATION: -26,-25,-24
<223> OTHER INFORMATION: Xaa = any one of the twenty amino acids

<400> SEQUENCE: 173

Met Gly Leu Leu Thr Phe Gly Tyr Ile Glu Xaa Xaa Xaa Lys Thr Glu
    -35                 -30                 -25

His Asn Pro Asp His His Ser Cys Leu Ala Val Ser Trp Glu Ala Ala
-20                 -15                 -10                 -5

Gly Cys His Gly Ala Gly Thr Gln Gln Ser Pro Leu Gly Val Ala Gly
              1                 5                   10

Pro Trp Arg Pro Arg Pro Pro Cys Val Gly Ser Leu Leu Ala Ala Arg
            15                  20                  25
```

```
Ser Leu His Lys Gln Val Ile Leu Phe Gly Leu Leu Gly Phe Ala Tyr
    30              35                  40

Asp His Ala Ala
45

<210> SEQ ID NO 174
<211> LENGTH: 131
<212> TYPE: PRT
<213> ORGANISM: Homo sapiens
<220> FEATURE:
<221> NAME/KEY: SIGNAL
<222> LOCATION: -20..-1
<220> FEATURE:
<221> NAME/KEY: UNSURE
<222> LOCATION: 40,41,43,60,70,76,82,86,105,107
<223> OTHER INFORMATION: Xaa = any one of the twenty amino acids

<400> SEQUENCE: 174

Met Glu Lys Ile Pro Val Ser Ala Phe Leu Leu Val Ala Leu Ser
-20              -15                 -10                 -5

Tyr Thr Leu Ala Arg Asp Thr Thr Val Lys Pro Gly Ala Lys Lys Asp
                1               5                  10

Thr Lys Asp Ser Arg Pro Lys Leu Pro Gln Thr Leu Ser Arg Gly Trp
        15                  20                  25

Gly Asp Gln Leu Ile Trp Thr Gln Thr Tyr Glu Xaa Xaa Leu Xaa Lys
        30                  35                  40

Ser Lys Thr Ser Asn Lys Pro Leu Met Ile His His Leu Asp Xaa
45                  50                  55                  60

Cys Pro His Ser Gln Ala Leu Lys Lys Xaa Phe Ala Glu Asn Lys Xaa
                65                  70                  75

Ile Gln Lys Leu Ala Xaa Gln Phe Val Xaa Leu Asn Leu Val Tyr Glu
                80                  85                  90

Thr Thr Asp Lys His Leu Ser Pro Asp Gly Gln Tyr Xaa Pro Xaa Asp
            95                  100                 105

Tyr Val Cys
    110

<210> SEQ ID NO 175
<211> LENGTH: 131
<212> TYPE: PRT
<213> ORGANISM: Homo sapiens
<220> FEATURE:
<221> NAME/KEY: SIGNAL
<222> LOCATION: -23..-1
<220> FEATURE:
<221> NAME/KEY: UNSURE
<222> LOCATION: 59,69,78,85,87
<223> OTHER INFORMATION: Xaa = any one of the twenty amino acids

<400> SEQUENCE: 175

Met Met Asn Phe Arg Gln Arg Met Gly Trp Ile Gly Val Gly Leu Tyr
            -20                 -15                 -10

Leu Leu Ala Ser Ala Ala Ala Phe Tyr Tyr Val Phe Glu Ile Ser Glu
        -5                  1                   5

Thr Tyr Asn Arg Leu Ala Leu Glu His Ile Gln Gln His Pro Gly Glu
10                  15                  20                  25

Pro Leu Glu Gly Thr Thr Trp Thr His Ser Leu Lys Ala Gln Leu Leu
                30                  35                  40

Ser Leu Pro Phe Trp Val Trp Val Ile Phe Leu Val Pro Tyr Leu
                45                  50                  55

Gln Xaa Phe Leu Phe Leu Tyr Ser Cys Thr Lys Xaa Asp Pro Lys Thr
```

```
              60              65              70
Val Gly Tyr Cys Xaa Ile Pro Ile Cys Leu Ala Xaa Ile Xaa Asn Arg
    75              80              85

His Gln Asp Phe Val Lys Ala Ser Asn Gln Ile Ser Lys Leu Gln Leu
90              95              100             105

Ile Asp Thr

<210> SEQ ID NO 176
<211> LENGTH: 335
<212> TYPE: PRT
<213> ORGANISM: Homo sapiens
<220> FEATURE:
<221> NAME/KEY: SIGNAL
<222> LOCATION: -16..-1
<220> FEATURE:
<221> NAME/KEY: UNSURE
<222> LOCATION: 70,139,141,154,156,165
<223> OTHER INFORMATION: Xaa = any one of the twenty amino acids

<400> SEQUENCE: 176

Met Ala Val Phe Val Val Leu Leu Ala Leu Val Ala Gly Val Leu Gly
    -15             -10             -5

Asn Glu Phe Ser Ile Leu Lys Ser Pro Gly Ser Val Val Phe Arg Asn
1               5               10              15

Gly Asn Trp Pro Ile Pro Gly Glu Arg Ile Pro Asp Val Ala Ala Leu
            20              25              30

Ser Met Gly Phe Ser Val Lys Glu Asp Leu Ser Trp Pro Gly Leu Ala
            35              40              45

Val Gly Asn Leu Phe His Arg Pro Arg Ala Ser Val Met Val Met Val
        50              55              60

Lys Gly Val Asn Asn Xaa Pro Leu Pro Pro Gly Cys Val Ile Ser Tyr
65              70              75              80

Pro Leu Glu Asn Ala Val Pro Phe Ser Leu Asp Ser Val Ala Asn Ser
                85              90              95

Ile His Ser Leu Phe Ser Glu Glu Thr Pro Val Val Leu Gln Leu Ala
                100             105             110

Pro Ser Glu Glu Arg Val Tyr Met Val Gly Lys Ala Asn Ser Val Trp
            115             120             125

Lys Thr Phe Gln Ser Leu Ala Pro Ala Pro Xaa Ile Xaa Cys Phe Lys
    130             135             140

Lys Thr Leu Phe Ser Val His Ser Pro Xaa Ile Xaa Leu Ser Arg Asn
145             150             155             160

Asn Glu Val Asp Xaa Leu Phe Leu Ser Glu Leu Gln Val Leu His Asp
            165             170             175

Ile Ser Ser Leu Leu Ser Arg His Lys His Leu Ala Lys Asp His Ser
            180             185             190

Pro Asp Leu Tyr Ser Leu Glu Leu Ala Gly Leu Asp Glu Ile Gly Lys
        195             200             205

Arg Tyr Gly Glu Asp Ser Glu Gln Phe Arg Asp Ala Ser Lys Ile Leu
    210             215             220

Val Asp Ala Leu Gln Lys Phe Ala Asp Met Tyr Ser Leu Tyr Gly
225             230             235             240

Gly Asn Ala Val Val Glu Leu Val Thr Val Lys Ser Phe Asp Thr Ser
            245             250             255

Leu Ile Arg Lys Thr Arg Thr Ile Leu Glu Ala Lys Gln Ala Lys Asn
            260             265             270
```

```
Pro Ala Ser Pro Tyr Asn Leu Ala Tyr Lys Tyr Asn Phe Glu Tyr Ser
            275                 280                 285

Val Val Phe Asn Met Val Leu Trp Ile Met Ile Ala Leu Ala Leu Ala
            290                 295                 300

Val Ile Ile Thr Ser Tyr Asn Ile Trp Asn Met Glu Ser Trp Ile
305                 310                 315

<210> SEQ ID NO 177
<211> LENGTH: 84
<212> TYPE: PRT
<213> ORGANISM: Homo sapiens
<220> FEATURE:
<221> NAME/KEY: SIGNAL
<222> LOCATION: -55..-1

<400> SEQUENCE: 177

Met Arg Lys Val Val Leu Ile Thr Gly Ala Ser Ser Gly Ile Gly Leu
-55                 -50                 -45                 -40

Ala Leu Cys Lys Arg Leu Leu Ala Glu Asp Asp Glu Leu His Leu Cys
            -35                 -30                 -25

Leu Ala Cys Arg Asn Met Ser Lys Ala Glu Ala Val Cys Ala Ala Leu
            -20                 -15                 -10

Leu Ala Ser His Pro Thr Ala Glu Val Thr Ile Val Gln Val Asp Val
            -5                   1                   5

Ser Asn Leu Gln Ser Phe Phe Arg Ala Ser Lys Glu Leu Lys Gln Arg
10                  15                  20                  25

Met Ile Ser Cys

<210> SEQ ID NO 178
<211> LENGTH: 280
<212> TYPE: PRT
<213> ORGANISM: Homo sapiens
<220> FEATURE:
<221> NAME/KEY: SIGNAL
<222> LOCATION: -18..-1

<400> SEQUENCE: 178

Met Glu Gly Pro Arg Gly Trp Leu Val Leu Cys Val Leu Ala Ile Ser
            -15                 -10                 -5

Leu Ala Ser Met Val Thr Glu Asp Leu Cys Arg Ala Pro Asp Gly Lys
             1                   5                  10

Lys Gly Glu Ala Gly Arg Pro Gly Arg Arg Gly Arg Pro Gly Leu Lys
15                  20                  25                  30

Gly Glu Gln Gly Glu Pro Gly Ala Pro Gly Ile Arg Thr Gly Ile Gln
            35                  40                  45

Gly Leu Lys Gly Asp Gln Gly Glu Pro Gly Pro Ser Gly Asn Pro Gly
            50                  55                  60

Lys Val Gly Tyr Pro Gly Pro Ser Gly Pro Leu Gly Ala Arg Gly Ile
            65                  70                  75

Pro Gly Ile Lys Gly Thr Lys Gly Ser Pro Gly Asn Ile Lys Asp Gln
            80                  85                  90

Pro Arg Pro Ala Phe Ser Ala Ile Arg Arg Asn Pro Pro Met Gly Gly
95                  100                 105                 110

Asn Val Val Ile Phe Asp Thr Val Ile Thr Asn Gln Glu Glu Pro Tyr
            115                 120                 125

Gln Asn His Ser Gly Arg Phe Val Cys Thr Val Pro Ala Thr Thr Thr
            130                 135                 140

Ser Pro Ser Arg Cys Cys Pro Ser Gly Lys Ser Ala Cys Pro Ser Ser
```

```
                    145                 150                 155
Pro Pro Gln Gly Ala Arg Ser Asp Ala Pro Trp Ala Ser Val Thr Pro
    160                 165                 170

Pro Thr Arg Gly Ser Ser Arg Trp Cys Gln Gly Ala Trp Cys Phe Ser
175                 180                 185                 190

Cys Ser Arg Val Thr Arg Ser Gly Leu Lys Lys Thr Pro Lys Arg Val
                195                 200                 205

Thr Phe Thr Arg Ala Leu Arg Pro Thr Ala Ser Ser Ala Ala Ser Ser
                210                 215                 220

Ser Ser His Leu Pro Glu Pro Gly Lys Asp Pro Leu Pro His Pro Pro
            225                 230                 235

Leu Trp Leu Pro Cys Ser Ala Cys Lys Met Gly Ala Leu Leu Leu Gln
    240                 245                 250

Leu Leu Lys Gly Gly Gly Trp Leu
255                 260

<210> SEQ ID NO 179
<211> LENGTH: 140
<212> TYPE: PRT
<213> ORGANISM: Homo sapiens
<220> FEATURE:
<221> NAME/KEY: SIGNAL
<222> LOCATION: -51...-1
<220> FEATURE:
<221> NAME/KEY: UNSURE
<222> LOCATION: 24,25,29,87
<223> OTHER INFORMATION: Xaa = any one of the twenty amino acids

<400> SEQUENCE: 179

Met Arg Lys Asp Pro Ser Gly Ala Gly Leu Trp Leu His Ser Gly Gly
    -50                 -45                 -40

Pro Val Leu Pro Tyr Val Arg Glu Ser Val Arg Arg Asn Pro Ala Ser
-35                 -30                 -25                 -20

Ala Ala Thr Pro Ser Thr Ala Val Gly Leu Phe Pro Ala Pro Thr Glu
                -15                 -10                 -5

Cys Phe Ala Arg Val Ser Cys Ser Gly Val Glu Ala Leu Gly Arg Arg
                1                   5                   10

Asp Trp Leu Gly Gly Pro Arg Ala His Xaa Xaa Ala Thr Glu Xaa
    15                  20                  25

Ser Ala Pro Lys Glu Ser Leu Gly Cys His Asp Cys His Ala Ile Lys
30                  35                  40                  45

Lys Cys Arg Lys Trp Glu Val Phe Arg Met Thr His Gln Val Leu Phe
                50                  55                  60

Pro Arg Val Trp Ala Leu Ser Trp Asn Pro Leu Ala Cys Thr Pro Ser
                65                  70                  75

Cys Leu Gln Arg Cys Thr Cys Ile Pro Xaa Cys Ser
        80                  85

<210> SEQ ID NO 180
<211> LENGTH: 279
<212> TYPE: DNA
<213> ORGANISM: Homo sapiens

<400> SEQUENCE: 180
atggcacctc tccaccacat cttggttttc tgtgtgggtc tcctcaccat ggccaaggca      60
gaaagtccaa aggaacacga cccgttcact tacgactacc agtccctgca gatcggaggc     120
ctcgtcatcg ccgggatcct cttcatcctg ggcatcctca tcgtgctgag cagaagatgc     180
```

| | |
|---|---|
| cggtgcaagt tcaaccagca gcagaggact ggggaacccg atgaagagga gggaactttc | 240 |
| cgcagctcca tccgccgtct gtccacccgc aggcggtag | 279 |

<210> SEQ ID NO 181
<211> LENGTH: 1082
<212> TYPE: DNA
<213> ORGANISM: Homo sapiens

<400> SEQUENCE: 181

| | |
|---|---|
| gatcccagac ctcggcttgc agtagtgtta gactgaagat aaagtaagtg ctgtttgggc | 60 |
| taacaggatc tcctcttgca gtctgcagcc caggacgctg attccagcag cgccttaccg | 120 |
| cgcagcccga agattcacta tggtgaaaat cgccttcaat acccctaccg ccgtgcaaaa | 180 |
| ggaggaggcg cggcaagacg tggaggccct cctgagccgc acggtcagaa ctcagatact | 240 |
| gaccggcaag gagctccgag ttgccaccca ggaaaaagag ggctcctctg ggagatgtat | 300 |
| gcttactctc ttaggccttt cattcatctt ggcaggactt attgttggtg gagcctgcat | 360 |
| ttacaagtac ttcatgccca agagcaccat ttaccgtgga gagatgtgct tttttgattc | 420 |
| tgaggatcct gcaaattccc ttcgtggagg agagcctaac ttcctgcctg tgactgagga | 480 |
| ggctgacatt cgtgaggatg acaacattgc aatcattgat gtgcctgtcc ccagtttctc | 540 |
| tgatagtgac cctgcagcaa ttattcatga cttttgaaaag ggaatgactg cttacctgga | 600 |
| cttgttgctg ggaactgct atctgatgcc cctcaatact tctattgtta tgcctccaaa | 660 |
| aaatctggta gagctctttg gcaaactggc gagtggcaga tatctgcctc aaacttatgt | 720 |
| ggttcgagaa gacctagttg ctgtggagga aattcgtgat gttagtaacc ttggcatctt | 780 |
| tatttaccaa ctttgcaata acagaaagtc cttccgcctt cgtcgcagag acctcttgct | 840 |
| gggtttcaac aaacgtgcca ttgataaatg ctggaagatt agacacttcc ccaacgaatt | 900 |
| tattgttgag accaagatct gtcaagagta agaggcaaca gatagagtgt ccttggtaat | 960 |
| aagaagtcag agatttacaa tatgacttta acattaaggt ttatgggata ctcaagatat | 1020 |
| ttactcatgc atttactcta ttgcttatgc cgtaaaaaaa aaaaaaaaaa aaaaaaaaa | 1080 |
| aa | 1082 |

<210> SEQ ID NO 182
<211> LENGTH: 1292
<212> TYPE: DNA
<213> ORGANISM: Mus musculus

<400> SEQUENCE: 182

| | |
|---|---|
| ctctccccgg ccgggagctc cggccgcgga gtgatggtgg caccggtggc gatgggccgg | 60 |
| gcagggacca tggaagtggc ggcagaggtg caggggagg ggcagctggc ggtggaggag | 120 |
| gctgtggtct tcagggtct gtaggtggag gcatggctcg ggccagcagc aggaacagca | 180 |
| gcgaagaggc ctgggggtca cttcaggcgc cgcaacagca gcagagtccg gcagcatctt | 240 |
| ctcttgaggg agcaatttgg agacgagctg gaacccagac tcgcgccctg gataccatcc | 300 |
| tttaccatcc acagcaatcc catctgcttc gagagctgtg cccaggagtg aatacccagc | 360 |
| cctacctctg tgagactggt cattgctgtg gggagactgg ctgctgcacc tactactatg | 420 |
| aactctggtg gttctggctg ctttggactg tcctcatcct ctttagctgc tgttgtgcct | 480 |
| tccgccaccg aagggctaaa ctcaggctgc aacagcaaca gcggcagcgt gaaatcaact | 540 |
| tgttggctta ccatggggca tgccacgggg ctggccctgt tccaaccggt tcactgcttg | 600 |
| accttcgcct cctcagcgcc ttcaaacccc cagcctacga ggatgtggtt caccacccag | 660 |

-continued

```
gcacaccgcc  acctccttac  actgtgggcc  caggctaccc  ttggactact  tccagtgaat    720
gcacccgctg  ctcttccgaa  tccagctgct  ctgcccactt  ggaggggaca  aatgtagaag    780
gtgtttcctc  ccagcagagt  gctctccctc  accaggaggg  tgagcccagg  gcaggattga    840
gcccagttca  catacccct   tcctgccgct  atcgtcgcct  aactggtgac  tcgggtattg    900
agctctgccc  ttgtcctgac  tccagtgaag  gtgagccact  caaggaagcg  agggctagtg    960
cctcccagcc  agatctggaa  gaccattccc  cttgtgcact  gcccccagat  tctgtgtccc   1020
aagttcctcc  catgggctg   gcttctagtt  gtgggacatc  ccataagtag  tttcaagagg   1080
gaaactgggt  attacttggc  caccaggatt  cagccctggt  ttcaactgca  gtcctccatg   1140
tgggaccgtc  cccaccctcc  tagaacacgc  ctgaaaggct  ggagccctga  agaggggcag   1200
caccgaggac  tgtgctatct  ttactcactc  ccaagacata  cacaggagcc  tttaatctca   1260
ttaaagagac  atgaaccagc  aaaaaaaaaa  aa                                   1292
```